United States Patent
Shapiro

(10) Patent No.: US 10,294,230 B2
(45) Date of Patent: May 21, 2019

(54) 3,3-DIFLUOROPIPERIDINE CARBAMATE HETEROCYCLIC COMPOUNDS AS NR2B NMDA RECEPTOR ANTAGONISTS

(71) Applicant: Rugen Holdings (Cayman) Limited, Grand Cayman (KY)

(72) Inventor: Gideon Shapiro, Gainesville, FL (US)

(73) Assignee: Rugen Holdings (Cayman) Limited, Grand Cayman (KY)

(*) Notice: Subject to any disclaimer, the term of this patent is extended or adjusted under 35 U.S.C. 154(b) by 0 days.

(21) Appl. No.: 16/100,596

(22) Filed: Aug. 10, 2018

(65) Prior Publication Data

US 2018/0346476 A1    Dec. 6, 2018

Related U.S. Application Data

(62) Division of application No. 15/578,460, filed as application No. PCT/US2016/035098 on May 31, 2016.

(60) Provisional application No. 62/169,107, filed on Jun. 1, 2015.

(51) Int. Cl.

| C07D 401/12 | (2006.01) |
|---|---|
| C07D 487/04 | (2006.01) |
| A61P 25/28 | (2006.01) |
| A61P 25/24 | (2006.01) |
| A61P 25/08 | (2006.01) |
| A61P 25/16 | (2006.01) |
| A61P 25/06 | (2006.01) |

(52) U.S. Cl.
CPC .......... *C07D 487/04* (2013.01); *A61P 25/06* (2018.01); *A61P 25/08* (2018.01); *A61P 25/16* (2018.01); *A61P 25/24* (2018.01); *A61P 25/28* (2018.01); *C07D 401/12* (2013.01)

(58) Field of Classification Search
CPC .................................................. C07D 401/12
USPC .......................................... 544/323; 514/275
See application file for complete search history.

(56) References Cited

U.S. PATENT DOCUMENTS

| 6,008,233 | A | 12/1999 | Andino et al. | |
|---|---|---|---|---|
| 7,592,360 | B2 | 9/2009 | Liverton et al. | |
| 9,387,212 | B2 * | 7/2016 | Michel | A61K 45/06 |
| 9,567,341 | B2 | 2/2017 | Shapiro | |
| 9,968,610 | B2 | 5/2018 | Shapiro | |
| 10,030,026 | B2 | 7/2018 | Shapiro | |
| 2002/0165241 | A1 | 11/2002 | Claiborne et al. | |
| 2003/0018038 | A1 | 1/2003 | Thompson et al. | |
| 2007/0149568 | A1 | 6/2007 | Liverton et al. | |
| 2007/0293515 | A1 | 12/2007 | Layton et al. | |
| 2008/0086006 | A1 * | 4/2008 | Nelson | C07D 211/72 546/236 |
| 2009/0062261 | A1 | 3/2009 | Masui et al. | |
| 2010/0105650 | A1 | 4/2010 | Plettenburg et al. | |
| 2011/0172415 | A1 | 7/2011 | Masui et al. | |
| 2011/0280808 | A1 | 11/2011 | Kroth et al. | |
| 2013/0096115 | A1 | 4/2013 | Lichter et al. | |
| 2013/0225575 | A1 | 8/2013 | Lichter et al. | |
| 2013/0231348 | A1 | 9/2013 | Campbell et al. | |
| 2014/0018348 | A1 | 1/2014 | Javitt | |
| 2014/0336185 | A1 | 11/2014 | Boehm et al. | |
| 2016/0075713 | A1 | 3/2016 | Shapiro | |
| 2017/0101412 | A1 | 4/2017 | Shapiro | |
| 2017/0209449 | A1 | 7/2017 | Shapiro | |
| 2018/0030055 | A1 | 2/2018 | Shapiro | |
| 2018/0170935 | A1 | 6/2018 | Shapiro | |
| 2018/0271869 | A1 | 9/2018 | Liu et al. | |
| 2018/0303834 | A1 | 10/2018 | Shapiro | |

FOREIGN PATENT DOCUMENTS

| CN | 1503793 A | 6/2004 |
|---|---|---|
| CN | 101163482 A | 4/2008 |
| EP | 3194403 A1 | 7/2017 |
| WO | WO-02068409 A1 | 9/2002 |
| WO | WO-2004/108705 A1 | 12/2004 |

(Continued)

OTHER PUBLICATIONS

Addy, C. et al., Single-dose administration of MK-0657, an NR2B-selective NMDA antagonist, does not result in clinically meaningful improvement in motor function in patients with moderate Parkinson's disease, J Clin Pharmacol, 49(7):856-864 (2009).

(Continued)

*Primary Examiner* — Patricia L Morris

(74) *Attorney, Agent, or Firm* — Choate, Hall & Stewart LLP; Brenda Herschbach Jarrell; Christopher K. Haley

(57) ABSTRACT

Disclosed are chemical entities of Formula (I):

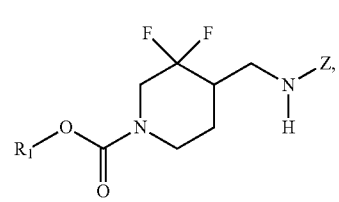

(I)

wherein $R^1$ and Z are defined herein, as NR2B subtype selective receptor antagonists. Also disclosed are pharmaceutical compositions comprising a chemical entity of Formula (I), and methods of treating various diseases and disorders associated with NR2B antagonism, e.g., diseases and disorders of the CNS, such as depression, by administering a chemical entity of Formula (I).

28 Claims, 18 Drawing Sheets

(56) References Cited

FOREIGN PATENT DOCUMENTS

| | | |
|---|---|---|
| WO | WO-2005/102390 A2 | 11/2005 |
| WO | WO-2006/113471 A2 | 10/2006 |
| WO | WO-2007/061868 A2 | 5/2007 |
| WO | WO-2010/015637 A1 | 2/2010 |
| WO | WO-2012/123312 A1 | 9/2012 |
| WO | WO-2014/120800 A1 | 8/2014 |
| WO | WO-2015/171770 A1 | 11/2015 |
| WO | WO-2015/187845 A1 | 12/2015 |
| WO | WO-2016/044323 A1 | 3/2016 |
| WO | WO-2016/049048 A1 | 3/2016 |
| WO | WO-2016/100349 A2 | 6/2016 |
| WO | WO-2016/126869 A1 | 8/2016 |
| WO | WO-2016/196513 A1 | 12/2016 |
| WO | WO-2018/098128 A1 | 5/2018 |

OTHER PUBLICATIONS

Ayata, C. et al., Suppression of cortical spreading depression in migraine prophylaxi, Ann Neurol, 59(4):652-661 (2006).

Bandyopadhyay, S. and Hablitz, J., NR2B antagonists restrict spatiotemporal spread of activity in a rat model of cortical dysplasia, Epilepsy Research, 72:127-139 (2006).

Barton, M. et al., Pharmacological characterization of the 6 Hz psychomotor seizure model of partial epilepsy, Epilepsy Res, 47(3):217-227 (2001).

Bausch, S. et al., Inverse relationship between seizure expression and extrasynaptic NMDAR function following chronic NMDAR inhibition, Epilepsia, 51(Suppl 3):102-105 (2010).

Beinat, C. et al., Insights into Structure-Activity Relationships and CNS Therapeutic Applications of NR2B Selective Antagonists, Current Medicinal Chemistry, 17:4166-4190 (2010).

Berge, S. et al., Pharmaceutical salts, J Pharm Sci, 66(1):1-19 (1977).

Bezzard et al., Neuroscience Disease Models, Neuroscience, 211:1 (2012).

Bogdanova, O. et al., Factors influencing behavior in the forced swim test, Physiol Behav, 118:227-239 (2013).

Borza, I. and Dománny, G., NR2B selective NMDA antagonists: the evolution of the ifenprodil-type pharmacophore, Curr Top Med Chem, 6(7):687-695 (2006).

Boyce-Rustay, J.M. and Holmes, A., Functional Roles of NMDA Receptor NR2A and NR2B Subunits in the Acute Intoxicating Effects of Ethanol in Mice, Synapse, 56:222-225 (2005).

Brown, D. et al., 2,6-Disubstituted pyrazines and related analogs as NR2B site antagonists of the NMDA receptor with anti-depressant activity, Bioorg Med Chem Lett, 21(11):3399-3403 (2011).

Brown, W. et al., Comparative assay of an antiepileptic drugs by psychomotor seizure test and minimal electroshock threshold test, J Pharmacol Exp Ther, 107(3):273-283 (1953).

Can, A. et al., The mouse forced swim test, J Vis Exp, (59):e3638 (2012).

Castel-Branco, M. et al., The maximal electroshock seizure (MES) model in the preclinical assessment of potential new antiepileptic drugs, Methods Find Exp Clin Pharmacol, 31(2):101-106 (2009).

Chen, M. et al., Differential Roles of NMDA Receptor Subtypes in Ischemic Neuronal Cell Death and Ischemic Tolerance, Stroke, 39:3042-3048 (2008).

Chenard, B. et al., (1S,2S)-1-(4-hydroxyphenyl)-2-(4-hydroxy-4-phenylpiperidino)-1-propanol: a potent new neuroprotectant which blocks N-methyl-D-aspartate responses, J Med Chem, 38(16):3138-3145 (1995).

Chermat and Simon, Fiche Technique, Journal of Pharmacology, 6:494-496 (1975).

Claiborne, C. et al., Orally efficacious NR2B-selective NMDA receptor antagonists, Bioorg Med Chem Lett, 13(4):697-700 (2003).

Cull-Candy, S. et al., NMDA receptor diversity in the cerebellum: identification of subunits contributing to functional receptors, Neuropharmacology, 37(10-11):1369-1380 (1998).

Curran, H. and Morgan, C., Cognitive, dissociative and psychotogenic effects of ketamine in recreational users on the night of drug use and 3 days later, Addiction, 95(4):575-590 (2000).

Curtis, N. et al., Novel N1-(benzyl)cinnamamidine derived NR2B subtype-selective NMDA receptor antagonists, Bioorg Med Chem Lett, 13(4):693-696 (2003).

Dalby, N. and Nielsen, E., Comparison of the preclinical anticonvulsant profiles of tiagabine, lamotrigine, gabapentin and vigabatrin, Epilepsy Res, 28(1):63-72 (1997).

Damasio, Antonio R., Alzheimer's Disease and Related Dementias, Cecil Textbook of Medicine, 20th Edition, 2:1992-1996 (1996).

Dubuisson, D. and Dennis, S., The formalin test: a quantitative study of the analgesic effects of morphine, meperidine, and brain stem stimulation in rats and cats, Pain, 4(2):161-74 (1977).

Duman, C., Models of depression, Vitam Horm, 82:1-21 (2010).

Esneault, E. et al., Evaluation of pro-convulsant risk in the rat: spontaneous and provoked convulsions, J Pharmacol Toxicol Methods, 72:59-66 (2015).

Fischer, G. et al., Ro 25-6981, a highly potent and selective blocker of N-methyl-D-aspartate receptors containing the NR2B subunit, Characterization in vitro, J Pharmacol Exp Ther, 283(3):1285-1292 (1997).

Fisher, R. et al., Epileptic seizures and epilepsy: definitions proposed by the International League Against Epilepsy (ILAE) and the International Bureau for Epilepsy (IBE), Epilepsia, 46(4):470-472 (2005).

Garner, R. et al., Preclinical pharmacology and pharmacokinetics of CERC-301, a GluN2B-selective N-methyl-D-aspartate receptor antagonist, Pharmacology Research & Perspectives, 3(6):e00198 (2015).

Ghasemi, M. and Schachter, S.C., The NMDA receptor complex as a therapeutic target in epilepsy: a review, Epilepsy & Behavior, 22:617-640 (2011).

Giannini, A. James et al., Phencyclidine and the Dissociativese, Psychiatric Medicine, 3:197-217 (1985).

Haas, D. and Harper, D., Ketamine: a review of its pharmacologic properties and use in ambulatory anesthesia, Anesth Prog, 39(3):61-68 (1992).

Hancox, J. and James, A., Refining insights into high-affinity drug binding to the human ether-à-go-go-related gene potassium channel, Mol Pharmacol, 73(6):1592-1595 (2008).

Hansen, K. et al., Pharmacological characterization of ligands at recombinant NMDA receptor subtypes by electrophysiological recordings and intracellular calcium measurements, Comb Chem High Throughput Screen, 11(4):304-315 (2008).

Hardy, J. et al., Randomized, double-blind, placebo-controlled study to assess the efficacy and toxicity of subcutaneous ketamine in the management of cancer pain, J Clin Oncol, 30(29):3611-3617 (2012).

Hooft, R. et al., Determination of absolute structure using Bayesian statistics on Bijvoet differences, J Appl Crystallogr, 41(Pt 1):96-103 (2008).

Ibrahim, L. et al., Randomized, placebo-controlled, crossover pilot trial of the oral selective NR2B antagonist MK-0657 in patients with treatment-resistant major depressive disorder, J Clin Psychopharmacol, 32(4):551-557 (2012).

International Search Report for PCT/US2015/034009, 3 pages (dated Sep. 30, 2015).

International Search Report for PCT/US2015/050267, 4 pages (dated Dec. 9, 2015).

International Search Report for PCT/US2015/051488, 4 pages (dated Jan. 27, 2016).

International Search Report for PCT/US2016/35098, 3 pages (dated Aug. 31, 2016).

International Search Report for PCT/US2017/062726 (Treatment of Autism Spectrum Disorders, Obsessive-Compulsive Disorder and Anxiety Disorders, filed Nov. 21, 2017), issued by ISA/EP, 7 pages (dated Apr. 3, 2018).

Jimenez-Sanchez, L. et al., The Role of GluN2A and GluN2B Subunits on the Effect of NMDA Receptor Antagonists in Modeling Schizophrenia and Treating Refractory Depression, Neuropsychopharmacology, 39:2673-2680 (2014).

Jordan, V. Craig, Tamoxifen: A Most Unlikely Pioneering Medicine, Nature Reviews: Drug Discovery, 2(3):205-213 (2003).

(56) References Cited

OTHER PUBLICATIONS

Kao, J. et al., NR2B subunit of NMDA receptor at nucleus accumbens is involved in morphine rewarding effect by siRNA study, Drug and Alcohol Dependence, 118:366-374 (2011).

Katalinic, N. et al., Ketamine as a new treatment for depression: a review of its efficacy and adverse effects, Aust N Z J Psychiatry, 47(8):710-727 (2013).

Kawai, M. et al., Discovery of novel and orally active NR2B-selective N-methyl-D-aspartate (NMDA) antagonists, pyridinol derivatives with reduced HERG binding affinity, Bioorg Med Chem Lett, 17(20):5533-5536 (2007).

Khisti, R. et al., Haloperidol-induced catalepsy: a model for screening antidepressants effective in treatment of depression with Parkinson's disease, Indian J Exp Biol, 35(12):1297-1301 (1997).

Kiss, L. et al., In vitro characterization of novel NR2B selective NMDA receptor antagonists, Neurochem Int, 46(6):453-464 (2005).

Kong, M. et al., NR2B antagonist CP-101,606 inhibits NR2B phosphorylation at tyrosine-1472 and its interactions with Fyn in levodopa-induced dyskinesia rat model, Behavioural Brain Research, 282:46-53 (2015).

Konitsiotis, S. et al., Effects of N-methyl-D-aspartate receptor antagonism on neuroleptic-indeuced orofacial dyskinesias, Physchopharmacology, 185:369-377 (2006).

Koudih, R. et al., Synthesis and in vitro characterization of trans- and cis-[(18)F]-4-methylbenzyl 4-[(pyrimidin-2-ylamino)methyl]-3-fluoropiperidine-1-carboxylates as new potential PET radiotracer candidates for the NR2B subtype N-methyl-D-aspartate receptor, Eur J Med Chem, 53:408-415 (2012).

Krall, R. et al., Antiepileptic drug development: II. Anticonvulsant drug screening, Epilepsia, 19(4):409-428 (1978).

Krska, S. et al., Enantioselective synthesis of a chiral fluoropiperidine via asymmetric hydrogenation of a vinyl fluoride, Tetrahedron, 65:8987-8994 (2009).

Layton, M. et al., Recent advances in the development of NR2B subtype-selective NMDA receptor antagonists, Curr Top Med Chem, 6(7):697-709 (2006).

Layton, M.E. et al., Discovery of 3-Substituted Aminocyclopentances as Potent and Orally Bioavailable NR2B Subtype-Selective NMDA Antagonists, ACS Chem. Neurosci., 2:352-362 (2011).

Lemke, J. et al., GRIN2B Mutations in West Syndrome and Intellectual Disability with Focal Epilepsy, Ann Neurol, 75:147-154 (2014).

Li, L. et al., Role of NR2B-type NMDA receptors in selective neurodegeneration in Huntington disease, Neurobiology of Aging, 24:1113-1121 (2003).

Lima-Ojeda, J.M. et al., Pharmacological blockad of GluN2B-containing NMDA reeptors induces antidepressant-like effects lacking psychotomimetic action and neurotoxicity in the perinatal and adult rodent brain, Progress in Neuro-Psychopharmacology & Biological Psychiatry, 45:28-33 (2013).

Liverton, N. et al., Identification and characterization of 4-methylbenzyl 4-[(pyrimidin-2-ylamino)methyl]piperidine-1-carboxylate, an orally bioavailable, brain penetrant NR2B selective N-methyl-D-aspartate receptor antagonist, J Med Chem, 50(4):807-819 (2007).

Loscher, Wolfgang, Critical review of current animal models of seizures and epilepsy used in the discovery and development of new antiepileptic drugs, Seizure, 20(5):359-368 (2011).

Lucki, I. et al., Sensitivity to the effects of pharmacologically selective antidepressants in different strains of mice, Psychopharmacology (Berl), 155(3):315-322 (2001).

Mares, P. and Mikulecka, A., Different effects of two N-methyl-D-aspartate receptor antagonists on seizures, spontaneous behavior, and motor performance in immature rats, Epilepsy & Behavior, 14:32-39 (2009).

Mares, P., Age and activation determines the anticonvulsant effect in ifenprodil in rats, Naunyn-Schmiedeberg's Arch Pharmacol, 387:753-761 (2014).

Mathews, D. and Zarate, C., Current status of ketamine and related compounds for depression, J Clin Psychiatry, 74(5):516-517 (2013).

Menniti, F. et al., CP-101,606: an NR2B-Selective NMDA Receptor Antagonist, CNS Drug Reviews, 4(4):307-322 (1998).

Menniti, F.S. et al., CP-101,606, an NR2B subunit selective NMDA receptor antagonist, inhibits NMDA and injury induced c-fos expression and corticol spreading depression in rodents, Neurpharmacology, 39:1147-1155 (2000).

Mony, L. et al., Allosteric modulators of NR2B-containing NMDA receptors: molecular mechanisms and therapeutic potential, Br J Pharmacol, 157(8):1301-1317 (2009).

Murrough, J. et al., Antidepressant efficacy of ketamine in treatment-resistant major depression: a two-site randomized controlled trial, Am J Psychiatry, 170(10):1134-1142 (2013).

Naspolini, A.P. et al., Traxoprodil decreases pentylenetetrazol-induced seizures, Epilepsy Research, 100:12-19 (2012).

Neligan, et al., The epidemiology of the epilepsies, Handb Clin Neurol, 107:113-133 (2012).

Nielsen, D. et al., Antidepressant-like activity of corticotropin-releasing factor type-1 receptor antagonists in mice, European Journal of Pharmacology, 499:135-146 (2004).

Niesters, M. et al., Ketamine for chronic pain: risks and benefits, British Journal of Clinical Pharmacology, 77(2):357-367 (2013).

Noppers, I. et al., Drug-induced liver injury following a repeated course of ketamine treatment for chronic pain in CRPS type 1 patients: a report of 3 cases, Pain, 152(9):2173-2178 (2011).

Nutt, J.G. et al., Effects of NR2B Selective NMDA Glutamate Antagonist, CP-101,606, on Dyskinesia and Parkinsonism, Movement Disorders, 23(13):1860-1866 (2008).

Paoletti, P. et al., NMDA receptor subunit diversity: impact on receptor properties, synaptic plasticity and disease, Nat Rev Neurosci, 14(6):383-400 (2013).

Peeters, M. et al., Effects of Pan- and Subtype-Selective N-Methyl-D-aspartate Receptor Antagonists on Cortical Spreading Depression in the Rat: Therapeutic Potential for Migraine, The Journal of Pharmacology and Experimental Therapeutics, 321(2):564-572 (2007).

Porsolt, et al., Behavioral Despair in Rats: A New Model Sensitive to Antidepressant Treatments, Eur. J. Pharmacol., 47:379-391 (1977).

Porsolt, R. et al., Behavioral despair in mice: a primary screening test for antidepressants, Arch Int Pharmacodyn Ther, 229(2):327-336 (1977).

Porsolt, R. et al., Depression: a new animal model sensitive to antidepressant treatments, Nature, 266(5604):730-732 (1977).

Preskorn, S. et al., An innovative design to establish proof of concept of the antidepressant effects of the NR2B subunit selective N-methyl-D-aspartate antagonist, CP-101,606, in patients with treatment-refractory major depressive disorder, J Clin Psychopharmacol, 28(6):631-637 (2008).

Reynolds, I. and Miller, R., Ifenprodil is a novel type of N-methyl-D-aspartate receptor antagonist: interaction with polyamines, Mol Pharmacol, 36(5):758-765 (1989).

Ruppa, K. et al., NMDA Antagonists of GluN2B Subtype and Modulators of GluN2A, GluN2C, and GluN2D Subtypes—Recent Results and Developments, Annual Reports in Medicinal Chemistry, 47:89-103 (2012).

Sanacora, G. et al., Targeting the glutamatergic system to develop novel, improved therapeutics for mood disorders, Nat Rev Drug Discov, 7(5):426-437 (2008).

Sang, C.N. et al., The NR2B subunit-selective NMDA receptor antagonist, CP-101,606, reduces spontaneous pain intensity in patients with central and peripheral neuropathic pain, Society for Neuroscience, Abstract 814.9 (2003).

Shatillo, A., et al., Involvement of NMDA receptor subtypes in cortical spreading depression in rats assessed by fMRI, Neuropharmacology, 93:164-170 (2015).

Shehadeh, J. et al., Striatal neuronal apoptosis is preferentially enhanced by NMDA receptor activation in YAC transgenic mouse model of Huntington disease, Neurobiology of Disease, 21:392-403 (2006).

Slattery, D. and Cryan, J., Using the rat forced swim test to assess antidepressant-like activity in rodents, Nat Protoc, 7(6):1009-1014 (2012).

Steece-Collier, K. et al., Antiparkinsonian actions of CP-101,606, an antagonist of NR2B subunit-containing N-methyl-d-aspartate receptors, Exp Neurol, 163(1):239-243 (2000).

(56) References Cited

OTHER PUBLICATIONS

Swinyard, E. et al., Comparative assays of antiepileptic drugs in mice and rats, J Pharmacol Exp Ther, 106(3):319-330 (1952).
Szczurowska, E. and Mares, P., Different action of a specific NR2B/NMDA antagonist Ro 25-6981 on cortical evoked potentials and epileptic afterdischarges in immature rats, Brain Research Bulletin, 111:1-8 (2015).
Tahirovic, Y.A. et al., Enantiomeric Propanolamines as selective N-Methyl-D-aspartate 2B Receptor Antagonists, J. Med. Chem., 51:5506-5521 (2008).
Tang, W. and Zhang, X., New chiral phosphorus ligands for enantioselective hydrogenation, Chem Rev,103(8):3029-3070 (2003).
Taniguchi, K. et al., Antinociceptive activity of CP-101,606 an NMDA receptor NR2B subunit antagonist, British Journal of Pharmacology, 122:809-812 (1997).
Traynelis, S. et al., Glutamate receptor ion channels: structure, regulation, and function, Pharmacol Rev, 62(3):405-496 (2010).
Tudge, M. et al., Development of a Kilogram-Scale Asymmetric Synthesis of a Potent DP Receptor Antagonist, Organic Process Research and Development, 14:787-798 (2010).
Vengeliene, V. et al., The role of the NMDA receptor in alcohol relapse: a pharmacological mapping study using the alcohol deprivation effect, Neuropharmacology, 48:822-829 (2005).
Wang, H. et al., pH-Sensitive NMDA Inhibitors Improve Outcome in a Murine Model of SAH, Neurocrit Care, 21:119-131 (2014).
Wang, X.M. and Bausch, S.B., Effects of distinct classes of N-methyl-D-aspartate receptor antagonist on seizures, axonal sprouting and neuronal loss in vitro: suppression by NR2B-selective antagonists, Neuropharmacology, 47:1008-1020 (2004).
Warraich, S.T. et al., Evaluation of behavioural effects of a selective NMDA NR1A/2B receptor antagonist in the unilateral 6-OHDA lesion rat model, Brain Research Bulletin, 79:85-90 (2009).
Wessel, R.H. et al., NR2B selective NMDA receptor antagonist CP-101,606 prevents levodopa-induced motor response alterations in hemi-parkinsonian rats, Neuropharmacology, 47:184-194 (2004).
Written Opinion for PCT/US2015/034009, 6 pages (dated Sep. 30, 2015).
Written Opinion for PCT/US2015/050267, 5 pages (dated Dec. 9, 2015).
Written Opinion for PCT/US2015/051488, 9 pages (dated Jan. 27, 2016).
Written Opinion for PCT/US2016/35098, 8 pages (dated Aug. 31, 2016).
Written Opinion for PCT/US2017/062726 (Treatment of Autism Spectrum Disorders, Obsessive-Compulsive Disorder and Anxiety Disorders, filed Nov. 21, 2017), issued by ISA/EP, 11 pages (dated Apr. 3, 2018).
Xie, X. et al., Role of a Hippocampal Src-Family Kinase-Mediated Glutamatergic Mechanism in Drug Context-Induced Cocaine Seeking, Neuropsychopharmacology, 38:2657-2665 (2013).
Yuan, H. et al., Context-Dependent GluN2B-Selective Inhibitors of NMDA Receptor Function Are Neuroprotective with Minimal Side Effects, Neuron, 85:1305-1318 (2015).
Zarate, C. et al., A randomized trial of an N-methyl-D-aspartate antagonist in treatment-resistant major depression, Arch Gen Psychiatry, 63(8):856-864 (2006).
Zarate, C. et al., Replication of ketamine's antidepressant efficacy in bipolar depression: a randomized controlled add-on trial, Biol Psychiatry, 71(11):939-946 (2012).
Zeron, M.M. et al., Increased Sensitivity to N-Methyl-D-Aspartate Receptor-Mediated Excitotoxicity in a Mouse Model of Huntington's Disease, Neuron, 33:849-860 (2002).
U.S. Appl. No. 15/513,112, Liu et al.
U.S. Appl. No. 15/961,553, Shapiro.
U.S. Appl. No. 16/100,596, Shapiro.
International Search Report for PCT/US2015/65829 (Bicyclic Azaheterocyclic Compounds as NR2B NMDA Receptor Antagonists, filed Dec. 15, 2015), issued by ISA/US, 3 pages (dated Feb. 25, 2016).
International Search Report for PCT/US2016/16442 (3,3-Difluoro-Piperidine Derivatives as NR2B NMDA Receptor Antagonists, filed Feb. 3, 2016), issued by ISA/US, 3 pages (dated Apr. 8, 2016).
Written Opinion for PCT/US2015/65829 (Bicyclic Azaheterocyclic Compounds as NR2B NMDA Receptor Antagonists, filed Dec. 15, 2015), issued by ISA/US, 9 pages (dated Feb. 25, 2016).
Written Opinion for PCT/US2016/16442 (3,3-Difluoro-Piperidine Derivatives as NR2B NMDA Receptor Antagonists, filed Feb. 3, 2016), issued by ISA/US, 9 pages (dated Apr. 8, 2016).
Patani, G. and Lavoie, E., Bioisosterism: A Rational Approach in Drug Design, Chem. Rev., 96:3147-3176 (1996).
Paterson, B., et al., A Randomized, double-blind, placebo-controlled, sequential parallel study of CERC-301 in the adjunctive treatment of subjects with severe depression and recent active suicidal ideation despite antidepressant treatment, Presented at the 2015 National Network of Depression Centers Annual Conference, Nov. 2015, Ann Arbor, MI, USA, Poster (2015).
Paterson, B., et al., A randomized, double-blind, placebo-controlled, parallel-group, three-part safety, pharmacokinetic, and pharmacodynamic study of CERC-301 in healthy subjects, Presented at the 2015 National Network of Depression Centers Annual Conference, Nov. 2015, Ann Arbor, MI, USA, Poster (2015).

\* cited by examiner

3,3-DIFLUOROPIPERIDINE CARBAMATE HETEROCYCLIC COMPOUNDS AS NR2B NMDA RECEPTOR ANTAGONISTS

BACKGROUND

Non-selective NMDA receptor antagonists, originally developed in stroke and head trauma, have more recently shown clinical efficacy in treating depression. The non-selective NMDA receptor antagonist, ketamine, has been shown to have rapid onset and efficacy in depression resistant to standard monoamine reuptake inhibitor therapy (Mathews and Zarate, 2013, *J. Clin. Psychiatry* 74:516-158). However, non-selective NMDA receptor antagonists such as ketamine have a range of undesirable pharmacological activities which limit application in humans. In particular dissociative or psychogenic side effects are particularly prominent for non-selective NMDA receptor antagonists. More recently, NR2B subtype selective NMDA receptor antagonists have demonstrated potential in a wide range of clinical indications. In particular, NR2B antagonists have also demonstrated antidepressant activity in early stage clinical trials (Ibrahim et al., 2012, *J. Clin. Psychopharmacol.* 32, 551-557; Preskorn et al., 2008, *J. Clin. Psychopharmacol.* 28, 631-637). Furthermore, selective NR2B antagonists have advantages over unselective NMDA receptor antagonists such as ketamine due to greatly diminished dissociative side effects. However, NR2B antagonists described to date have generally exhibited drawbacks with regard to other drug properties which have limited potential use in human drug therapy.

SUMMARY

For broad scope of application and safe human use in a range of clinical indications including depression, improved NR2B subtype selective antagonists are needed. The present invention, among other things, addresses the need for NR2B receptor antagonists that are improved in one or more aspects exemplified by pharmacokinetic performance, oral activity, cardiovascular safety, and in vitro and in vivo therapeutic safety index measures.

In some embodiments, the present invention encompasses the insight that chemical entities of Formula (I):

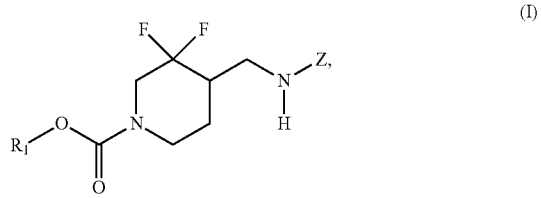

(I)

wherein $R^1$ and Z are defined herein, are NR2B subtype selective receptor antagonists. Chemical entities of Formula (I), and pharmaceutically acceptable compositions thereof, are useful for treating a variety of diseases and disorders associated with NR2B receptor antagonism. Such diseases and disorders include those described herein.

DETAILED DESCRIPTION OF CERTAIN EMBODIMENTS

General Description of Chemical Entities

Figure 1A:
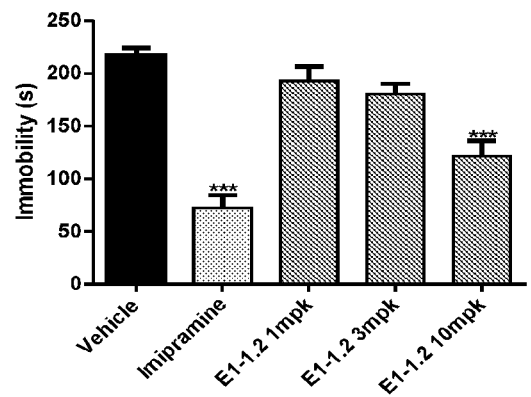
FIG. 1A shows results of the Forced Swim Test in mice as described in Example 2.4.1 with compound E1-1.2.

In some embodiments, the present invention provides chemical entities of Formula I:

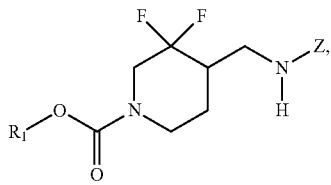

wherein:
$R^1$ is alkyl, cycloalkyl, (cycloalkyl)alkyl, heterocyclyl, (heterocyclyl)alkyl, aryl, (aryl)alkyl, heteroaryl or (heteroaryl)alkyl,
  wherein each of cycloalkyl, (cycloalkyl)alkyl, heterocyclyl, (heterocyclyl)alkyl, aryl, (aryl)alkyl, heteroaryl and (heteroaryl)alkyl is independently optionally substituted with 1 to 3 groups independently selected from —F, —Cl, $C_1$-$C_4$ alkyl, cyclopropyl, —C≡CH, —CFH$_2$, —CF$_2$H, —CF$_3$, —CF$_2$CH$_3$, —CH$_2$CF$_3$, $C_1$-$C_4$ alkoxy, —OCFH$_2$, —OCF$_2$H, —OCF$_3$, —CN, —N($R^2$)($R^3$), —NO$_2$, $C_1$-$C_4$ alkylthio, $C_1$-$C_4$ alkylsulfonyl and —S(O)$_2$CF$_3$;
    wherein each instance of $R^2$ and $R^3$ independently is —H or $C_1$-$C_4$ alkyl, or —N($R^2$)($R^3$) is

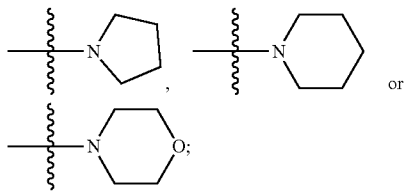

Z is 5- or 6-membered monocyclic or 9- or 10-membered bicyclic heteroaryl having ring carbon atoms, 1 nitrogen ring atom and 0-3 additional ring heteroatoms independently selected from N, O and S, which is optionally substituted with 1 or 2 $R^x$ groups and optionally substituted with 1 $R^a$ group, wherein each $R^x$ is attached to a ring carbon atom and $R^a$ is attached to a ring nitrogen atom;
  wherein:
    each instance of $R^x$ independently is —F, —Cl, —CH$_3$, —CFH$_2$, —CF$_2$H, —CF$_3$, —OH, —OCH$_3$, —OCF$_3$ or —CN; and
    $R^a$ is $C_{1-4}$ alkyl, $C_{3-4}$ cycloalkyl or —S(O)$_2$—$C_{1-4}$ alkyl.

Unless otherwise specified or clear from context, the term "chemical entity" refers to a compound having the indicated structure, whether in its "free" form (e.g., "free compound" or "free base" or "free acid" form, as applicable), or in a salt form, particularly a pharmaceutically acceptable salt form, and furthermore whether in solid state form or otherwise. In some embodiments, a solid state form is an amorphous (i.e., non-crystalline) form; in some embodiments, a solid state form is a crystalline form. In some embodiments, a crystalline form (e.g., a polymorph, pseudohydrate, or hydrate).

Similarly, the term encompasses the compound whether provided in solid form or otherwise. Unless otherwise specified, all statements made herein regarding "compounds" apply to the associated chemical entities, as defined.

Chemical Entities and Definitions

Unless otherwise specified, the word "includes" (or any variation thereon, e.g., "include", "including", etc.) is intended to be open-ended. For example, "A includes 1, 2 and 3" means that A includes but is not limited to 1, 2 and 3.

Unless otherwise specified, the phrase "such as" is intended to be open-ended. For example, "A can be a halogen, such as chlorine or bromine" means that A can be, but is not limited to, chlorine or bromine.

Chemical entities of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

The term "alkyl", used alone or as part of a larger moiety, means a substituted or unsubstituted, linear or branched, univalent hydrocarbon chain that is completely saturated or that contains one or more units of unsaturation. Unless otherwise specified, alkyl groups contain 1 to 7 carbon atoms ("$C_1$-$C_7$ alkyl"). In some embodiments, alkyl groups contain 1 to 6 carbon atoms ("$C_1$-$C_6$ alkyl"). In some embodiments, alkyl groups contain 1 to 5 carbon atoms ("$C_1$-$C_5$ alkyl"). In some embodiments, alkyl groups contain 1 to 4 carbon atoms ("$C_1$-$C_4$ alkyl"). In some embodiments, alkyl groups contain 3 to 7 carbon atoms ("$C_3$-$C_7$ alkyl"). Examples of saturated alkyl groups include methyl, ethyl, n-propyl, i-propyl, n-butyl, t-butyl, i-butyl, s-butyl, homologs and isomers of, for example, n-pentyl, n-hexyl, n-heptyl, n-octyl, and the like. An unsaturated alkyl group is one having one or more carbon-carbon double bonds or carbon-carbon triple bonds. Examples of unsaturated alkyl groups include allyl, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the like. The term "lower alkyl" refers to alkyl groups having 1 to 4 (if saturated) or 2 to 4 (if unsaturated) carbon atoms. Exemplary lower alkyl groups include methyl, ethyl, n-propyl, i-propyl, n-butyl, s-butyl, i-butyl, t-butyl and the like. The term "alkenyl" refers to alkyl groups having at least two carbon atoms and at least one carbon-carbon double bond. The term "alkynyl" refers to alkyl groups having at least two carbon atoms and at least one carbon-carbon triple bond.

The term "cycloalkyl", used alone or as part of a larger moiety, e.g., "(cycloalkyl)alkyl", refers to a univalent monocyclic hydrocarbon that is completely saturated or that contains one or more units of unsaturation, but which is not aromatic; or bicyclo[2.2.1]heptanyl (also called norbornyl) or bicyclo[2.2.2]octanyl. In some embodiments, cycloalkyl groups contain 3 to 8 ring carbon atoms ("$C_3$-$C_8$ cycloalkyl"). Examples of cycloalkyl include cyclopropyl, cyclobutyl, cyclopentyl, cyclohexyl, 1-cyclohexenyl, 3-cyclohexenyl, cycloheptyl, and the like, as well as bicyclo [2.2.1]heptanyl and bicyclo[2.2.2]octanyl.

The term "alkoxy", used alone or as part of a larger moiety, refers to the group —O-alkyl.

The term "halogen" or "halo", used alone or as part of a larger moiety, refers to fluoro, chloro, bromo or iodo.

The term "aryl", used alone or as part of a larger moiety, e.g., "(aryl)alkyl", refers to a univalent monocyclic or bicyclic carbocyclic aromatic ring system. Unless otherwise specified, aryl groups contain 6 or 10 ring members. Examples of aryl include phenyl, naphthyl, and the like.

The term "heteroaryl", used alone or as part of a larger moiety, e.g., "(heteroaryl)alkyl", refers to a univalent monocyclic or bicyclic group having 5 to 10 ring atoms, preferably 5, 6, 9 or 10 ring atoms, having 6, 10, or 14 n electrons shared in a cyclic array, and having, in addition to ring carbon atoms, from one to four ring heteroatoms. Examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, and the like.

The term "heterocyclyl", used alone or as part of a larger moiety, e.g., "(heterocyclyl)alkyl", refers to a univalent stable 5- to 7-membered monocyclic or 7- to 10-membered bicyclic heterocyclic moiety that is either saturated or partially unsaturated, and having, in addition to ring carbon atoms, one to four heteroatoms. Examples of heterocycyl groups include tetrahydrofuranyl, pyrrolidinyl, tetrahydropyranyl, piperidinyl, morpholinyl, and the like.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66:1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "subject" includes a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered. In some embodiments, a subject is a fetus, an infant, a child, a teenager, an adult, or a senior citizen (i.e., the subject is of advanced age, such as older than 50). In some embodiments, a child refers to a human between two and 18 years of age. In some embodiments, an adult refers to a human eighteen years of age or older.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement hydrogen, carbon, nitrogen, oxygen, chlorine or fluorine with $^2$H, $^3$H, $^{11}$C, $^3$C, $^{14}$C, $^{13}$N, $^{15}$N, $^{17}$O, $^{18}$O, $^{36}$Cl or $^{18}$F, respectively, are within the scope of this invention. Such compounds are useful, for example, as analytical tools, as probes in biological assays, or as therapeutic agents in accordance with the present invention. Additionally, incorporation of heavier isotopes such as deuterium ($^2$H) can afford certain therapeutic advantages resulting from greater metabolic stability, for example, increase in vivo half-life, or reduced dosage requirements.

Diastereomeric excess is expressed as % de, i.e., for diastereomers X and Y, the diastereomeric excess of $X=((x-y)/(x+y))*100$, where x and y are the fractions of X and Y, respectively.

Enantiomeric excess is expressed as % ee, i.e., for enantiomers X and Y, the entiomeric excess of $X=((x-y)/(x+y))*100$, where x and y are the fractions of X and Y, respectively.

Exemplary Embodiments of Chemical Entities

In some embodiments, the present invention provides chemical entities of Formula (I):

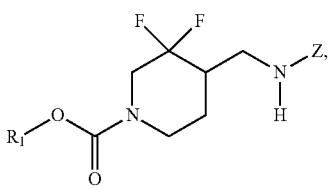

(I)

wherein R¹ and Z are as described above.

In some embodiments, R¹ is optionally substituted alkyl.

In some embodiments, R¹ is optionally substituted cycloalkyl or optionally substituted (cycloalkyl)alkyl. In some embodiments, R¹ is optionally substituted cycloalkyl. In some embodiments, R¹ is optionally substituted cyclohexyl. In some embodiments, R¹ is cyclohexyl. In some embodiments, R¹ is 4,4-difluorocyclohexyl. In some embodiments, R¹ is 4,4-dimethylcyclohexyl. In some embodiments, R¹ is 4-methylcyclohexyl. In some embodiments, R¹ is 4-ethylcyclohexyl. In some embodiments, R¹ is 4-cyclopropylcyclohexyl. In some embodiments, R¹ is optionally substituted norbornanyl. In some embodiments, R¹ is optionally substituted (cycloalkyl)alkyl. In some embodiments, R¹ is bicyclo[2.2.1]heptan-2-ylmethyl. In some embodiments, R¹ is optionally substituted cyclohexylmethyl. In some embodiments, R¹ is cyclohexylmethyl. In some embodiments, R¹ is (4,4-dimethylcyclohexyl)methyl. In some embodiments, R¹ is (4,4-difluorocyclohexyl)methyl.

In some embodiments, R¹ is optionally substituted heterocyclyl or optionally substituted (heterocyclyl)alkyl. In some embodiments, R¹ is optionally substituted heterocyclyl. In some embodiments, R¹ is optionally substituted tetrahydropyranyl. In some embodiments, R¹ is tetrahydropyran-4-yl. In some embodiments, R¹ is optionally substituted (heterocyclyl)alkyl. In some embodiments, R¹ is optionally substituted tetrahydropyranylmethyl. In some embodiments, R¹ is tetrahydropyran-4-ylmethyl.

In some embodiments, R¹ is optionally substituted aryl or optionally substituted (aryl)alkyl. In some embodiments, R¹ is optionally substituted (aryl)alkyl. In some embodiments, R¹ is optionally substituted benzyl. In some embodiments, R¹ is 4-methylbenzyl. In some embodiments, R¹ is 4-ethylbenzyl. In some embodiments, R¹ is 4-isopropylbenzyl. In some embodiments, R¹ is 4-(2,2,2-tri-fluoroethyl)benzyl. In some embodiments, R¹ is 4-(1,1-difluoroethyl)benzyl. In some embodiments, R¹ is 4-t-butylbenzyl. In some embodiments, R¹ is 4-chlorobenzyl. In some embodiments, R¹ is 4-fluorobenzyl. In some embodiments, R¹ is 4-difluoromethylbenzyl. In some embodiments, R¹ is 4-trifluoromethylbenzyl. In some embodiments, R¹ is 4-difluoromethoxybenzyl. In some embodiments, R¹ is 4-trifluoromethoxybenzyl. In some embodiments, R¹ is 4-methylthiobenzyl. In some embodiments, R¹ is 4-ethylthiobenzyl. In some embodiments, R¹ is 4-methylsulfonylbenzyl. In some embodiments R¹ is 4-ethylsulfonylbenzyl. In some embodiments, R¹ is 4-trifluoromethyl-sulfonylbenzyl.

In some embodiments, R¹ is optionally substituted heteroaryl or optionally substituted (heteroaryl)alkyl. In some embodiments, R¹ is optionally substituted (heteroaryl)alkyl. In some embodiments, R¹ is optionally substituted (pyridin-2-yl)methyl. In some embodiments, R¹ is optionally (5-chloro-pyridin-2-yl)methyl. In some embodiments, R¹ is optionally (5-methyl-pyridin-2-yl)methyl. In some embodiments, R¹ is optionally substituted (pyridin-3-yl)methyl. In some embodiments, R¹ is (5-methyl-pyridin-3-yl)methyl.

In some embodiments, Z is 5- or 6-membered monocyclic or 9- or 10-membered bicyclic heteroaryl having ring carbon atoms, 1 ring nitrogen atom and 0-3 additional ring heteroatoms independently selected from N, O and S, which is optionally substituted with 1 or 2 $R^x$ groups and optionally substituted with 1 $R^a$ group, wherein each $R^x$ is attached to a ring carbon atom and $R^a$ is attached to a ring nitrogen atom.

In some embodiments, Z is 9-membered optionally substituted bicyclic heteroaromatic ring system having ring carbon atoms, 1 ring nitrogen atom and 0-3 additional ring heteroatoms independently selected from N, O and S.

In some embodiments, Z is a 9-membered optionally substituted bicyclic hetearomatic ring system having ring carbon atoms, 1 ring nitrogen heteroatom and 1 oxygen ring heteroatom.

In some embodiments, Z is a 9-membered optionally substituted bicyclic hetearomatic ring system having ring carbon atoms and 2 ring nitrogen heteroatoms.

In some embodiments, Z is a 9-membered optionally substituted bicyclic hetearomatic ring system having ring carbon atoms and 3 ring nitrogen heteroatoms.

In some embodiments, Z is a 9-membered optionally substituted bicyclic hetearomatic ring system having ring carbon atoms and 4 ring nitrogen heteroatoms.

In some embodiments, Z is a 5- or 6-membered optionally substituted monocyclic hetearomatic ring system having ring carbon atoms, 1 ring nitrogen atom and 0-2 additional ring heteroatoms independently selected from N, O and S.

In some embodiments, Z is a 6-membered optionally substituted monocyclic hetearomatic ring system having ring carbon atoms, 1 ring nitrogen atom and 0 or 1 additional ring nitrogen atoms. In some embodiments, Z is pyridyl. In some embodiments, Z is pyrimidinyl. In some embodiments, Z is pyridazinyl.

In some embodiments, Z is a 6-membered optionally substituted monocyclic hetearomatic ring system having ring carbon atoms and 2 ring nitrogen atoms. In some embodiments, Z is a 6-membered monocyclic hetearomatic ring system having ring carbon atoms and 2 ring nitrogen atoms, wherein Z is substituted with 1 or 2 $R^x$ groups. In certain embodiments, Z is a 6-membered monocyclic hetearomatic ring system having ring carbon atoms and 2 ring nitrogen atoms, wherein Z is substituted with 1 $R^x$ group. Thus, in some embodiments, Z is a 6-membered monocyclic heteroaromatic ring system having ring carbon atoms and 2 ring nitrogen atoms, wherein Z is monosubstituted with $R^x$. In some embodiments, Z is pyridyl monosubstituted with $R^x$. In some embodiments, Z is pyrimidinyl monosubstituted with $R^x$. In some embodiments, Z is pyridazinyl monosubstituted with $R^x$. In some embodiments, Z is a 5-membered optionally substituted monocyclic hetearomatic ring system having ring carbon atoms, 1 ring nitrogen atom and 0-2 additional ring heteroatoms independently selected from N, O and S.

In some embodiments, Z is a 5-membered optionally substituted monocyclic hetearomatic ring system having ring carbon atoms, 1 ring nitrogen atom and 0 or 1 additional ring heteroatoms independently selected from N, O and S. In some embodiments, Z is imidazolyl or thiazolyl. In some embodiments, Z is imidazolyl. In some embodiments, Z is thiazolyl.

In some embodiments, Z is a 5-membered optionally substituted monocyclic hetearomatic ring system having ring carbon atoms, 1 ring nitrogen atom and 0-2 additional ring heteroatoms independently selected from N, O and S. In some embodiments, Z is triazolyl, oxadiazolyl or thiadiazolyl. In some embodiments, Z is triazolyl. In some embodiments, Z is oxadiazolyl. In some embodiments, Z is thiadiazolyl.

In some embodiments, Z is optionally substituted with 1 or 2 $R^x$ groups and optionally substituted with 1 $R^a$ group, wherein each $R^x$ is attached to a ring carbon atom and $R^a$ is attached to a ring nitrogen atom. In some embodiments, each $R^x$ is independently selected from —F, —Cl, —CH$_3$, —CFH$_2$, —CF$_2$H, —CF$_3$, —OH, —OCH$_3$, —OCF$_3$ or —CN. In some embodiments, $R^x$ is —F or —Cl. In some embodiments, $R^x$ is —F, —Cl or —CN. In some embodiments, $R^x$ is —CH$_3$, —CFH$_2$, —CF$_2$H or —CF$_3$. In some such embodiments, $R^x$ is —CFH$_2$, —CF$_2$H or —CF$_3$. In some embodiments, $R^x$ is —CH$_3$ or —CF$_3$. In some embodiments, $R^x$ is —OH, —OCH$_3$ or —OCF$_3$.

In some embodiments, each $R^a$ is independently selected from $C_{1-4}$ alkyl, $C_{3-4}$ cycloalkyl or —S(O)$_2$—$C_{1-4}$ alkyl. In some embodiments, $R^a$ is $C_{1-4}$ alkyl or $C_{3-4}$ cycloalkyl. In some embodiments, $R^a$ is $C_{1-4}$ alkyl. In some embodiments, $R^a$ is —S(O)$_2$—$C_{1-4}$ alkyl.

In some embodiments Z is one of Formulas Z1-Z36, wherein Z is optionally substituted with 1 or 2 $R^x$ groups, wherein each $R^x$ is attached to a ring carbon atom:

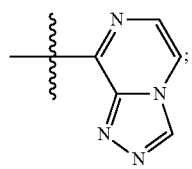
Z1

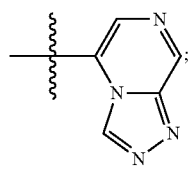
Z2

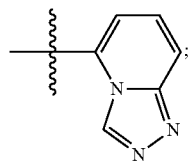
Z3

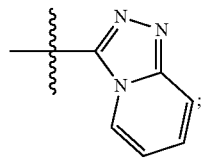
Z4

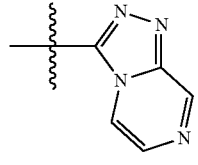
Z5

-continued

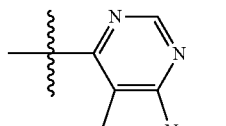
Z6

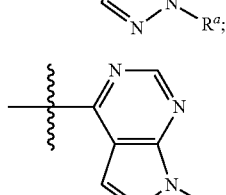
Z7

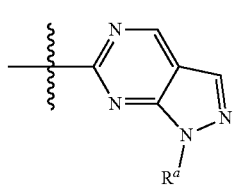
Z8

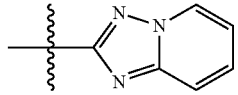
Z9

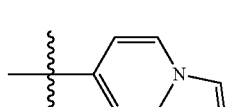
Z10

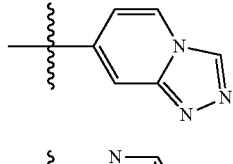
Z11

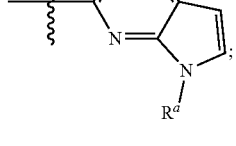
Z12

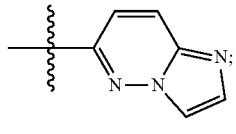
Z13

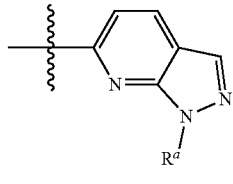
Z14

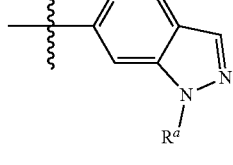
Z15

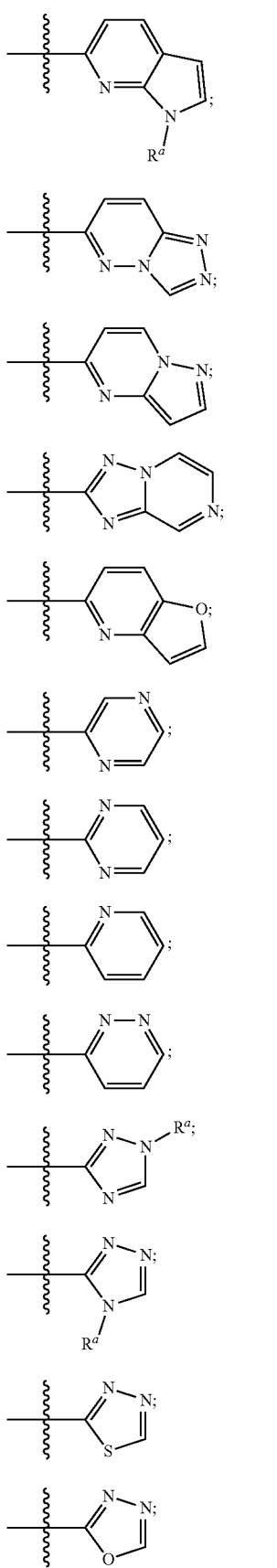
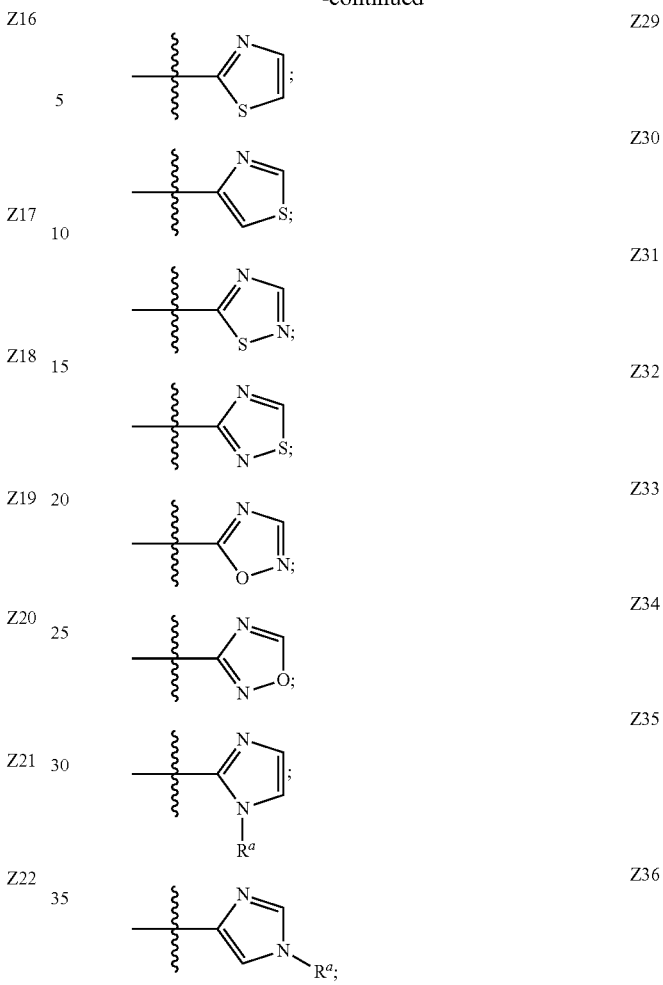

wherein:
each instance of $R^x$ independently is —F, —Cl, —CH$_3$, —CFH$_2$, —CF$_2$H, —CF$_3$, —OH, —OCH$_3$, —OCF$_3$ or —CN; and
$R^a$ is C$_{1-4}$ alkyl, C$_{3-4}$ cycloalkyl or —S(O)$_2$—C$_{1-4}$ alkyl.

In some embodiments, Z is Z1, Z2, Z3, Z4, Z5, Z6, Z7, Z8, Z9, Z10, Z11, Z12, Z13, Z14, Z15, Z16, Z17, Z18, Z19, Z20, Z21, Z22, Z23, Z24, Z25, Z26, Z27, Z28, Z29, Z30, Z31, Z32, Z33, Z34, Z35 or Z36.

In some embodiments, Z is Z1, Z2, Z3, Z4, Z5, Z6, Z7, Z8, Z9, Z10, Z11, Z12, Z13, Z14, Z15, Z16, Z17, Z18, Z19, or Z20.

In some embodiments, Z is Z1, Z2, Z5, Z6, Z8, Z17 or Z19. In some embodiments, Z is Z1 or Z2. In some embodiments, Z is Z1. In some embodiments, Z is Z2. In some embodiments, Z is Z6 or Z8. In some embodiments, Z is Z6. In some embodiments, Z is Z8.

In some embodiments, Z is Z3, Z4, Z7, Z9, Z10, Z11, Z12, Z13, Z14 or Z18. In some embodiments, Z is Z7 or Z9. In some embodiments, Z is Z7. In some embodiments, Z is Z9.

In some embodiments, Z is Z15, Z16 or Z20. In some embodiments, Z is Z15 or Z16. In some embodiments, Z is Z15. In some embodiments, Z is Z16. In some embodiments, Z is 20.

In some embodiments, Z is Z21, Z22, Z23, Z24, Z25, Z26, Z27, Z28, Z29, Z30, Z31, Z32, Z33, Z34, Z35 or Z36.

In some embodiments, Z is Z21, Z22, Z23 or Z24. In some embodiments, Z is Z25, Z26, Z27, Z28, Z29, Z30, Z31, Z32, Z33, Z34, Z35 or Z36.

In some embodiments, Z is Z23.

In some embodiments, Z is Z21, Z22, Z24, Z29, Z30, Z35 or Z36. In some embodiments, Z is Z21, Z22, Z24, Z35 or Z36. In some embodiments, Z is Z21 or Z22. In some embodiments, Z is Z21. In some embodiments, Z is Z22. In some embodiments, Z is Z29 or Z30.

In some embodiments, Z is Z25, Z26, Z27, Z28, Z31, Z32, Z33 or Z34. In some embodiments, Z is Z25 or Z26. In some embodiments, Z is Z25. In some embodiments, Z is Z26. In some embodiments, Z is Z27, Z31 or Z32. In some embodiments, Z is Z28, Z33 or Z34.

In some embodiments, Z is Z27, Z29, Z30, Z31 or Z32. In some embodiments, Z is Z29 or Z30. In some embodiments, Z is Z27, Z31 or Z32.

In some embodiments, Z is Z28, Z33 or Z34. In some embodiments, Z is Z28.

In some embodiments, each instance of $R^x$ independently is —F, —Cl, —CH$_3$, —CF$_3$ or —CN. In some embodiments, each instance of $R^x$ independently is —CH$_3$ or —CF$_3$.

In some embodiments, $R^a$ is —CH$_3$.

In some embodiments, a chemical entity of Formula (I) is a chemical entity of Formula (II):

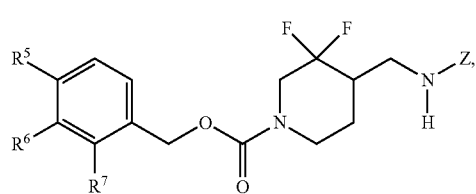

(II)

wherein Z is as described in embodiments of Formula (I), supra, or described in embodiments herein, both singly and in combination; and wherein $R^5$, $R^6$ and $R^7$ independently are —H, —F, —Cl, $C_1$-$C_4$ alkyl, cyclopropyl, —C≡CH, —CFH$_2$, —CF$_2$H, —CF$_3$, —CF$_2$CH$_3$, —CH$_2$CF$_3$, $C_1$-$C_4$ alkoxy, —OCFH$_2$, —OCF$_2$H, —OCF$_3$, —CN, —N($R^2$)($R^3$), —NO$_2$, $C_1$-$C_4$ alkylthio, $C_1$-$C_4$ alkylsulfonyl or —S(O)$_2$CF$_3$;

wherein each instance of $R^2$ and $R^3$ independently is —H or $C_1$-$C_4$ alkyl, or —N($R^2$)($R^3$) is

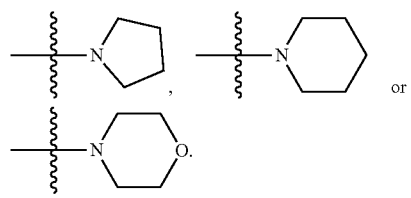

In some embodiments, Z is selected from formulas Z1-Z36, wherein: $R^x$ and $R^a$ are as described in embodiments of formulas Z1-Z36, supra, or described in embodiments herein, both singly and in combination.

In some embodiments, a provided chemical entity is a chemical entity of Formula (II), wherein each of $R^5$, $R^6$ and $R^7$ independently is —H, —F, —Cl, —CH$_3$, —CFH$_2$, —CF$_2$H, —CF$_3$, —CH$_2$CH$_3$, —CF$_2$CH$_3$, —CH$_2$CF$_3$, isopropyl, tert-butyl, cyclopropyl, —OCF$_3$, —OCF$_2$H, —SCH$_3$, —SCH$_2$CH$_3$, —S(O)$_2$CH$_3$, —S(O)$_2$CH$_2$CH$_3$, —S(O)$_2$CF$_3$ or —C≡CH.

In some embodiments, a provided chemical entity is a chemical entity of Formula (II), wherein each of $R^5$, $R^6$ and $R^7$ independently is —H, —F, —Cl, —CH$_3$, —CFH$_2$, —CF$_2$H, —CF$_3$, —CH$_2$CH$_3$, —CF$_2$CH$_3$, —CH$_2$CF$_3$, cyclopropyl, —OCF$_3$, —OCF$_2$H, —SCH$_3$, —S(O)$_2$CH$_3$ or —C≡CH.

In some embodiments, a provided chemical entity is a chemical entity of Formula (II), wherein:
$R^5$ is —H, —F, —Cl, —CH$_3$, —CFH$_2$, —CF$_2$H, —CF$_3$, —CH$_2$CH$_3$, —CF$_2$CH$_3$, —CH$_2$CF$_3$, cyclopropyl, —OCF$_3$, —OCF$_2$H, —SCH$_3$, —S(O)$_2$CH$_3$ or —C≡CH;
$R^6$ is —H or —F; and
$R^7$ is —H, —F, —Cl or —CH$_3$.

In some embodiments, a provided chemical entity is a chemical entity of Formula (II), wherein each of $R^5$, $R^6$ and $R^7$ independently is —H, —F, —Cl, —CH$_3$, —CFH$_2$, —CF$_2$H, —CF$_3$, —CH$_2$CH$_3$, —CF$_2$CH$_3$, —CH$_2$CF$_3$, isopropyl, tert-butyl, cyclopropyl, —OCF$_3$, —OCF$_2$H, —SCH$_3$, —SCH$_2$CH$_3$, —S(O)$_2$CH$_3$, —S(O)$_2$CH$_2$CH$_3$, —S(O)$_2$CF$_3$ or —C≡CH; and Z is Z1, Z2, Z6, Z7, Z8, Z9, Z21 or Z22. In some embodiments, Z is Z1, Z2, Z8, Z9, Z21 or Z22. In some embodiments, Z is Z1 or Z2. In some embodiments, Z is Z1. In some embodiments, Z is Z2.

In some embodiments, a provided chemical entity is a chemical entity of Formula (II), wherein each of $R^5$, $R^6$ and $R^7$ independently is —H, —F, —Cl, —CH$_3$, —CFH$_2$, —CF$_2$H, —CF$_3$, —CH$_2$CH$_3$, —CF$_2$CH$_3$, —CH$_2$CF$_3$, cyclopropyl, —OCF$_3$, —OCF$_2$H, —SCH$_3$, —S(O)$_2$CH$_3$ or —C≡CH; and Z is Z1, Z2, Z8, Z9, Z21 or Z22. In some embodiments, Z is Z1 or Z2. In some embodiments, Z is Z1. In some embodiments, Z is Z2.

In some embodiments, a provided chemical entity is a chemical entity of Formula (II), wherein:
$R^5$ is —H, —F, —Cl, —CH$_3$, —CFH$_2$, —CF$_2$H, —CF$_3$, —CH$_2$CH$_3$, —CF$_2$CH$_3$, —CH$_2$CF$_3$, cyclopropyl, —OCF$_3$, —OCF$_2$H, —SCH$_3$, —S(O)$_2$CH$_3$ or —C≡CH;
$R^6$ is —H or —F;
$R^7$ is —H, —F, —Cl or —CH$_3$; and
Z is Z1, Z2, Z8, Z9, Z21 or Z22. In some embodiments, Z is Z1 or Z2. In some embodiments, Z is Z1. In some embodiments, Z is Z2.

Designation of the stereocenter as R indicates that the R isomer is present in greater amount than the corresponding S isomer. For example, the R isomer can be present in an enantiomeric excess of 50%, 60%, 70%, 80%, 85%, 90%, 92%, 94%, 96% or 98% relative to the S isomer. Similarly, in synthetic intermediates in which more than one stereocenter may be indicated, the R isomer can be present in a diastereomeric excess of 50%, 60%, 70%, 80%, 85%, 90%, 92%, 94%, 96% or 98% relative to the S isomer.

Designation of the stereocenter as S indicates that the S isomer is present in greater amount than the corresponding R isomer. For example, the S isomer can be present in an enantiomeric excess of 50%, 60%, 70%, 80%, 85%, 90%, 92%, 94%, 96% or 98% relative to the R isomer. Similarly, in synthetic intermediates in which more than one stereocenter may be indicated, the S isomer can be present in a diastereomeric excess of 50%, 60%, 70%, 80%, 85%, 90%, 92%, 94%, 96% or 98% relative to the R isomer.

Designation of the optical rotation of a chemical entity indicates that the indicated enantiomer is present in greater amount than the opposite enantiomer. For example, the (−) isomer can be present in an enantiomeric excess of 50%, 60%, 70%, 80%, 85%, 90%, 92%, 94%, 96% or 98% relative to the (+) isomer. Similarly, the (+) isomer can be present in an enantiomeric excess of 50%, 60%, 70%, 80%, 85%, 90%, 92%, 94%, 96% or 98% relative to the (−) isomer.

Exemplary chemical entities of Formula (I) are shown in Tables 1.C, 1.E1 and 1.E2, below.

TABLE 1.C

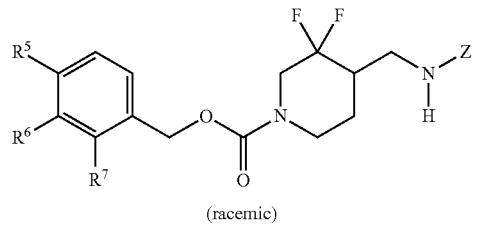

(racemic)

| compound | Z | $R^5$ | $R^6$ | $R^7$ |
|---|---|---|---|---|
| C-1.1 | Z1 | H | H | H |
| C-1.2 | Z1 | $CH_3$ | H | H |
| C-1.3 | Z1 | Cl | H | H |
| C-1.4 | Z1 | F | H | H |
| C-1.5 | Z1 | $CH_2CH_3$ | H | H |
| C-1.6 | Z1 | $CF_2H$ | H | H |
| C-1.7 | Z1 | $CH_2F$ | H | H |
| C-1.8 | Z1 | $CF_3$ | H | H |
| C-1.9 | Z1 | $CF_2CH_3$ | H | H |
| C-1.10 | Z1 | $CH_2CF_3$ | H | H |
| C-1.11 | Z1 | cyclopropyl | H | H |
| C-1.12 | Z1 | $OCF_3$ | H | H |
| C-1.13 | Z1 | $OCF_2H$ | H | H |
| C-1.14 | Z1 | Cl | H | F |
| C-1.15 | Z1 | $CH_3$ | H | F |
| C-1.16 | Z1 | $CH_3$ | F | H |
| C-1.17 | Z1 | Cl | F | H |
| C-1.18 | Z1 | F | F | H |
| C-1.19 | Z1 | F | H | F |
| C-1.20 | Z1 | F | H | Cl |
| C-1.21 | Z1 | F | H | $CH_3$ |
| C-1.22 | Z1 | Cl | H | $CH_3$ |
| C-1.23 | Z1 | $SCH_3$ | H | H |
| C-1.24 | Z1 | $SO_2CH_3$ | H | H |
| C-1.25 | Z1 | ethynyl | H | H |
| C-2.1 | Z2 | H | H | H |
| C-2.2 | Z2 | $CH_3$ | H | H |
| C-2.3 | Z2 | Cl | H | H |
| C-2.4 | Z2 | F | H | H |
| C-2.5 | Z2 | $CH_2CH_3$ | H | H |
| C-2.6 | Z2 | $CF_2H$ | H | H |
| C-2.7 | Z2 | $CH_2F$ | H | H |
| C-2.8 | Z2 | $CF_3$ | H | H |
| C-2.9 | Z2 | $CF_2CH_3$ | H | H |
| C-2.10 | Z2 | $CH_2CF_3$ | H | H |
| C-2.11 | Z2 | cyclopropyl | H | H |
| C-2.12 | Z2 | $OCF_3$ | H | H |
| C-2.13 | Z2 | $OCF_2H$ | H | H |
| C-2.14 | Z2 | Cl | H | F |
| C-2.15 | Z2 | $CH_3$ | H | F |
| C-2.16 | Z2 | $CH_3$ | F | H |
| C-2.17 | Z2 | Cl | F | H |
| C-2.18 | Z2 | F | F | H |
| C-2.19 | Z2 | F | H | F |
| C-2.20 | Z2 | F | H | Cl |
| C-2.21 | Z2 | F | H | $CH_3$ |
| C-2.22 | Z2 | Cl | H | $CH_3$ |
| C-2.23 | Z2 | $SCH_3$ | H | H |
| C-2.24 | Z2 | $SO_2CH_3$ | H | H |
| C-2.25 | Z2 | ethynyl | H | H |
| C-3.1 | Z3 | H | H | H |
| C-3.2 | Z3 | $CH_3$ | H | H |
| C-3.3 | Z3 | Cl | H | H |
| C-3.4 | Z3 | F | H | H |
| C-3.5 | Z3 | $CH_2CH_3$ | H | H |
| C-3.6 | Z3 | $CF_2H$ | H | H |
| C-3.7 | Z3 | $CH_2F$ | H | H |
| C-3.8 | Z3 | $CF_3$ | H | H |
| C-3.9 | Z3 | $CF_2CH_3$ | H | H |
| C-3.10 | Z3 | $CH_2CF_3$ | H | H |
| C-3.11 | Z3 | cyclopropyl | H | H |
| C-3.12 | Z3 | $OCF_3$ | H | H |
| C-3.13 | Z3 | $OCF_2H$ | H | H |
| C-3.14 | Z3 | Cl | H | F |
| C-3.15 | Z3 | $CH_3$ | H | F |
| C-3.16 | Z3 | $CH_3$ | F | H |
| C-3.17 | Z3 | Cl | F | H |
| C-3.18 | Z3 | F | F | H |
| C-3.19 | Z3 | F | H | F |
| C-3.20 | Z3 | F | H | Cl |
| C-3.21 | Z3 | F | H | $CH_3$ |
| C-3.22 | Z3 | Cl | H | $CH_3$ |
| C-3.23 | Z3 | $SCH_3$ | H | H |
| C-3.24 | Z3 | $SO_2CH_3$ | H | H |
| C-3.25 | Z3 | ethynyl | H | H |
| C-4.1 | Z4 | H | H | H |
| C-4.2 | Z4 | $CH_3$ | H | H |
| C-4.3 | Z4 | Cl | H | H |
| C-4.4 | Z4 | F | H | H |
| C-4.5 | Z4 | $CH_2CH_3$ | H | H |
| C-4.6 | Z4 | $CF_2H$ | H | H |
| C-4.7 | Z4 | $CH_2F$ | H | H |
| C-4.8 | Z4 | $CF_3$ | H | H |
| C-4.9 | Z4 | $CF_2CH_3$ | H | H |
| C-4.10 | Z4 | $CH_2CF_3$ | H | H |
| C-4.11 | Z4 | cyclopropyl | H | H |
| C-4.12 | Z4 | $OCF_3$ | H | H |
| C-4.13 | Z4 | $OCF_2H$ | H | H |
| C-4.14 | Z4 | Cl | H | F |
| C-4.15 | Z4 | $CH_3$ | H | F |
| C-4.16 | Z4 | $CH_3$ | F | H |
| C-4.17 | Z4 | Cl | F | H |
| C-4.18 | Z4 | F | F | H |
| C-4.19 | Z4 | F | H | F |
| C-4.20 | Z4 | F | H | Cl |
| C-4.21 | Z4 | F | H | $CH_3$ |
| C-4.22 | Z4 | Cl | H | $CH_3$ |
| C-4.23 | Z4 | $SCH_3$ | H | H |
| C-4.24 | Z4 | $SO_2CH_3$ | H | H |
| C-4.25 | Z4 | ethynyl | H | H |
| C-5.1 | Z5 | H | H | H |
| C-5.2 | Z5 | $CH_3$ | H | H |
| C-5.3 | Z5 | Cl | H | H |
| C-5.4 | Z5 | F | H | H |
| C-5.5 | Z5 | $CH_2CH_3$ | H | H |
| C-5.6 | Z5 | $CF_2H$ | H | H |
| C-5.7 | Z5 | $CH_2F$ | H | H |
| C-5.8 | Z5 | $CF_3$ | H | H |
| C-5.9 | Z5 | $CF_2CH_3$ | H | H |
| C-5.10 | Z5 | $CH_2CF_3$ | H | H |
| C-5.11 | Z5 | cyclopropyl | H | H |
| C-5.12 | Z5 | $OCF_3$ | H | H |
| C-5.13 | Z5 | $OCF_2H$ | H | H |
| C-5.14 | Z5 | Cl | H | F |
| C-5.15 | Z5 | $CH_3$ | H | F |
| C-5.16 | Z5 | $CH_3$ | F | H |
| C-5.17 | Z5 | Cl | F | H |
| C-5.18 | Z5 | F | F | H |
| C-5.19 | Z5 | F | H | F |
| C-5.20 | Z5 | F | H | Cl |
| C-5.21 | Z5 | F | H | $CH_3$ |
| C-5.22 | Z5 | Cl | H | $CH_3$ |

TABLE 1.C-continued

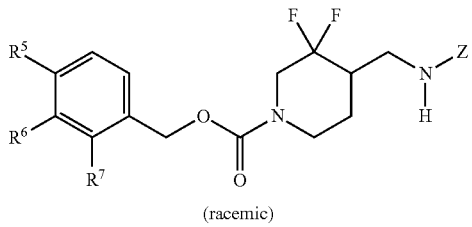
(racemic)

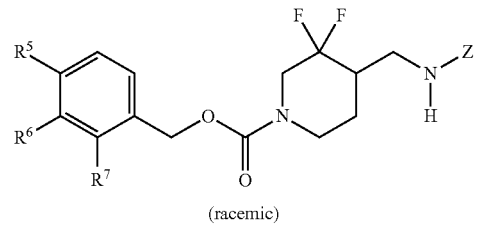
(racemic)

| compound | Z | R⁵ | R⁶ | R⁷ |
|---|---|---|---|---|
| C-5.23 | Z5 | SCH₃ | H | H |
| C-5.24 | Z5 | SO₂CH₃ | H | H |
| C-5.25 | Z5 | ethynyl | H | H |
| C-6.1 | Z6, Rᵃ is H | H | H | H |
| C-6.2 | Z6, Rᵃ is H | CH₃ | H | H |
| C-6.3 | Z6, Rᵃ is H | Cl | H | H |
| C-6.4 | Z6, Rᵃ is H | F | H | H |
| C-6.5 | Z6, Rᵃ is H | CH₂CH₃ | H | H |
| C-6.6 | Z6, Rᵃ is H | CF₂H | H | H |
| C-6.7 | Z6, Rᵃ is H | CH₂F | H | H |
| C-6.8 | Z6, Rᵃ is H | CF₃ | H | H |
| C-6.9 | Z6, Rᵃ is H | CF₂CH₃ | H | H |
| C-6.10 | Z6, Rᵃ is H | CH₂CF₃ | H | H |
| C-6.11 | Z6, Rᵃ is H | cyclopropyl | H | H |
| C-6.12 | Z6, Rᵃ is H | OCF₃ | H | H |
| C-6.13 | Z6, Rᵃ is H | OCF₂H | H | H |
| C-6.14 | Z6, Rᵃ is H | Cl | H | F |
| C-6.15 | Z6, Rᵃ is H | CH₃ | H | F |
| C-6.16 | Z6, Rᵃ is H | CH₃ | F | H |
| C-6.17 | Z6, Rᵃ is H | Cl | F | H |
| C-6.18 | Z6, Rᵃ is H | F | F | H |
| C-6.19 | Z6, Rᵃ is H | F | H | F |
| C-6.20 | Z6, Rᵃ is H | F | H | Cl |
| C-6.21 | Z6, Rᵃ is H | F | H | CH₃ |
| C-6.22 | Z6, Rᵃ is H | Cl | H | CH₃ |
| C-6.23 | Z6, Rᵃ is H | SCH₃ | H | H |
| C-6.24 | Z6, Rᵃ is H | SO₂CH₃ | H | H |
| C-6.25 | Z6, Rᵃ is H | ethynyl | H | H |
| C-7.1 | Z7, Rᵃ is H | H | H | H |
| C-7.2 | Z7, Rᵃ is H | CH₃ | H | H |
| C-7.3 | Z7, Rᵃ is H | Cl | H | H |
| C-7.4 | Z7, Rᵃ is H | F | H | H |
| C-7.5 | Z7, Rᵃ is H | CH₂CH₃ | H | H |
| C-7.6 | Z7, Rᵃ is H | CF₂H | H | H |
| C-7.7 | Z7, Rᵃ is H | CH₂F | H | H |
| C-7.8 | Z7, Rᵃ is H | CF₃ | H | H |
| C-7.9 | Z7, Rᵃ is H | CF₂CH₃ | H | H |
| C-7.10 | Z7, Rᵃ is H | CH₂CF₃ | H | H |
| C-7.11 | Z7, Rᵃ is H | cyclopropyl | H | H |
| C-7.12 | Z7, Rᵃ is H | OCF₃ | H | H |
| C-7.13 | Z7, Rᵃ is H | OCF₂H | H | H |
| C-7.14 | Z7, Rᵃ is H | Cl | H | F |
| C-7.15 | Z7, Rᵃ is H | CH₃ | H | F |
| C-7.16 | Z7, Rᵃ is H | CH₃ | F | H |
| C-7.17 | Z7, Rᵃ is H | Cl | F | H |
| C-7.18 | Z7, Rᵃ is H | F | F | H |
| C-7.19 | Z7, Rᵃ is H | F | H | F |
| C-7.20 | Z7, Rᵃ is H | F | H | Cl |
| C-7.21 | Z7, Rᵃ is H | F | H | CH₃ |
| C-7.22 | Z7, Rᵃ is H | Cl | H | CH₃ |
| C-7.23 | Z7, Rᵃ is H | SCH₃ | H | H |
| C-7.24 | Z7, Rᵃ is H | SO₂CH₃ | H | H |
| C-7.25 | Z7, Rᵃ is H | ethynyl | H | H |
| C-8.1 | Z8, Rᵃ is H | H | H | H |
| C-8.2 | Z8, Rᵃ is H | CH₃ | H | H |
| C-8.3 | Z8, Rᵃ is H | Cl | H | H |
| C-8.4 | Z8, Rᵃ is H | F | H | H |
| C-8.5 | Z8, Rᵃ is H | CH₂CH₃ | H | H |
| C-8.6 | Z8, Rᵃ is H | CF₂H | H | H |
| C-8.7 | Z8, Rᵃ is H | CH₂F | H | H |
| C-8.8 | Z8, Rᵃ is H | CF₃ | H | H |
| C-8.9 | Z8, Rᵃ is H | CF₂CH₃ | H | H |
| C-8.10 | Z8, Rᵃ is H | CH₂CF₃ | H | H |
| C-8.11 | Z8, Rᵃ is H | cyclopropyl | H | H |
| C-8.12 | Z8, Rᵃ is H | OCF₃ | H | H |
| C-8.13 | Z8, Rᵃ is H | OCF₂H | H | H |
| C-8.14 | Z8, Rᵃ is H | Cl | H | F |
| C-8.15 | Z8, Rᵃ is H | CH₃ | H | F |
| C-8.16 | Z8, Rᵃ is H | CH₃ | F | H |
| C-8.17 | Z8, Rᵃ is H | Cl | F | H |
| C-8.18 | Z8, Rᵃ is H | F | F | H |
| C-8.19 | Z8, Rᵃ is H | F | H | F |
| C-8.20 | Z8, Rᵃ is H | F | H | Cl |
| C-8.21 | Z8, Rᵃ is H | F | H | CH₃ |
| C-8.22 | Z8, Rᵃ is H | Cl | H | CH₃ |
| C-8.23 | Z8, Rᵃ is H | SCH₃ | H | H |
| C-8.24 | Z8, Rᵃ is H | SO₂CH₃ | H | H |
| C-8.25 | Z8, Rᵃ is H | ethynyl | H | H |
| C-9.1 | Z9 | H | H | H |
| C-9.2 | Z9 | CH₃ | H | H |
| C-9.3 | Z9 | Cl | H | H |
| C-9.4 | Z9 | F | H | H |
| C-9.5 | Z9 | CH₂CH₃ | H | H |
| C-9.6 | Z9 | CF₂H | H | H |
| C-9.7 | Z9 | CH₂F | H | H |
| C-9.8 | Z9 | CF₃ | H | H |
| C-9.9 | Z9 | CF₂CH₃ | H | H |
| C-9.10 | Z9 | CH₂CF₃ | H | H |
| C-9.11 | Z9 | cyclopropyl | H | H |
| C-9.12 | Z9 | OCF₃ | H | H |
| C-9.13 | Z9 | OCF₂H | H | H |
| C-9.14 | Z9 | Cl | H | F |
| C-9.15 | Z9 | CH₃ | H | F |
| C-9.16 | Z9 | CH₃ | F | H |
| C-9.17 | Z9 | Cl | F | H |
| C-9.18 | Z9 | F | F | H |
| C-9.19 | Z9 | F | H | F |
| C-9.20 | Z9 | F | H | Cl |
| C-9.21 | Z9 | F | H | CH₃ |
| C-9.22 | Z9 | Cl | H | CH₃ |
| C-9.23 | Z9 | SCH₃ | H | H |
| C-9.24 | Z9 | SO₂CH₃ | H | H |
| C-9.25 | Z9 | ethynyl | H | H |
| C-10.1 | Z10 | H | H | H |
| C-10.2 | Z10 | CH₃ | H | H |
| C-10.3 | Z10 | Cl | H | H |
| C-10.4 | Z10 | F | H | H |
| C-10.5 | Z10 | CH₂CH₃ | H | H |
| C-10.6 | Z10 | CF₂H | H | H |
| C-10.7 | Z10 | CH₂F | H | H |
| C-10.8 | Z10 | CF₃ | H | H |
| C-10.9 | Z10 | CF₂CH₃ | H | H |
| C-10.10 | Z10 | CH₂CF₃ | H | H |
| C-10.11 | Z10 | cyclopropyl | H | H |
| C-10.12 | Z10 | OCF₃ | H | H |
| C-10.13 | Z10 | OCF₂H | H | H |
| C-10.14 | Z10 | Cl | H | F |
| C-10.15 | Z10 | CH₃ | H | F |
| C-10.16 | Z10 | CH₃ | F | H |
| C-10.17 | Z10 | Cl | F | H |
| C-10.18 | Z10 | F | F | H |
| C-10.19 | Z10 | F | H | F |
| C-10.20 | Z10 | F | H | Cl |
| C-10.21 | Z10 | F | H | CH₃ |
| C-10.22 | Z10 | Cl | H | CH₃ |
| C-10.23 | Z10 | SCH₃ | H | H |
| C-10.24 | Z10 | SO₂CH₃ | H | H |
| C-10.25 | Z10 | ethynyl | H | H |
| C-11.1 | Z11, Rᵃ is H | H | H | H |
| C-11.2 | Z11, Rᵃ is H | CH₃ | H | H |

TABLE 1.C-continued

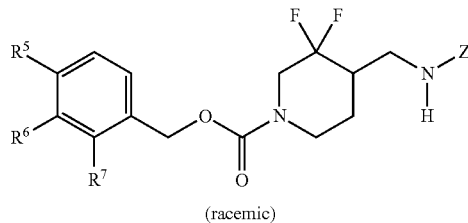

(racemic)

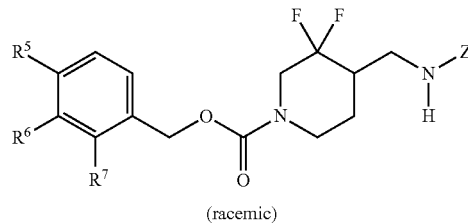

(racemic)

| compound | Z | R⁵ | R⁶ | R⁷ |
|---|---|---|---|---|
| C-11.3 | Z11, Rᵃ is H | Cl | H | H |
| C-11.4 | Z11, Rᵃ is H | F | H | H |
| C-11.5 | Z11, Rᵃ is H | CH₂CH₃ | H | H |
| C-11.6 | Z11, Rᵃ is H | CF₂H | H | H |
| C-11.7 | Z11, Rᵃ is H | CH₂F | H | H |
| C-11.8 | Z11, Rᵃ is H | CF₃ | H | H |
| C-11.9 | Z11, Rᵃ is H | CF₂CH₃ | H | H |
| C-11.10 | Z11, Rᵃ is H | CH₂CF₃ | H | H |
| C-11.11 | Z11, Rᵃ is H | cyclopropyl | H | H |
| C-11.12 | Z11, Rᵃ is H | OCF₃ | H | H |
| C-11.13 | Z11, Rᵃ is H | OCF₂H | H | H |
| C-11.14 | Z11, Rᵃ is H | Cl | H | F |
| C-11.15 | Z11, Rᵃ iS H | CH₃ | H | F |
| C-11.16 | Z11, Rᵃ is H | CH₃ | F | H |
| C-11.17 | Z11, Rᵃ is H | Cl | F | H |
| C-11.18 | Z11, Rᵃ is H | F | F | H |
| C-11.19 | Z11, Rᵃ is H | F | H | F |
| C-11.20 | Z11, Rᵃ is H | F | H | Cl |
| C-11.21 | Z11, Rᵃ is H | F | H | CH₃ |
| C-11.22 | Z11, Rᵃ is H | Cl | H | CH₃ |
| C-11.23 | Z11, Rᵃ is H | SCH₃ | H | H |
| C-11.24 | Z11, Rᵃ is H | SO₂CH₃ | H | H |
| C-11.25 | Z11, Rᵃ is H | ethynyl | H | H |
| C-12.1 | Z12 | H | H | H |
| C-12.2 | Z12 | CH₃ | H | H |
| C-12.3 | Z12 | Cl | H | H |
| C-12.4 | Z12 | F | H | H |
| C-12.5 | Z12 | CH₂CH₃ | H | H |
| C-12.6 | Z12 | CF₂H | H | H |
| C-12.7 | Z12 | CH₂F | H | H |
| C-12.8 | Z12 | CF₃ | H | H |
| C-12.9 | Z12 | CF₂CH₃ | H | H |
| C-12.10 | Z12 | CH₂CF₃ | H | H |
| C-12.11 | Z12 | cyclopropyl | H | H |
| C-12.12 | Z12 | OCF₃ | H | H |
| C-12.13 | Z12 | OCF₂H | H | H |
| C-12.14 | Z12 | Cl | H | F |
| C-12.15 | Z12 | CH₃ | H | F |
| C-12.16 | Z12 | CH₃ | F | H |
| C-12.17 | Z12 | Cl | F | H |
| C-12.18 | Z12 | F | F | H |
| C-12.19 | Z12 | F | H | F |
| C-12.20 | Z12 | F | H | Cl |
| C-12.21 | Z12 | F | H | CH₃ |
| C-12.22 | Z12 | Cl | H | CH₃ |
| C-12.23 | Z12 | SCH₃ | H | H |
| C-12.24 | Z12 | SO₂CH₃ | H | H |
| C-12.25 | Z12 | ethynyl | H | H |
| C-13.1 | Z13, Rᵃ is H | H | H | H |
| C-13.2 | Z13, Rᵃ is H | CH₃ | H | H |
| C-13.3 | Z13, Rᵃ is H | Cl | H | H |
| C-13.4 | Z13, Rᵃ is H | F | H | H |
| C-13.5 | Z13, Rᵃ is H | CH₂CH₃ | H | H |
| C-13.6 | Z13, Rᵃ is H | CF₂H | H | H |
| C-13.7 | Z13, Rᵃ iS H | CH₂F | H | H |
| C-13.8 | Z13, Rᵃ is H | CF₃ | H | H |
| C-13.9 | Z13, Rᵃ is H | CF₂CH₃ | H | H |
| C-13.10 | Z13, Rᵃ is H | CH₂CF₃ | H | H |
| C-13.11 | Z13, Rᵃ is H | cyclopropyl | H | H |
| C-13.12 | Z13, Rᵃ is H | OCF₃ | H | H |
| C-13.13 | Z13, Rᵃ is H | OCF₂H | H | H |
| C-13.14 | Z13, Rᵃ is H | Cl | H | F |
| C-13.15 | Z13, Rᵃ is H | CH₃ | H | F |
| C-13.16 | Z13, Rᵃ is H | CH₃ | F | H |
| C-13.17 | Z13, Rᵃ is H | Cl | F | H |
| C-13.18 | Z13, Rᵃ is H | F | F | H |
| C-13.19 | Z13, Rᵃ is H | F | H | F |
| C-13.20 | Z13, Rᵃ is H | F | H | Cl |
| C-13.21 | Z13, Rᵃ is H | F | H | CH₃ |
| C-13.22 | Z13, Rᵃ is H | Cl | H | CH₃ |
| C-13.23 | Z13, Rᵃ is H | SCH₃ | H | H |
| C-13.24 | Z13, Rᵃ is H | SO₂CH₃ | H | H |
| C-13.25 | Z13, Rᵃ is H | ethynyl | H | H |
| C-14.1 | Z14, Rᵃ is H | H | H | H |
| C-14.2 | Z14, Rᵃ is H | CH₃ | H | H |
| C-14.3 | Z14, Rᵃ is H | Cl | H | H |
| C-14.4 | Z14, Rᵃ is H | F | H | H |
| C-14.5 | Z14, Rᵃ is H | CH₂CH₃ | H | H |
| C-14.6 | Z14, Rᵃ is H | CF₂H | H | H |
| C-14.7 | Z14, Rᵃ is H | CH₂F | H | H |
| C-14.8 | Z14, Rᵃ iS H | CF₃ | H | H |
| C-14.9 | Z14, Rᵃ is H | CF₂CH₃ | H | H |
| C-14.10 | Z14, Rᵃ is H | CH₂CF₃ | H | H |
| C-14.11 | Z14, Rᵃ is H | cyclopropyl | H | H |
| C-14.12 | Z14, Rᵃ is H | OCF₃ | H | H |
| C-14.13 | Z14, Rᵃ is H | OCF₂H | H | H |
| C-14.14 | Z14, Rᵃ is H | Cl | H | F |
| C-14.15 | Z14, Rᵃ is H | CH₃ | H | F |
| C-14.16 | Z14, Rᵃ is H | CH₃ | F | H |
| C-14.17 | Z14, Rᵃ is H | Cl | F | H |
| C-14.18 | Z14, Rᵃ is H | F | F | H |
| C-14.19 | Z14, Rᵃ is H | F | H | F |
| C-14.20 | Z14, Rᵃ is H | F | H | Cl |
| C-14.21 | Z14, Rᵃ is H | F | H | CH₃ |
| C-14.22 | Z14, Rᵃ is H | Cl | H | CH₃ |
| C-14.23 | Z14, Rᵃ is H | SCH₃ | H | H |
| C-14.24 | Z14, Rᵃ is H | SO₂CH₃ | H | H |
| C-14.25 | Z14, Rᵃ is H | ethynyl | H | H |
| C-15.1 | Z15, Rᵃ is H | H | H | H |
| C-15.2 | Z15, Rᵃ is H | CH₃ | H | H |
| C-15.3 | Z15, Rᵃ is H | Cl | H | H |
| C-15.4 | Z15, Rᵃ is H | F | H | H |
| C-15.5 | Z15, Rᵃ is H | CH₂CH₃ | H | H |
| C-15.6 | Z15, Rᵃ is H | CF₂H | H | H |
| C-15.7 | Z15, Rᵃ is H | CH₂F | H | H |
| C-15.8 | Z15, Rᵃ is H | CF₃ | H | H |
| C-15.9 | Z15, Rᵃ iS H | CF₂CH₃ | H | H |
| C-15.10 | Z15, Rᵃ is H | CH₂CF₃ | H | H |
| C-15.11 | Z15, Rᵃ is H | cyclopropyl | H | H |
| C-15.12 | Z15, Rᵃ is H | OCF₃ | H | H |
| C-15.13 | Z15, Rᵃ is H | OCF₂H | H | H |
| C-15.14 | Z15, Rᵃ is H | Cl | H | F |
| C-15.15 | Z15, Rᵃ is H | CH₃ | H | F |
| C-15.16 | Z15, Rᵃ is H | CH₃ | F | H |
| C-15.17 | Z15, Rᵃ is H | Cl | F | H |
| C-15.18 | Z15, Rᵃ is H | F | F | H |
| C-15.19 | Z15, Rᵃ is H | F | H | F |
| C-15.20 | Z15, Rᵃ is H | F | H | Cl |
| C-15.21 | Z15, Rᵃ is H | F | H | CH₃ |
| C-15.22 | Z15, Rᵃ is H | Cl | H | CH₃ |
| C-15.23 | Z15, Rᵃ is H | SCH₃ | H | H |
| C-15.24 | Z15, Rᵃ is H | SO₂CH₃ | H | H |
| C-15.25 | Z15, Rᵃ is H | ethynyl | H | H |
| C-16.1 | Z16, Rᵃ is H | H | H | H |
| C-16.2 | Z16, Rᵃ is H | CH₃ | H | H |
| C-16.3 | Z16, Rᵃ is H | Cl | H | H |
| C-16.4 | Z16, Rᵃ is H | F | H | H |
| C-16.5 | Z16, Rᵃ is H | CH₂CH₃ | H | H |
| C-16.6 | Z16, Rᵃ is H | CF₂H | H | H |
| C-16.7 | Z16, Rᵃ is H | CH₂F | H | H |

TABLE 1.C-continued

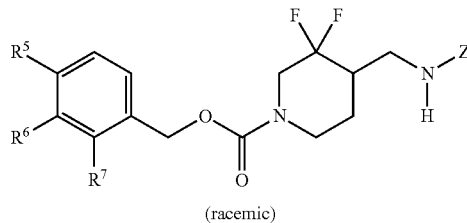

(racemic)

TABLE 1.C-continued

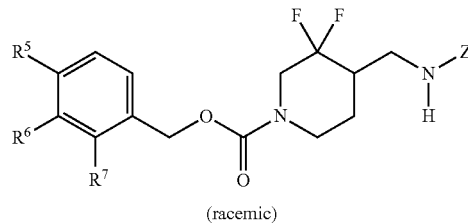

(racemic)

| compound | Z | R5 | R6 | R7 |
|---|---|---|---|---|
| C-16.8 | Z16, $R^a$ is H | $CF_3$ | H | H |
| C-16.9 | Z16, $R^a$ is H | $CF_2CH_3$ | H | H |
| C-16.10 | Z16, $R^a$ is H | $CH_2CF_3$ | H | H |
| C-16.11 | Z16, $R^a$ is H | cyclopropyl | H | H |
| C-16.12 | Z16, $R^a$ is H | $OCF_3$ | H | H |
| C-16.13 | Z16, $R^a$ is H | $OCF_2H$ | H | H |
| C-16.14 | Z16, $R^a$ is H | Cl | H | F |
| C-16.15 | Z16, $R^a$ is H | $CH_3$ | H | F |
| C-16.16 | Z16, $R^a$ is H | $CH_3$ | F | H |
| C-16.17 | Z16, $R^a$ is H | Cl | F | H |
| C-16.18 | Z16, $R^a$ is H | F | F | H |
| C-16.19 | Z16, $R^a$ is H | F | H | F |
| C-16.20 | Z16, $R^a$ is H | F | H | Cl |
| C-16.21 | Z16, $R^a$ is H | F | H | $CH_3$ |
| C-16.22 | Z16, $R^a$ is H | Cl | H | $CH_3$ |
| C-16.23 | Z16, $R^a$ is H | $SCH_3$ | H | H |
| C-16.24 | Z16, $R^a$ is H | $SO_2CH_3$ | H | H |
| C-16.25 | Z16, $R^a$ is H | ethynyl | H | H |
| C-17.1 | Z17 | H | H | H |
| C-17.2 | Z17 | $CH_3$ | H | H |
| C-17.3 | Z17 | Cl | H | H |
| C-17.4 | Z17 | F | H | H |
| C-17.5 | Z17 | $CH_2CH_3$ | H | H |
| C-17.6 | Z17 | $CF_2H$ | H | H |
| C-17.7 | Z17 | $CH_2F$ | H | H |
| C-17.8 | Z17 | $CF_3$ | H | H |
| C-17.9 | Z17 | $CF_2CH_3$ | H | H |
| C-17.10 | Z17 | $CH_2CF_3$ | H | H |
| C-17.11 | Z17 | cyclopropyl | H | H |
| C-17.12 | Z17 | $OCF_3$ | H | H |
| C-17.13 | Z17 | $OCF_2H$ | H | H |
| C-17.14 | Z17 | Cl | H | F |
| C-17.15 | Z17 | $CH_3$ | H | F |
| C-17.16 | Z17 | $CH_3$ | F | H |
| C-17.17 | Z17 | Cl | F | H |
| C-17.18 | Z17 | F | F | H |
| C-17.19 | Z17 | F | H | F |
| C-17.20 | Z17 | F | H | Cl |
| C-17.21 | Z17 | F | H | $CH_3$ |
| C-17.22 | Z17 | Cl | H | $CH_3$ |
| C-17.23 | Z17 | $SCH_3$ | H | H |
| C-17.24 | Z17 | $SO_2CH_3$ | H | H |
| C-17.25 | Z17 | ethynyl | H | H |
| C-18.1 | Z18 | H | H | H |
| C-18.2 | Z18 | $CH_3$ | H | H |
| C-18.3 | Z18 | Cl | H | H |
| C-18.4 | Z18 | F | H | H |
| C-18.5 | Z18 | $CH_2CH_3$ | H | H |
| C-18.6 | Z18 | $CF_2H$ | H | H |
| C-18.7 | Z18 | $CH_2F$ | H | H |
| C-18.8 | Z18 | $CF_3$ | H | H |
| C-18.9 | Z18 | $CF_2CH_3$ | H | H |
| C-18.10 | Z18 | $CH_2CF_3$ | H | H |
| C-18.11 | Z18 | cyclopropyl | H | H |
| C-18.12 | Z18 | $OCF_3$ | H | H |
| C-18.13 | Z18 | $OCF_2H$ | H | H |
| C-18.14 | Z18 | Cl | H | F |
| C-18.15 | Z18 | $CH_3$ | H | F |
| C-18.16 | Z18 | $CH_3$ | F | H |
| C-18.17 | Z18 | Cl | F | H |
| C-18.18 | Z18 | F | F | H |
| C-18.19 | Z18 | F | H | F |
| C-18.20 | Z18 | F | H | Cl |
| C-18.21 | Z18 | F | H | $CH_3$ |
| C-18.22 | Z18 | Cl | H | $CH_3$ |
| C-18.23 | Z18 | $SCH_3$ | H | H |
| C-18.24 | Z18 | $SO_2CH_3$ | H | H |
| C-18.25 | Z18 | ethynyl | H | H |
| C-19.1 | Z19 | H | H | H |
| C-19.2 | Z19 | $CH_3$ | H | H |
| C-19.3 | Z19 | Cl | H | H |
| C-19.4 | Z19 | F | H | H |
| C-19.5 | Z19 | $CH_2CH_3$ | H | H |
| C-19.6 | Z19 | $CF_2H$ | H | H |
| C-19.7 | Z19 | $CH_2F$ | H | H |
| C-19.8 | Z19 | $CF_3$ | H | H |
| C-19.9 | Z19 | $CF_2CH_3$ | H | H |
| C-19.10 | Z19 | $CH_2CF_3$ | H | H |
| C-19.11 | Z19 | cyclopropyl | H | H |
| C-19.12 | Z19 | $OCF_3$ | H | H |
| C-19.13 | Z19 | $OCF_2H$ | H | H |
| C-19.14 | Z19 | Cl | H | F |
| C-19.15 | Z19 | $CH_3$ | H | F |
| C-19.16 | Z19 | $CH_3$ | F | H |
| C-19.17 | Z19 | Cl | F | H |
| C-19.18 | Z19 | F | F | H |
| C-19.19 | Z19 | F | H | F |
| C-19.20 | Z19 | F | H | Cl |
| C-19.21 | Z19 | F | H | $CH_3$ |
| C-19.22 | Z19 | Cl | H | $CH_3$ |
| C-19.23 | Z19 | $SCH_3$ | H | H |
| C-19.24 | Z19 | $SO_2CH_3$ | H | H |
| C-19.25 | Z19 | ethynyl | H | H |
| C-19.26 | Z19 | $CH_3$ | H | H |
| C-20.1 | Z20 | H | H | H |
| C-20.2 | Z20 | $CH_3$ | H | H |
| C-20.3 | Z20 | Cl | H | H |
| C-20.4 | Z20 | F | H | H |
| C-20.5 | Z20 | $CH_2CH_3$ | H | H |
| C-20.6 | Z20 | $CF_2H$ | H | H |
| C-20.7 | Z20 | $CH_2F$ | H | H |
| C-20.8 | Z20 | $CF_3$ | H | H |
| C-20.9 | Z20 | $CF_2CH_3$ | H | H |
| C-20.10 | Z20 | $CH_2CF_3$ | H | H |
| C-20.11 | Z20 | cyclopropyl | H | H |
| C-20.12 | Z20 | $OCF_3$ | H | H |
| C-20.13 | Z20 | $OCF_2H$ | H | H |
| C-20.14 | Z20 | Cl | H | F |
| C-20.15 | Z20 | $CH_3$ | H | F |
| C-20.16 | Z20 | $CH_3$ | F | H |
| C-20.17 | Z20 | Cl | F | H |
| C-20.18 | Z20 | F | F | H |
| C-20.19 | Z20 | F | H | F |
| C-20.20 | Z20 | F | H | Cl |
| C-20.21 | Z20 | F | H | $CH_3$ |
| C-20.22 | Z20 | Cl | H | $CH_3$ |
| C-20.23 | Z20 | $SCH_3$ | H | H |
| C-20.24 | Z20 | $SO_2CH_3$ | H | H |
| C-20.25 | Z20 | ethynyl | H | H |
| C-21.1 | Z21 | H | H | H |
| C-21.2 | Z21 | $CH_3$ | H | H |
| C-21.3 | Z21 | Cl | H | H |
| C-21.4 | Z21 | F | H | H |
| C-21.5 | Z21 | $CH_2CH_3$ | H | H |
| C-21.6 | Z21 | $CF_2H$ | H | H |
| C-21.7 | Z21 | $CH_2F$ | H | H |
| C-21.8 | Z21 | $CF_3$ | H | H |
| C-21.9 | Z21 | $CF_2CH_3$ | H | H |
| C-21.10 | Z21 | $CH_2CF_3$ | H | H |
| C-21.11 | Z21 | cyclopropyl | H | H |

TABLE 1.C-continued

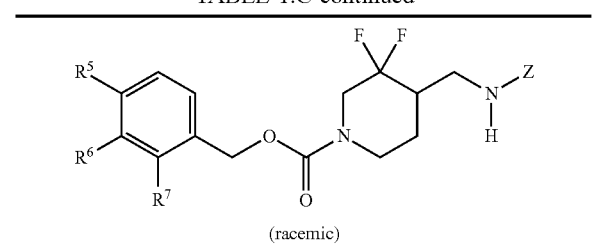

(racemic)

TABLE 1.C-continued

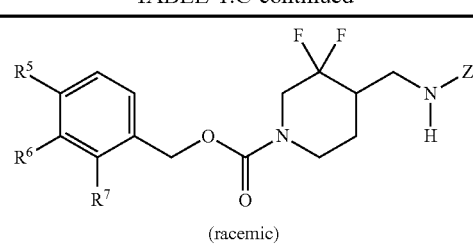

(racemic)

| compound | Z | R⁵ | R⁶ | R⁷ |
|---|---|---|---|---|
| C-21.12 | Z21 | OCF₃ | H | H |
| C-21.13 | Z21 | OCF₂H | H | H |
| C-21.14 | Z21 | Cl | H | F |
| C-21.15 | Z21 | CH₃ | H | F |
| C-21.16 | Z21 | CH₃ | F | H |
| C-21.17 | Z21 | Cl | F | H |
| C-21.18 | Z21 | F | F | H |
| C-21.19 | Z21 | F | H | F |
| C-21.20 | Z21 | F | H | Cl |
| C-21.21 | Z21 | F | H | CH₃ |
| C-21.22 | Z21 | Cl | H | CH₃ |
| C-21.23 | Z21 | SCH₃ | H | H |
| C-21.24 | Z21 | SO₂CH₃ | H | H |
| C-21.25 | Z21 | ethynyl | H | H |
| C-21.26 | (pyrazine, Rˣ, Rˣ is CH₃) | CH₃ | H | H |
| C-22.1 | Z22 | H | H | H |
| C-22.2 | Z22 | CH₃ | H | H |
| C-22.3 | Z22 | Cl | H | H |
| C-22.4 | Z22 | F | H | H |
| C-22.5 | Z22 | CH₂CH₃ | H | H |
| C-22.6 | Z22 | CF₂H | H | H |
| C-22.7 | Z22 | CH₂F | H | H |
| C-22.8 | Z22 | CF₃ | H | H |
| C-22.9 | Z22 | CF₂CH₃ | H | H |
| C-22.10 | Z22 | CH₂CF₃ | H | H |
| C-22.11 | Z22 | cyclopropyl | H | H |
| C-22.12 | Z22 | OCF₃ | H | H |
| C-22.13 | Z22 | OCF₂H | H | H |
| C-22.14 | Z22 | Cl | H | F |
| C-22.15 | Z22 | CH₃ | H | F |
| C-22.16 | Z22 | CH₃ | F | H |
| C-22.17 | Z22 | Cl | F | H |
| C-22.18 | Z22 | F | F | H |
| C-22.19 | Z22 | F | H | F |
| C-22.20 | Z22 | F | H | Cl |
| C-22.21 | Z22 | F | H | CH₃ |
| C-22.22 | Z22 | Cl | H | CH₃ |
| C-22.23 | Z22 | SCH₃ | H | H |
| C-22.24 | Z22 | SO₂CH₃ | H | H |
| C-22.25 | Z22 | ethynyl | H | H |
| C-23.1 | Z23 | H | H | H |
| C-23.2 | Z23 | CH₃ | H | H |
| C-23.3 | Z23 | Cl | H | H |
| C-23.4 | Z23 | F | H | H |
| C-23.5 | Z23 | CH₂CH₃ | H | H |
| C-23.6 | Z23 | CF₂H | H | H |
| C-23.7 | Z23 | CH₂F | H | H |
| C-23.8 | Z23 | CF₃ | H | H |
| C-23.9 | Z23 | CF₂CH₃ | H | H |
| C-23.10 | Z23 | CH₂CF₃ | H | H |
| C-23.11 | Z23 | cyclopropyl | H | H |
| C-23.12 | Z23 | OCF₃ | H | H |
| C-23.13 | Z23 | OCF₂H | H | H |
| C-23.14 | Z23 | Cl | H | F |
| C-23.15 | Z23 | CH₃ | H | F |
| C-23.16 | Z23 | CH₃ | F | H |
| C-23.17 | Z23 | Cl | F | H |
| C-23.18 | Z23 | F | F | H |
| C-23.19 | Z23 | F | H | F |
| C-23.20 | Z23 | F | H | Cl |
| C-23.21 | Z23 | F | H | CH₃ |
| C-23.22 | Z23 | Cl | H | CH₃ |
| C-23.23 | Z23 | SCH₃ | H | H |
| C-23.24 | Z23 | SO₂CH₃ | H | H |
| C-23.25 | Z23 | ethynyl | H | H |
| C-24.1 | Z24 | H | H | H |
| C-24.2 | Z24 | CH₃ | H | H |
| C-24.3 | Z24 | Cl | H | H |
| C-24.4 | Z24 | F | H | H |
| C-24.5 | Z24 | CH₂CH₃ | H | H |
| C-24.6 | Z24 | CF₂H | H | H |
| C-24.7 | Z24 | CH₂F | H | H |
| C-24.8 | Z24 | CF₃ | H | H |
| C-24.9 | Z24 | CF₂CH₃ | H | H |
| C-24.10 | Z24 | CH₂CF₃ | H | H |
| C-24.11 | Z24 | cyclopropyl | H | H |
| C-24.12 | Z24 | OCF₃ | H | H |
| C-24.13 | Z24 | OCF₂H | H | H |
| C-24.14 | Z24 | Cl | H | F |
| C-24.15 | Z24 | CH₃ | H | F |
| C-24.16 | Z24 | CH₃ | F | H |
| C-24.17 | Z24 | Cl | F | H |
| C-24.18 | Z24 | F | F | H |
| C-24.19 | Z24 | F | H | F |
| C-24.20 | Z24 | F | H | Cl |
| C-24.21 | Z24 | F | H | CH₃ |
| C-24.22 | Z24 | Cl | H | CH₃ |
| C-24.23 | Z24 | SCH₃ | H | H |
| C-24.24 | Z24 | SO₂CH₃ | H | H |
| C-24.25 | Z24 | ethynyl | H | H |
| C-25.1 | Z25, Rᵃ is H | H | H | H |
| C-25.2 | Z25, Rᵃ is H | CH₃ | H | H |
| C-25.3 | Z25, Rᵃ is H | Cl | H | H |
| C-25.4 | Z25, Rᵃ is H | F | H | H |
| C-25.5 | Z25, Rᵃ is H | CH₂CH₃ | H | H |
| C-25.6 | Z25, Rᵃ is H | CF₂H | H | H |
| C-25.7 | Z25, Rᵃ is H | CH₂F | H | H |
| C-25.8 | Z25, Rᵃ is H | CF₃ | H | H |
| C-25.9 | Z25, Rᵃ is H | CF₂CH₃ | H | H |
| C-25.10 | Z25, Rᵃ is H | CH₂CF₃ | H | H |
| C-25.11 | Z25, Rᵃ is H | cyclopropyl | H | H |
| C-25.12 | Z25, Rᵃ is H | OCF₃ | H | H |
| C-25.13 | Z25, Rᵃ is H | OCF₂H | H | H |
| C-25.14 | Z25, Rᵃ is H | Cl | H | F |
| C-25.15 | Z25, Rᵃ is H | CH₃ | H | F |
| C-25.16 | Z25, Rᵃ is H | CH₃ | F | H |
| C-25.17 | Z25, Rᵃ is H | Cl | F | H |
| C-25.18 | Z25, Rᵃ is H | F | F | H |
| C-25.19 | Z25, Rᵃ is H | F | H | F |
| C-25.20 | Z25, Rᵃ is H | F | H | Cl |
| C-25.21 | Z25, Rᵃ is H | F | H | CH₃ |
| C-25.22 | Z25, Rᵃ is H | Cl | H | CH₃ |
| C-25.23 | Z25, Rᵃ is H | SCH₃ | H | H |
| C-25.24 | Z25, Rᵃ is H | SO₂CH₃ | H | H |
| C-25.25 | Z25, Rᵃ is H | ethynyl | H | H |
| C-26.1 | Z26, Rᵃ is H | H | H | H |
| C-26.2 | Z26, Rᵃ is H | CH₃ | H | H |
| C-26.3 | Z26, Rᵃ is H | Cl | H | H |
| C-26.4 | Z26, Rᵃ is H | F | H | H |
| C-26.5 | Z26, Rᵃ is H | CH₂CH₃ | H | H |
| C-26.6 | Z26, Rᵃ is H | CF₂H | H | H |
| C-26.7 | Z26, Rᵃ is H | CH₂F | H | H |
| C-26.8 | Z26, Rᵃ is H | CF₃ | H | H |
| C-26.9 | Z26, Rᵃ is H | CF₂CH₃ | H | H |
| C-26.10 | Z26, Rᵃ is H | CH₂CF₃ | H | H |
| C-26.11 | Z26, Rᵃ is H | cyclopropyl | H | H |

TABLE 1.C-continued

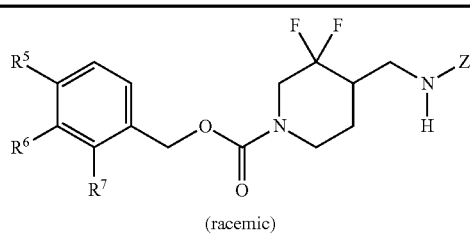

(racemic)

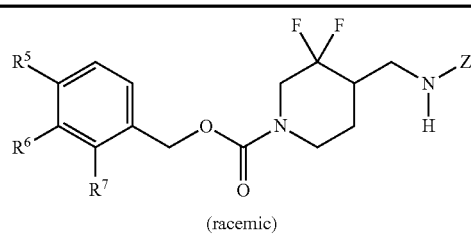

(racemic)

| compound | Z | R⁵ | R⁶ | R⁷ |
|---|---|---|---|---|
| C-26.12 | Z26, $R^a$ is H | OCF₃ | H | H |
| C-26.13 | Z26, $R^a$ is H | OCF₂H | H | H |
| C-26.14 | Z26, $R^a$ is H | Cl | H | F |
| C-26.15 | Z26, $R^a$ is H | CH₃ | H | F |
| C-26.16 | Z26, $R^a$ is H | CH₃ | F | H |
| C-26.17 | Z26, $R^a$ is H | Cl | F | H |
| C-26.18 | Z26, $R^a$ is H | F | F | H |
| C-26.19 | Z26, $R^a$ is H | F | H | F |
| C-26.20 | Z26, $R^a$ is H | F | H | Cl |
| C-26.21 | Z26, $R^a$ is H | F | H | CH₃ |
| C-26.22 | Z26, $R^a$ is H | Cl | H | CH₃ |
| C-26.23 | Z26, $R^a$ is H | SCH₃ | H | H |
| C-26.24 | Z26, $R^a$ is H | SO₂CH₃ | H | H |
| C-26.25 | Z26, $R^a$ is H | ethynyl | H | H |
| C-27.1 | Z27 | H | H | H |
| C-27.2 | Z27 | CH₃ | H | H |
| C-27.3 | Z27 | Cl | H | H |
| C-27.4 | Z27 | F | H | H |
| C-27.5 | Z27 | CH₂CH₃ | H | H |
| C-27.6 | Z27 | CF₂H | H | H |
| C-27.7 | Z27 | CH₂F | H | H |
| C-27.8 | Z27 | CF₃ | H | H |
| C-27.9 | Z27 | CF₂CH₃ | H | H |
| C-27.10 | Z27 | CH₂CF₃ | H | H |
| C-27.11 | Z27 | cyclopropyl | H | H |
| C-27.12 | Z27 | OCF₃ | H | H |
| C-27.13 | Z27 | OCF₂H | H | H |
| C-27.14 | Z27 | Cl | H | F |
| C-27.15 | Z27 | CH₃ | H | F |
| C-27.16 | Z27 | CH₃ | F | H |
| C-27.17 | Z27 | Cl | F | H |
| C-27.18 | Z27 | F | F | H |
| C-27.19 | Z27 | F | H | F |
| C-27.20 | Z27 | F | H | Cl |
| C-27.21 | Z27 | F | H | CH₃ |
| C-27.22 | Z27 | Cl | H | CH₃ |
| C-27.23 | Z27 | SCH₃ | H | H |
| C-27.24 | Z27 | SO₂CH₃ | H | H |
| C-27.25 | Z27 | ethynyl | H | H |
| C-28.1 | Z28 | H | H | H |
| C-28.2 | Z28 | CH₃ | H | H |
| C-28.3 | Z28 | Cl | H | H |
| C-28.4 | Z28 | F | H | H |
| C-28.5 | Z28 | CH₂CH₃ | H | H |
| C-28.6 | Z28 | CF₂H | H | H |
| C-28.7 | Z28 | CH₂F | H | H |
| C-28.8 | Z28 | CF₃ | H | H |
| C-28.9 | Z28 | CF₂CH₃ | H | H |
| C-28.10 | Z28 | CH₂CF₃ | H | H |
| C-28.11 | Z28 | cyclopropyl | H | H |
| C-28.12 | Z28 | OCF₃ | H | H |
| C-28.13 | Z28 | OCF₂H | H | H |
| C-28.14 | Z28 | Cl | H | F |
| C-28.15 | Z28 | CH₃ | H | F |
| C-28.16 | Z28 | CH₃ | F | H |
| C-28.17 | Z28 | Cl | F | H |
| C-28.18 | Z28 | F | F | H |
| C-28.19 | Z28 | F | H | F |
| C-28.20 | Z28 | F | H | Cl |
| C-28.21 | Z28 | F | H | CH₃ |
| C-28.22 | Z28 | Cl | H | CH₃ |
| C-28.23 | Z28 | SCH₃ | H | H |
| C-28.24 | Z28 | SO₂CH₃ | H | H |
| C-28.25 | Z28 | ethynyl | H | H |
| C-29.1 | Z29 | H | H | H |
| C-29.2 | Z29 | CH₃ | H | H |
| C-29.3 | Z29 | Cl | H | H |
| C-29.4 | Z29 | F | H | H |
| C-29.5 | Z29 | CH₂CH₃ | H | H |
| C-29.6 | Z29 | CF₂H | H | H |
| C-29.7 | Z29 | CH₂F | H | H |
| C-29.8 | Z29 | CF₃ | H | H |
| C-29.9 | Z29 | CF₂CH₃ | H | H |
| C-29.10 | Z29 | CH₂CF₃ | H | H |
| C-29.11 | Z29 | cyclopropyl | H | H |
| C-29.12 | Z29 | OCF₃ | H | H |
| C-29.13 | Z29 | OCF₂H | H | H |
| C-29.14 | Z29 | Cl | H | F |
| C-29.15 | Z29 | CH₃ | H | F |
| C-29.16 | Z29 | CH₃ | F | H |
| C-29.17 | Z29 | Cl | F | H |
| C-29.18 | Z29 | F | F | H |
| C-29.19 | Z29 | F | H | F |
| C-29.20 | Z29 | F | H | Cl |
| C-29.21 | Z29 | F | H | CH₃ |
| C-29.22 | Z29 | Cl | H | CH₃ |
| C-29.23 | Z29 | SCH₃ | H | H |
| C-29.24 | Z29 | SO₂CH₃ | H | H |
| C-29.25 | Z29 | ethynyl | H | H |
| C-30.1 | Z30 | H | H | H |
| C-30.2 | Z30 | CH₃ | H | H |
| C-30.3 | Z30 | Cl | H | H |
| C-30.4 | Z30 | F | H | H |
| C-30.5 | Z30 | CH₂CH₃ | H | H |
| C-30.6 | Z30 | CF₂H | H | H |
| C-30.7 | Z30 | CH₂F | H | H |
| C-30.8 | Z30 | CF₃ | H | H |
| C-30.9 | Z30 | CF₂CH₃ | H | H |
| C-30.10 | Z30 | CH₂CF₃ | H | H |
| C-30.11 | Z30 | cyclopropyl | H | H |
| C-30.12 | Z30 | OCF₃ | H | H |
| C-30.13 | Z30 | OCF₂H | H | H |
| C-30.14 | Z30 | Cl | H | F |
| C-30.15 | Z30 | CH₃ | H | F |
| C-30.16 | Z30 | CH₃ | F | H |
| C-30.17 | Z30 | Cl | F | H |
| C-30.18 | Z30 | F | F | H |
| C-30.19 | Z30 | F | H | F |
| C-30.20 | Z30 | F | H | Cl |
| C-30.21 | Z30 | F | H | CH₃ |
| C-30.22 | Z30 | Cl | H | CH₃ |
| C-30.23 | Z30 | SCH₃ | H | H |
| C-30.24 | Z30 | SO₂CH₃ | H | H |
| C-30.25 | Z30 | ethynyl | H | H |
| C-31.1 | Z31 | H | H | H |
| C-31.2 | Z31 | CH₃ | H | H |
| C-31.3 | Z31 | Cl | H | H |
| C-31.4 | Z31 | F | H | H |
| C-31.5 | Z31 | CH₂CH₃ | H | H |
| C-31.6 | Z31 | CF₂H | H | H |
| C-31.7 | Z31 | CH₂F | H | H |
| C-31.8 | Z31 | CF₃ | H | H |
| C-31.9 | Z31 | CF₂CH₃ | H | H |
| C-31.10 | Z31 | CH₂CF₃ | H | H |
| C-31.11 | Z31 | cyclopropyl | H | H |
| C-31.12 | Z31 | OCF₃ | H | H |
| C-31.13 | Z31 | OCF₂H | H | H |
| C-31.14 | Z31 | Cl | H | F |
| C-31.15 | Z31 | CH₃ | H | F |
| C-31.16 | Z31 | CH₃ | F | H |

TABLE 1.C-continued

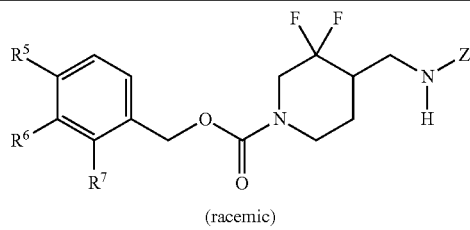
(racemic)

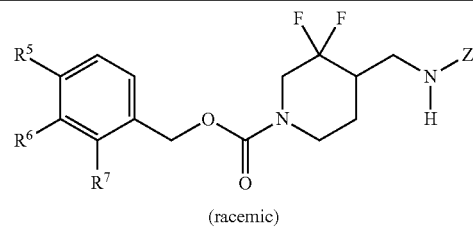
(racemic)

| compound | Z | R⁵ | R⁶ | R⁷ |
|---|---|---|---|---|
| C-31.17 | Z31 | Cl | F | H |
| C-31.18 | Z31 | F | F | H |
| C-31.19 | Z31 | F | H | F |
| C-31.20 | Z31 | F | H | Cl |
| C-31.21 | Z31 | F | H | CH₃ |
| C-31.22 | Z31 | Cl | H | CH₃ |
| C-31.23 | Z31 | SCH₃ | H | H |
| C-31.24 | Z31 | SO₂CH₃ | H | H |
| C-31.25 | Z31 | ethynyl | H | H |
| C-32.1 | Z32 | H | H | H |
| C-32.2 | Z32 | CH₃ | H | H |
| C-32.3 | Z32 | Cl | H | H |
| C-32.4 | Z32 | F | H | H |
| C-32.5 | Z32 | CH₂CH₃ | H | H |
| C-32.6 | Z32 | CF₂H | H | H |
| C-32.7 | Z32 | CH₂F | H | H |
| C-32.8 | Z32 | CF₃ | H | H |
| C-32.9 | Z32 | CF₂CH₃ | H | H |
| C-32.10 | Z32 | CH₂CF₃ | H | H |
| C-32.11 | Z32 | cyclopropyl | H | H |
| C-32.12 | Z32 | OCF₃ | H | H |
| C-32.13 | Z32 | OCF₂H | H | H |
| C-32.14 | Z32 | Cl | H | F |
| C-32.15 | Z32 | CH₃ | H | F |
| C-32.16 | Z32 | CH₃ | F | H |
| C-32.17 | Z32 | Cl | F | H |
| C-32.18 | Z32 | F | F | H |
| C-32.19 | Z32 | F | H | F |
| C-32.20 | Z32 | F | H | Cl |
| C-32.21 | Z32 | F | H | CH₃ |
| C-32.22 | Z32 | Cl | H | CH₃ |
| C-32.23 | Z32 | SCH₃ | H | H |
| C-32.24 | Z32 | SO₂CH₃ | H | H |
| C-32.25 | Z32 | ethynyl | H | H |
| C-33.1 | Z33 | H | H | H |
| C-33.2 | Z33 | CH₃ | H | H |
| C-33.3 | Z33 | Cl | H | H |
| C-33.4 | Z33 | F | H | H |
| C-33.5 | Z33 | CH₂CH₃ | H | H |
| C-33.6 | Z33 | CF₂H | H | H |
| C-33.7 | Z33 | CH₂F | H | H |
| C-33.8 | Z33 | CF₃ | H | H |
| C-33.9 | Z33 | CF₂CH₃ | H | H |
| C-33.10 | Z33 | CH₂CF₃ | H | H |
| C-33.11 | Z33 | cyclopropyl | H | H |
| C-33.12 | Z33 | OCF₃ | H | H |
| C-33.13 | Z33 | OCF₂H | H | H |
| C-33.14 | Z33 | Cl | H | F |
| C-33.15 | Z33 | CH₃ | H | F |
| C-33.16 | Z33 | CH₃ | F | H |
| C-33.17 | Z33 | Cl | F | H |
| C-33.18 | Z33 | F | F | H |
| C-33.19 | Z33 | F | H | F |
| C-33.20 | Z33 | F | H | Cl |
| C-33.21 | Z33 | F | H | CH₃ |
| C-33.22 | Z33 | Cl | H | CH₃ |
| C-33.23 | Z33 | SCH₃ | H | H |
| C-33.24 | Z33 | SO₂CH₃ | H | H |
| C-33.25 | Z33 | ethynyl | H | H |
| C-34.1 | Z34 | H | H | H |
| C-34.2 | Z34 | CH₃ | H | H |
| C-34.3 | Z34 | Cl | H | H |
| C-34.4 | Z34 | F | H | H |
| C-34.5 | Z34 | CH₂CH₃ | H | H |
| C-34.6 | Z34 | CF₂H | H | H |
| C-34.7 | Z34 | CH₂F | H | H |
| C-34.8 | Z34 | CF₃ | H | H |
| C-34.9 | Z34 | CF₂CH₃ | H | H |
| C-34.10 | Z34 | CH₂CF₃ | H | H |
| C-34.11 | Z34 | cyclopropyl | H | H |
| C-34.12 | Z34 | OCF₃ | H | H |
| C-34.13 | Z34 | OCF₂H | H | H |
| C-34.14 | Z34 | Cl | H | F |
| C-34.15 | Z34 | CH₃ | H | F |
| C-34.16 | Z34 | CH₃ | F | H |
| C-34.17 | Z34 | Cl | F | H |
| C-34.18 | Z34 | F | F | H |
| C-34.19 | Z34 | F | H | F |
| C-34.20 | Z34 | F | H | Cl |
| C-34.21 | Z34 | F | H | CH₃ |
| C-34.22 | Z34 | Cl | H | CH₃ |
| C-34.23 | Z34 | SCH₃ | H | H |
| C-34.24 | Z34 | SO₂CH₃ | H | H |
| C-34.25 | Z34 | ethynyl | H | H |
| C-35.1 | Z35, Rᵃ is H | H | H | H |
| C-35.2 | Z35, Rᵃ is H | CH₃ | H | H |
| C-35.3 | Z35, Rᵃ is H | Cl | H | H |
| C-35.4 | Z35, Rᵃ is H | F | H | H |
| C-35.5 | Z35, Rᵃ is H | CH₂CH₃ | H | H |
| C-35.6 | Z35, Rᵃ is H | CF₂H | H | H |
| C-35.7 | Z35, Rᵃ is H | CH₂F | H | H |
| C-35.8 | Z35, Rᵃ is H | CF₃ | H | H |
| C-35.9 | Z35, Rᵃ is H | CF₂CH₃ | H | H |
| C-35.10 | Z35, Rᵃ is H | CH₂CF₃ | H | H |
| C-35.11 | Z35, Rᵃ is H | cyclopropyl | H | H |
| C-35.12 | Z35, Rᵃ is H | OCF₃ | H | H |
| C-35.13 | Z35, Rᵃ is H | OCF₂H | H | H |
| C-35.14 | Z35, Rᵃ is H | Cl | H | F |
| C-35.15 | Z35, Rᵃ is H | CH₃ | H | F |
| C-35.16 | Z35, Rᵃ is H | CH₃ | F | H |
| C-35.17 | Z35, Rᵃ is H | Cl | F | H |
| C-35.18 | Z35, Rᵃ is H | F | F | H |
| C-35.19 | Z35, Rᵃ is H | F | H | F |
| C-35.20 | Z35, Rᵃ is H | F | H | Cl |
| C-35.21 | Z35, Rᵃ is H | F | H | CH₃ |
| C-35.22 | Z35, Rᵃ is H | Cl | H | CH₃ |
| C-35.23 | Z35, Rᵃ is H | SCH₃ | H | H |
| C-35.24 | Z35, Rᵃ is H | SO₂CH₃ | H | H |
| C-35.25 | Z35, Rᵃ is H | ethynyl | H | H |
| C-36.1 | Z36, Rᵃ is H | H | H | H |
| C-36.2 | Z36, Rᵃ is H | CH₃ | H | H |
| C-36.3 | Z36, Rᵃ is H | Cl | H | H |
| C-36.4 | Z36, Rᵃ is H | F | H | H |
| C-36.5 | Z36, Rᵃ is H | CH₂CH₃ | H | H |
| C-36.6 | Z36, Rᵃ is H | CF₂H | H | H |
| C-36.7 | Z36, Rᵃ is H | CH₂F | H | H |
| C-36.8 | Z36, Rᵃ is H | CF₃ | H | H |
| C-36.9 | Z36, Rᵃ is H | CF₂CH₃ | H | H |
| C-36.10 | Z36, Rᵃ is H | CH₂CF₃ | H | H |
| C-36.11 | Z36, Rᵃ is H | cyclopropyl | H | H |
| C-36.12 | Z36, Rᵃ is H | OCF₃ | H | H |
| C-36.13 | Z36, Rᵃ is H | OCF₂H | H | H |
| C-36.14 | Z36, Rᵃ is H | Cl | H | F |
| C-36.15 | Z36, Rᵃ is H | CH₃ | H | F |
| C-36.16 | Z36, Rᵃ is H | CH₃ | F | H |
| C-36.17 | Z36, Rᵃ is H | Cl | F | H |
| C-36.18 | Z36, Rᵃ is H | F | F | H |
| C-36.19 | Z36, Rᵃ is H | F | H | F |
| C-36.20 | Z36, Rᵃ is H | F | H | Cl |
| C-36.21 | Z36, Rᵃ is H | F | H | CH₃ |

TABLE 1.C-continued

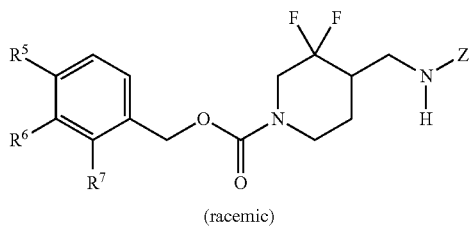

(racemic)

| compound | Z | R⁵ | R⁶ | R⁷ |
|---|---|---|---|---|
| C-36.22 | Z36, Rᵃ is H | Cl | H | CH₃ |
| C-36.23 | Z36, Rᵃ is H | SCH₃ | H | H |
| C-36.24 | Z36, Rᵃ is H | SO₂CH₃ | H | H |
| C-36.25 | Z36, Rᵃ is H | ethynyl | H | H |

TABLE 1.E1

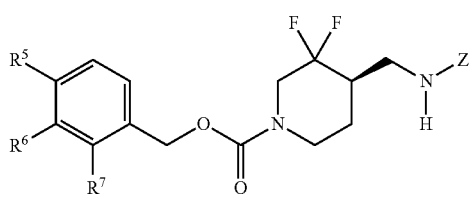

(R)

| compound | Z | R⁵ | R⁶ | R⁷ |
|---|---|---|---|---|
| E1-1.1 | Z1 | H | H | H |
| E1-1.2 | Z1 | CH₃ | H | H |
| E1-1.3 | Z1 | Cl | H | H |
| E1-1.4 | Z1 | F | H | H |
| E1-1.5 | Z1 | CH₂CH₃ | H | H |
| E1-1.6 | Z1 | CF₂H | H | H |
| E1-1.7 | Z1 | CH₂F | H | H |
| E1-1.8 | Z1 | CF₃ | H | H |
| E1-1.9 | Z1 | CF₂CH₃ | H | H |
| E1-1.10 | Z1 | CH₂CF₃ | H | H |
| E1-1.11 | Z1 | cyclopropyl | H | H |
| E1-1.12 | Z1 | OCF₃ | H | H |
| E1-1.13 | Z1 | OCF₂H | H | H |
| E1-1.14 | Z1 | Cl | H | F |
| E1-1.15 | Z1 | CH₃ | H | F |
| E1-1.16 | Z1 | CH₃ | F | H |
| E1-1.17 | Z1 | Cl | F | H |
| E1-1.18 | Z1 | F | F | H |
| E1-1.19 | Z1 | F | H | F |
| E1-1.20 | Z1 | F | H | Cl |
| E1-1.21 | Z1 | F | H | CH₃ |
| E1-1.22 | Z1 | Cl | H | CH₃ |
| E1-1.23 | Z1 | SCH₃ | H | H |
| E1-1.24 | Z1 | SO₂CH₃ | H | H |
| E1-1.25 | Z1 | ethynyl | H | H |
| E1-2.1 | Z2 | H | H | H |
| E1-2.2 | Z2 | CH₃ | H | H |
| E1-2.3 | Z2 | Cl | H | H |
| E1-2.4 | Z2 | F | H | H |
| E1-2.5 | Z2 | CH₂CH₃ | H | H |
| E1-2.6 | Z2 | CF₂H | H | H |
| E1-2.7 | Z2 | CH₂F | H | H |
| E1-2.8 | Z2 | CF₃ | H | H |
| E1-2.9 | Z2 | CF₂CH₃ | H | H |
| E1-2.10 | Z2 | CH₂CF₃ | H | H |
| E1-2.11 | Z2 | cyclopropyl | H | H |
| E1-2.12 | Z2 | OCF₃ | H | H |
| E1-2.13 | Z2 | OCF₂H | H | H |
| E1-2.14 | Z2 | Cl | H | F |
| E1-2.15 | Z2 | CH₃ | H | F |
| E1-2.16 | Z2 | CH₃ | F | H |
| E1-2.17 | Z2 | Cl | F | H |
| E1-2.18 | Z2 | F | F | H |

TABLE 1.E1-continued

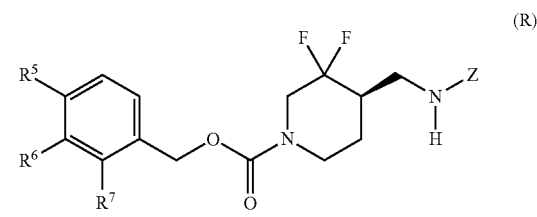

(R)

| compound | Z | R⁵ | R⁶ | R⁷ |
|---|---|---|---|---|
| E1-2.19 | Z2 | F | H | F |
| E1-2.20 | Z2 | F | H | Cl |
| E1-2.21 | Z2 | F | H | CH₃ |
| E1-2.22 | Z2 | Cl | H | CH₃ |
| E1-2.23 | Z2 | SCH₃ | H | H |
| E1-2.24 | Z2 | SO₂CH₃ | H | H |
| E1-2.25 | Z2 | ethynyl | H | H |
| E1-3.1 | Z3 | H | H | H |
| E1-3.2 | Z3 | CH₃ | H | H |
| E1-3.3 | Z3 | Cl | H | H |
| E1-3.4 | Z3 | F | H | H |
| E1-3.5 | Z3 | CH₂CH₃ | H | H |
| E1-3.6 | Z3 | CF₂H | H | H |
| E1-3.7 | Z3 | CH₂F | H | H |
| E1-3.8 | Z3 | CF₃ | H | H |
| E1-3.9 | Z3 | CF₂CH₃ | H | H |
| E1-3.10 | Z3 | CH₂CF₃ | H | H |
| E1-3.11 | Z3 | cyclopropyl | H | H |
| E1-3.12 | Z3 | OCF₃ | H | H |
| E1-3.13 | Z3 | OCF₂H | H | H |
| E1-3.14 | Z3 | Cl | H | F |
| E1-3.15 | Z3 | CH₃ | H | F |
| E1-3.16 | Z3 | CH₃ | F | H |
| E1-3.17 | Z3 | Cl | F | H |
| E1-3.18 | Z3 | F | F | H |
| E1-3.19 | Z3 | F | H | F |
| E1-3.20 | Z3 | F | H | Cl |
| E1-3.21 | Z3 | F | H | CH₃ |
| E1-3.22 | Z3 | Cl | H | CH₃ |
| E1-3.23 | Z3 | SCH₃ | H | H |
| E1-3.24 | Z3 | SO₂CH₃ | H | H |
| E1-3.25 | Z3 | ethynyl | H | H |
| E1-4.1 | Z4 | H | H | H |
| E1-4.2 | Z4 | CH₃ | H | H |
| E1-4.3 | Z4 | Cl | H | H |
| E1-4.4 | Z4 | F | H | H |
| E1-4.5 | Z4 | CH₂CH₃ | H | H |
| E1-4.6 | Z4 | CF₂H | H | H |
| E1-4.7 | Z4 | CH₂F | H | H |
| E1-4.8 | Z4 | CF₃ | H | H |
| E1-4.9 | Z4 | CF₂CH₃ | H | H |
| E1-4.10 | Z4 | CH₂CF₃ | H | H |
| E1-4.11 | Z4 | cyclopropyl | H | H |
| E1-4.12 | Z4 | OCF₃ | H | H |
| E1-4.13 | Z4 | OCF₂H | H | H |
| E1-4.14 | Z4 | Cl | H | F |
| E1-4.15 | Z4 | CH₃ | H | F |
| E1-4.16 | Z4 | CH₃ | F | H |
| E1-4.17 | Z4 | Cl | F | H |
| E1-4.18 | Z4 | F | F | H |
| E1-4.19 | Z4 | F | H | F |
| E1-4.20 | Z4 | F | H | Cl |
| E1-4.21 | Z4 | F | H | CH₃ |
| E1-4.22 | Z4 | Cl | H | CH₃ |
| E1-4.23 | Z4 | SCH₃ | H | H |
| E1-4.24 | Z4 | SO₂CH₃ | H | H |
| E1-4.25 | Z4 | ethynyl | H | H |
| E1-5.1 | Z5 | H | H | H |
| E1-5.2 | Z5 | CH₃ | H | H |
| E1-5.3 | Z5 | Cl | H | H |
| E1-5.4 | Z5 | F | H | H |
| E1-5.5 | Z5 | CH₂CH₃ | H | H |
| E1-5.6 | Z5 | CF₂H | H | H |
| E1-5.7 | Z5 | CH₂F | H | H |
| E1-5.8 | Z5 | CF₃ | H | H |
| E1-5.9 | Z5 | CF₂CH₃ | H | H |
| E1-5.10 | Z5 | CH₂CF₃ | H | H |

TABLE 1.E1-continued

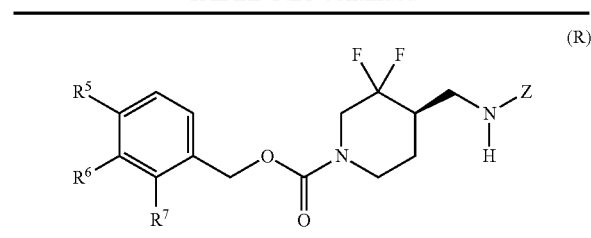

(R)

| compound | Z | R⁵ | R⁶ | R⁷ |
|---|---|---|---|---|
| E1-5.11 | Z5 | cyclopropyl | H | H |
| E1-5.12 | Z5 | OCF₃ | H | H |
| E1-5.13 | Z5 | OCF₂H | H | H |
| E1-5.14 | Z5 | Cl | H | F |
| E1-5.15 | Z5 | CH₃ | H | F |
| E1-5.16 | Z5 | CH₃ | F | H |
| E1-5.17 | Z5 | Cl | F | H |
| E1-5.18 | Z5 | F | F | H |
| E1-5.19 | Z5 | F | H | F |
| E1-5.20 | Z5 | F | H | Cl |
| E1-5.21 | Z5 | F | H | CH₃ |
| E1-5.22 | Z5 | Cl | H | CH₃ |
| E1-5.23 | Z5 | SCH₃ | H | H |
| E1-5.24 | Z5 | SO₂CH₃ | H | H |
| E1-5.25 | Z5 | ethynyl | H | H |
| E1-6.1 | Z6, Rᵃ is H | H | H | H |
| E1-6.2 | Z6, Rᵃ is H | CH₃ | H | H |
| E1-6.3 | Z6, Rᵃ is H | Cl | H | H |
| E1-6.4 | Z6, Rᵃ is H | F | H | H |
| E1-6.5 | Z6, Rᵃ is H | CH₂CH₃ | H | H |
| E1-6.6 | Z6, Rᵃ is H | CF₂H | H | H |
| E1-6.7 | Z6, Rᵃ is H | CH₂F | H | H |
| E1-6.8 | Z6, Rᵃ is H | CF₃ | H | H |
| E1-6.9 | Z6, Rᵃ is H | CF₂CH₃ | H | H |
| E1-6.10 | Z6, Rᵃ is H | CH₂CF₃ | H | H |
| E1-6.11 | Z6, Rᵃ is H | cyclopropyl | H | H |
| E1-6.12 | Z6, Rᵃ is H | OCF₃ | H | H |
| E1-6.13 | Z6, Rᵃ is H | OCF₂H | H | H |
| E1-6.14 | Z6, Rᵃ is H | Cl | H | F |
| E1-6.15 | Z6, Rᵃ is H | CH₃ | H | F |
| E1-6.16 | Z6, Rᵃ is H | CH₃ | F | H |
| E1-6.17 | Z6, Rᵃ is H | Cl | F | H |
| E1-6.18 | Z6, Rᵃ is H | F | F | H |
| E1-6.19 | Z6, Rᵃ is H | F | H | F |
| E1-6.20 | Z6, Rᵃ is H | F | H | Cl |
| E1-6.21 | Z6, Rᵃ is H | F | H | CH₃ |
| E1-6.22 | Z6, Rᵃ is H | Cl | H | CH₃ |
| E1-6.23 | Z6, Rᵃ is H | SCH₃ | H | H |
| E1-6.24 | Z6, Rᵃ is H | SO₂CH₃ | H | H |
| E1-6.25 | Z6, Rᵃ is H | ethynyl | H | H |
| E1-7.1 | Z7, Rᵃ is H | H | H | H |
| E1-7.2 | Z7, Rᵃ is H | CH₃ | H | H |
| E1-7.3 | Z7, Rᵃ is H | Cl | H | H |
| E1-7.4 | Z7, Rᵃ is H | F | H | H |
| E1-7.5 | Z7, Rᵃ is H | CH₂CH₃ | H | H |
| E1-7.6 | Z7, Rᵃ is H | CF₂H | H | H |
| E1-7.7 | Z7, Rᵃ is H | CH₂F | H | H |
| E1-7.8 | Z7, Rᵃ is H | CF₃ | H | H |
| E1-7.9 | Z7, Rᵃ is H | CF₂CH₃ | H | H |
| E1-7.10 | Z7, Rᵃ is H | CH₂CF₃ | H | H |
| E1-7.11 | Z7, Rᵃ is H | cyclopropyl | H | H |
| E1-7.12 | Z7, Rᵃ is H | OCF₃ | H | H |
| E1-7.13 | Z7, Rᵃ is H | OCF₂H | H | H |
| E1-7.14 | Z7, Rᵃ is H | Cl | H | F |
| E1-7.15 | Z7, Rᵃ is H | CH₃ | H | F |
| E1-7.16 | Z7, Rᵃ is H | CH₃ | F | H |
| E1-7.17 | Z7, Rᵃ is H | Cl | F | H |
| E1-7.18 | Z7, Rᵃ is H | F | F | H |
| E1-7.19 | Z7, Rᵃ is H | F | H | F |
| E1-7.20 | Z7, Rᵃ is H | F | H | Cl |
| E1-7.21 | Z7, Rᵃ is H | F | H | CH₃ |
| E1-7.22 | Z7, Rᵃ is H | Cl | H | CH₃ |
| E1-7.23 | Z7, Rᵃ is H | SCH₃ | H | H |
| E1-7.24 | Z7, Rᵃ is H | SO₂CH₃ | H | H |
| E1-7.25 | Z7, Rᵃ is H | ethynyl | H | H |
| E1-8.1 | Z8, Rᵃ is H | H | H | H |
| E1-8.2 | Z8, Rᵃ is H | CH₃ | H | H |
| E1-8.3 | Z8, Rᵃ is H | Cl | H | H |
| E1-8.4 | Z8, Rᵃ is H | F | H | H |
| E1-8.5 | Z8, Rᵃ is H | CH₂CH₃ | H | H |
| E1-8.6 | Z8, Rᵃ is H | CF₂H | H | H |
| E1-8.7 | Z8, Rᵃ is H | CH₂F | H | H |
| E1-8.8 | Z8, Rᵃ is H | CF₃ | H | H |
| E1-8.9 | Z8, Rᵃ is H | CF₂CH₃ | H | H |
| E1-8.10 | Z8, Rᵃ is H | CH₂CF₃ | H | H |
| E1-8.11 | Z8, Rᵃ is H | cyclopropyl | H | H |
| E1-8.12 | Z8, Rᵃ is H | OCF₃ | H | H |
| E1-8.13 | Z8, Rᵃ is H | OCF₂H | H | H |
| E1-8.14 | Z8, Rᵃ is H | Cl | H | F |
| E1-8.15 | Z8, Rᵃ is H | CH₃ | H | F |
| E1-8.16 | Z8, Rᵃ is H | CH₃ | F | H |
| E1-8.17 | Z8, Rᵃ is H | Cl | F | H |
| E1-8.18 | Z8, Rᵃ is H | F | F | H |
| E1-8.19 | Z8, Rᵃ is H | F | H | F |
| E1-8.20 | Z8, Rᵃ is H | F | H | Cl |
| E1-8.21 | Z8, Rᵃ is H | F | H | CH₃ |
| E1-8.22 | Z8, Rᵃ is H | Cl | H | CH₃ |
| E1-8.23 | Z8, Rᵃ is H | SCH₃ | H | H |
| E1-8.24 | Z8, Rᵃ is H | SO₂CH₃ | H | H |
| E1-8.25 | Z8, Rᵃ is H | ethynyl | H | H |
| E1-9.1 | Z9 | H | H | H |
| E1-9.2 | Z9 | CH₃ | H | H |
| E1-9.3 | Z9 | Cl | H | H |
| E1-9.4 | Z9 | F | H | H |
| E1-9.5 | Z9 | CH₂CH₃ | H | H |
| E1-9.6 | Z9 | CF₂H | H | H |
| E1-9.7 | Z9 | CH₂F | H | H |
| E1-9.8 | Z9 | CF₃ | H | H |
| E1-9.9 | Z9 | CF₂CH₃ | H | H |
| E1-9.10 | Z9 | CH₂CF₃ | H | H |
| E1-9.11 | Z9 | cyclopropyl | H | H |
| E1-9.12 | Z9 | OCF₃ | H | H |
| E1-9.13 | Z9 | OCF₂H | H | H |
| E1-9.14 | Z9 | Cl | H | F |
| E1-9.15 | Z9 | CH₃ | H | F |
| E1-9.16 | Z9 | CH₃ | F | H |
| E1-9.17 | Z9 | Cl | F | H |
| E1-9.18 | Z9 | F | F | H |
| E1-9.19 | Z9 | F | H | F |
| E1-9.20 | Z9 | F | H | Cl |
| E1-9.21 | Z9 | F | H | CH₃ |
| E1-9.22 | Z9 | Cl | H | CH₃ |
| E1-9.23 | Z9 | SCH₃ | H | H |
| E1-9.24 | Z9 | SO₂CH₃ | H | H |
| E1-9.25 | Z9 | ethynyl | H | H |
| E1-10.1 | Z10 | H | H | H |
| E1-10.2 | Z10 | CH₃ | H | H |
| E1-10.3 | Z10 | Cl | H | H |
| E1-10.4 | Z10 | F | H | H |
| E1-10.5 | Z10 | CH₂CH₃ | H | H |
| E1-10.6 | Z10 | CF₂H | H | H |
| E1-10.7 | Z10 | CH₂F | H | H |
| E1-10.8 | Z10 | CF₃ | H | H |
| E1-10.9 | Z10 | CF₂CH₃ | H | H |
| E1-10.10 | Z10 | CH₂CF₃ | H | H |
| E1-10.11 | Z10 | cyclopropyl | H | H |
| E1-10.12 | Z10 | OCF₃ | H | H |
| E1-10.13 | Z10 | OCF₂H | H | H |
| E1-10.14 | Z10 | Cl | H | F |
| E1-10.15 | Z10 | CH₃ | H | F |
| E1-10.16 | Z10 | CH₃ | F | H |
| E1-10.17 | Z10 | Cl | F | H |
| E1-10.18 | Z10 | F | F | H |
| E1-10.19 | Z10 | F | H | F |

TABLE 1.E1-continued

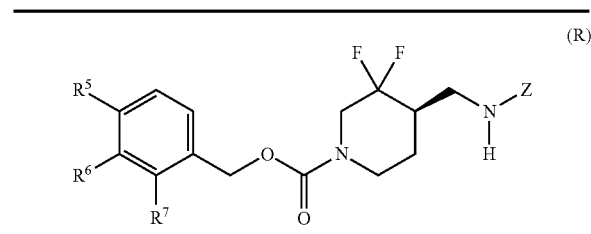

| compound | Z | R⁵ | R⁶ | R⁷ |
|---|---|---|---|---|
| E1-10.20 | Z10 | F | H | Cl |
| E1-10.21 | Z10 | F | H | CH₃ |
| E1-10.22 | Z10 | Cl | H | CH₃ |
| E1-10.23 | Z10 | SCH₃ | H | H |
| E1-10.24 | Z10 | SO₂CH₃ | H | H |
| E1-10.25 | Z10 | ethynyl | H | H |
| E1-11.1 | Z11, Rᵃ is H | H | H | H |
| E1-11.2 | Z11, Rᵃ is H | CH₃ | H | H |
| E1-11.3 | Z11, Rᵃ is H | Cl | H | H |
| E1-11.4 | Z11, Rᵃ is H | F | H | H |
| E1-11.5 | Z11, Rᵃ is H | CH₂CH₃ | H | H |
| E1-11.6 | Z11, Rᵃ is H | CF₂H | H | H |
| E1-11.7 | Z11, Rᵃ is H | CH₂F | H | H |
| E1-11.8 | Z11, Rᵃ is H | CF₃ | H | H |
| E1-11.9 | Z11, Rᵃ is H | CF₂CH₃ | H | H |
| E1-11.10 | Z11, Rᵃ is H | CH₂CF₃ | H | H |
| E1-11.11 | Z11, Rᵃ is H | cyclopropyl | H | H |
| E1-11.12 | Z11, Rᵃ is H | OCF₃ | H | H |
| E1-11.13 | Z11, Rᵃ is H | OCF₂H | H | H |
| E1-11.14 | Z11, Rᵃ is H | Cl | H | F |
| E1-11.15 | Z11, Rᵃ is H | CH₃ | H | F |
| E1-11.16 | Z11, Rᵃ is H | CH₃ | F | H |
| E1-11.17 | Z11, Rᵃ is H | Cl | F | H |
| E1-11.18 | Z11, Rᵃ is H | F | F | H |
| E1-11.19 | Z11, Rᵃ is H | F | H | F |
| E1-11.20 | Z11, Rᵃ is H | F | H | Cl |
| E1-11.21 | Z11, Rᵃ is H | F | H | CH₃ |
| E1-11.22 | Z11, Rᵃ is H | Cl | H | CH₃ |
| E1-11.23 | Z11, Rᵃ is H | SCH₃ | H | H |
| E1-11.24 | Z11, Rᵃ is H | SO₂CH₃ | H | H |
| E1-11.25 | Z11, Rᵃ is H | ethynyl | H | H |
| E1-12.1 | Z12 | H | H | H |
| E1-12.2 | Z12 | CH₃ | H | H |
| E1-12.3 | Z12 | Cl | H | H |
| E1-12.4 | Z12 | F | H | H |
| E1-12.5 | Z12 | CH₂CH₃ | H | H |
| E1-12.6 | Z12 | CF₂H | H | H |
| E1-12.7 | Z12 | CH₂F | H | H |
| E1-12.8 | Z12 | CF₃ | H | H |
| E1-12.9 | Z12 | CF₂CH₃ | H | H |
| E1-12.10 | Z12 | CH₂CF₃ | H | H |
| E1-12.11 | Z12 | cyclopropyl | H | H |
| E1-12.12 | Z12 | OCF₃ | H | H |
| E1-12.13 | Z12 | OCF₂H | H | H |
| E1-12.14 | Z12 | Cl | H | F |
| E1-12.15 | Z12 | CH₃ | H | F |
| E1-12.16 | Z12 | CH₃ | F | H |
| E1-12.17 | Z12 | Cl | F | H |
| E1-12.18 | Z12 | F | F | H |
| E1-12.19 | Z12 | F | H | F |
| E1-12.20 | Z12 | F | H | Cl |
| E1-12.21 | Z12 | F | H | CH₃ |
| E1-12.22 | Z12 | Cl | H | CH₃ |
| E1-12.23 | Z12 | SCH₃ | H | H |
| E1-12.24 | Z12 | SO₂CH₃ | H | H |
| E1-12.25 | Z12 | ethynyl | H | H |
| E1-13.1 | Z13, Rᵃ is H | H | H | H |
| E1-13.2 | Z13, Rᵃ is H | CH₃ | H | H |
| E1-13.3 | Z13, Rᵃ is H | Cl | H | H |
| E1-13.4 | Z13, Rᵃ is H | F | H | H |
| E1-13.5 | Z13, Rᵃ is H | CH₂CH₃ | H | H |
| E1-13.6 | Z13, Rᵃ is H | CF₂H | H | H |
| E1-13.7 | Z13, Rᵃ is H | CH₂F | H | H |
| E1-13.8 | Z13, Rᵃ is H | CF₃ | H | H |
| E1-13.9 | Z13, Rᵃ is H | CF₂CH₃ | H | H |
| E1-13.10 | Z13, Rᵃ is H | CH₂CF₃ | H | H |
| E1-13.11 | Z13, Rᵃ is H | cyclopropyl | H | H |
| E1-13.12 | Z13, Rᵃ is H | OCF₃ | H | H |
| E1-13.13 | Z13, Rᵃ is H | OCF₂H | H | H |
| E1-13.14 | Z13, Rᵃ is H | Cl | H | F |
| E1-13.15 | Z13, Rᵃ is H | CH₃ | H | F |
| E1-13.16 | Z13, Rᵃ is H | CH₃ | F | H |
| E1-13.17 | Z13, Rᵃ is H | Cl | F | H |
| E1-13.18 | Z13, Rᵃ is H | F | F | H |
| E1-13.19 | Z13, Rᵃ is H | F | H | F |
| E1-13.20 | Z13, Rᵃ is H | F | H | Cl |
| E1-13.21 | Z13, Rᵃ is H | F | H | CH₃ |
| E1-13.22 | Z13, Rᵃ is H | Cl | H | CH₃ |
| E1-13.23 | Z13, Rᵃ is H | SCH₃ | H | H |
| E1-13.24 | Z13, Rᵃ is H | SO₂CH₃ | H | H |
| E1-13.25 | Z13, Rᵃ is H | ethynyl | H | H |
| E1-14.1 | Z14, Rᵃ is H | H | H | H |
| E1-14.2 | Z14, Rᵃ is H | CH₃ | H | H |
| E1-14.3 | Z14, Rᵃ is H | Cl | H | H |
| E1-14.4 | Z14, Rᵃ is H | F | H | H |
| E1-14.5 | Z14, Rᵃ is H | CH₂CH₃ | H | H |
| E1-14.6 | Z14, Rᵃ is H | CF₂H | H | H |
| E1-14.7 | Z14, Rᵃ is H | CH₂F | H | H |
| E1-14.8 | Z14, Rᵃ is H | CF₃ | H | H |
| E1-14.9 | Z14, Rᵃ is H | CF₂CH₃ | H | H |
| E1-14.10 | Z14, Rᵃ is H | CH₂CF₃ | H | H |
| E1-14.11 | Z14, Rᵃ is H | cyclopropyl | H | H |
| E1-14.12 | Z14, Rᵃ is H | OCF₃ | H | H |
| E1-14.13 | Z14, Rᵃ is H | OCF₂H | H | H |
| E1-14.14 | Z14, Rᵃ is H | Cl | H | F |
| E1-14.15 | Z14, Rᵃ is H | CH₃ | H | F |
| E1-14.16 | Z14, Rᵃ is H | CH₃ | F | H |
| E1-14.17 | Z14, Rᵃ is H | Cl | F | H |
| E1-14.18 | Z14, Rᵃ is H | F | F | H |
| E1-14.19 | Z14, Rᵃ is H | F | H | F |
| E1-14.20 | Z14, Rᵃ is H | F | H | Cl |
| E1-14.21 | Z14, Rᵃ is H | F | H | CH₃ |
| E1-14.22 | Z14, Rᵃ is H | Cl | H | CH₃ |
| E1-14.23 | Z14, Rᵃ is H | SCH₃ | H | H |
| E1-14.24 | Z14, Rᵃ is H | SO₂CH₃ | H | H |
| E1-14.25 | Z14, Rᵃ is H | ethynyl | H | H |
| E1-15.1 | Z15, Rᵃ is H | H | H | H |
| E1-15.2 | Z15, Rᵃ is H | CH₃ | H | H |
| E1-15.3 | Z15, Rᵃ is H | Cl | H | H |
| E1-15.4 | Z15, Rᵃ is H | F | H | H |
| E1-15.5 | Z15, Rᵃ is H | CH₂CH₃ | H | H |
| E1-15.6 | Z15, Rᵃ is H | CF₂H | H | H |
| E1-15.7 | Z15, Rᵃ is H | CH₂F | H | H |
| E1-15.8 | Z15, Rᵃ is H | CF₃ | H | H |
| E1-15.9 | Z15, Rᵃ is H | CF₂CH₃ | H | H |
| E1-15.10 | Z15, Rᵃ is H | CH₂CF₃ | H | H |
| E1-15.11 | Z15, Rᵃ is H | cyclopropyl | H | H |
| E1-15.12 | Z15, Rᵃ is H | OCF₃ | H | H |
| E1-15.13 | Z15, Rᵃ is H | OCF₂H | H | H |
| E1-15.14 | Z15, Rᵃ is H | Cl | H | F |
| E1-15.15 | Z15, Rᵃ is H | CH₃ | H | F |
| E1-15.16 | Z15, Rᵃ is H | CH₃ | F | H |
| E1-15.17 | Z15, Rᵃ is H | Cl | F | H |
| E1-15.18 | Z15, Rᵃ is H | F | F | H |
| E1-15.19 | Z15, Rᵃ is H | F | H | F |
| E1-15.20 | Z15, Rᵃ is H | F | H | Cl |
| E1-15.21 | Z15, Rᵃ is H | F | H | CH₃ |
| E1-15.22 | Z15, Rᵃ is H | Cl | H | CH₃ |
| E1-15.23 | Z15, Rᵃ is H | SCH₃ | H | H |
| E1-15.24 | Z15, Rᵃ is H | SO₂CH₃ | H | H |
| E1-15.25 | Z15, Rᵃ is H | ethynyl | H | H |
| E1-16.1 | Z16, Rᵃ is H | H | H | H |
| E1-16.2 | Z16, Rᵃ is H | CH₃ | H | H |
| E1-16.3 | Z16, Rᵃ is H | Cl | H | H |

TABLE 1.E1-continued

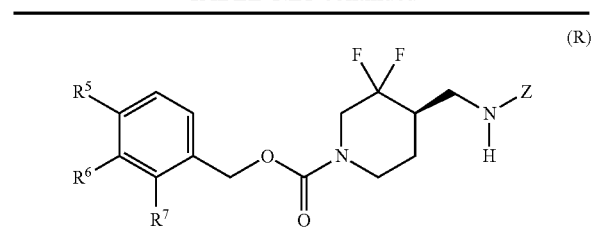

(R)

| compound | Z | R⁵ | R⁶ | R⁷ |
|---|---|---|---|---|
| E1-16.4 | Z16, Rᵃ is H | F | H | H |
| E1-16.5 | Z16, Rᵃ is H | CH₂CH₃ | H | H |
| E1-16.6 | Z16, Rᵃ is H | CF₂H | H | H |
| E1-16.7 | Z16, Rᵃ is H | CH₂F | H | H |
| E1-16.8 | Z16, Rᵃ is H | CF₃ | H | H |
| E1-16.9 | Z16, Rᵃ is H | CF₂CH₃ | H | H |
| E1-16.10 | Z16, Rᵃ is H | CH₂CF₃ | H | H |
| E1-16.11 | Z16, Rᵃ is H | cyclopropyl | H | H |
| E1-16.12 | Z16, Rᵃ is H | OCF₃ | H | H |
| E1-16.13 | Z16, Rᵃ is H | OCF₂H | H | H |
| E1-16.14 | Z16, Rᵃ is H | Cl | H | F |
| E1-16.15 | Z16, Rᵃ is H | CH₃ | H | F |
| E1-16.16 | Z16, Rᵃ is H | CH₃ | F | H |
| E1-16.17 | Z16, Rᵃ is H | Cl | F | H |
| E1-16.18 | Z16, Rᵃ is H | F | F | H |
| E1-16.19 | Z16, Rᵃ is H | F | H | F |
| E1-16.20 | Z16, Rᵃ is H | F | H | Cl |
| E1-16.21 | Z16, Rᵃ is H | F | H | CH₃ |
| E1-16.22 | Z16, Rᵃ is H | Cl | H | CH₃ |
| E1-16.23 | Z16, Rᵃ is H | SCH₃ | H | H |
| E1-16.24 | Z16, Rᵃ is H | SO₂CH₃ | H | H |
| E1-16.25 | Z16, Rᵃ is H | ethynyl | H | H |
| E1-17.1 | Z17 | H | H | H |
| E1-17.2 | Z17 | CH₃ | H | H |
| E1-17.3 | Z17 | Cl | H | H |
| E1-17.4 | Z17 | F | H | H |
| E1-17.5 | Z17 | CH₂CH₃ | H | H |
| E1-17.6 | Z17 | CF₂H | H | H |
| E1-17.7 | Z17 | CH₂F | H | H |
| E1-17.8 | Z17 | CF₃ | H | H |
| E1-17.9 | Z17 | CF₂CH₃ | H | H |
| E1-17.10 | Z17 | CH₂CF₃ | H | H |
| E1-17.11 | Z17 | cyclopropyl | H | H |
| E1-17.12 | Z17 | OCF₃ | H | H |
| E1-17.13 | Z17 | OCF₂H | H | H |
| E1-17.14 | Z17 | Cl | H | F |
| E1-17.15 | Z17 | CH₃ | H | F |
| E1-17.16 | Z17 | CH₃ | F | H |
| E1-17.17 | Z17 | Cl | F | H |
| E1-17.18 | Z17 | F | F | H |
| E1-17.19 | Z17 | F | H | F |
| E1-17.20 | Z17 | F | H | Cl |
| E1-17.21 | Z17 | F | H | CH₃ |
| E1-17.22 | Z17 | Cl | H | CH₃ |
| E1-17.23 | Z17 | SCH₃ | H | H |
| E1-17.24 | Z17 | SO₂CH₃ | H | H |
| E1-17.25 | Z17 | ethynyl | H | H |
| E1-18.1 | Z18 | H | H | H |
| E1-18.2 | Z18 | CH₃ | H | H |
| E1-18.3 | Z18 | Cl | H | H |
| E1-18.4 | Z18 | F | H | H |
| E1-18.5 | Z18 | CH₂CH₃ | H | H |
| E1-18.6 | Z18 | CF₂H | H | H |
| E1-18.7 | Z18 | CH₂F | H | H |
| E1-18.8 | Z18 | CF₃ | H | H |
| E1-18.9 | Z18 | CF₂CH₃ | H | H |
| E1-18.10 | Z18 | CH₂CF₃ | H | H |
| E1-18.11 | Z18 | cyclopropyl | H | H |
| E1-18.12 | Z18 | OCF₃ | H | H |
| E1-18.13 | Z18 | OCF₂H | H | H |
| E1-18.14 | Z18 | Cl | H | F |
| E1-18.15 | Z18 | CH₃ | H | F |
| E1-18.16 | Z18 | CH₃ | F | H |
| E1-18.17 | Z18 | Cl | F | H |
| E1-18.18 | Z18 | F | F | H |
| E1-18.19 | Z18 | F | H | F |
| E1-18.20 | Z18 | F | H | Cl |

TABLE 1.E1-continued

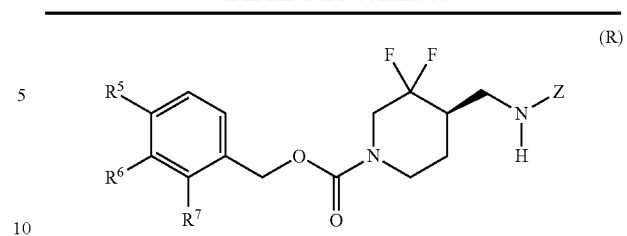

(R)

| compound | Z | R⁵ | R⁶ | R⁷ |
|---|---|---|---|---|
| E1-18.21 | Z18 | F | H | CH₃ |
| E1-18.22 | Z18 | Cl | H | CH₃ |
| E1-18.23 | Z18 | SCH₃ | H | H |
| E1-18.24 | Z18 | SO₂CH₃ | H | H |
| E1-18.25 | Z18 | ethynyl | H | H |
| E1-19.1 | Z19 | H | H | H |
| E1-19.2 | Z19 | CH₃ | H | H |
| E1-19.3 | Z19 | Cl | H | H |
| E1-19.4 | Z19 | F | H | H |
| E1-19.5 | Z19 | CH₂CH₃ | H | H |
| E1-19.6 | Z19 | CF₂H | H | H |
| E1-19.7 | Z19 | CH₂F | H | H |
| E1-19.8 | Z19 | CF₃ | H | H |
| E1-19.9 | Z19 | CF₂CH₃ | H | H |
| E1-19.10 | Z19 | CH₂CF₃ | H | H |
| E1-19.11 | Z19 | cyclopropyl | H | H |
| E1-19.12 | Z19 | OCF₃ | H | H |
| E1-19.13 | Z19 | OCF₂H | H | H |
| E1-19.14 | Z19 | Cl | H | F |
| E1-19.15 | Z19 | CH₃ | H | F |
| E1-19.16 | Z19 | CH₃ | F | H |
| E1-19.17 | Z19 | Cl | F | H |
| E1-19.18 | Z19 | F | F | H |
| E1-19.19 | Z19 | F | H | F |
| E1-19.20 | Z19 | F | H | Cl |
| E1-19.21 | Z19 | F | H | CH₃ |
| E1-19.22 | Z19 | Cl | H | CH₃ |
| E1-19.23 | Z19 | SCH₃ | H | H |
| E1-19.24 | Z19 | SO₂CH₃ | H | H |
| E1-19.25 | Z19 | ethynyl | H | H |
| E1-19.26 | Z19 | CH₃ | H | H |
| E1-20.1 | Z20 | H | H | H |
| E1-20.2 | Z20 | CH₃ | H | H |
| E1-20.3 | Z20 | Cl | H | H |
| E1-20.4 | Z20 | F | H | H |
| E1-20.5 | Z20 | CH₂CH₃ | H | H |
| E1-20.6 | Z20 | CF₂H | H | H |
| E1-20.7 | Z20 | CH₂F | H | H |
| E1-20.8 | Z20 | CF₃ | H | H |
| E1-20.9 | Z20 | CF₂CH₃ | H | H |
| E1-20.10 | Z20 | CH₂CF₃ | H | H |
| E1-20.11 | Z20 | cyclopropyl | H | H |
| E1-20.12 | Z20 | OCF₃ | H | H |
| E1-20.13 | Z20 | OCF₂H | H | H |
| E1-20.14 | Z20 | Cl | H | F |
| E1-20.15 | Z20 | CH₃ | H | F |
| E1-20.16 | Z20 | CH₃ | F | H |
| E1-20.17 | Z20 | Cl | F | H |
| E1-20.18 | Z20 | F | F | H |
| E1-20.19 | Z20 | F | H | F |
| E1-20.20 | Z20 | F | H | Cl |
| E1-20.21 | Z20 | F | H | CH₃ |
| E1-20.22 | Z20 | Cl | H | CH₃ |
| E1-20.23 | Z20 | SCH₃ | H | H |
| E1-20.24 | Z20 | SO₂CH₃ | H | H |
| E1-20.25 | Z20 | ethynyl | H | H |
| E1-21.1 | Z21 | H | H | H |
| E1-21.2 | Z21 | CH₃ | H | H |
| E1-21.3 | Z21 | Cl | H | H |
| E1-21.4 | Z21 | F | H | H |
| E1-21.5 | Z21 | CH₂CH₃ | H | H |
| E1-21.6 | Z21 | CF₂H | H | H |
| E1-21.7 | Z21 | CH₂F | H | H |
| E1-21.8 | Z21 | CF₃ | H | H |
| E1-21.9 | Z21 | CF₂CH₃ | H | H |
| E1-21.10 | Z21 | CH₂CF₃ | H | H |
| E1-21.11 | Z21 | cyclopropyl | H | H |

TABLE 1.E1-continued

| compound | Z | R⁵ | R⁶ | R⁷ |
|---|---|---|---|---|
| E1-21.12 | Z21 | OCF₃ | H | H |
| E1-21.13 | Z21 | OCF₂H | H | H |
| E1-21.14 | Z21 | Cl | H | F |
| E1-21.15 | Z21 | CH₃ | H | F |
| E1-21.16 | Z21 | CH₃ | F | H |
| E1-21.17 | Z21 | Cl | F | H |
| E1-21.18 | Z21 | F | F | H |
| E1-21.19 | Z21 | F | H | F |
| E1-21.20 | Z21 | F | H | Cl |
| E1-21.21 | Z21 | F | H | CH₃ |
| E1-21.22 | Z21 | Cl | H | CH₃ |
| E1-21.23 | Z21 | SCH₃ | H | H |
| E1-21.24 | Z21 | SO₂CH₃ | H | H |
| E1-21.25 | Z21 | ethynyl | H | H |
| E1-21.26 | pyrazine-Rˣ, Rˣ is CH₃ | CH₃ | H | H |
| E1-22.1 | Z22 | H | H | H |
| E1-22.2 | Z22 | CH₃ | H | H |
| E1-22.3 | Z22 | Cl | H | H |
| E1-22.4 | Z22 | F | H | H |
| E1-22.5 | Z22 | CH₂CH₃ | H | H |
| E1-22.6 | Z22 | CF₂H | H | H |
| E1-22.7 | Z22 | CH₂F | H | H |
| E1-22.8 | Z22 | CF₃ | H | H |
| E1-22.9 | Z22 | CF₂CH₃ | H | H |
| E1-22.10 | Z22 | CH₂CF₃ | H | H |
| E1-22.11 | Z22 | cyclopropyl | H | H |
| E1-22.12 | Z22 | OCF₃ | H | H |
| E1-22.13 | Z22 | OCF₂H | H | H |
| E1-22.14 | Z22 | Cl | H | F |
| E1-22.15 | Z22 | CH₃ | H | F |
| E1-22.16 | Z22 | CH₃ | F | H |
| E1-22.17 | Z22 | Cl | F | H |
| E1-22.18 | Z22 | F | F | H |
| E1-22.19 | Z22 | F | H | F |
| E1-22.20 | Z22 | F | H | Cl |
| E1-22.21 | Z22 | F | H | CH₃ |
| E1-22.22 | Z22 | Cl | H | CH₃ |
| E1-22.23 | Z22 | SCH₃ | H | H |
| E1-22.24 | Z22 | SO₂CH₃ | H | H |
| E1-22.25 | Z22 | ethynyl | H | H |
| E1-23.1 | Z23 | H | H | H |
| E1-23.2 | Z23 | CH₃ | H | H |
| E1-23.3 | Z23 | Cl | H | H |
| E1-23.4 | Z23 | F | H | H |
| E1-23.5 | Z23 | CH₂CH₃ | H | H |
| E1-23.6 | Z23 | CF₂H | H | H |
| E1-23.7 | Z23 | CH₂F | H | H |
| E1-23.8 | Z23 | CF₃ | H | H |
| E1-23.9 | Z23 | CF₂CH₃ | H | H |
| E1-23.10 | Z23 | CH₂CF₃ | H | H |
| E1-23.11 | Z23 | cyclopropyl | H | H |
| E1-23.12 | Z23 | OCF₃ | H | H |
| E1-23.13 | Z23 | OCF₂H | H | H |
| E1-23.14 | Z23 | Cl | H | F |
| E1-23.15 | Z23 | CH₃ | H | F |
| E1-23.16 | Z23 | CH₃ | F | H |
| E1-23.17 | Z23 | Cl | F | H |
| E1-23.18 | Z23 | F | F | H |
| E1-23.19 | Z23 | F | H | F |
| E1-23.20 | Z23 | F | H | Cl |
| E1-23.21 | Z23 | F | H | CH₃ |
| E1-23.22 | Z23 | Cl | H | CH₃ |
| E1-23.23 | Z23 | SCH₃ | H | H |
| E1-23.24 | Z23 | SO₂CH₃ | H | H |
| E1-23.25 | Z23 | ethynyl | H | H |
| E1-24.1 | Z24 | H | H | H |
| E1-24.2 | Z24 | CH₃ | H | H |
| E1-24.3 | Z24 | Cl | H | H |
| E1-24.4 | Z24 | F | H | H |
| E1-24.5 | Z24 | CH₂CH₃ | H | H |
| E1-24.6 | Z24 | CF₂H | H | H |
| E1-24.7 | Z24 | CH₂F | H | H |
| E1-24.8 | Z24 | CF₃ | H | H |
| E1-24.9 | Z24 | CF₂CH₃ | H | H |
| E1-24.10 | Z24 | CH₂CF₃ | H | H |
| E1-24.11 | Z24 | cyclopropyl | H | H |
| E1-24.12 | Z24 | OCF₃ | H | H |
| E1-24.13 | Z24 | OCF₂H | H | H |
| E1-24.14 | Z24 | Cl | H | F |
| E1-24.15 | Z24 | CH₃ | H | F |
| E1-24.16 | Z24 | CH₃ | F | H |
| E1-24.17 | Z24 | Cl | F | H |
| E1-24.18 | Z24 | F | F | H |
| E1-24.19 | Z24 | F | H | F |
| E1-24.20 | Z24 | F | H | Cl |
| E1-24.21 | Z24 | F | H | CH₃ |
| E1-24.22 | Z24 | Cl | H | CH₃ |
| E1-24.23 | Z24 | SCH₃ | H | H |
| E1-24.24 | Z24 | SO₂CH₃ | H | H |
| E1-24.25 | Z24 | ethynyl | H | H |
| E1-25.1 | Z25, Rᵃ is H | H | H | H |
| E1-25.2 | Z25, Rᵃ is H | CH₃ | H | H |
| E1-25.3 | Z25, Rᵃ is H | Cl | H | H |
| E1-25.4 | Z25, Rᵃ is H | F | H | H |
| E1-25.5 | Z25, Rᵃ is H | CH₂CH₃ | H | H |
| E1-25.6 | Z25, Rᵃ is H | CF₂H | H | H |
| E1-25.7 | Z25, Rᵃ is H | CH₂F | H | H |
| E1-25.8 | Z25, Rᵃ is H | CF₃ | H | H |
| E1-25.9 | Z25, Rᵃ is H | CF₂CH₃ | H | H |
| E1-25.10 | Z25, Rᵃ is H | CH₂CF₃ | H | H |
| E1-25.11 | Z25, Rᵃ is H | cyclopropyl | H | H |
| E1-25.12 | Z25, Rᵃ is H | OCF₃ | H | H |
| E1-25.13 | Z25, Rᵃ is H | OCF₂H | H | H |
| E1-25.14 | Z25, Rᵃ is H | Cl | H | F |
| E1-25.15 | Z25, Rᵃ is H | CH₃ | H | F |
| E1-25.16 | Z25, Rᵃ is H | CH₃ | F | H |
| E1-25.17 | Z25, Rᵃ is H | Cl | F | H |
| E1-25.18 | Z25, Rᵃ is H | F | F | H |
| E1-25.19 | Z25, Rᵃ is H | F | H | F |
| E1-25.20 | Z25, Rᵃ is H | F | H | Cl |
| E1-25.21 | Z25, Rᵃ is H | F | H | CH₃ |
| E1-25.22 | Z25, Rᵃ is H | Cl | H | CH₃ |
| E1-25.23 | Z25, Rᵃ is H | SCH₃ | H | H |
| E1-25.24 | Z25, Rᵃ is H | SO₂CH₃ | H | H |
| E1-25.25 | Z25, Rᵃ is H | ethynyl | H | H |
| E1-26.1 | Z26, Rᵃ is H | H | H | H |
| E1-26.2 | Z26, Rᵃ is H | CH₃ | H | H |
| E1-26.3 | Z26, Rᵃ is H | Cl | H | H |
| E1-26.4 | Z26, Rᵃ is H | F | H | H |
| E1-26.5 | Z26, Rᵃ is H | CH₂CH₃ | H | H |
| E1-26.6 | Z26, Rᵃ is H | CF₂H | H | H |
| E1-26.7 | Z26, Rᵃ is H | CH₂F | H | H |
| E1-26.8 | Z26, Rᵃ is H | CF₃ | H | H |
| E1-26.9 | Z26, Rᵃ is H | CF₂CH₃ | H | H |
| E1-26.10 | Z26, Rᵃ is H | CH₂CF₃ | H | H |
| E1-26.11 | Z26, Rᵃ is H | cyclopropyl | H | H |
| E1-26.12 | Z26, Rᵃ is H | OCF₃ | H | H |
| E1-26.13 | Z26, Rᵃ is H | OCF₂H | H | H |
| E1-26.14 | Z26, Rᵃ is H | Cl | H | F |

TABLE 1.E1-continued

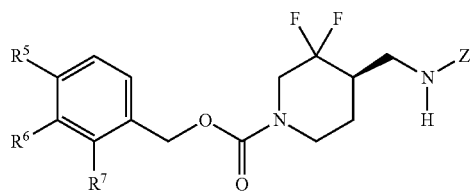

TABLE 1.E1-continued

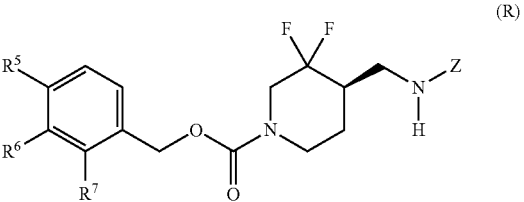

| compound | Z | R⁵ | R⁶ | R⁷ | compound | Z | R⁵ | R⁶ | R⁷ |
|---|---|---|---|---|---|---|---|---|---|
| E1-26.15 | Z26, Rᵃ is H | CH₃ | H | F | E1-29.7 | Z29 | CH₂F | H | H |
| E1-26.16 | Z26, Rᵃ is H | CH₃ | F | H | E1-29.8 | Z29 | CF₃ | H | H |
| E1-26.17 | Z26, Rᵃ is H | Cl | F | H | E1-29.9 | Z29 | CF₂CH₃ | H | H |
| E1-26.18 | Z26, Rᵃ is H | F | F | H | E1-29.10 | Z29 | CH₂CF₃ | H | H |
| E1-26.19 | Z26, Rᵃ is H | F | H | F | E1-29.11 | Z29 | cyclopropyl | H | H |
| E1-26.20 | Z26, Rᵃ is H | F | H | Cl | E1-29.12 | Z29 | OCF₃ | H | H |
| E1-26.21 | Z26, Rᵃ is H | F | H | CH₃ | E1-29.13 | Z29 | OCF₂H | H | H |
| E1-26.22 | Z26, Rᵃ is H | Cl | H | CH₃ | E1-29.14 | Z29 | Cl | H | F |
| E1-26.23 | Z26, Rᵃ is H | SCH₃ | H | H | E1-29.15 | Z29 | CH₃ | H | F |
| E1-26.24 | Z26, Rᵃ is H | SO₂CH₃ | H | H | E1-29.16 | Z29 | CH₃ | F | H |
| E1-26.25 | Z26, Rᵃ is H | ethynyl | H | H | E1-29.17 | Z29 | Cl | F | H |
| E1-27.1 | Z27 | H | H | H | E1-29.18 | Z29 | F | F | H |
| E1-27.2 | Z27 | CH₃ | H | H | E1-29.19 | Z29 | F | H | F |
| E1-27.3 | Z27 | Cl | H | H | E1-29.20 | Z29 | F | H | Cl |
| E1-27.4 | Z27 | F | H | H | E1-29.21 | Z29 | F | H | CH₃ |
| E1-27.5 | Z27 | CH₂CH₃ | H | H | E1-29.22 | Z29 | Cl | H | CH₃ |
| E1-27.6 | Z27 | CF₂H | H | H | E1-29.23 | Z29 | SCH₃ | H | H |
| E1-27.7 | Z27 | CH₂F | H | H | E1-29.24 | Z29 | SO₂CH₃ | H | H |
| E1-27.8 | Z27 | CF₃ | H | H | E1-29.25 | Z29 | ethynyl | H | H |
| E1-27.9 | Z27 | CF₂CH₃ | H | H | E1-30.1 | Z30 | H | H | H |
| E1-27.10 | Z27 | CH₂CF₃ | H | H | E1-30.2 | Z30 | CH₃ | H | H |
| E1-27.11 | Z27 | cyclopropyl | H | H | E1-30.3 | Z30 | Cl | H | H |
| E1-27.12 | Z27 | OCF₃ | H | H | E1-30.4 | Z30 | F | H | H |
| E1-27.13 | Z27 | OCF₂H | H | H | E1-30.5 | Z30 | CH₂CH₃ | H | H |
| E1-27.14 | Z27 | Cl | H | F | E1-30.6 | Z30 | CF₂H | H | H |
| E1-27.15 | Z27 | CH₃ | H | F | E1-30.7 | Z30 | CH₂F | H | H |
| E1-27.16 | Z27 | CH₃ | F | H | E1-30.8 | Z30 | CF₃ | H | H |
| E1-27.17 | Z27 | Cl | F | H | E1-30.9 | Z30 | CF₂CH₃ | H | H |
| E1-27.18 | Z27 | F | F | H | E1-30.10 | Z30 | CH₂CF₃ | H | H |
| E1-27.19 | Z27 | F | H | F | E1-30.11 | Z30 | cyclopropyl | H | H |
| E1-27.20 | Z27 | F | H | Cl | E1-30.12 | Z30 | OCF₃ | H | H |
| E1-27.21 | Z27 | F | H | CH₃ | E1-30.13 | Z30 | OCF₂H | H | H |
| E1-27.22 | Z27 | Cl | H | CH₃ | E1-30.14 | Z30 | Cl | H | F |
| E1-27.23 | Z27 | SCH₃ | H | H | E1-30.15 | Z30 | CH₃ | H | F |
| E1-27.24 | Z27 | SO₂CH₃ | H | H | E1-30.16 | Z30 | CH₃ | F | H |
| E1-27.25 | Z27 | ethynyl | H | H | E1-30.17 | Z30 | Cl | F | H |
| E1-28.1 | Z28 | H | H | H | E1-30.18 | Z30 | F | F | H |
| E1-28.2 | Z28 | CH₃ | H | H | E1-30.19 | Z30 | F | H | F |
| E1-28.3 | Z28 | Cl | H | H | E1-30.20 | Z30 | F | H | Cl |
| E1-28.4 | Z28 | F | H | H | E1-30.21 | Z30 | F | H | CH₃ |
| E1-28.5 | Z28 | CH₂CH₃ | H | H | E1-30.22 | Z30 | Cl | H | CH₃ |
| E1-28.6 | Z28 | CF₂H | H | H | E1-30.23 | Z30 | SCH₃ | H | H |
| E1-28.7 | Z28 | CH₂F | H | H | E1-30.24 | Z30 | SO₂CH₃ | H | H |
| E1-28.8 | Z28 | CF₃ | H | H | E1-30.25 | Z30 | ethynyl | H | H |
| E1-28.9 | Z28 | CF₂CH₃ | H | H | E1-31.1 | Z31 | H | H | H |
| E1-28.10 | Z28 | CH₂CF₃ | H | H | E1-31.2 | Z31 | CH₃ | H | H |
| E1-28.11 | Z28 | cyclopropyl | H | H | E1-31.3 | Z31 | Cl | H | H |
| E1-28.12 | Z28 | OCF₃ | H | H | E1-31.4 | Z31 | F | H | H |
| E1-28.13 | Z28 | OCF₂H | H | H | E1-31.5 | Z31 | CH₂CH₃ | H | H |
| E1-28.14 | Z28 | Cl | H | F | E1-31.6 | Z31 | CF₂H | H | H |
| E1-28.15 | Z28 | CH₃ | H | F | E1-31.7 | Z31 | CH₂F | H | H |
| E1-28.16 | Z28 | CH₃ | F | H | E1-31.8 | Z31 | CF₃ | H | H |
| E1-28.17 | Z28 | Cl | F | H | E1-31.9 | Z31 | CF₂CH₃ | H | H |
| E1-28.18 | Z28 | F | F | H | E1-31.10 | Z31 | CH₂CF₃ | H | H |
| E1-28.19 | Z28 | F | H | F | E1-31.11 | Z31 | cyclopropyl | H | H |
| E1-28.20 | Z28 | F | H | Cl | E1-31.12 | Z31 | OCF₃ | H | H |
| E1-28.21 | Z28 | F | H | CH₃ | E1-31.13 | Z31 | OCF₂H | H | H |
| E1-28.22 | Z28 | Cl | H | CH₃ | E1-31.14 | Z31 | Cl | H | F |
| E1-28.23 | Z28 | SCH₃ | H | H | E1-31.15 | Z31 | CH₃ | H | F |
| E1-28.24 | Z28 | SO₂CH₃ | H | H | E1-31.16 | Z31 | CH₃ | F | H |
| E1-28.25 | Z28 | ethynyl | H | H | E1-31.17 | Z31 | Cl | F | H |
| E1-29.1 | Z29 | H | H | H | E1-31.18 | Z31 | F | F | H |
| E1-29.2 | Z29 | CH₃ | H | H | E1-31.19 | Z31 | F | H | F |
| E1-29.3 | Z29 | Cl | H | H | E1-31.20 | Z31 | F | H | Cl |
| E1-29.4 | Z29 | F | H | H | E1-31.21 | Z31 | F | H | CH₃ |
| E1-29.5 | Z29 | CH₂CH₃ | H | H | E1-31.22 | Z31 | Cl | H | CH₃ |
| E1-29.6 | Z29 | CF₂H | H | H | E1-31.23 | Z31 | SCH₃ | H | H |

TABLE 1.E1-continued

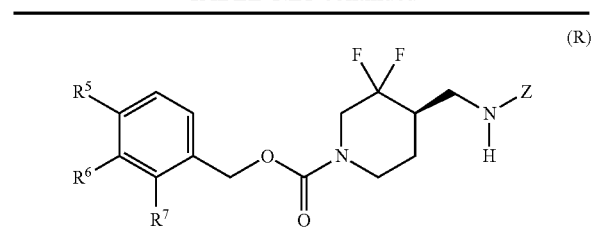

(R)

| compound | Z | R⁵ | R⁶ | R⁷ |
|---|---|---|---|---|
| E1-31.24 | Z31 | SO₂CH₃ | H | H |
| E1-31.25 | Z31 | ethynyl | H | H |
| E1-32.1 | Z32 | H | H | H |
| E1-32.2 | Z32 | CH₃ | H | H |
| E1-32.3 | Z32 | Cl | H | H |
| E1-32.4 | Z32 | F | H | H |
| E1-32.5 | Z32 | CH₂CH₃ | H | H |
| E1-32.6 | Z32 | CF₂H | H | H |
| E1-32.7 | Z32 | CH₂F | H | H |
| E1-32.8 | Z32 | CF₃ | H | H |
| E1-32.9 | Z32 | CF₂CH₃ | H | H |
| E1-32.10 | Z32 | CH₂CF₃ | H | H |
| E1-32.11 | Z32 | cyclopropyl | H | H |
| E1-32.12 | Z32 | OCF₃ | H | H |
| E1-32.13 | Z32 | OCF₂H | H | H |
| E1-32.14 | Z32 | Cl | H | F |
| E1-32.15 | Z32 | CH₃ | H | F |
| E1-32.16 | Z32 | CH₃ | F | H |
| E1-32.17 | Z32 | Cl | F | H |
| E1-32.18 | Z32 | F | F | H |
| E1-32.19 | Z32 | F | H | F |
| E1-32.20 | Z32 | F | H | Cl |
| E1-32.21 | Z32 | F | H | CH₃ |
| E1-32.22 | Z32 | Cl | H | CH₃ |
| E1-32.23 | Z32 | SCH₃ | H | H |
| E1-32.24 | Z32 | SO₂CH₃ | H | H |
| E1-32.25 | Z32 | ethynyl | H | H |
| E1-33.1 | Z33 | H | H | H |
| E1-33.2 | Z33 | CH₃ | H | H |
| E1-33.3 | Z33 | Cl | H | H |
| E1-33.4 | Z33 | F | H | H |
| E1-33.5 | Z33 | CH₂CH₃ | H | H |
| E1-33.6 | Z33 | CF₂H | H | H |
| E1-33.7 | Z33 | CH₂F | H | H |
| E1-33.8 | Z33 | CF₃ | H | H |
| E1-33.9 | Z33 | CF₂CH₃ | H | H |
| E1-33.10 | Z33 | CH₂CF₃ | H | H |
| E1-33.11 | Z33 | cyclopropyl | H | H |
| E1-33.12 | Z33 | OCF₃ | H | H |
| E1-33.13 | Z33 | OCF₂H | H | H |
| E1-33.14 | Z33 | Cl | H | F |
| E1-33.15 | Z33 | CH₃ | H | F |
| E1-33.16 | Z33 | CH₃ | F | H |
| E1-33.17 | Z33 | Cl | F | H |
| E1-33.18 | Z33 | F | F | H |
| E1-33.19 | Z33 | F | H | F |
| E1-33.20 | Z33 | F | H | Cl |
| E1-33.21 | Z33 | F | H | CH₃ |
| E1-33.22 | Z33 | Cl | H | CH₃ |
| E1-33.23 | Z33 | SCH₃ | H | H |
| E1-33.24 | Z33 | SO₂CH₃ | H | H |
| E1-33.25 | Z33 | ethynyl | H | H |
| E1-34.1 | Z34 | H | H | H |
| E1-34.2 | Z34 | CH₃ | H | H |
| E1-34.3 | Z34 | Cl | H | H |
| E1-34.4 | Z34 | F | H | H |
| E1-34.5 | Z34 | CH₂CH₃ | H | H |
| E1-34.6 | Z34 | CF₂H | H | H |
| E1-34.7 | Z34 | CH₂F | H | H |
| E1-34.8 | Z34 | CF₃ | H | H |
| E1-34.9 | Z34 | CF₂CH₃ | H | H |
| E1-34.10 | Z34 | CH₂CF₃ | H | H |
| E1-34.11 | Z34 | cyclopropyl | H | H |
| E1-34.12 | Z34 | OCF₃ | H | H |
| E1-34.13 | Z34 | OCF₂H | H | H |
| E1-34.14 | Z34 | Cl | H | F |
| E1-34.15 | Z34 | CH₃ | H | F |
| E1-34.16 | Z34 | CH₃ | F | H |
| E1-34.17 | Z34 | Cl | F | H |
| E1-34.18 | Z34 | F | F | H |
| E1-34.19 | Z34 | F | H | F |
| E1-34.20 | Z34 | F | H | Cl |
| E1-34.21 | Z34 | F | H | CH₃ |
| E1-34.22 | Z34 | Cl | H | CH₃ |
| E1-34.23 | Z34 | SCH₃ | H | H |
| E1-34.24 | Z34 | SO₂CH₃ | H | H |
| E1-34.25 | Z34 | ethynyl | H | H |
| E1-35.1 | Z35, Rᵃ is H | H | H | H |
| E1-35.2 | Z35, Rᵃ is H | CH₃ | H | H |
| E1-35.3 | Z35, Rᵃ is H | Cl | H | H |
| E1-35.4 | Z35, Rᵃ is H | F | H | H |
| E1-35.5 | Z35, Rᵃ is H | CH₂CH₃ | H | H |
| E1-35.6 | Z35, Rᵃ is H | CF₂H | H | H |
| E1-35.7 | Z35, Rᵃ is H | CH₂F | H | H |
| E1-35.8 | Z35, Rᵃ is H | CF₃ | H | H |
| E1-35.9 | Z35, Rᵃ is H | CF₂CH₃ | H | H |
| E1-35.10 | Z35, Rᵃ is H | CH₂CF₃ | H | H |
| E1-35.11 | Z35, Rᵃ is H | cyclopropyl | H | H |
| E1-35.12 | Z35, Rᵃ is H | OCF₃ | H | H |
| E1-35.13 | Z35, Rᵃ is H | OCF₂H | H | H |
| E1-35.14 | Z35, Rᵃ is H | Cl | H | F |
| E1-35.15 | Z35, Rᵃ is H | CH₃ | H | F |
| E1-35.16 | Z35, Rᵃ is H | CH₃ | F | H |
| E1-35.17 | Z35, Rᵃ is H | Cl | F | H |
| E1-35.18 | Z35, Rᵃ is H | F | F | H |
| E1-35.19 | Z35, Rᵃ is H | F | H | F |
| E1-35.20 | Z35, Rᵃ is H | F | H | Cl |
| E1-35.21 | Z35, Rᵃ is H | F | H | CH₃ |
| E1-35.22 | Z35, Rᵃ is H | Cl | H | CH₃ |
| E1-35.23 | Z35, Rᵃ is H | SCH₃ | H | H |
| E1-35.24 | Z35, Rᵃ is H | SO₂CH₃ | H | H |
| E1-35.25 | Z35, Rᵃ is H | ethynyl | H | H |
| E1-36.1 | Z36, Rᵃ is H | H | H | H |
| E1-36.2 | Z36, Rᵃ is H | CH₃ | H | H |
| E1-36.3 | Z36, Rᵃ is H | Cl | H | H |
| E1-36.4 | Z36, Rᵃ is H | F | H | H |
| E1-36.5 | Z36, Rᵃ is H | CH₂CH₃ | H | H |
| E1-36.6 | Z36, Rᵃ is H | CF₂H | H | H |
| E1-36.7 | Z36, Rᵃ is H | CH₂F | H | H |
| E1-36.8 | Z36, Rᵃ is H | CF₃ | H | H |
| E1-36.9 | Z36, Rᵃ is H | CF₂CH₃ | H | H |
| E1-36.10 | Z36, Rᵃ is H | CH₂CF₃ | H | H |
| E1-36.11 | Z36, Rᵃ is H | cyclopropyl | H | H |
| E1-36.12 | Z36, Rᵃ is H | OCF₃ | H | H |
| E1-36.13 | Z36, Rᵃ is H | OCF₂H | H | H |
| E1-36.14 | Z36, Rᵃ is H | Cl | H | F |
| E1-36.15 | Z36, Rᵃ is H | CH₃ | H | F |
| E1-36.16 | Z36, Rᵃ is H | CH₃ | F | H |
| E1-36.17 | Z36, Rᵃ is H | Cl | F | H |
| E1-36.18 | Z36, Rᵃ is H | F | F | H |
| E1-36.19 | Z36, Rᵃ is H | F | H | F |
| E1-36.20 | Z36, Rᵃ is H | F | H | Cl |
| E1-36.21 | Z36, Rᵃ is H | F | H | CH₃ |
| E1-36.22 | Z36, Rᵃ is H | Cl | H | CH₃ |
| E1-36.23 | Z36, Rᵃ is H | SCH₃ | H | H |
| E1-36.24 | Z36, Rᵃ is H | SO₂CH₃ | H | H |
| E1-36.25 | Z36, Rᵃ is H | ethynyl | H | H |

TABLE 1.E2

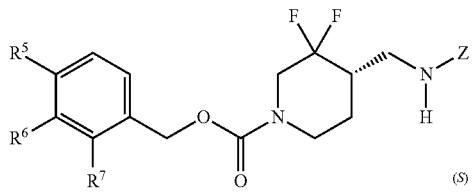

| compound | Z | R⁵ | R⁶ | R⁷ |
|---|---|---|---|---|
| E2-1.1 | Z1 | H | H | H |
| E2-1.2 | Z1 | CH₃ | H | H |
| E2-1.3 | Z1 | Cl | H | H |
| E2-1.4 | Z1 | F | H | H |
| E2-1.5 | Z1 | CH₂CH₃ | H | H |
| E2-1.6 | Z1 | CF₂H | H | H |
| E2-1.7 | Z1 | CH₂F | H | H |
| E2-1.8 | Z1 | CF₃ | H | H |
| E2-1.9 | Z1 | CF₂CH₃ | H | H |
| E2-1.10 | Z1 | CH₂CF₃ | H | H |
| E2-1.11 | Z1 | cyclopropyl | H | H |
| E2-1.12 | Z1 | OCF₃ | H | H |
| E2-1.13 | Z1 | OCF₂H | H | H |
| E2-1.14 | Z1 | Cl | H | F |
| E2-1.15 | Z1 | CH₃ | H | F |
| E2-1.16 | Z1 | CH₃ | F | H |
| E2-1.17 | Z1 | Cl | F | H |
| E2-1.18 | Z1 | F | F | H |
| E2-1.19 | Z1 | F | H | F |
| E2-1.20 | Z1 | F | H | Cl |
| E2-1.21 | Z1 | F | H | CH₃ |
| E2-1.22 | Z1 | Cl | H | CH₃ |
| E2-1.23 | Z1 | SCH₃ | H | H |
| E2-1.24 | Z1 | SO₂CH₃ | H | H |
| E2-1.25 | Z1 | ethynyl | H | H |
| E2-2.1 | Z2 | H | H | H |
| E2-2.2 | Z2 | CH₃ | H | H |
| E2-2.3 | Z2 | Cl | H | H |
| E2-2.4 | Z2 | F | H | H |
| E2-2.5 | Z2 | CH₂CH₃ | H | H |
| E2-2.6 | Z2 | CF₂H | H | H |
| E2-2.7 | Z2 | CH₂F | H | H |
| E2-2.8 | Z2 | CF₃ | H | H |
| E2-2.9 | Z2 | CF₂CH₃ | H | H |
| E2-2.10 | Z2 | CH₂CF₃ | H | H |
| E2-2.11 | Z2 | cyclopropyl | H | H |
| E2-2.12 | Z2 | OCF₃ | H | H |
| E2-2.13 | Z2 | OCF₂H | H | H |
| E2-2.14 | Z2 | Cl | H | F |
| E2-2.15 | Z2 | CH₃ | H | F |
| E2-2.16 | Z2 | CH₃ | F | H |
| E2-2.17 | Z2 | Cl | F | H |
| E2-2.18 | Z2 | F | F | H |
| E2-2.19 | Z2 | F | H | F |
| E2-2.20 | Z2 | F | H | Cl |
| E2-2.21 | Z2 | F | H | CH₃ |
| E2-2.22 | Z2 | Cl | H | CH₃ |
| E2-2.23 | Z2 | SCH₃ | H | H |
| E2-2.24 | Z2 | SO₂CH₃ | H | H |
| E2-2.25 | Z2 | ethynyl | H | H |
| E2-3.1 | Z3 | H | H | H |
| E2-3.2 | Z3 | CH₃ | H | H |
| E2-3.3 | Z3 | Cl | H | H |
| E2-3.4 | Z3 | F | H | H |
| E2-3.5 | Z3 | CH₂CH₃ | H | H |
| E2-3.6 | Z3 | CF₂H | H | H |
| E2-3.7 | Z3 | CH₂F | H | H |
| E2-3.8 | Z3 | CF₃ | H | H |
| E2-3.9 | Z3 | CF₂CH₃ | H | H |
| E2-3.10 | Z3 | CH₂CF₃ | H | H |
| E2-3.11 | Z3 | cyclopropyl | H | H |
| E2-3.12 | Z3 | OCF₃ | H | H |
| E2-3.13 | Z3 | OCF₂H | H | H |
| E2-3.14 | Z3 | Cl | H | F |
| E2-3.15 | Z3 | CH₃ | H | F |
| E2-3.16 | Z3 | CH₃ | F | H |
| E2-3.17 | Z3 | Cl | F | H |
| E2-3.18 | Z3 | F | F | H |
| E2-3.19 | Z3 | F | H | F |
| E2-3.20 | Z3 | F | H | Cl |
| E2-3.21 | Z3 | F | H | CH₃ |
| E2-3.22 | Z3 | Cl | H | CH₃ |
| E2-3.23 | Z3 | SCH₃ | H | H |
| E2-3.24 | Z3 | SO₂CH₃ | H | H |
| E2-3.25 | Z3 | ethynyl | H | H |
| E2-4.1 | Z4 | H | H | H |
| E2-4.2 | Z4 | CH₃ | H | H |
| E2-4.3 | Z4 | Cl | H | H |
| E2-4.4 | Z4 | F | H | H |
| E2-4.5 | Z4 | CH₂CH₃ | H | H |
| E2-4.6 | Z4 | CF₂H | H | H |
| E2-4.7 | Z4 | CH₂F | H | H |
| E2-4.8 | Z4 | CF₃ | H | H |
| E2-4.9 | Z4 | CF₂CH₃ | H | H |
| E2-4.10 | Z4 | CH₂CF₃ | H | H |
| E2-4.11 | Z4 | cyclopropyl | H | H |
| E2-4.12 | Z4 | OCF₃ | H | H |
| E2-4.13 | Z4 | OCF₂H | H | H |
| E2-4.14 | Z4 | Cl | H | F |
| E2-4.15 | Z4 | CH₃ | H | F |
| E2-4.16 | Z4 | CH₃ | F | H |
| E2-4.17 | Z4 | Cl | F | H |
| E2-4.18 | Z4 | F | F | H |
| E2-4.19 | Z4 | F | H | F |
| E2-4.20 | Z4 | F | H | Cl |
| E2-4.21 | Z4 | F | H | CH₃ |
| E2-4.22 | Z4 | Cl | H | CH₃ |
| E2-4.23 | Z4 | SCH₃ | H | H |
| E2-4.24 | Z4 | SO₂CH₃ | H | H |
| E2-4.25 | Z4 | ethynyl | H | H |
| E2-5.1 | Z5 | H | H | H |
| E2-5.2 | Z5 | CH₃ | H | H |
| E2-5.3 | Z5 | Cl | H | H |
| E2-5.4 | Z5 | F | H | H |
| E2-5.5 | Z5 | CH₂CH₃ | H | H |
| E2-5.6 | Z5 | CF₂H | H | H |
| E2-5.7 | Z5 | CH₂F | H | H |
| E2-5.8 | Z5 | CF₃ | H | H |
| E2-5.9 | Z5 | CF₂CH₃ | H | H |
| E2-5.10 | Z5 | CH₂CF₃ | H | H |
| E2-5.11 | Z5 | cyclopropyl | H | H |
| E2-5.12 | Z5 | OCF₃ | H | H |
| E2-5.13 | Z5 | OCF₂H | H | H |
| E2-5.14 | Z5 | Cl | H | F |
| E2-5.15 | Z5 | CH₃ | H | F |
| E2-5.16 | Z5 | CH₃ | F | H |
| E2-5.17 | Z5 | Cl | F | H |
| E2-5.18 | Z5 | F | F | H |
| E2-5.19 | Z5 | F | H | F |
| E2-5.20 | Z5 | F | H | Cl |
| E2-5.21 | Z5 | F | H | CH₃ |
| E2-5.22 | Z5 | Cl | H | CH₃ |
| E2-5.23 | Z5 | SCH₃ | H | H |
| E2-5.24 | Z5 | SO₂CH₃ | H | H |
| E-5.25 | Z5 | ethynyl | H | H |
| E2-6.1 | Z6, Rᵃ is H | H | H | H |
| E2-6.2 | Z6, Rᵃ is H | CH₃ | H | H |
| E2-6.3 | Z6, Rᵃ is H | Cl | H | H |
| E2-6.4 | Z6, Rᵃ is H | F | H | H |
| E2-6.5 | Z6, Rᵃ is H | CH₂CH₃ | H | H |
| E2-6.6 | Z6, Rᵃ is H | CF₂H | H | H |
| E2-6.7 | Z6, Rᵃ is H | CH₂F | H | H |
| E2-6.8 | Z6, Rᵃ is H | CF₃ | H | H |
| E2-6.9 | Z6, Rᵃ is H | CF₂CH₃ | H | H |

TABLE 1.E2-continued

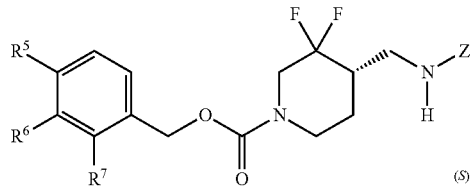

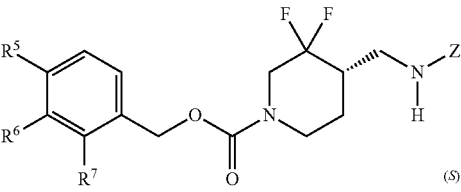

| compound | Z | R⁵ | R⁶ | R⁷ |
|---|---|---|---|---|
| E2-6.10 | Z6, R$^a$ is H | CH$_2$CF$_3$ | H | H |
| E2-6.11 | Z6, R$^a$ is H | cyclopropyl | H | H |
| E2-6.12 | Z6, R$^a$ is H | OCF$_3$ | H | H |
| E2-6.13 | Z6, R$^a$ is H | OCF$_2$H | H | H |
| E2-6.14 | Z6, R$^a$ is H | Cl | H | F |
| E2-6.15 | Z6, R$^a$ is H | CH$_3$ | H | F |
| E2-6.16 | Z6, R$^a$ is H | CH$_3$ | F | H |
| E2-6.17 | Z6, R$^a$ is H | Cl | F | H |
| E2-6.18 | Z6, R$^a$ is H | F | F | H |
| E2-6.19 | Z6, R$^a$ is H | F | H | F |
| E2-6.20 | Z6, R$^a$ is H | F | H | Cl |
| E2-6.21 | Z6, R$^a$ is H | F | H | CH$_3$ |
| E2-6.22 | Z6, R$^a$ is H | Cl | H | CH$_3$ |
| E2-6.23 | Z6, R$^a$ is H | SCH$_3$ | H | H |
| E2-6.24 | Z6, R$^a$ is H | SO$_2$CH$_3$ | H | H |
| E2-6.25 | Z6, R$^a$ is H | ethynyl | H | H |
| E2-7.1 | Z7, R$^a$ is H | H | H | H |
| E2-7.2 | Z7, R$^a$ is H | CH$_3$ | H | H |
| E2-7.3 | Z7, R$^a$ is H | Cl | H | H |
| E2-7.4 | Z7, R$^a$ is H | F | H | H |
| E2-7.5 | Z7, R$^a$ is H | CH$_2$CH$_3$ | H | H |
| E2-7.6 | Z7, R$^a$ is H | CF$_2$H | H | H |
| E2-7.7 | Z7, R$^a$ is H | CH$_2$F | H | H |
| E2-7.8 | Z7, R$^a$ is H | CF$_3$ | H | H |
| E2-7.9 | Z7, R$^a$ is H | CF$_2$CH$_3$ | H | H |
| E2-7.10 | Z7, R$^a$ is H | CH$_2$CF$_3$ | H | H |
| E2-7.11 | Z7, R$^a$ is H | cyclopropyl | H | H |
| E2-7.12 | Z7, R$^a$ is H | OCF$_3$ | H | H |
| E2-7.13 | Z7, R$^a$ is H | OCF$_2$H | H | H |
| E2-7.14 | Z7, R$^a$ is H | Cl | H | F |
| E2-7.15 | Z7, R$^a$ is H | CH$_3$ | H | F |
| E2-7.16 | Z7, R$^a$ is H | CH$_3$ | F | H |
| E2-7.17 | Z7, R$^a$ is H | Cl | F | H |
| E2-7.18 | Z7, R$^a$ is H | F | F | H |
| E2-7.19 | Z7, R$^a$ is H | F | H | F |
| E2-7.20 | Z7, R$^a$ is H | F | H | Cl |
| E2-7.21 | Z7, R$^a$ is H | F | H | CH$_3$ |
| E2-7.22 | Z7, R$^a$ is H | Cl | H | CH$_3$ |
| E2-7.23 | Z7, R$^a$ is H | SCH$_3$ | H | H |
| E2-7.24 | Z7, R$^a$ is H | SO$_2$CH$_3$ | H | H |
| E2-7.25 | Z7, R$^a$ is H | ethynyl | H | H |
| E2-8.1 | Z8, R$^a$ is H | H | H | H |
| E2-8.2 | Z8, R$^a$ is H | CH$_3$ | H | H |
| E2-8.3 | Z8, R$^a$ is H | Cl | H | H |
| E2-8.4 | Z8, R$^a$ is H | F | H | H |
| E2-8.5 | Z8, R$^a$ is H | CH$_2$CH$_3$ | H | H |
| E2-8.6 | Z8, R$^a$ is H | CF$_2$H | H | H |
| E2-8.7 | Z8, R$^a$ is H | CH$_2$F | H | H |
| E2-8.8 | Z8, R$^a$ is H | CF$_3$ | H | H |
| E2-8.9 | Z8, R$^a$ is H | CF$_2$CH$_3$ | H | H |
| E2-8.10 | Z8, R$^a$ is H | CH$_2$CF$_3$ | H | H |
| E2-8.11 | Z8, R$^a$ is H | cyclopropyl | H | H |
| E2-8.12 | Z8, R$^a$ is H | OCF$_3$ | H | H |
| E2-8.13 | Z8, R$^a$ is H | OCF$_2$H | H | H |
| E2-8.14 | Z8, R$^a$ is H | Cl | H | F |
| E2-8.15 | Z8, R$^a$ is H | CH$_3$ | H | F |
| E2-8.16 | Z8, R$^a$ is H | CH$_3$ | F | H |
| E2-8.17 | Z8, R$^a$ is H | Cl | F | H |
| E2-8.18 | Z8, R$^a$ is H | F | F | H |
| E2-8.19 | Z8, R$^a$ is H | F | H | F |
| E2-8.20 | Z8, R$^a$ is H | F | H | Cl |
| E2-8.21 | Z8, R$^a$ is H | F | H | CH$_3$ |
| E2-8.22 | Z8, R$^a$ is H | Cl | H | CH$_3$ |
| E2-8.23 | Z8, R$^a$ is H | SCH$_3$ | H | H |
| E2-8.24 | Z8, R$^a$ is H | SO$_2$CH$_3$ | H | H |
| E2-8.25 | Z8, R$^a$ is H | ethynyl | H | H |
| E2-9.1 | Z9 | H | H | H |
| E2-9.2 | Z9 | CH$_3$ | H | H |
| E2-9.3 | Z9 | Cl | H | H |
| E2-9.4 | Z9 | F | H | H |
| E2-9.5 | Z9 | CH$_2$CH$_3$ | H | H |
| E2-9.6 | Z9 | CF$_2$H | H | H |
| E2-9.7 | Z9 | CH$_2$F | H | H |
| E2-9.8 | Z9 | CF$_3$ | H | H |
| E2-9.9 | Z9 | CF$_2$CH$_3$ | H | H |
| E2-9.10 | Z9 | CH$_2$CF$_3$ | H | H |
| E2-9.11 | Z9 | cyclopropyl | H | H |
| E2-9.12 | Z9 | OCF$_3$ | H | H |
| E2-9.13 | Z9 | OCF$_2$H | H | H |
| E2-9.14 | Z9 | Cl | H | F |
| E2-9.15 | Z9 | CH$_3$ | H | F |
| E2-9.16 | Z9 | CH$_3$ | F | H |
| E2-9.17 | Z9 | Cl | F | H |
| E2-9.18 | Z9 | F | F | H |
| E2-9.19 | Z9 | F | H | F |
| E2-9.20 | Z9 | F | H | Cl |
| E2-9.21 | Z9 | F | H | CH$_3$ |
| E2-9.22 | Z9 | Cl | H | CH$_3$ |
| E2-9.23 | Z9 | SCH$_3$ | H | H |
| E2-9.24 | Z9 | SO$_2$CH$_3$ | H | H |
| E2-9.25 | Z9 | ethynyl | H | H |
| E2-10.1 | Z10 | H | H | H |
| E2-10.2 | Z10 | CH$_3$ | H | H |
| E2-10.3 | Z10 | Cl | H | H |
| E2-10.4 | Z10 | F | H | H |
| E2-10.5 | Z10 | CH$_2$CH$_3$ | H | H |
| E2-10.6 | Z10 | CF$_2$H | H | H |
| E2-10.7 | Z10 | CH$_2$F | H | H |
| E2-10.8 | Z10 | CF$_3$ | H | H |
| E2-10.9 | Z10 | CF$_2$CH$_3$ | H | H |
| E2-10.10 | Z10 | CH$_2$CF$_3$ | H | H |
| E2-10.11 | Z10 | cyclopropyl | H | H |
| E2-10.12 | Z10 | OCF$_3$ | H | H |
| E2-10.13 | Z10 | OCF$_2$H | H | H |
| E2-10.14 | Z10 | Cl | H | F |
| E2-10.15 | Z10 | CH$_3$ | H | F |
| E2-10.16 | Z10 | CH$_3$ | F | H |
| E2-10.17 | Z10 | Cl | F | H |
| E2-10.18 | Z10 | F | F | H |
| E2-10.19 | Z10 | F | H | F |
| E2-10.20 | Z10 | F | H | Cl |
| E2-10.21 | Z10 | F | H | CH$_3$ |
| E2-10.22 | Z10 | Cl | H | CH$_3$ |
| E2-10.23 | Z10 | SCH$_3$ | H | H |
| E2-10.24 | Z10 | SO$_2$CH$_3$ | H | H |
| E2-10.25 | Z10 | ethynyl | H | H |
| E2-11.1 | Z11, R$^a$ is H | H | H | H |
| E2-11.2 | Z11, R$^a$ is H | CH$_3$ | H | H |
| E2-11.3 | Z11, R$^a$ is H | Cl | H | H |
| E2-11.4 | Z11, R$^a$ is H | F | H | H |
| E2-11.5 | Z11, R$^a$ is H | CH$_2$CH$_3$ | H | H |
| E2-11.6 | Z11, R$^a$ is H | CF$_2$H | H | H |
| E2-11.7 | Z11, R$^a$ is H | CH$_2$F | H | H |
| E2-11.8 | Z11, R$^a$ is H | CF$_3$ | H | H |
| E2-11.9 | Z11, R$^a$ is H | CF$_2$CH$_3$ | H | H |
| E2-11.10 | Z11, R$^a$ is H | CH$_2$CF$_3$ | H | H |
| E2-11.11 | Z11, R$^a$ is H | cyclopropyl | H | H |
| E2-11.12 | Z11, R$^a$ is H | OCF$_3$ | H | H |
| E2-11.13 | Z11, R$^a$ is H | OCF$_2$H | H | H |
| E2-11.14 | Z11, R$^a$ is H | Cl | H | F |
| E2-11.15 | Z11, R$^a$ is H | CH$_3$ | H | F |
| E2-11.16 | Z11, R$^a$ is H | CH$_3$ | F | H |
| E2-11.17 | Z11, R$^a$ is H | Cl | F | H |
| E2-11.18 | Z11, R$^a$ is H | F | F | H |

TABLE 1.E2-continued

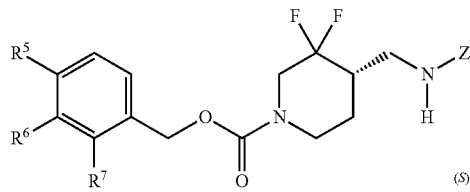

(S)

TABLE 1.E2-continued

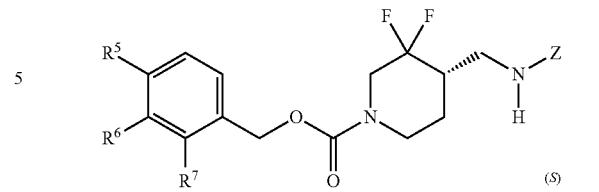

(S)

| compound | Z | R⁵ | R⁶ | R⁷ |
|---|---|---|---|---|
| E2-11.19 | Z11, Rᵃ is H | F | H | F |
| E2-11.20 | Z11, Rᵃ is H | F | H | Cl |
| E2-11.21 | Z11, Rᵃ is H | F | H | CH₃ |
| E2-11.22 | Z11, Rᵃ is H | Cl | H | CH₃ |
| E2-11.23 | Z11, Rᵃ is H | SCH₃ | H | H |
| E2-11.24 | Z11, Rᵃ is H | SO₂CH₃ | H | H |
| E2-11.25 | Z11, Rᵃ is H | ethynyl | H | H |
| E2-12.1 | Z12 | H | H | H |
| E2-12.2 | Z12 | CH₃ | H | H |
| E2-12.3 | Z12 | Cl | H | H |
| E2-12.4 | Z12 | F | H | H |
| E2-12.5 | Z12 | CH₂CH₃ | H | H |
| E2-12.6 | Z12 | CF₂H | H | H |
| E2-12.7 | Z12 | CH₂F | H | H |
| E2-12.8 | Z12 | CF₃ | H | H |
| E2-12.9 | Z12 | CF₂CH₃ | H | H |
| E2-12.10 | Z12 | CH₂CF₃ | H | H |
| E2-12.11 | Z12 | cyclopropyl | H | H |
| E2-12.12 | Z12 | OCF₃ | H | H |
| E2-12.13 | Z12 | OCF₂H | H | H |
| E2-12.14 | Z12 | Cl | H | F |
| E2-12.15 | Z12 | CH₃ | H | F |
| E2-12.16 | Z12 | CH₃ | F | H |
| E2-12.17 | Z12 | Cl | F | H |
| E2-12.18 | Z12 | F | F | H |
| E2-12.19 | Z12 | F | H | F |
| E2-12.20 | Z12 | F | H | Cl |
| E2-12.21 | Z12 | F | H | CH₃ |
| E2-12.22 | Z12 | Cl | H | CH₃ |
| E2-12.23 | Z12 | SCH₃ | H | H |
| E2-12.24 | Z12 | SO₂CH₃ | H | H |
| E2-12.25 | Z12 | ethynyl | H | H |
| E2-13.1 | Z13, Rᵃ is H | H | H | H |
| E2-13.2 | Z13, Rᵃ is H | CH₃ | H | H |
| E2-13.3 | Z13, Rᵃ is H | Cl | H | H |
| E2-13.4 | Z13, Rᵃ is H | F | H | H |
| E2-13.5 | Z13, Rᵃ is H | CH₂CH₃ | H | H |
| E2-13.6 | Z13, Rᵃ is H | CF₂H | H | H |
| E2-13.7 | Z13, Rᵃ is H | CH₂F | H | H |
| E2-13.8 | Z13, Rᵃ is H | CF₃ | H | H |
| E2-13.9 | Z13, Rᵃ is H | CF₂CH₃ | H | H |
| E2-13.10 | Z13, Rᵃ is H | CH₂CF₃ | H | H |
| E2-13.11 | Z13, Rᵃ is H | cyclopropyl | H | H |
| E2-13.12 | Z13, Rᵃ is H | OCF₃ | H | H |
| E2-13.13 | Z13, Rᵃ is H | OCF₂H | H | H |
| E2-13.14 | Z13, Rᵃ is H | Cl | H | F |
| E2-13.15 | Z13, Rᵃ is H | CH₃ | H | F |
| E2-13.16 | Z13, Rᵃ is H | CH₃ | F | H |
| E2-13.17 | Z13, Rᵃ is H | Cl | F | H |
| E2-13.18 | Z13, Rᵃ is H | F | F | H |
| E2-13.19 | Z13, Rᵃ is H | F | H | F |
| E2-13.20 | Z13, Rᵃ is H | F | H | Cl |
| E2-13.21 | Z13, Rᵃ is H | F | H | CH₃ |
| E2-13.22 | Z13, Rᵃ is H | Cl | H | CH₃ |
| E2-13.23 | Z13, Rᵃ is H | SCH₃ | H | H |
| E2-13.24 | Z13, Rᵃ is H | SO₂CH₃ | H | H |
| E2-13.25 | Z13, Rᵃ is H | ethynyl | H | H |
| E2-14.1 | Z14, Rᵃ is H | H | H | H |
| E2-14.2 | Z14, Rᵃ is H | CH₃ | H | H |
| E2-14.3 | Z14, Rᵃ is H | Cl | H | H |
| E2-14.4 | Z14, Rᵃ is H | F | H | H |
| E2-14.5 | Z14, Rᵃ is H | CH₂CH₃ | H | H |
| E2-14.6 | Z14, Rᵃ is H | CF₂H | H | H |
| E2-14.7 | Z14, Rᵃ is H | CH₂F | H | H |
| E2-14.8 | Z14, Rᵃ is H | CF₃ | H | H |
| E2-14.9 | Z14, Rᵃ is H | CF₂CH₃ | H | H |
| E2-14.10 | Z14, Rᵃ is H | CH₂CF₃ | H | H |
| E2-14.11 | Z14, Rᵃ is H | cyclopropyl | H | H |
| E2-14.12 | Z14, Rᵃ is H | OCF₃ | H | H |
| E2-14.13 | Z14, Rᵃ is H | OCF₂H | H | H |
| E2-14.14 | Z14, Rᵃ is H | Cl | H | F |
| E2-14.15 | Z14, Rᵃ is H | CH₃ | H | F |
| E2-14.16 | Z14, Rᵃ is H | CH₃ | F | H |
| E2-14.17 | Z14, Rᵃ is H | Cl | F | H |
| E2-14.18 | Z14, Rᵃ is H | F | F | H |
| E2-14.19 | Z14, Rᵃ is H | F | H | F |
| E2-14.20 | Z14, Rᵃ is H | F | H | Cl |
| E2-14.21 | Z14, Rᵃ is H | F | H | CH₃ |
| E2-14.22 | Z14, Rᵃ is H | Cl | H | CH₃ |
| E2-14.23 | Z14, Rᵃ is H | SCH₃ | H | H |
| E2-14.24 | Z14, Rᵃ is H | SO₂CH₃ | H | H |
| E2-14.25 | Z14, Rᵃ is H | ethynyl | H | H |
| E2-15.1 | Z15, Rᵃ is H | H | H | H |
| E2-15.2 | Z15, Rᵃ is H | CH₃ | H | H |
| E2-15.3 | Z15, Rᵃ is H | Cl | H | H |
| E2-15.4 | Z15, Rᵃ is H | F | H | H |
| E2-15.5 | Z15, Rᵃ is H | CH₂CH₃ | H | H |
| E2-15.6 | Z15, Rᵃ is H | CF₂H | H | H |
| E2-15.7 | Z15, Rᵃ is H | CH₂F | H | H |
| E2-15.8 | Z15, Rᵃ is H | CF₃ | H | H |
| E2-15.9 | Z15, Rᵃ is H | CF₂CH₃ | H | H |
| E2-15.10 | Z15, Rᵃ is H | CH₂CF₃ | H | H |
| E2-15.11 | Z15, Rᵃ is H | cyclopropyl | H | H |
| E2-15.12 | Z15, Rᵃ is H | OCF₃ | H | H |
| E2-15.13 | Z15, Rᵃ is H | OCF₂H | H | H |
| E2-15.14 | Z15, Rᵃ is H | Cl | H | F |
| E2-15.15 | Z15, Rᵃ is H | CH₃ | H | F |
| E2-15.16 | Z15, Rᵃ is H | CH₃ | F | H |
| E2-15.17 | Z15, Rᵃ is H | Cl | F | H |
| E2-15.18 | Z15, Rᵃ is H | F | F | H |
| E2-15.19 | Z15, Rᵃ is H | F | H | F |
| E2-15.20 | Z15, Rᵃ is H | F | H | Cl |
| E2-15.21 | Z15, Rᵃ is H | F | H | CH₃ |
| E2-15.22 | Z15, Rᵃ is H | Cl | H | CH₃ |
| E2-15.23 | Z15, Rᵃ is H | SCH₃ | H | H |
| E2-15.24 | Z15, Rᵃ is H | SO₂CH₃ | H | H |
| E2-15.25 | Z15, Rᵃ is H | ethynyl | H | H |
| E2-16.1 | Z16, Rᵃ is H | H | H | H |
| E2-16.2 | Z16, Rᵃ is H | CH₃ | H | H |
| E2-16.3 | Z16, Rᵃ is H | Cl | H | H |
| E2-16.4 | Z16, Rᵃ is H | F | H | H |
| E2-16.5 | Z16, Rᵃ is H | CH₂CH₃ | H | H |
| E2-16.6 | Z16, Rᵃ is H | CF₂H | H | H |
| E2-16.7 | Z16, Rᵃ is H | CH₂F | H | H |
| E2-16.8 | Z16, Rᵃ is H | CF₃ | H | H |
| E2-16.9 | Z16, Rᵃ is H | CF₂CH₃ | H | H |
| E2-16.10 | Z16, Rᵃ is H | CH₂CF₃ | H | H |
| E2-16.11 | Z16, Rᵃ is H | cyclopropyl | H | H |
| E2-16.12 | Z16, Rᵃ is H | OCF₃ | H | H |
| E2-16.13 | Z16, Rᵃ is H | OCF₂H | H | H |
| E2-16.14 | Z16, Rᵃ is H | Cl | H | F |
| E2-16.15 | Z16, Rᵃ is H | CH₃ | H | F |
| E2-16.16 | Z16, Rᵃ is H | CH₃ | F | H |
| E2-16.17 | Z16, Rᵃ is H | Cl | F | H |
| E2-16.18 | Z16, Rᵃ is H | F | F | H |
| E2-16.19 | Z16, Rᵃ is H | F | H | F |
| E2-16.20 | Z16, Rᵃ is H | F | H | Cl |
| E2-16.21 | Z16, Rᵃ is H | F | H | CH₃ |
| E2-16.22 | Z16, Rᵃ is H | Cl | H | CH₃ |
| E2-16.23 | Z16, Rᵃ is H | SCH₃ | H | H |
| E2-16.24 | Z16, Rᵃ is H | SO₂CH₃ | H | H |
| E2-16.25 | Z16, Rᵃ is H | ethynyl | H | H |
| E2-17.1 | Z17 | H | H | H |
| E2-17.2 | Z17 | CH₃ | H | H |

TABLE 1.E2-continued

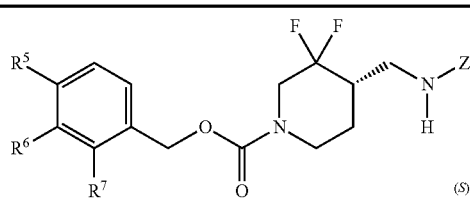

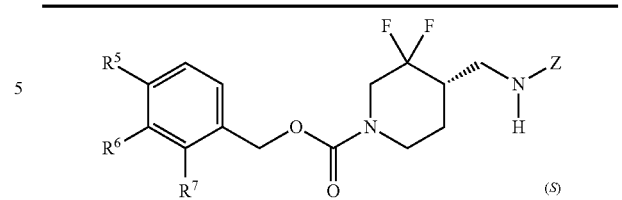

| compound | Z | R⁵ | R⁶ | R⁷ |
|---|---|---|---|---|
| E2-17.3 | Z17 | Cl | H | H |
| E2-17.4 | Z17 | F | H | H |
| E2-17.5 | Z17 | CH₂CH₃ | H | H |
| E2-17.6 | Z17 | CF₂H | H | H |
| E2-17.7 | Z17 | CH₂F | H | H |
| E2-17.8 | Z17 | CF₃ | H | H |
| E2-17.9 | Z17 | CF₂CH₃ | H | H |
| E2-17.10 | Z17 | CH₂CF₃ | H | H |
| E2-17.11 | Z17 | cyclopropyl | H | H |
| E2-17.12 | Z17 | OCF₃ | H | H |
| E2-17.13 | Z17 | OCF₂H | H | H |
| E2-17.14 | Z17 | Cl | H | F |
| E2-17.15 | Z17 | CH₃ | H | F |
| E2-17.16 | Z17 | CH₃ | F | H |
| E2-17.17 | Z17 | Cl | F | H |
| E2-17.18 | Z17 | F | F | H |
| E2-17.19 | Z17 | F | H | F |
| E2-17.20 | Z17 | F | H | Cl |
| E2-17.21 | Z17 | F | H | CH₃ |
| E2-17.22 | Z17 | Cl | H | CH₃ |
| E2-17.23 | Z17 | SCH₃ | H | H |
| E2-17.24 | Z17 | SO₂CH₃ | H | H |
| E2-17.25 | Z17 | ethynyl | H | H |
| E2-18.1 | Z18 | H | H | H |
| E2-18.2 | Z18 | CH₃ | H | H |
| E2-18.3 | Z18 | Cl | H | H |
| E2-18.4 | Z18 | F | H | H |
| E2-18.5 | Z18 | CH₂CH₃ | H | H |
| E2-18.6 | Z18 | CF₂H | H | H |
| E2-18.7 | Z18 | CH₂F | H | H |
| E2-18.8 | Z18 | CF₃ | H | H |
| E2-18.9 | Z18 | CF₂CH₃ | H | H |
| E2-18.10 | Z18 | CH₂CF₃ | H | H |
| E2-18.11 | Z18 | cyclopropyl | H | H |
| E2-18.12 | Z18 | OCF₃ | H | H |
| E2-18.13 | Z18 | OCF₂H | H | H |
| E2-18.14 | Z18 | Cl | H | F |
| E2-18.15 | Z18 | CH₃ | H | F |
| E2-18.16 | Z18 | CH₃ | F | H |
| E2-18.17 | Z18 | Cl | F | H |
| E2-18.18 | Z18 | F | F | H |
| E2-18.19 | Z18 | F | H | F |
| E2-18.20 | Z18 | F | H | Cl |
| E2-18.21 | Z18 | F | H | CH₃ |
| E2-18.22 | Z18 | Cl | H | CH₃ |
| E2-18.23 | Z18 | SCH₃ | H | H |
| E2-18.24 | Z18 | SO₂CH₃ | H | H |
| E2-18.25 | Z18 | ethynyl | H | H |
| E2-19.1 | Z19 | H | H | H |
| E2-19.2 | Z19 | CH₃ | H | H |
| E2-19.3 | Z19 | Cl | H | H |
| E2-19.4 | Z19 | F | H | H |
| E2-19.5 | Z19 | CH₂CH₃ | H | H |
| E2-19.6 | Z19 | CF₂H | H | H |
| E2-19.7 | Z19 | CH₂F | H | H |
| E2-19.8 | Z19 | CF₃ | H | H |
| E2-19.9 | Z19 | CF₂CH₃ | H | H |
| E2-19.10 | Z19 | CH₂CF₃ | H | H |
| E2-19.11 | Z19 | cyclopropyl | H | H |
| E2-19.12 | Z19 | OCF₃ | H | H |
| E2-19.13 | Z19 | OCF₂H | H | H |
| E2-19.14 | Z19 | Cl | H | F |
| E2-19.15 | Z19 | CH₃ | H | F |
| E2-19.16 | Z19 | CH₃ | F | H |
| E2-19.17 | Z19 | Cl | F | H |
| E2-19.18 | Z19 | F | F | H |
| E2-19.19 | Z19 | F | H | F |
| E2-19.20 | Z19 | F | H | Cl |
| E2-19.21 | Z19 | F | H | CH₃ |
| E2-19.22 | Z19 | Cl | H | CH₃ |
| E2-19.23 | Z19 | SCH₃ | H | H |
| E2-19.24 | Z19 | SO₂CH₃ | H | H |
| E2-19.25 | Z19 | ethynyl | H | H |
| E2-19.26 | Z19 | CH₃ | H | H |
| E2-20.1 | Z20 | H | H | H |
| E2-20.2 | Z20 | CH₃ | H | H |
| E2-20.3 | Z20 | Cl | H | H |
| E2-20.4 | Z20 | F | H | H |
| E2-20.5 | Z20 | CH₂CH₃ | H | H |
| E2-20.6 | Z20 | CF₂H | H | H |
| E2-20.7 | Z20 | CH₂F | H | H |
| E2-20.8 | Z20 | CF₃ | H | H |
| E2-20.9 | Z20 | CF₂CH₃ | H | H |
| E2-20.10 | Z20 | CH₂CF₃ | H | H |
| E2-20.11 | Z20 | cyclopropyl | H | H |
| E2-20.12 | Z20 | OCF₃ | H | H |
| E2-20.13 | Z20 | OCF₂H | H | H |
| E2-20.14 | Z20 | Cl | H | F |
| E2-20.15 | Z20 | CH₃ | H | F |
| E2-20.16 | Z20 | CH₃ | F | H |
| E2-20.17 | Z20 | Cl | F | H |
| E2-20.18 | Z20 | F | F | H |
| E2-20.19 | Z20 | F | H | F |
| E2-20.20 | Z20 | F | H | Cl |
| E2-20.21 | Z20 | F | H | CH₃ |
| E2-20.22 | Z20 | Cl | H | CH₃ |
| E2-20.23 | Z20 | SCH₃ | H | H |
| E2-20.24 | Z20 | SO₂CH₃ | H | H |
| E2-20.25 | Z20 | ethynyl | H | H |
| E2-21.1 | Z21 | H | H | H |
| E2-21.2 | Z21 | CH₃ | H | H |
| E2-21.3 | Z21 | Cl | H | H |
| E2-21.4 | Z21 | F | H | H |
| E2-21.5 | Z21 | CH₂CH₃ | H | H |
| E2-21.6 | Z21 | CF₂H | H | H |
| E2-21.7 | Z21 | CH₂F | H | H |
| E2-21.8 | Z21 | CF₃ | H | H |
| E2-21.9 | Z21 | CF₂CH₃ | H | H |
| E2-21.10 | Z21 | CH₂CF₃ | H | H |
| E2-21.11 | Z21 | cyclopropyl | H | H |
| E2-21.12 | Z21 | OCF₃ | H | H |
| E2-21.13 | Z21 | OCF₂H | H | H |
| E2-21.14 | Z21 | Cl | H | F |
| E2-21.15 | Z21 | CH₃ | H | F |
| E2-21.16 | Z21 | CH₃ | F | H |
| E2-21.17 | Z21 | Cl | F | H |
| E2-21.18 | Z21 | F | F | H |
| E2-21.19 | Z21 | F | H | F |
| E2-21.20 | Z21 | F | H | Cl |
| E2-21.21 | Z21 | F | H | CH₃ |
| E2-21.22 | Z21 | Cl | H | CH₃ |
| E2-21.23 | Z21 | SCH₃ | H | H |
| E2-21.24 | Z21 | SO₂CH₃ | H | H |
| E2-21.25 | Z21 | ethynyl | H | H |
| E2-21.26 | (pyrazine structure), Rˣ is CH₃ | CH₃ | H | H |
| E2-22.1 | Z22 | H | H | H |
| E2-22.2 | Z22 | CH₃ | H | H |

TABLE 1.E2-continued

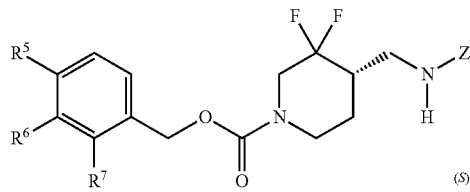

| compound | Z | R^5 | R^6 | R^7 |
|---|---|---|---|---|
| E2-22.3 | Z22 | Cl | H | H |
| E2-22.4 | Z22 | F | H | H |
| E2-22.5 | Z22 | $CH_2CH_3$ | H | H |
| E2-22.6 | Z22 | $CF_2H$ | H | H |
| E2-22.7 | Z22 | $CH_2F$ | H | H |
| E2-22.8 | Z22 | $CF_3$ | H | H |
| E2-22.9 | Z22 | $CF_2CH_3$ | H | H |
| E2-22.10 | Z22 | $CH_2CF_3$ | H | H |
| E2-22.11 | Z22 | cyclopropyl | H | H |
| E2-22.12 | Z22 | $OCF_3$ | H | H |
| E2-22.13 | Z22 | $OCF_2H$ | H | H |
| E2-22.14 | Z22 | Cl | H | F |
| E2-22.15 | Z22 | $CH_3$ | H | F |
| E2-22.16 | Z22 | $CH_3$ | F | H |
| E2-22.17 | Z22 | Cl | F | H |
| E2-22.18 | Z22 | F | F | H |
| E2-22.19 | Z22 | F | H | F |
| E2-22.20 | Z22 | F | H | Cl |
| E2-22.21 | Z22 | F | H | $CH_3$ |
| E2-22.22 | Z22 | Cl | H | $CH_3$ |
| E2-22.23 | Z22 | $SCH_3$ | H | H |
| E2-22.24 | Z22 | $SO_2CH_3$ | H | H |
| E2-22.25 | Z22 | ethynyl | H | H |
| E2-23.1 | Z23 | H | H | H |
| E2-23.2 | Z23 | $CH_3$ | H | H |
| E2-23.3 | Z23 | Cl | H | H |
| E2-23.4 | Z23 | F | H | H |
| E2-23.5 | Z23 | $CH_2CH_3$ | H | H |
| E2-23.6 | Z23 | $CF_2H$ | H | H |
| E2-23.7 | Z23 | $CH_2F$ | H | H |
| E2-23.8 | Z23 | $CF_3$ | H | H |
| E2-23.9 | Z23 | $CF_2CH_3$ | H | H |
| E2-23.10 | Z23 | $CH_2CF_3$ | H | H |
| E2-23.11 | Z23 | cyclopropyl | H | H |
| E2-23.12 | Z23 | $OCF_3$ | H | H |
| E2-23.13 | Z23 | $OCF_2H$ | H | H |
| E2-23.14 | Z23 | Cl | H | F |
| E2-23.15 | Z23 | $CH_3$ | H | F |
| E2-23.16 | Z23 | $CH_3$ | F | H |
| E2-23.17 | Z23 | Cl | F | H |
| E2-23.18 | Z23 | F | F | H |
| E2-23.19 | Z23 | F | H | F |
| E2-23.20 | Z23 | F | H | Cl |
| E2-23.21 | Z23 | F | H | $CH_3$ |
| E2-23.22 | Z23 | Cl | H | $CH_3$ |
| E2-23.23 | Z23 | $SCH_3$ | H | H |
| E2-23.24 | Z23 | $SO_2CH_3$ | H | H |
| E2-23.25 | Z23 | ethynyl | H | H |
| E2-24.1 | Z24 | H | H | H |
| E2-24.2 | Z24 | $CH_3$ | H | H |
| E2-24.3 | Z24 | Cl | H | H |
| E2-24.4 | Z24 | F | H | H |
| E2-24.5 | Z24 | $CH_2CH_3$ | H | H |
| E2-24.6 | Z24 | $CF_2H$ | H | H |
| E2-24.7 | Z24 | $CH_2F$ | H | H |
| E2-24.8 | Z24 | $CF_3$ | H | H |
| E2-24.9 | Z24 | $CF_2CH_3$ | H | H |
| E2-24.10 | Z24 | $CH_2CF_3$ | H | H |
| E2-24.11 | Z24 | cyclopropyl | H | H |
| E2-24.12 | Z24 | $OCF_3$ | H | H |
| E2-24.13 | Z24 | $OCF_2H$ | H | H |
| E2-24.14 | Z24 | Cl | H | F |
| E2-24.15 | Z24 | $CH_3$ | H | F |
| E2-24.16 | Z24 | $CH_3$ | F | H |
| E2-24.17 | Z24 | Cl | F | H |
| E2-24.18 | Z24 | F | F | H |
| E2-24.19 | Z24 | F | H | F |
| E2-24.20 | Z24 | F | H | Cl |
| E2-24.21 | Z24 | F | H | $CH_3$ |
| E2-24.22 | Z24 | Cl | H | $CH_3$ |
| E2-24.23 | Z24 | $SCH_3$ | H | H |
| E2-24.24 | Z24 | $SO_2CH_3$ | H | H |
| E2-24.25 | Z24 | ethynyl | H | H |
| E2-25.1 | Z25, $R^a$ is H | H | H | H |
| E2-25.2 | Z25, $R^a$ is H | $CH_3$ | H | H |
| E2-25.3 | Z25, $R^a$ is H | Cl | H | H |
| E2-25.4 | Z25, $R^a$ is H | F | H | H |
| E2-25.5 | Z25, $R^a$ is H | $CH_2CH_3$ | H | H |
| E2-25.6 | Z25, $R^a$ is H | $CF_2H$ | H | H |
| E2-25.7 | Z25, $R^a$ is H | $CH_2F$ | H | H |
| E2-25.8 | Z25, $R^a$ is H | $CF_3$ | H | H |
| E2-25.9 | Z25, $R^a$ is H | $CF_2CH_3$ | H | H |
| E2-25.10 | Z25, $R^a$ is H | $CH_2CF_3$ | H | H |
| E2-25.11 | Z25, $R^a$ is H | cyclopropyl | H | H |
| E2-25.12 | Z25, $R^a$ is H | $OCF_3$ | H | H |
| E2-25.13 | Z25, $R^a$ is H | $OCF_2H$ | H | H |
| E2-25.14 | Z25, $R^a$ is H | Cl | H | F |
| E2-25.15 | Z25, $R^a$ is H | $CH_3$ | H | F |
| E2-25.16 | Z25, $R^a$ is H | $CH_3$ | F | H |
| E2-25.17 | Z25, $R^a$ is H | Cl | F | H |
| E2-25.18 | Z25, $R^a$ is H | F | F | H |
| E2-25.19 | Z25, $R^a$ is H | F | H | F |
| E2-25.20 | Z25, $R^a$ is H | F | H | Cl |
| E2-25.21 | Z25, $R^a$ is H | F | H | $CH_3$ |
| E2-25.22 | Z25, $R^a$ is H | Cl | H | $CH_3$ |
| E2-25.23 | Z25, $R^a$ is H | $SCH_3$ | H | H |
| E2-25.24 | Z25, $R^a$ is H | $SO_2CH_3$ | H | H |
| E2-25.25 | Z25, $R^a$ is H | ethynyl | H | H |
| E2-26.1 | Z26, $R^a$ is H | H | H | H |
| E2-26.2 | Z26, $R^a$ is H | $CH_3$ | H | H |
| E2-26.3 | Z26, $R^a$ is H | Cl | H | H |
| E2-26.4 | Z26, $R^a$ is H | F | H | H |
| E2-26.5 | Z26, $R^a$ is H | $CH_2CH_3$ | H | H |
| E2-26.6 | Z26, $R^a$ is H | $CF_2H$ | H | H |
| E2-26.7 | Z26, $R^a$ is H | $CH_2F$ | H | H |
| E2-26.8 | Z26, $R^a$ is H | $CF_3$ | H | H |
| E2-26.9 | Z26, $R^a$ is H | $CF_2CH_3$ | H | H |
| E2-26.10 | Z26, $R^a$ is H | $CH_2CF_3$ | H | H |
| E2-26.11 | Z26, $R^a$ is H | cyclopropyl | H | H |
| E2-26.12 | Z26, $R^a$ is H | $OCF_3$ | H | H |
| E2-26.13 | Z26, $R^a$ is H | $OCF_2H$ | H | H |
| E2-26.14 | Z26, $R^a$ is H | Cl | H | F |
| E2-26.15 | Z26, $R^a$ is H | $CH_3$ | H | F |
| E2-26.16 | Z26, $R^a$ is H | $CH_3$ | F | H |
| E2-26.17 | Z26, $R^a$ is H | Cl | F | H |
| E2-26.18 | Z26, $R^a$ is H | F | F | H |
| E2-26.19 | Z26, $R^a$ is H | F | H | F |
| E2-26.20 | Z26, $R^a$ is H | F | H | Cl |
| E2-26.21 | Z26, $R^a$ is H | F | H | $CH_3$ |
| E2-26.22 | Z26, $R^a$ is H | Cl | H | $CH_3$ |
| E2-26.23 | Z26, $R^a$ is H | $SCH_3$ | H | H |
| E2-26.24 | Z26, $R^a$ is H | $SO_2CH_3$ | H | H |
| E2-26.25 | Z26, $R^a$ is H | ethynyl | H | H |
| E2-27.1 | Z27 | H | H | H |
| E2-27.2 | Z27 | $CH_3$ | H | H |
| E2-27.3 | Z27 | Cl | H | H |
| E2-27.4 | Z27 | F | H | H |
| E2-27.5 | Z27 | $CH_2CH_3$ | H | H |
| E2-27.6 | Z27 | $CF_2H$ | H | H |
| E2-27.7 | Z27 | $CH_2F$ | H | H |
| E2-27.8 | Z27 | $CF_3$ | H | H |
| E2-27.9 | Z27 | $CF_2CH_3$ | H | H |
| E2-27.10 | Z27 | $CH_2CF_3$ | H | H |
| E2-27.11 | Z27 | cyclopropyl | H | H |

TABLE 1.E2-continued

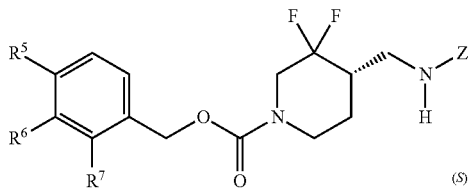

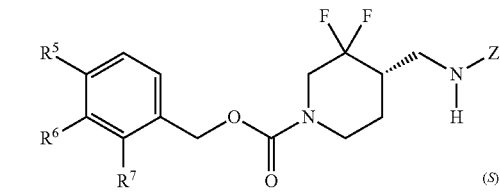

| compound | Z | R⁵ | R⁶ | R⁷ |
|---|---|---|---|---|
| E2-27.12 | Z27 | OCF₃ | H | H |
| E2-27.13 | Z27 | OCF₂H | H | H |
| E2-27.14 | Z27 | Cl | H | F |
| E2-27.15 | Z27 | CH₃ | H | F |
| E2-27.16 | Z27 | CH₃ | F | H |
| E2-27.17 | Z27 | Cl | F | H |
| E2-27.18 | Z27 | F | F | H |
| E2-27.19 | Z27 | F | H | F |
| E2-27.20 | Z27 | F | H | Cl |
| E2-27.21 | Z27 | F | H | CH₃ |
| E2-27.22 | Z27 | Cl | H | CH₃ |
| E2-27.23 | Z27 | SCH₃ | H | H |
| E2-27.24 | Z27 | SO₂CH₃ | H | H |
| E2-27.25 | Z27 | ethynyl | H | H |
| E2-28.1 | Z28 | H | H | H |
| E2-28.2 | Z28 | CH₃ | H | H |
| E2-28.3 | Z28 | Cl | H | H |
| E2-28.4 | Z28 | F | H | H |
| E2-28.5 | Z28 | CH₂CH₃ | H | H |
| E2-28.6 | Z28 | CF₂H | H | H |
| E2-28.7 | Z28 | CH₂F | H | H |
| E2-28.8 | Z28 | CF₃ | H | H |
| E2-28.9 | Z28 | CF₂CH₃ | H | H |
| E2-28.10 | Z28 | CH₂CF₃ | H | H |
| E2-28.11 | Z28 | cyclopropyl | H | H |
| E2-28.12 | Z28 | OCF₃ | H | H |
| E2-28.13 | Z28 | OCF₂H | H | H |
| E2-28.14 | Z28 | Cl | H | F |
| E2-28.15 | Z28 | CH₃ | H | F |
| E2-28.16 | Z28 | CH₃ | F | H |
| E2-28.17 | Z28 | Cl | F | H |
| E2-28.18 | Z28 | F | F | H |
| E2-28.19 | Z28 | F | H | F |
| E2-28.20 | Z28 | F | H | Cl |
| E2-28.21 | Z28 | F | H | CH₃ |
| E2-28.22 | Z28 | Cl | H | CH₃ |
| E2-28.23 | Z28 | SCH₃ | H | H |
| E2-28.24 | Z28 | SO₂CH₃ | H | H |
| E2-28.25 | Z28 | ethynyl | H | H |
| E2-29.1 | Z29 | H | H | H |
| E2-29.2 | Z29 | CH₃ | H | H |
| E2-29.3 | Z29 | Cl | H | H |
| E2-29.4 | Z29 | F | H | H |
| E2-29.5 | Z29 | CH₂CH₃ | H | H |
| E2-29.6 | Z29 | CF₂H | H | H |
| E2-29.7 | Z29 | CH₂F | H | H |
| E2-29.8 | Z29 | CF₃ | H | H |
| E2-29.9 | Z29 | CF₂CH₃ | H | H |
| E2-29.10 | Z29 | CH₂CF₃ | H | H |
| E2-29.11 | Z29 | cyclopropyl | H | H |
| E2-29.12 | Z29 | OCF₃ | H | H |
| E2-29.13 | Z29 | OCF₂H | H | H |
| E2-29.14 | Z29 | Cl | H | F |
| E2-29.15 | Z29 | CH₃ | H | F |
| E2-29.16 | Z29 | CH₃ | F | H |
| E2-29.17 | Z29 | Cl | F | H |
| E2-29.18 | Z29 | F | F | H |
| E2-29.19 | Z29 | F | H | F |
| E2-29.20 | Z29 | F | H | Cl |
| E2-29.21 | Z29 | F | H | CH₃ |
| E2-29.22 | Z29 | Cl | H | CH₃ |
| E2-29.23 | Z29 | SCH₃ | H | H |
| E2-29.24 | Z29 | SO₂CH₃ | H | H |
| E2-29.25 | Z29 | ethynyl | H | H |
| E2-30.1 | Z30 | H | H | H |
| E2-30.2 | Z30 | CH₃ | H | H |
| E2-30.3 | Z30 | Cl | H | H |
| E2-30.4 | Z30 | F | H | H |
| E2-30.5 | Z30 | CH₂CH₃ | H | H |
| E2-30.6 | Z30 | CF₂H | H | H |
| E2-30.7 | Z30 | CH₂F | H | H |
| E2-30.8 | Z30 | CF₃ | H | H |
| E2-30.9 | Z30 | CF₂CH₃ | H | H |
| E2-30.10 | Z30 | CH₂CF₃ | H | H |
| E2-30.11 | Z30 | cyclopropyl | H | H |
| E2-30.12 | Z30 | OCF₃ | H | H |
| E2-30.13 | Z30 | OCF₂H | H | H |
| E2-30.14 | Z30 | Cl | H | F |
| E2-30.15 | Z30 | CH₃ | H | F |
| E2-30.16 | Z30 | CH₃ | F | H |
| E2-30.17 | Z30 | Cl | F | H |
| E2-30.18 | Z30 | F | F | H |
| E2-30.19 | Z30 | F | H | F |
| E2-30.20 | Z30 | F | H | Cl |
| E2-30.21 | Z30 | F | H | CH₃ |
| E2-30.22 | Z30 | Cl | H | CH₃ |
| E2-30.23 | Z30 | SCH₃ | H | H |
| E2-30.24 | Z30 | SO₂CH₃ | H | H |
| E2-30.25 | Z30 | ethynyl | H | H |
| E2-31.1 | Z31 | H | H | H |
| E2-31.2 | Z31 | CH₃ | H | H |
| E2-31.3 | Z31 | Cl | H | H |
| E2-31.4 | Z31 | F | H | H |
| E2-31.5 | Z31 | CH₂CH₃ | H | H |
| E2-31.6 | Z31 | CF₂H | H | H |
| E2-31.7 | Z31 | CH₂F | H | H |
| E2-31.8 | Z31 | CF₃ | H | H |
| E2-31.9 | Z31 | CF₂CH₃ | H | H |
| E2-31.10 | Z31 | CH₂CF₃ | H | H |
| E2-31.11 | Z31 | cyclopropyl | H | H |
| E2-31.12 | Z31 | OCF₃ | H | H |
| E2-31.13 | Z31 | OCF₂H | H | H |
| E2-31.14 | Z31 | Cl | H | F |
| E2-31.15 | Z31 | CH₃ | H | F |
| E2-31.16 | Z31 | CH₃ | F | H |
| E2-31.17 | Z31 | Cl | F | H |
| E2-31.18 | Z31 | F | F | H |
| E2-31.19 | Z31 | F | H | F |
| E2-31.20 | Z31 | F | H | Cl |
| E2-31.21 | Z31 | F | H | CH₃ |
| E2-31.22 | Z31 | Cl | H | CH₃ |
| E2-31.23 | Z31 | SCH₃ | H | H |
| E2-31.24 | Z31 | SO₂CH₃ | H | H |
| E2-31.25 | Z31 | ethynyl | H | H |
| E2-32.1 | Z32 | H | H | H |
| E2-32.2 | Z32 | CH₃ | H | H |
| E2-32.3 | Z32 | Cl | H | H |
| E2-32.4 | Z32 | F | H | H |
| E2-32.5 | Z32 | CH₂CH₃ | H | H |
| E2-32.6 | Z32 | CF₂H | H | H |
| E2-32.7 | Z32 | CH₂F | H | H |
| E2-32.8 | Z32 | CF₃ | H | H |
| E2-32.9 | Z32 | CF₂CH₃ | H | H |
| E2-32.10 | Z32 | CH₂CF₃ | H | H |
| E2-32.11 | Z32 | cyclopropyl | H | H |
| E2-32.12 | Z32 | OCF₃ | H | H |
| E2-32.13 | Z32 | OCF₂H | H | H |
| E2-32.14 | Z32 | Cl | H | F |
| E2-32.15 | Z32 | CH₃ | H | F |
| E2-32.16 | Z32 | CH₃ | F | H |
| E2-32.17 | Z32 | Cl | F | H |
| E2-32.18 | Z32 | F | F | H |
| E2-32.19 | Z32 | F | H | F |
| E2-32.20 | Z32 | F | H | Cl |

TABLE 1.E2-continued

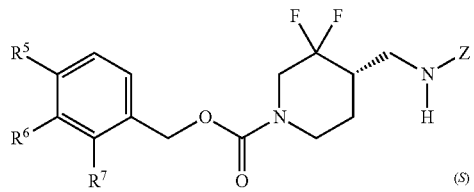

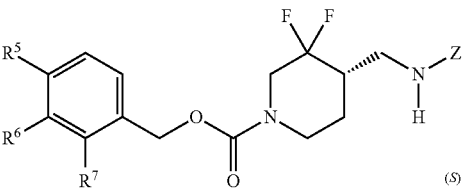

| compound | Z | R⁵ | R⁶ | R⁷ |
|---|---|---|---|---|
| E2-32.21 | Z32 | F | H | CH₃ |
| E2-32.22 | Z32 | Cl | H | CH₃ |
| E2-32.23 | Z32 | SCH₃ | H | H |
| E2-32.24 | Z32 | SO₂CH₃ | H | H |
| E2-32.25 | Z32 | ethynyl | H | H |
| E2-33.1 | Z33 | H | H | H |
| E2-33.2 | Z33 | CH₃ | H | H |
| E2-33.3 | Z33 | Cl | H | H |
| E2-33.4 | Z33 | F | H | H |
| E2-33.5 | Z33 | CH₂CH₃ | H | H |
| E2-33.6 | Z33 | CF₂H | H | H |
| E2-33.7 | Z33 | CH₂F | H | H |
| E2-33.8 | Z33 | CF₃ | H | H |
| E2-33.9 | Z33 | CF₂CH₃ | H | H |
| E2-33.10 | Z33 | CH₂CF₃ | H | H |
| E2-33.11 | Z33 | cyclopropyl | H | H |
| E2-33.12 | Z33 | OCF₃ | H | H |
| E2-33.13 | Z33 | OCF₂H | H | H |
| E2-33.14 | Z33 | Cl | H | F |
| E2-33.15 | Z33 | CH₃ | H | F |
| E2-33.16 | Z33 | CH₃ | F | H |
| E2-33.17 | Z33 | Cl | F | H |
| E2-33.18 | Z33 | F | F | H |
| E2-33.19 | Z33 | F | H | F |
| E2-33.20 | Z33 | F | H | Cl |
| E2-33.21 | Z33 | F | H | CH₃ |
| E2-33.22 | Z33 | Cl | H | CH₃ |
| E2-33.23 | Z33 | SCH₃ | H | H |
| E2-33.24 | Z33 | SO₂CH₃ | H | H |
| E2-33.25 | Z33 | ethynyl | H | H |
| E2-34.1 | Z34 | H | H | H |
| E2-34.2 | Z34 | CH₃ | H | H |
| E2-34.3 | Z34 | Cl | H | H |
| E2-34.4 | Z34 | F | H | H |
| E2-34.5 | Z34 | CH₂CH₃ | H | H |
| E2-34.6 | Z34 | CF₂H | H | H |
| E2-34.7 | Z34 | CH₂F | H | H |
| E2-34.8 | Z34 | CF₃ | H | H |
| E2-34.9 | Z34 | CF₂CH₃ | H | H |
| E2-34.10 | Z34 | CH₂CF₃ | H | H |
| E2-34.11 | Z34 | cyclopropyl | H | H |
| E2-34.12 | Z34 | OCF₃ | H | H |
| E2-34.13 | Z34 | OCF₂H | H | H |
| E2-34.14 | Z34 | Cl | H | F |
| E2-34.15 | Z34 | CH₃ | H | F |
| E2-34.16 | Z34 | CH₃ | F | H |
| E2-34.17 | Z34 | Cl | F | H |
| E2-34.18 | Z34 | F | F | H |
| E2-34.19 | Z34 | F | H | F |
| E2-34.20 | Z34 | F | H | Cl |
| E2-34.21 | Z34 | F | H | CH₃ |
| E2-34.22 | Z34 | Cl | H | CH₃ |
| E2-34.23 | Z34 | SCH₃ | H | H |
| E2-34.24 | Z34 | SO₂CH₃ | H | H |
| E2-34.25 | Z34 | ethynyl | H | H |
| E2-35.1 | Z35, Rᵃ is H | H | H | H |
| E2-35.2 | Z35, Rᵃ is H | CH₃ | H | H |
| E2-35.3 | Z35, Rᵃ is H | Cl | H | H |
| E2-35.4 | Z35, Rᵃ is H | F | H | H |
| E2-35.5 | Z35, Rᵃ is H | CH₂CH₃ | H | H |
| E2-35.6 | Z35, Rᵃ is H | CF₂H | H | H |
| E2-35.7 | Z35, Rᵃ is H | CH₂F | H | H |
| E2-35.8 | Z35, Rᵃ is H | CF₃ | H | H |
| E2-35.9 | Z35, Rᵃ is H | CF₂CH₃ | H | H |
| E2-35.10 | Z35, Rᵃ is H | CH₂CF₃ | H | H |
| E2-35.11 | Z35, Rᵃ is H | cyclopropyl | H | H |
| E2-35.12 | Z35, Rᵃ is H | OCF₃ | H | H |
| E2-35.13 | Z35, Rᵃ is H | OCF₂H | H | H |
| E2-35.14 | Z35, Rᵃ is H | Cl | H | F |
| E2-35.15 | Z35, Rᵃ is H | CH₃ | H | F |
| E2-35.16 | Z35, Rᵃ is H | CH₃ | F | H |
| E2-35.17 | Z35, Rᵃ is H | Cl | F | H |
| E2-35.18 | Z35, Rᵃ is H | F | F | H |
| E2-35.19 | Z35, Rᵃ is H | F | H | F |
| E2-35.20 | Z35, Rᵃ is H | F | H | Cl |
| E2-35.21 | Z35, Rᵃ is H | F | H | CH₃ |
| E2-35.22 | Z35, Rᵃ is H | Cl | H | CH₃ |
| E2-35.23 | Z35, Rᵃ is H | SCH₃ | H | H |
| E2-35.24 | Z35, Rᵃ is H | SO₂CH₃ | H | H |
| E2-35.25 | Z35, Rᵃ is H | ethynyl | H | H |
| E2-36.1 | Z36, Rᵃ is H | H | H | H |
| E2-36.2 | Z36, Rᵃ is H | CH₃ | H | H |
| E2-36.3 | Z36, Rᵃ is H | Cl | H | H |
| E2-36.4 | Z36, Rᵃ is H | F | H | H |
| E2-36.5 | Z36, Rᵃ is H | CH₂CH₃ | H | H |
| E2-36.6 | Z36, Rᵃ is H | CF₂H | H | H |
| E2-36.7 | Z36, Rᵃ is H | CH₂F | H | H |
| E2-36.8 | Z36, Rᵃ is H | CF₃ | H | H |
| E2-36.9 | Z36, Rᵃ is H | CF₂CH₃ | H | H |
| E2-36.10 | Z36, Rᵃ is H | CH₂CF₃ | H | H |
| E2-36.11 | Z36, Rᵃ is H | cyclopropyl | H | H |
| E2-36.12 | Z36, Rᵃ is H | OCF₃ | H | H |
| E2-36.13 | Z36, Rᵃ is H | OCF₂H | H | H |
| E2-36.14 | Z36, Rᵃ is H | Cl | H | F |
| E2-36.15 | Z36, Rᵃ is H | CH₃ | H | F |
| E2-36.16 | Z36, Rᵃ is H | CH₃ | F | H |
| E2-36.17 | Z36, Rᵃ is H | Cl | F | H |
| E2-36.18 | Z36, Rᵃ is H | F | F | H |
| E2-36.19 | Z36, Rᵃ is H | F | H | F |
| E2-36.20 | Z36, Rᵃ is H | F | H | Cl |
| E2-36.21 | Z36, Rᵃ is H | F | H | CH₃ |
| E2-36.22 | Z36, Rᵃ is H | Cl | H | CH₃ |
| E2-36.23 | Z36, Rᵃ is H | SCH₃ | H | H |
| E2-36.24 | Z36, Rᵃ is H | SO₂CH₃ | H | H |
| E2-36.25 | Z36, Rᵃ is H | ethynyl | H | H |

Pharmacology

Glutamate (GLU) is a fundamental excitatory neurotransmitter in the mammalian brain and central nervous system (CNS). The effects of this endogenous neurotransmitter are mediated through binding to and activation of GLU to glutamate receptors (GLURs), which are broadly classified into metabotropic G-protein coupled (mGluRs) and ligand gated ion channels or ionotropic GluRs. The ionotropic GLURs are pharmacologically classified into three main types based on the actions of selective receptor agonists: NMDA (N-methyl D-aspartate selective), KA (kainic acid selective) and AMPA (α-amino-3-hydroxy-5-methyl-4-isoxazolepropionic acid) receptors whose structure and pharmacological function has been recently reviewed in detail (S. F. Traynelis et al. *Pharmacology Reviews*, 2010, 62, 405-496). Electrophysiology studies have demonstrated NMDARs to be cation ion channels that are subject to voltage-dependent channel block by endogenous $Mg^{2+}$. Activation of NMDARs by glutamate in the presence of glycine as a co-agonist results in opening of the receptor ion channel. This in turn allows for the flow of $Na^+$ and $Ca^{2+}$ into the cell generating excitatory postsynaptic potentials (EPSPs) and $Ca^{2+}$ activated second messenger signaling pathways in neurons. By virtue of their permeability to $Ca^{2+}$, activation of NMDA receptors regulates long-term changes in neuronal communication such as learning and memory and synaptic plasticity.

Since the original pharmacological characterization with selective ligands, molecular biology and cloning studies have enabled detailed characterization of NMDARs at the molecular level (Paoletti et al., 2013, *Nat. Rev. Neurosci.* 14:383-400). Thus, NMDARs are heterotetramers comprised of two NR1 subunits and two NR2 subunits. NR1 subunits contain the binding site for the glycine co-agonist while NR2 subunits contain the binding site for glutamate. The existence of multiple splice variants for NR1 and four isoforms of NR2 (NR2A, NR2B, NR2C and NR2D) from different genes results in a diverse molecular array and of NMDARs. The pharmacological and electrophysiological properties of NMDARs vary depending on the particular NR1 isoform and NR2 subtype composition. Furthermore, the NR2 subtype isoforms are differentially expressed across cell types and brain regions. Thus, compounds that interact selectivity with NR2 subunits can exert specific pharmacological effects in particular brain regions and have potential to treat CNS diseases with a high degree of specificity and selectivity (e.g. vz side effects). For example the low expression of the NR2B subtype in the cerebellum relative to other brain structures (Cull-Candy et al., 1998, *Neuropharmacol.* 37:1369-1380) indicated lower motor side effects for this subtype.

NMDA receptor antagonism has been extensively investigated for its potential to treat a variety of CNS diseases including stroke, epilepsy, pain, depression Parkinson's Disease and Alzheimer's disease (Paoletti et al., Nat. Rev. Neurosci 14:383-400; Sancora, 2008, *Nature Rev. Drug Disc.*, 7, 426-437). The NMDA receptor offers a number of pharmacological entry points for developing receptor inhibitors. Direct blockers of the NMDAR ion channel pore represent one family of antagonist compounds for which efficacy could be demonstrated in diverse in vitro and in vivo CNS disease models including, epilepsy, pain and neurodegeneration/stroke. However, compounds from this class, as exemplified by phencyclidine (PCP), MK-801, and ketamine, are generally categorized as unselective across the diversity of NMDA receptor subtypes.

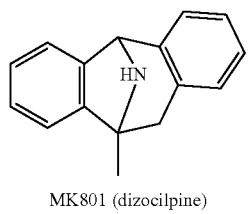

MK801 (dizocilpine)

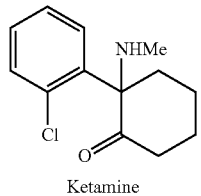

Ketamine

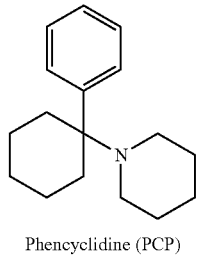

Phencyclidine (PCP)

In humans unselective, high-affinity NMDAR antagonists have generally been associated with serious clinical side effects including hallucinations, dysphoria and lack of coordination. Nevertheless, ketamine, an intravenous drug originally approved for use in anesthesia (Haas et. al, 1992, *Anesthesia Prog.*, 39, 61-68) has more recently demonstrated clinical efficacy as an antidepressant therapy (Katalinic et al. 2013, *Aust. N. Z. J. Psychiatry*, 47, 710-727). The antidepressant action of acute ketamine therapy has an essentially immediate onset compared to approximately six weeks required for standard serotonin reuptake inhibitor (SSRI) drug therapy. Thus, intravenous administration of the drug has shown rapid onset and prolonged efficacy that can be maintained with continued intermittent administrations (Zarate et al., 2006, *Arch. Gen. Psychiatry* 63, 856-864). Finally, ketamine has been shown to be effective in cases of depression resistant to standard drug therapies (Murrough et al., 2013, *American J. Psychiatry*, 170, 1134-1142) including bipolar depression (Zarate et al. 2012, *Biol. Psychiatry*, 71, 939-946). However, as an intravenous drug with serious side effects (Gianni et. al 1985, *Psychiatric Medicine*, 3, 197-217; Curran et al 2000, *Addiction*, 95, 575-590) and potential chronic toxicity (Hardy et al., 2012, *J. Clin. Oncol.* 30:3611-3617; Noppers et al., 2011, *Pain* 152:2173-2178) ketamine therapy is of limited utility and restricted to acute or intermittent administration. To have broader scope of application and utility as a therapy for depression and other CNS diseases, orally active selective NMDA antagonists with reduced side effects are needed that can be administered chronically.

Ifenprodil, a vasodilator al-adrenergic antagonist drug, was determined to have a novel allosteric modulator mechanism of action at the NR2B NMDA receptor subtype (Reynolds et al. 1989, *Mol. Pharmacol.*, 36, 758-765). This new mechanism held promise for a new class of NMDA antagonist drugs having therapeutic efficacy without the limiting side effects of subtype unselective ion channel blockers. Following this discovery, NR2B selective antagonist analogs of ifenprodil (Borza et al., 2006, *Current Topics in Medicinal Chemistry*, 6, 687-695; Layton et al. *Current Topics in Medicinal Chemistry*, 6, 697-709) optimized against the undesirable al-adrenergic activity included Ro-25,6981 (Fischer et al. 1997, *J. Pharmacol. Exp. Ther.*, 283, 1285-1292) and CP-101,606 otherwise known as traxoprodil (Chenard et al. 1995, *Journal of Medicinal Chemistry*, 38, 3138-3145; Menniti et al. 1998, *CNS Drug Reviews.*, 4, 307-322). In a clinical study, CP-101,606 evidenced antidepressant activity in humans after intravenous administration with a favorable dissociative side effect profile relative to unselective NMDA antagonists (Preskorn et al. 2008, *Journal of Clinical Psychopharmacology*, 28, 631-637). However, CP-101,606 has suboptimal pharmacokinetic properties and requires limiting intravenous administration. For CP-101,606 a slow intravenous infusion protocol was required for optimal results in the aforementioned antidepressant clinical study (Preskorn et al. 2008, *Journal of Clinical Psychopharmacology*, 28, 631-637).

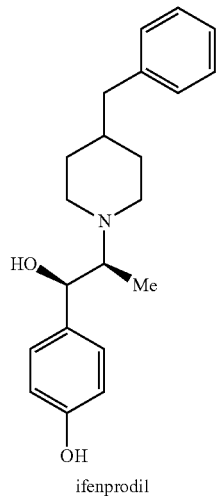

ifenprodil

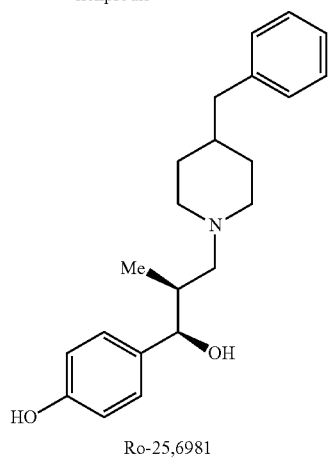

Ro-25,6981

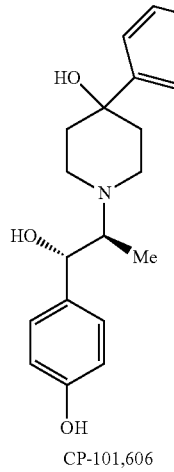

CP-101,606

Other NR2B antagonists which have been described as reviewed by B. Ruppa et al. (K. B. Ruppa et al., *Annual Reports in Medicinal Chemistry* 2012, 47:89-103) include MK0657 (J. A. McCauley et al., 3$^{rd}$ *Anglo-Swedish Medicinal Chemistry Symposium*, Åre, Sweden, Mar. 11-14, 2007; L. Mony et al., *British J. of Pharmacology* 2009, 157:1301-1317; see also Intl. Appl. Publ. No. WO 2004/108705; U.S. Pat. No. 7,592,360) and compounds of formula LX (Intl. Appl. Publ. No. WO 2006/113471), below, including the specific analog LX-1 depicted below.

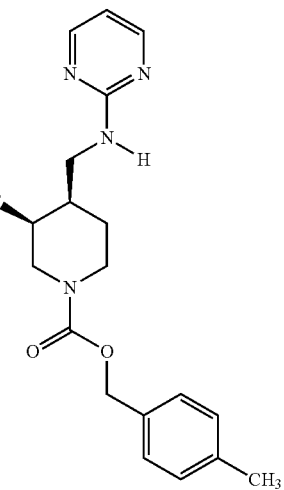

MK0657

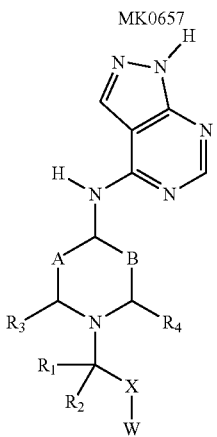

LX

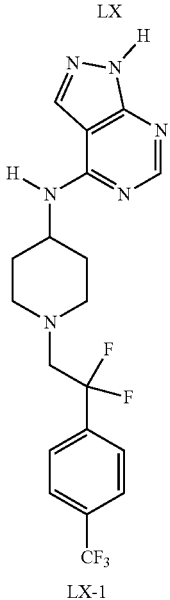

LX-1

The difficulties presented by NR2B antagonists having basic amine moieties with regard to overcoming hERG and CYP2D6 safety liabilities while maintaining NR2B in vitro and in vivo potency are well established as noted by Kawai et al. (M. Kawai et al., *Bioorganic and Medicinal Chem. Lett.* 2007, v17:5533-5536) and Brown et al. (Brown et al., *Bioorganic and Medicinal Chem. Lett.* 2011, v21:3399-3403). Compound inhibition of hERG channels and associated QT prolongation in the electrocardiograph (ECG) represents a well recognized serious human cardiovascular safety risk (Hancox et al., *Molecular Pharmacology* 2008, 73:1592-1595). QT prolongation can lead to torsades de pointes (TdP) cardiac arrhythmia which can degenerate into ventricular tachycardia and sudden death.

Compound inhibition of human metabolic cytochrome P-450 enzymes including CYP2D6 represents a risk with regard to human drug safety due to drug-drug interactions (*Drug Metabolism Handbook: Concepts and Applications*, ed. Ala F. Nassar copyright 2009 Wiley & Sons, Hoboken, N.J.). Thus, the clearance of drugs that are substrates of CYP2D6 can be reduced by compounds that inhibit CYP2D6. The result can be toxic or side effect overload due to accumulation of the given CYP2D6 drug substrate. CNS drugs including antidepressant drugs feature prominently among the established CYP2D6 substrates. Therefore, CYP2D6 inhibition is highly undesirable for an NR2B antagonist drug especially given the common application of comedications or polypharmacy in CNS indications including depression. Examples of CY2D6 substrates include antidepressants from the SSRI class such as fluoxetine, paroxetine, and fluvoxamine, duloxetine, an antidepressants from the SSNI class, numerous antipsychotics including haloperidol, risperidone and aripiperazole, numerous beta-blocker antihypertensives including metaprolol, propranolol, timolol and alprenolol and the Alzheimer's disease anticholinesterase inhibitor drug donepezil (Flockhart D A (2007). "Drug Interactions: Cytochrome P450 Drug Interaction Table", Indiana University School of Medicine, accessed at <<http://medicine.iupui.edu/clinpharm/ddis/>> on May 28, 2014).

MK0657 and closely related analogs (Liverton et al., *J. Med. Chem.* 2007, v50:807-819) represent an improved generation of NR2B antagonists with respect to human oral bioavailability. However, drug-related systolic as well as diastolic blood pressure elevation cardiovascular side effects for MK0657 after oral dosing have been described in a published clinical efficacy trial study in patients with Parkinson's Disease (Addy et al., *J. Clin. Pharm.* 2009, v49:856-864). Similar blood pressure effects were reported to have also been observed after single doses of MK0657 in safety studies with healthy subjects. (Peterson et al., "A randomized, double-blind, placebo-controlled, parallel-group, three-part safety, pharmacokinetic, and pharmacodynamic study of CERC-301 in healthy subjects", National Network of Depression Centers Annual Conference, Ann Arbor, Nov. 5-6, 2015). Interestingly, MK0657 and its enantiomer (the 3R,4S compound) show similar potency against NR2B (MK0657=13.8 nM; 3R,4S enantiomer=25.5 nM). Even more remarkable is that the potency of the cis and trans diastereomers show similar potency against NR2B (see Koudih et al., *European J. Med. Chem.* 53 (2012), 408-415).

Compound LX-1 demonstrates oral bioavailability in animals and lacks a phenolic group which can compromise oral bioavailability in humans. However, not inconsistent with other NR2B antagonists having basic amine moieties, compound LX-1, which has a basic piperidine nitrogen atom, notwithstanding the basicity-attenuating vicinal difluoro moiety beta to this nitrogen exhibits human hERG channel inhibition with an $IC_{50}$<10 µM (~4.5 µM), and exhibits human CYP2D6 metabolic enzyme inhibition activity ($IC_{50}$~1.0 µM).

For broad scope of application and safe human use, improved NR2B selective antagonists are needed, as also noted in K. B. Ruppa et al., *Annual Reports in Medicinal Chemistry* 2012, 47:89-103. There is a need for NR2B antagonist compounds which are improved in one or more aspects exemplified by pharmacokinetic, absorption, metabolism, excretion (ADME, e.g., oral activity), improved efficacy, off-target activity, improved therapeutic safety index relative and compatibility with chronic oral therapy. For example, drug-related systolic as well as diastolic blood pressure elevation cardiovascular side effect for MK0657 after oral dosing have been described in a published clinical efficacy trial study in patients with Parkinson's Disease (Addy et al., *J. Clin. Pharm.* 2009, v49:856-864). Similar blood pressure effects were reported to have also been observed after single doses of MK0657 in safety studies with healthy elderly subjects.

Provided chemical entities are antagonists of the NR2B receptor and have technical advantages with regard to one or more pharmaceutical drug properties, such as oral bioavailability, pharmacokinetic parameters, ADME properties (e.g., CYP inhibition, metabolite formation), in vivo and/or in vitro pharmacological safety.

In some embodiments, a provided chemical entity has NR2B functional NMDA receptor selectivity versus NR2A ("NR2B selectivity", determined as the ratio NR2A $IC_{50}$/NR2B $IC_{50}$, in which the $IC_{50}$ values are measured according to the procedure of Example 2.1) ≥400. In some embodiments, a provided chemical entity has NR2B selectivity ≥300. In some embodiments, a provided chemical entity has NR2B selectivity ≥200. In some embodiments, a provided chemical entity has NR2B selectivity ≥100. In some embodiments, a provided chemical entity has NR2B selectivity ≥50. In some embodiments, a provided chemical entity has NR2B selectivity ≥20.

In some embodiments, a provided chemical entity has hERG activity (determined as hERG $IC_{50}$ measured according to the procedure of Example 2.2) ≥5 µM. In some embodiments, a provided chemical entity has hERG $IC_{50}$≥10 µM. In some embodiments, a provided chemical entity has hERG $IC_{50}$≥15 µM. In some embodiments, a provided chemical entity has hERG $IC_{50}$≥20 µM. In some embodiments, a provided chemical entity has hERG $IC_{50}$≥25 µM. In some embodiments, a provided chemical entity has hERG $IC_{50}$≥30 µM. In some embodiments, a provided chemical entity has hERG $IC_{50}$≥40 µM.

In some embodiments, a provided chemical entity has NR2B functional antagonist activity (determined as NR2B $IC_{50}$ measured according to the procedure of Example 2.1) ≤200 nM and hERG activity (determined as hERG $IC_{50}$ measured according to the procedure of Example 2.2) ≥5 µM. In some embodiments, a provided chemical entity has NR2B $IC_{50}$≤200 nM and hERG $IC_{50}$≥10 µM. In some embodiments, a provided chemical entity has NR2B $IC_{50}$≤200 nM and hERG $IC_{50}$≥15 µM. In some embodiments, a provided chemical entity has NR2B $IC_{50}$≤200 nM and hERG $IC_{50}$≥20 µM. In some embodiments, a provided chemical entity has NR2B $IC_{50}$≤200 nM and hERG $IC_{50}$≥25 µM. In some embodiments, a provided chemical entity has NR2B $IC_{50}$≤200 nM and hERG $IC_{50}$≥30 µM. In some embodiments, a provided chemical entity has NR2B $IC_{50}$≤200 nM and hERG $IC_{50}$≥40 µM. In some embodiments, a provided chemical entity has NR2B $IC_{50}$≤100 nM and hERG $IC_{50}$≥5 µM. In some embodiments, a provided chemical entity has NR2B $IC_{50} \leq 100$ nM and hERG $IC_{50} \geq 10$ µM. In some embodiments, a provided chemical entity has NR2B $IC_{50} \leq 50$ nM and hERG $IC_{50} \geq 5$ µM. In some embodiments, a provided chemical entity has NR2B $IC_{50} \leq 50$ nM and hERG $IC_{50} \geq 10$ µM.

In some embodiments, a provided chemical entity has NR2B functional antagonist activity (determined as NR2B $IC_{50}$ measured according to the procedure of Example 2.1) $\leq 200$ nM and CYP2D6 inhibition (measured as CYP2D6 $IC_{50}$ determined according to the procedure of Example 2.3) $\geq 2$ µM. In some embodiments, a provided chemical entity has NR2B $IC_{50} \geq 200$ nM and CYP2D6 $IC_{50} \geq 3$ µM. In some embodiments, a provided chemical entity has NR2B $IC_{50} \leq 200$ nM and CYP2D6 $IC_{50} \geq 4$ µM. In some embodiments, a provided chemical entity has NR2B $IC_{50} \leq 200$ nM and CYP2D6 $IC_{50} \geq 5$ µM. In some embodiments, a provided chemical entity has NR2B $IC_{50} \leq 200$ nM and CYP2D6 $IC_{50}$ of about 5-10 µM. In some embodiments, a provided chemical entity has NR2B $IC_{50} \leq 200$ nM and CYP2D6 $IC_{50} \geq 10$ µM. In some embodiments, a provided chemical entity has NR2B $IC_{50} \leq 100$ nM and CYP2D6 $IC_{50} \geq 2$ µM. In some embodiments, a provided chemical entity has NR2B $IC_{50} \leq 100$ nM and CYP2D6 $IC_{50} \geq 3$ µM. In some embodiments, a provided chemical entity has NR2B $IC_{50} \leq 100$ nM and CYP2D6 $IC_{50} \geq 4$ µM. In some embodiments, a provided chemical entity has NR2B $IC_{50} \leq 100$ nM and CYP2D6 $IC_{50} \geq 5$ µM. In some embodiments, a provided chemical entity has NR2B $IC_{50} \leq 100$ nM and CYP2D6 $IC_{50}$ of about 5-10 µM. In some embodiments, a provided chemical entity has NR2B $IC_{50} \leq 100$ nM and CYP2D6 $IC_{50} \geq 10$ µM. In some embodiments, a provided chemical entity has NR2B $IC_{50} \leq 50$ nM and CYP2D6 $IC_{50} \geq 2$ µM. In some embodiments, a provided chemical entity has NR2B $IC_{50} \leq 50$ nM and CYP2D6 $IC_{50} \geq 3$ µM. In some embodiments, a provided chemical entity has NR2B $IC_{50} \leq 50$ nM and CYP2D6 $IC_{50} \geq 4$ µM. In some embodiments, a provided chemical entity has NR2B $IC_{50} \leq 50$ nM and CYP2D6 $IC_{50} \geq 5$ µM. In some embodiments, a provided chemical entity has NR2B $IC_{50} \leq 50$ nM and CYP2D6 $IC_{50}$ of about 5-10 µM. In some embodiments, a provided chemical entity has NR2B $IC_{50} \leq 50$ nM and CYP2D6 $IC_{50} \geq 10$ µM.

Uses, Formulation and Administration, and Pharmaceutically Acceptable Compositions In some embodiments, the invention provides a composition comprising a chemical entity of the invention or a pharmaceutically acceptable derivative thereof and a pharmaceutically acceptable carrier, adjuvant, or vehicle. The amount of chemical entity in compositions of this invention is such that is effective to measurably inhibit NR2B, in a biological sample or in a patient. In some embodiments, the amount of chemical entity in compositions of this invention is such that is effective to measurably inhibit NR2B, in a biological sample or in a patient. In some embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the chemical entity with which it is formulated. Pharmaceutically acceptable carriers, adjuvants or vehicles that may be used in the compositions of this invention include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic ester, salt of an ester or other derivative of a chemical entity of this invention (e.g., a prodrug) that, upon administration to a recipient, is capable of providing, either directly or indirectly, a chemical entity of this invention or an inhibitorily active metabolite or residue thereof.

As used herein, the term "inhibitorily active metabolite or residue thereof" means that a metabolite or residue thereof is also an inhibitor of NR2B.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon a variety of factors, including the host treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Chemical Entities and Pharmaceutically Acceptable Compositions

Human therapeutic applications of NR2B receptor antagonists have been summarized in reviews by Traynelis et al. (S. F. Traynelis et al., *Pharmacology Reviews*, 2010, 62:405-496), Beinat et al. (C. Beinat et al., *Current Medicinal Chemistry*, 2010, 17:4166-4190) and Mony et al. (L. Mony et al., *British J. of Pharmacology*, 2009, 157:1301-1317). Antagonism of NR2B can be useful in the treatment of diseases and disorders including depression, pain, Parkinson's disease, Huntington's disease, Alzheimer's disease, cerebral ischaemia, traumatic brain injury, seizure disorders (e.g., epilepsy) and migraine. (S. B. Bausch et al., *Epilepsia*, 2010, 51:102-105; P. Mares, *Naunyn-Schmiedeberg's Arch Pharmacol*, 2014, 387:753-761; E. Szczurowska et al., *Brain Research Bulletin*, 2015, 111:1-8).

The activity of a chemical entity utilized in this invention as an antagonist of NR2B or a treatment for a disease or disorder of the central nervous system (CNS) may be assayed in vitro or in vivo. An in vivo assessment of the efficacy of the compounds of the invention may be made using an animal model of a disease or disorder of the CNS, e.g., a rodent or primate model. Cell-based assays may be performed using, e.g., a cell line isolated from a tissue that expresses NR2B, or a cell line that recombinantly expresses NR2B. Additionally, biochemical or mechanism-based assays, e.g., measuring cAMP or cGMP levels, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with chemical entities of the invention. Alternate in vitro assays quantify the ability of the inhibitor to bind to protein or nucleic acid molecules within the cell. Inhibitor binding may be measured by radiolabelling the inhibitor prior to binding, isolating the inhibitor/target molecule complex and determining the amount of radiolabel bound. Alternatively, inhibitor binding may be determined by running a competition experiment where new inhibitors are incubated with purified proteins or nucleic acids bound to known radioligands. Detailed conditions for assaying a compound utilized in this invention as an antagonist of NR2B are set forth in the Examples below. The aforementioned assays are exemplary and not intended to limit the scope of the invention. A person skilled in the art can appreciate that modifications can be made to conventional assays to develop equivalent assays that obtain the same result.

Those skilled in the art appreciate that identification and/or characterization of desirable or effective compounds commonly involves assessment of one or more activities in an animal model. Those skilled in the art further appreciate that such animal models do not always accurately recapitulate human experience. (Bezard et al. *Neuroscience* 211:1, 2012). Among other things, animal models are often developed to mimic one or more symptoms of a particular human condition, but it is not always feasible to ensure that, or possibly even determine whether, symptoms observed in the animal result from or are attributable to the same mechanism as that which causes the symptom(s) in humans. Furthermore, it is not uncommon for multiple animal models to be developed for the same disease, disorder or condition, each of which may reflect or mimic one or more features of the disease, disorder or condition; those skilled in the art appreciate that results are not always precisely consistent across such models, and that judgment and/or interpretation may be required to draw conclusions reasonably predictive of human responses. Still further, particularly for animal models of neurological conditions as described herein, different measurements or responses observed within the model may be more reliable than others in modeling or predicting human response.

To give but a few examples, it is known in the art that available animal models for depression have varying degrees of face, construct, and predictive validity for depression and contribute differently to our understanding of antidepressant processes. (Duman C. H. Vitamins & Hormones 82:1-21, 2010).

Commonly employed models relevant to work described herein include, for example, the rodent forced swim test, which is often used for evaluation of antidepressant efficacy. (Can et al. *J. Vis. Exp.* 2012, 59:3638; Bogdanova et al. *Physiol. Behav.* 118:227, 2013). Different protocols are available for performance of forced swim tests. (Slattery & Cryan *Nature Protocols* 7:1009, 2012; Lucki et el., 2001, *Psychopharmacology* 155:315-322).

The haloperidol-induced catalepsy (HIC) model has been used to characterize therapeutic agents for treating certain neurological conditions and/or symptoms. For example, the HIC model has been particularly recommended for use in characterizing therapeutic agents for their potential utility in protection against catalepsy associated with PD. (Steece-Collier et al. *Exp. Neurol.* 163: 239, 2000). Additionally, the HIC model has been used for characterizing antidepressants, and has been reported to be able to reveal differing activities among antidepressants that may have performed comparably in one or more other assays such as, for example, in forced swim tests. (Khisti et al. *Indian J. Exp. Biol.* 35:1297, 1997).

Various different models have been reported to provide information relevant to treatment of epilepsy, though the diversity of epilepsy syndromes and their causes may preclude use of any single model or test as definitive of efficacy. Most animal models used in epilepsy research are models of epileptic seizure rather than models of epilepsy. Epilepsy is characterized by spontaneous recurrent seizures, therefore, a test such as the 6 Hz seizure test described herein, in which an acute seizure is electrically induced in a normal non-epileptic animal, may not fully represent a model of epilepsy. (Löscher Seizure 2011, 20:359-368). Conversely, the 6 Hz seizure test is considered to be a potential screen for therapy-resistant epilepsy. The 6 Hz seizure test assay described herein uses a current of 44 mA which typically results in most antiepileptic drugs losing their efficacy. Accordingly, the 6 Hz seizure test has been suggested to be a useful model of therapy-resistant limbic seizures. (Barton et al. *Epilepsy Res.* 47(3):217-27, 2001).

The PTZ test, described herein, is thought to be predictive of anticonvulsant drug activity against nonconvulsive (absence or myoclonic) epileptic seizures. As described in a review by Löscher, various antiepileptic drugs that protect against nonconvulsive seizures in epilepsy patients failed in the PTZ test. (Löscher W. *Seizure* 20:359-368, 2011). Therefore, inconclusive or negative data resulting from the PTZ test does not necessarily mean that the tested therapy (e.g., compound) will be ineffective in epilepsy patients. Further, such compounds could be effective in a different animal model of epilepsy. For example, an antiepileptic drug may fail in the 6 Hz seizure test (electrically induced seizures) but prove efficacious in the PTZ test (chemically induced seizures).

Those of ordinary skill in the art will appreciate that any effect observed in a specific animal model test can be significant. Furthermore, those skilled in the art will appreciate that use of multiple and various animal models of diseases can be beneficial to characterize the efficacy of a particular agent or treatment. Moreover, those skilled in the art will appreciate that it is not required that every assessment of a particular agent in an animal model provide strong evidence of activity; in some circumstances, positive evidence of activity in one context may be more significant than absence of evidence of activity in another, particularly as it is understood that optimization of reaction conditions may reveal activity not observed in initial studies.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The chemical entities and compositions, according to the method of the present invention, may be administered using any amount and any route of administration effective for treating or lessening the severity of a CNS disease or disorder.

In some embodiments, the chemical entities and compositions, according to the method of the present invention, may be administered using any amount and any route of administration effective for treating or lessening the severity of a disease or disorder associated with NR2B.

In some embodiments, the chemical entities and compositions, according to the method of the present invention, may be administered using any amount and any route of administration effective for treating or lessening the severity of a CNS disease or disorder.

In some embodiments, the disease or disorder is depression with or without concomitant anxiety disorder, e.g., single episode and recurrent depressive disorder, dysthymic disorder, major depressive disorder, psychotic depression, premenstrual dysphoric disorder, postpartum depression, seasonal affective disorder (SAD), mood disorder, treatment-resistant depression (TRD, i.e., major depressive disorder that has not responded to other drug therapies), depression caused by a chronic medical condition such as cancer or chronic pain, chemotherapy, chronic stress, and post traumatic stress disorders.

In some embodiments, the disease or disorder is an acute affective disorder, e.g., selected from bipolar disorders including bipolar I and bipolar II manic disorders.

In some embodiments, the present invention provides a method of treating substance abuse disorders, wherein treatment results in decreased tolerance and/or dependence to opioid treatment of pain, and/or by treating withdrawal syndrome of e.g., alcohol, opioids, heroin, and cocaine. As used herein, the term "substance abuse disorders" includes substance dependence or abuse with or without physiological dependence. The substances associated with these disorders include: alcohol, amphetamines (or amphetamine-like substances), caffeine, cannabis, cocaine, hallucinogens, inhalants, marijuana, nicotine, opioids, phencyclidine (or phencyclidine-like compounds), sedative-hypnotics or benzodiazepines, and other (or unknown) substances and combinations of all of the above.

In some embodiments, a substance abuse disorder includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation. Other substance abuse disorders include substance-induced anxiety disorder with onset during withdrawal; substance-induced mood disorder with onset during withdrawal; and substance-induced sleep disorder with onset during withdrawal.

In some embodiments, the disease or disorder is pain, e.g., selected from pain states arising from a variety of sources including neuropathic pain (such as post herpetic neuralgia, nerve injury/damage, the "dynias", e.g., vulvodynia, phantom limb pain, root avulsions, painful diabetic neuropathy, compressive mononeuropathy, ischemic neuropathy, painful traumatic mononeuropathy, or painful polyneuropathy), central pain syndromes (potentially caused by virtually any lesion at any level of the nervous system), and postsurgical pain syndromes (e.g., postmastectomy syndrome, postthoracotomy syndrome, stump pain), bone and joint pain (osteoarthritis, rheumatoid arthritis, ankylosing spondylitis), repetitive motion pain, carpal tunnel syndrome, dental pain, cancer pain, myofascial pain (muscular injury, fibromyalgia), perioperative pain (general surgery, gynecological), chronic pain, dysmenorrhea, as well as pain associated with angina, and inflammatory pain of varied origins (e.g. osteoarthritis, rheumatoid arthritis, rheumatic disease, tenosynovitis and gout), headache, migraine and cluster headache. In some embodiments, the disease or disorder is associated with intractable pain, such as migraine, fibromyalgia, and trigeminal neuralgia.

In some embodiments, the disease or disorder is a migraine disorder. Migraine is among the most common neurological disorders with a prevalence of 10-15% worldwide. A third of patients with migraine also suffer from transient focal neurological symptoms, termed aura. Aura typically begins minutes to hours prior to the headache, but may occur during the headache phase or even in the absence of headache. The most interesting aspects of aura are the 'spreading' character, suggesting an underlying mechanism that propagates slowly along adjacent brain tissue.

A large body of data has accumulated suggesting that spreading depression (SD), which can also refer to cortical spreading depression (CSD), is the electrophysiological substrate of migraine aura and a potential trigger for headache. Occasionally, an aura can occur with little or no headache following it. SD takes place in a number of major neurological disorders besides migraine with aura, for example stroke and brain trauma. Moreover, SD is capable of activating central and peripheral trigeminovascular nociceptive pathways with a latency matching that occurs between aura and headache in migraineurs. Last, but not least, migraine prophylactic drugs have been shown to suppress SD, suggesting that SD is a relevant pharmacological target in migraine. (Shatillo et al. *Neuropharm.* 2015, 93:164-170).

SD is an intense depolarization of neuronal and glial membranes that propagates in brain tissue at a rate of approximately 3 mm/min. The depolarization wave will be recognized by DC (direct current) recording on cortex in anesthetized rats. Simultaneously, CBF (cerebral blood flow) increase on dura can be measured indicating the vasodilatation of dural veins. Evoked when local extracellular $K^+$ concentrations exceed a critical threshold, SD is associated with disruption of membrane ionic gradients, with massive $K^+$ and glutamate efflux believed to first depolarize and then hyperpolarize adjacent neurons to facilitate spread. SD can be evoked pharmacologically by application of glutamate, $K^+$ and $Na^+/K^+$-pump inhibitors, by electrical stimulation and by tissue injury, such as trauma, hemorrhage or ischemia. Direct evidence for the occurrence of SD in human brain in situ has been obtained using subdural electrophysiological recordings and intracortical multiparametric electrodes. (Ayata et al. *Ann. Neurol.* 2006, 59:652-61).

In some embodiments, the disease or disorder is a migraine without aura. In some embodiments, the disease or disorder is a migraine with aura. In some embodiments, the disease or disorder is a migraine with typical aura. In some embodiments, the disease or disorder includes migraine with brainstem aura, hemiplegic migraine, retinal migraine, and/or chronic migraine.

In some embodiments, a migraine may be a stress migraine, silent or acephalgic migraine, sinus migraine, ocular migraine, seasonal migraine, cyclic migraine syndrome, gastric stasis migraine, and/or tension migraine.

In some embodiments, the disease or disorder is a primary headache disorder characterized by recurrent headaches that are moderate to severe. A headache can affect one half of the head and last from one hour to several days. In some embodiments, the disease or disorder is a tension headache and/or trigeminal autonomic cephalagias.

In some embodiments, the disease or disorder is cluster headache. Cluster headache is a type of headache that recurs over a period of time. Generally, patients who suffer from cluster headaches experience an episode one to three times per day during a period of time (the cluster period), which may last from two weeks to three months. A cluster headache typically awakens a person from sleep one to two hours after going to bed. Cluster headaches may disappear or go into remission for months or years, only to recur without any warning. In some embodiments, the cluster headache is chronic (e.g., the cluster period is measured by months or years, rather than weeks). In certain embodiments, the cluster headache is episodic.

In some embodiments, a headache may result in symptoms comprising nausea, vomiting, and sensitivity to light, sound, or smell. In some embodiments, a migraine may result in symptoms comprising nausea, vomiting, and sensitivity to light, sound, or smell. In some embodiments, complications of migraine include status migrainosus, persistent aura without infarction, migrainosus infarction, and/or migraine aura-triggered seizure.

In some embodiments, the disease or disorder is selected from sleep disorders and their sequelae including insomnia, narcolepsy and idiopathic hypersomnia.

In some embodiments, the disease or disorder is selected from CNS disorders characterized by neuronal hyperexcitablity, such as epilepsy, convulsions, seizures, partial seizure disorders, generalized seizure disorders such as absence seizures, atonic, myoclonic, tonic, tonic-clonic or "grand-mal" seizures, status epilepticus, cortical spreading depression, migraine headaches, cerebral palsy, Ohtahara Syndrome, Fragile X Syndrome, pediatric or genetic seizures such as West syndrome, Lennox-Gastaut syndrome and Angleman syndrome, tuberosclerosis, intracranial hypertension, central nervous system edema, neuronal toxicity, such as toxicity induced by alcohol exposure, pathophysiological effects of head trauma, stroke, ischemia, hypoxia and other conditions resulting from or producing ionic imbalances in the central nervous system, or synchronized discharges of neuronal populations.

In some embodiments, the disease or disorder is characterized by the occurrence of a seizure. Seizures are a result of uncontrolled discharges of electrical activity in the brain. A seizure typically manifests as sudden, involuntary, disruptive, and often destructive sensory, motor, and cognitive phenomena. Seizures are frequently associated with physical harm to the body (e.g., tongue biting, limb breakage, and burns), a complete loss of consciousness, and incontinence. A typical seizure, for example, might begin as spontaneous shaking of an arm or leg and progress over seconds or minutes to rhythmic movement of the entire body, loss of consciousness, and voiding of urine or stool. There are both convulsive and non-convulsive seizures. Convulsive seizures can be generalized seizures or partial seizures. There are six main types of generalized seizures: tonic-clonic, tonic, clonic, myoclonic, absence, and atonic seizures. A non-convulsive seizure, for example an absence seizure, presents as a decreased level of consciousness and usually lasts about 10 seconds.

In some embodiments, the disease or disorder is epilepsy. Epilepsy is a disorder of the brain characterized by an enduring predisposition to generate epileptic seizures and by the neurobiologic, cognitive, psychological, and social consequences of this condition. (R. S. Fisher et al., *Epilepsia*, 2005, 46(4):470-472). Epilepsy can be the occurrence of at least one epileptic seizure. An epileptic seizure is a transient occurrence of signs and/or symptoms due to abnormal excessive or synchronous neuronal activity in the brain. Epilepsy affects people of all ages; however, epilepsy most often occurs in childhood and older adulthood (Institute of Medicine 2012). The exact cause of epilepsy is uncertain. Some known causes of epilepsy include head trauma, stroke, tumors, infection, or abnormalities of the brain.

Epilepsy is categorized as idiopathic (genetic cause) or symptomatic (cause unknown), and is further grouped into either generalized, affecting both hemispheres of the brain, or partial epilepsy, which affects one hemisphere of the brain. Examples of idiopathic generalized epilepsy include childhood absence epilepsy, juvenile myoclonic epilepsy and epilepsy with grand mal seizures. Examples of idiopathic partial epilepsy include benign focal epilepsy of childhood. Symptomatic generalized epilepsy includes West syndrome, Lennox-Gastaut syndrome and others. Symptomatic partial epilepsy includes temporal lobe epilepsy, frontal lobe epilepsy and others.

In some embodiments, the seizure disorder is a pediatric seizure disorder. The ability to categorize a case of a seizure disorder, e.g. epilepsy, into a specific syndrome occurs more often with children since the onset of seizures is commonly early. Less serious examples are benign rolandic epilepsy, childhood absence epilepsy and juvenile myoclonic epilepsy (A. Neligan et al., *Handbook of clinical neurology* 2012, 107:113-33). Other examples of pediatric seizures include febrile seizures, infantile spasms and neonatal seizures.

In some embodiments, the seizure disorder is frontal lobe epilepsy, juvenile myoclonic epilepsy, myoclonic epilepsy, absence epilepsy, Lennox-Gastaut syndrome, Landau-Kleffner syndrome, Dravet syndrome, progressive myoclonus epilepsies, reflex epilepsy, Rasmussen's syndrome, temporal lobe epilepsy, limbic epilepsy, status epilepticus, abdominal epilepsy, massive bilateral myoclonus, catamenial epilepsy, Jacksonian seizure disorder, Lafora disease or photosensitive epilepsy, or a combination of one or more of these.

For most cases of epilepsy, the disease is chronic and requires chronic medications for treatment. Antiepileptic drugs (AEDs) generally suppress neural activity by a variety of mechanisms, including altering the activity of cell membrane ion channels and the propensity of action potentials or bursts of action potentials to be generated. These desired therapeutic effects are often accompanied by the undesired side effect of sedation. Other medications have significant non-neurological side effects, such as gingival hyperplasia, a cosmetically undesirable overgrowth of the gums, and/or a thickening of the skull, as occurs with phenytoin. While chronic usage of AEDs has proven to be effective for a majority of patients suffering from epilepsy, the persistent side effects can cause a significant impairment to a patient's quality of life. Furthermore, in spite of the currently available arsenal of old and new AEDs, almost one-third of epileptic patients are non-responsive (e.g. refractory) to all pharmacological regimens. (M. M. Castel-Branco et al., *Methods Find Exp Clin Pharmacol*, 2009, 31(2):101-106). Subsequently, there is a substantial need to develop new and more effective AEDs.

In some embodiments, the seizure disorder is refractory to treatment. Severe syndromes with diffuse brain dysfunction, also referred to as epileptic encephalopathies, are refractory to current treatment. Epileptic encephalopathies constitute a group of disorders in which the epileptic activity itself is considered to contribute to severe cognitive impairment or decline above and beyond what might be expected from the underlying pathology alone. In further embodiments, the refractory seizure disorder is a disorder associated with neuronal migration, such as human microgyria. (S. Bandyopadhyay et al., *Epilepsy Research*, 2006, 72:127-139). Another important disturbance in a subgroup of patients surgically treated for intractable seizures is focal dysplasia of the cerebral cortex. Anticonvulsant drug therapy is often ineffective in patients with such cortical malformations. In some embodiments, the seizure disorder involves cortical hyperexcitability in focal cortical dysplasia (malformations). (S. Bandyopadhyay et al., *Epilepsy Research*, 2006, 72:127-139).

In some embodiments, the seizure or epilepsy disorder is caused by a genetic abnormality. Genetics is believed to play an important role in epilepsies by a number of mechanisms. Simple and complex modes of inheritance have been identified for some of them. Recent exome and genome sequencing studies have begun to reveal a number of de novo gene mutations that are responsible for some epileptic encephalopathies, including CHD2 and SYNGAP1 and DMN1, GABBR2, FASN and RYR3. Patients with the epileptic encephalopathie, West syndrome, present distinct clinical electrophysiological features usually manifesting between 3 and 12 months as clusters of infantile spasms (IS) and a characteristic electroencephalogram (EEG) pattern called hypsarrhythmia. West syndrome has been associated with mutations in ARX, CDKL5, STXBP1, and ST3GAL3 as well as various copy number variations (CNVs). (J. R. Lemke et al., *Ann Neurol*, 2014, 75(1), 147-154). Mutations in GRIN2A and GRIN2B encoding the NR2A and NR2B of the NMDA receptor are associated with several neurodevelopmental disorders. Mutations in GRIN2A have recently been detected in idiopathic focal epilepsy with rolandic spikes and related epileptic encephalopathies, that is, in Landau-Kleffner syndrome, epilepsy with continuous spike-and-waves during slow sleep syndrome, and nonsyndromic epilepsy associated with intellectual disability. By contrast, GRIN2B has not been described as an epilepsy gene to date but has repeatedly been considered as a putative candidate gene for seizures, and mutations were detected in patients with ID and schizophrenia. (J. R. Lemke et al., *Ann Neurol*, 2014, 75(1), 147-154).

In some embodiments, the disease or disorder is a movement disorder. Movement disorders include Parkinson's disease, dyskinesias (including the side effects accompanying normal doses of L-Dopa), tardive dyskinesia, drug-induced parkinsonism, postencephalitic parkinsonism, progressive supranuclear palsy, multiple system atrophy, corticobasal degeneration, parkinsonian-ALS dementia complex, basal ganglia calcification, akinesia, akinetic-rigid syndrome, bradykinesia, dystonia, medication-induced parkinsonian, Gilles de la Tourette syndrome, Huntingon's disease, tremor, chorea, myoclonus, tick disorder and dystonia.

In some embodiments, the movement disorder is one or more of akinesias and akinetic-rigid syndromes, dyskinesias and medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor). Examples of "akinetic-rigid syndromes" include Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification. Examples of dyskinesias include tremor (including rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia).

In some embodiments, the disease or disorder is Parkinson's disease.

In some embodiments, the disease or disorder is Huntington's disease.

In some embodiments, the disease or disorder is cognitive dysfunction associated with disorders including schizophrenia, Alzheimer's disease, fronto-temporal dementia, Pick's disease, Lewy body disease, and other senile dementias (e.g., vascular dementia).

In some embodiments, the present invention provides a method of treating a disorder described herein, comprising administering a chemical entity of the invention in conjunction with one or more pharmaceutical agents. Suitable pharmaceutical agents that may be used in combination with the chemical entities of the present invention include selective serotonin reuptake inhibitors (SSRIs), e.g., in the treatment of depression; dopamine replacement therapy regimens and dopamine agonists, e.g., in the treatment of Parkinson's disease; typical antipsychotics; atypical antipsychotics; anticonvulsants; stimulants; Alzheimer's disease therapies; anti-migraine agents; and anxiolytic agents.

Suitable SSRIs include citalopram, dapoxetine, escitalopram, fluoxetine, fluvoxamine, indalpine, paroxetine, sertraline, vilazodone and zimelidine.

Suitable dopamine replacement therapy regimens include replacement of L-DOPA with a DOPA decarboxylase inhibitor such as carbidopa.

Suitable dopamine receptor agonists include aplindore, apomorphine, bromocriptine, cabergoline, ciladopa, dihydroergocryptine, lisuride, pardoprunox, pergolide, piribedil, pramipexole, ropinirole and rotigotine.

Suitable typical antipsychotics include chlorpromazine, thioridazine, mesoridazine, levomepromazine, loxapine, molindone, perphenazine, thiothixene, trifluoperazine, haloperidol, fluphenazine, droperidol, zuclopenthixol, flupentixol and prochlorperazine.

Suitable atypical antipsychotics include amisulpride, aripiprazole, asenapine, blonanserin, clotiapine, clozapine, iloperidone, Ilurasidone, mosapramine, olanzapine, paliperidone, perospirone, quetiapine, remoxipride, risperidone, sertindole, sulpiride, ziprasidone, zotepine, bifeprunox, pimavanserin and vabicaserin.

Suitable anticonvulsants include phenytoin, carbamazepine, barbiturates, phenobarbital, phenobarbital, mephobarbital, trimethadione, mephenytoin, paramethadione, phenthenylate, phenacemide, metharbital, benzchlorpropamide, phensuximide, priraidone, methsuximide, ethotoin, aminoglutethinide, diazepam, clonazepam, clorazepate, fosphenytoin, ethosuximide, valproate, felbamate, gabapentin, lamotrigine, topiramate, vigrabatrin, tiagabine, ziamide, clobazam, thiopental, midazolam, propofol, levetiracetam, oxcarbazepine, CCPene, and GYKI 52466.

Suitable stimulants include Adderall (amphetamine, dextroamphetamine mixed salts), methylphenidate, dextroamphetamine, dexmethylphenidate and lisdexamfetamine.

Suitable Alzheimer's disease therapies include acetylcholinesterase inhibitors such as rivastigmine, donepezil, galanthamine and huperazine; alpha-7 nicotinic agonists such as encenicline; and drugs that reduce A1342 such as BACE inhibitors, gamma secretase modulators and beta amyloid peptide antibodies.

Suitable anti-migraine drugs include Ergot alkaloids (e.g., ergotamine and dihydroergotamine mesylate). Other suitable anti-migraine drugs include 5-HT1D agonist triptans such as sumitriptan, almotriptan, eletriptan, frovatriptan, naratriptan, rizatriptan, and zolmitriptan.

Other suitable agents for use in treating or preventing headache(s) or migraine include pain medication (e.g., aspirin, naproxen, ibuprofen, and acetaminophen), medication for nasuea, caffeine, antihistamines, isometheptene mucate, divalproex sodium/sodium valproate, topiramate, metoprolol, propranolol, timolol, lisinopril, candesartan, atenolol, nadolol, diltiazem, nimodipine, verapamil, amitriptyline, nortriptyline, imipramine, doxepin, protriptyline, paroxetine, fluoxetine, sertraline, topiramate, gabapentin, and divalproex sodium.

In some embodiments, one or more other suitable agents can be combined with a chemical entity of the invention to prevent and/or treat a headache. In some embodiments, one or more other suitable agents can be combined with a chemical entity of the invention to prevent and/or treat a migraine. In some embodiments, one or more other suitable agents can be combined with a chemical entity of the invention to prevent and/or treat a migraine with aura.

In some embodiments, one or more other suitable agents can be combined with a chemical entity of the invention to prevent and/or treat cluster headache. Blood pressure lowering medications have been shown to treat cluster headache. Accordingly, in some such embodiments, a chemical entity of the invention can be combined with, for example, verapamil, lithium, divalproex sodium, prednisone, ergotamine tartrate, melatonin, a triptan (e.g., sumatriptan), oxygen, intranasal lidocaine, or any other suitable agent to prevent and/or treat cluster headache.

Suitable anxiolytic drugs include benzodiazepine receptor modulators such as diazepam, alprazolam, lorazepam and clonazepam.

Other suitable agents for use in conjunction with a chemical entity of the invention include memantine and modafinil.

The exact amount required will vary from subject to subject, depending on the species, age, and general condition of the subject, the severity of the infection, the particular agent, its mode of administration, and the like. The chemical entities of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the chemical entities and compositions of the present invention will be decided by the attending physician within the scope of sound medical judgment. The specific effective dose level for any particular patient or organism will depend upon a variety of factors including the disorder being treated and the severity of the disorder; the activity of the specific chemical entity employed; the specific composition employed; the age, body weight, general health, sex and diet of the patient; the time of administration, route of administration, and rate of excretion of the specific chemical entity employed; the duration of the treatment; drugs used in combination or coincidental with the specific chemical entity employed, and like factors well known in the medical arts. The term "patient", as used herein, means an animal, preferably a mammal, and most preferably a human.

In some embodiments, administration may involve dosing that is intermittent (e.g., a plurality (i.e., at least two) of doses separated in time) and/or periodic (e.g., individual doses separated by a common period of time) dosing. In some embodiments, a dosing regimen for a particular active agent may involve intermittent or continuous administration, for example to achieve a particular desired pharmacokinetic profile or other pattern of exposure in one or more tissues or fluids of interest in the subject receiving therapy. In some embodiments, intermittent dosing may include dosing that occurs once a day, once every other day, once a week, once every two weeks, or once a month.

In some embodiments, administration may involve dosing that is titrated over time in order to reach a target dosage. In some embodiments, increases in dosing amount and/or schedule can occur at weekly intervals based on the subject's clinical response and tolerability.

In some embodiments, one or more features of a dosing regimen may be modified over time (e.g., increasing or decreasing amount of active in any individual dose, increasing or decreasing time intervals between doses, etc.), for example in order to optimize a desired therapeutic effect or response.

In some embodiments, pharmaceutically acceptable compositions of the present invention can be administered once a week. In some embodiments, pharmaceutically acceptable compositions of the present invention can be administered once a day. In some embodiments, pharmaceutically acceptable compositions of the present invention can be administered twice a day. In some embodiments, pharmaceutically acceptable compositions of the present invention can be administered three times a day. In some embodiments, pharmaceutically acceptable compositions of the present invention can be administered with or without regard to food.

In some embodiments, pharmaceutically acceptable compositions of the present invention can be administered to treat acute conditions. Acute conditions may be sudden in onset. Acute condition symptoms may appear and change or worsen rapidly. In some embodiments, pharmaceutically acceptable compositions of the present invention can be administered to treat chronic conditions. Chronic conditions may be long-developing conditions. A chronic condition may develop and worsen over an extended period of time.

In some embodiments, pharmaceutically acceptable compositions of the present invention can be administered prior to a seizure. In some embodiments, pharmaceutically acceptable compositions of the present invention can be administered after a seizure. In some embodiments, pharmaceutically acceptable compositions of the present invention can be administered to a patient at risk of seizure.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the chemical entities of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a chemical entity of the present invention, it is often desirable to slow the absorption of the chemical entity from subcutaneous or intramuscular injection. This may be accomplished by the use of a liquid suspension of crystalline or amorphous material with poor water solubility. The rate of absorption of the chemical entity then depends upon its rate of dissolution that, in turn, may depend upon crystal size and crystalline form. Alternatively, delayed absorption of a parenterally administered chemical entity form is accomplished by dissolving or suspending the chemical entity in an oil vehicle. Injectable depot forms are made by forming microencapsule matrices of the chemical entity in biodegradable polymers such as polylactide-polyglycolide. Depending upon the ratio of chemical entity to polymer and the nature of the particular polymer employed, the rate of chemical entity release can be controlled. Examples of other biodegradable polymers include poly(orthoesters) and poly(anhydrides). Depot injectable formulations are also prepared by entrapping the chemical entity in liposomes or microemulsions that are compatible with body tissues.

Compositions for rectal or vaginal administration are preferably suppositories which can be prepared by mixing the chemical entities of this invention with suitable non-irritating excipients or carriers such as cocoa butter, polyethylene glycol or a suppository wax which are solid at ambient temperature but liquid at body temperature and therefore melt in the rectum or vaginal cavity and release the active chemical entity.

Solid dosage forms for oral administration include capsules, tablets, pills, powders, and granules. In such solid dosage forms, the active chemical entity is mixed with at least one inert, pharmaceutically acceptable carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active chemical entities can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active chemical entity may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a chemical entity of the invention include ointments, pastes, creams, lotions, gels, powders, solutions, sprays, inhalants or patches. The active chemical entity is admixed under sterile conditions with a pharmaceutically acceptable carrier and any needed preservatives or buffers as may be required. Ophthalmic formulation, ear drops, and eye drops are also contemplated as being within the scope of the invention. Additionally, the present invention contemplates the use of transdermal patches, which have the added advantage of providing controlled delivery of a chemical entity to the body. Such dosage forms can be made by dissolving or dispensing the chemical entity in the proper medium. Absorption enhancers can also be used to increase the flux of the chemical entity across the skin. The rate can be controlled by either providing a rate controlling membrane or by dispersing the chemical entity in a polymer matrix or gel.

As used herein, the term "combination," "combined," and related terms refers to the simultaneous or sequential administration of therapeutic agents in accordance with this invention. For example, a chemical entity of the present invention may be administered with another therapeutic agent simultaneously or sequentially in separate unit dosage forms or together in a single unit dosage form. Accordingly, the present invention provides a single unit dosage form comprising a chemical entity of Formula (I), an additional therapeutic agent, and a pharmaceutically acceptable carrier, adjuvant, or vehicle.

In some embodiments, different agents administered in combination may be administered via different routes of delivery and/or according to different schedules. Alternatively or additionally, in some embodiments, one or more doses of a first active agent is administered substantially simultaneously with, and in some embodiments via a common route and/or as part of a single composition with, one or more other active agents.

The amount of both, a provided chemical entity and additional therapeutic agent (in those compositions which comprise an additional therapeutic agent as described above), that may be combined with the carrier materials to produce a single dosage form will vary depending upon the host treated and the particular mode of administration. Preferably, compositions of this invention should be formulated so that a dosage of between 0.01-100 mg/kg body weight/day of a provided chemical entity can be administered.

In those compositions which comprise an additional therapeutic agent, that additional therapeutic agent and the chemical entity of this invention may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, the present invention provides a medicament comprising at least one chemical entity of Formula (I) and a pharmaceutically acceptable carrier, adjuvant or vehicle.

In some embodiments, the present invention provides the use of a chemical entity of Formula (I) in the manufacture of a medicament for the treatment of a CNS disease or disorder.

General Synthetic Methods

Chemical entities of Formula (I) can be synthesized according to Scheme 1 and/or using methods known in the art.

reaction such as chlorine or bromine. In certain cases the coupling reaction can be conducted as a base mediated nucleophilic aromatic substitution reaction. In certain cases the coupling reaction can be conducted as a Buchwald reaction mediated by palladium catalysis. Aromatic substitution coupling reactions can be conducted in suitable protic (e.g., isopropanol, n-butanol) or aprotic (e.g., $CH_2Cl_2$, DMF, DMSO, $CH_3CN$) solvents at temperatures from ambient to 160° C., for example, between 50° C. and 120° C. with intermediates of formula Z—Cl in the presence of a suitable base (e.g., triethylamine, diisopropylethylamine). Buchwald coupling reactions (Buchwald, S.; Muci, A. Top. Curr. Chem. 2002; 219, 133-209) can be conducted in suitable organic solvents (e.g., t-butanol, toluene, DMF, DMSO, $CH_3CN$) in the presence of a suitable palladium catalyst and phosphine ligand system (e.g., Brettphos/Brettphos precatalyst, BINAP/$Pd_2(dba)_3$) at temperatures from 70° C. to 150° C., for example, between 80° C. and 130° C. with intermediates of formula Z—Br, in the presence of a suitable base (e.g., $Cs_2CO_3$) under inert (e.g., nitrogen) atmosphere. In the case where $R^{1'}=R^1$, compounds of formula XII are equivalent to compounds of formula I. In the case where $R^{1'}$ is a protecting group then intermediate compounds of formula XII can be converted to intermediate compounds of formula XIII using deprotection conditions known in the art. For example, when $R^{1'}$ is a t-butyl group (i.e., where the $R^{1'}$—OC(O)— moiety is a Boc group), intermediate compounds of formula XII can be converted to intermediate compounds of formula XIII using a number of known methods. Typically the Boc deprotection is conducted under acidic conditions using either HCl (e.g., 1-4N HCl in ether or dioxane in a suitable organic solvent, e.g., dichloromethane, methanol or THF) at temperatures between 0° C. and 50° C., or Scheme 1

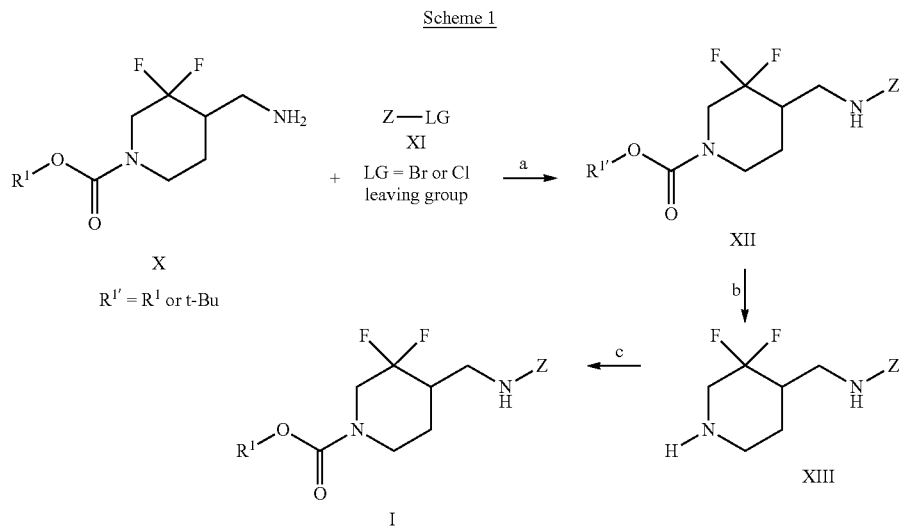

a. base (e.g., diisopropylethylamine), organic solvent (e.g., n-butanol), heat or Buchwald coupling conditions (e.g., Pd catalyst, base, organic solvent, heat) b. deprotection conditions (e.g., $CF_3CO_2H$ or HCl, room temperature when $R^{1'}$ = t-butyl) c. carbamate formation conditions (e.g., carbonyldiimidazole, $R^1$-OH, DMSO, room temperature).

In the method depicted in Scheme 1, in a first step, compounds of formula XII may be prepared by coupling of intermediates of formula X, wherein $R^{1'}=R^1$ or a protecting group (e.g., where $R^{1'}$ is t-butyl, the moiety $R^{1'}$—OC(O)— is a Boc group), with intermediates Z-LG of formula XI. For compounds of formula XI the Z is a heterocyclic group as defined above and LG is a suitable group for the coupling using trifluoroacetic acid in an aprotic solvent (e.g., dichloromethane) at temperatures between 0° C. and room temperature. The latter is particularly useful for compounds which are sensitive to chloride-mediated side reactions. Intermediate compounds of formula XIII can be can be converted to compounds of formula I by carbamoylation reaction with a carbamoylating reagent of formula $R^1$OC (O)X wherein X is a suitable leaving group (e.g., Cl, imidazolyl, hydroxysuccinyl). Reagents of formula R¹OC(O)X may be implemented in isolated form or generated in situ. For example, an alcohol of formula R¹OH can be treated with carbonyldiimidazole in an aprotic organic solvent at between 0° C. and room temperature to first form the R¹OC(O)imidazolyl carbamoylating reagent. In situ reaction of the R¹OC(O)imidazolyl carbamoylating reagent with intermediate compounds of formula XIII (in free base or acid addition salt form, at temperatures between 0° C. and 70° C.) in an aprotic solvent (e.g., DMSO) yields compounds of formula I.

The heteroaryl chloride or bromide coupling reagents Z—LG are either commercially available, can be prepared according to known literature procedures for the exact compound or can be prepared using methods known in the art for synthesizing heteroaryl chlorides and bromides. For example, the heteroaryl compound Z—H can be brominated or chlorinated using methods known in the art (e.g. by treatment with bromine or N-bromosuccinimide or another brominating reagent or treatment with a chlorinating reagent such as sulfurylchloride) the desired Z—Br or Z—Cl heteroaryl coupling reagent can then be isolated by the appropriate procedure (e.g. by chromatography as needed to separate regioisomers). Heteroaryl coupling reagents Z—Cl wherein the chloro group is part of an iminochloride substructure can be prepared under standard conditions (e.g., using phosphorus oxychloride at elevated temperature as solvent itself or in a suitable aprotic organic solvent) from the corresponding Z—OH starting material which has the corresponding amido tautomeric substructure. Other heteroaryl coupling reagents can be prepared from the corresponding Z—NH₂ starting material under Sandmeyer reaction-type conditions which are well established in the art (i.e., diazotization reaction followed by chlorination or bromination with CuCl or CuBr). In some cases the required Z—H, Z—OH or Z—NH₂ starting materials can be prepared using methods known in the art for synthesizing heteroaryl compounds.

Chemical entities of Formula (I) can be obtained as individual enantiomers from racemic mixtures using methods known in the art such as chiral chromatography or recrystallization of diastereomeric acid addition salts. Alternatively, chemical entities of Formula (I) can be obtained as individual enantiomers by asymmetric synthesis or from the corresponding individual enantiomer intermediates. For example, the individual enantiomers of chemical entities of Formula (I) can be prepared from enantiomers of the intermediates of formula X having the corresponding absolute stereochemical configuration at C-4 of the piperidine ring system. Intermediates of formula X can in turn be prepared by an asymmetric synthesis process as depicted in Scheme 2. In this process the known starting material XIV (Madaiah M. et. Al. *Tetrahedron Lett.* 2013, 54, 1424-27) is converted in three steps to an α,β-unsaturated acyl intermediate XV substituted with an optically pure R=(XVa) or S=(XVb) oxazolidinone chiral auxiliary system. In the case of XVa, with the R-absolute stereochemistry chiral auxiliary, standard catalytic hydrogenation using 10% Pd—C in ethyl acetate affords a ca. 5:1 mixture of diasteromeric products (R)-XVIa (major) and (S)-XVIa (minor). This mixture can be separated by standard chromatography over silica gel to give (R)-XVIa in pure form. As depicted in Scheme 2, hydrolysis of the chiral auxiliary of pure intermediate (R)-XVIa gives the pure enantiomer acid intermediate (R)-XVII. From (R)-XVII, a two-step Curtius reaction process gives the (−)-(R)-X enantiomer. The (+)-(S)-X enantiomer can be prepared in analogous fashion starting from intermediate XVb. Pure enantiomers of formula X may also be prepared from enantiomerically enriched or racemic mixtures by chiral acid addition salt formation and recrystallization (e.g., using a chirally pure tartaric acid) methods standard in the art.

Scheme 2

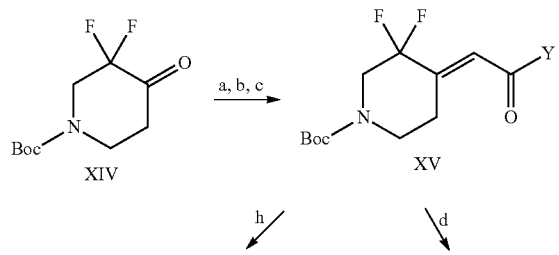

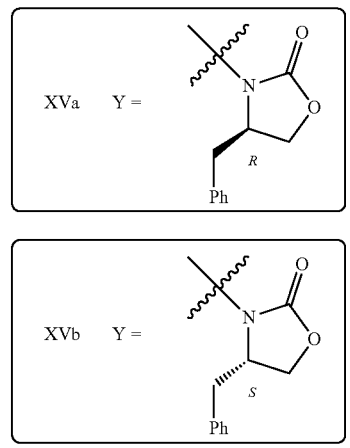

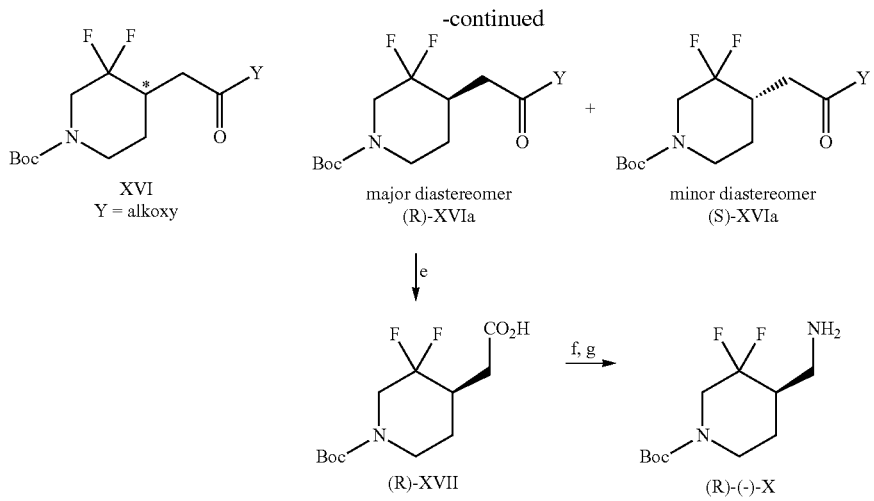

a. methyl (triphenylphosphoranylidene)acetate, toluene, rt b. NaOH, THF, water 50° C. c. triethylamine, pivaloylchloride, THF -78° C., R-4-benzyl-3-lithio-2-oxazolidinone d. 10% Pd/C, H₂, ethyl acetate rt, separation of product diastereomers by column chromatography over silica gel e. LiOH, 30% H₂SO₂, THF, 50° C. f. diphenylphosphorylazide, PhCH₂OH, trimethylamine, toluene, reflux g. 10% Pd/C, H₂, ethyl acetate rt h. asymmetric hydrogenation Enantiomer intermediates of formula XVI can also be prepared by catalytic asymmetric hydrogenation of the intermediates of formula XV wherein Y forms simple achiral ester group (e.g., Y=OMe, OEt). To this end chiral catalysts comprising a chiral phosphine ligand (e.g., Waldphos ligands) and a transition metal (e.g., Ir, Rh or Ru) can be employed in asymmetric catalytic hydrogenation conditions at elevated temperature and pressure to give simple ester intermediates XVI of high enantiomeric purity. The latter can be converted to pure enantiomers of X using standard methods in the art such as those described above. Hydrogenation of α,β-unsaturated acid and ester systems have been reviewed by Tang et al. (Tang W. et al., *Chem Rev.* 2003, 103, 3029), and additional useful catalytic asymmetric hydrogenation methods have been described by Krska et al. (Krska S. W. et al., *Tetrahedron* 2009, 65, 8987-8994) and Tudge et al. (Tudge M. et al., *Organic Process Research and Development* 2010, 14, 787-798).

Pure enantiomer intermediates for synthesizing enantiomers of compounds of Formula I may also be prepared by variants of the above methods using intermediates with alternative protecting groups or double bond isomers as exemplified in Scheme 3.

Scheme 3

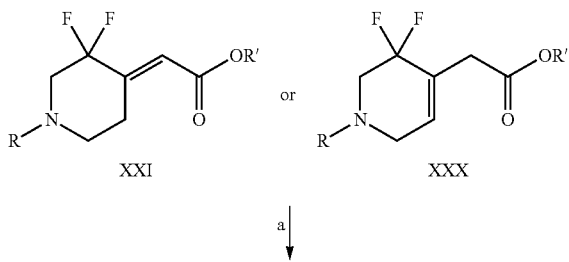

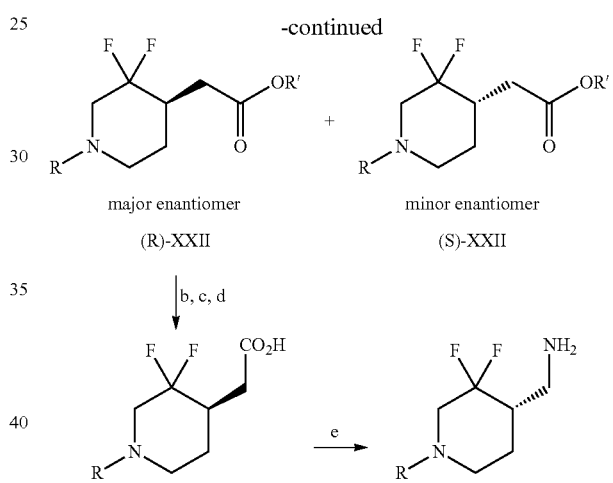

a. R = CH₂Ph, R' = hydrogen or alkyl, (e.g., Me or Et), asymmetric catalytic hydrogenation b. H₂ 10% Pd/C to remove benzyl protecting group to give R = H c. carbamoylation, e.g., carbonyldiimidazole, R¹—OH, DMSO, to give R = R¹—OC(O)— d. ester saponification, e.g., NaOH, THF e. Hofmann degradation or Curtius rearrangement protocol.

For example, an intermediate of formula XXI wherein R=benzyl can be subjected to the above-described reduction processes (e.g., catalytic asymmetric hydrogenation) to generate intermediates of formula (R)-XXII that are chirally pure at the C-4 piperidine stereocenter. In subsequent steps the benzyl group can be removed and exchanged for another protecting group (e.g., Boc) or the CO₂R¹ group present in the compound of Formula I. Alternatively, the same reaction scheme can be implemented via asymmetric hydrogenation of the double bond isomer starting material XXX.

Example 1. Chemical Entities

As depicted in the Examples below, in certain exemplary embodiments, chemical entities are prepared according to the following procedures. It will be appreciated that, although the general methods depict the synthesis of certain chemical entities of the present invention, the following methods, and other methods known to persons skilled in the art, can be applied to all chemical entities and subclasses and species of each of these chemical entities, as described herein.

Temperatures are given in degrees centigrade. If not mentioned otherwise, all evaporations are performed under reduced pressure, preferably between 15 mm Hg and 100 mm Hg. The structures of intermediates and final products are confirmed by standard analytical methods, for example, mass spectrometry and NMR spectroscopy. Optical rotations are measured at the sodium D line and given in degrees. Enantiomeric excess can be determined via chiral HPLC methods (e.g., using CHIRALPAK AD-H4.6*150 mm, 5 μm columns and suitable mobile phase selection, e.g., hexane/isopropanol (80:20), and flow rates, e.g., 1.5 mL/min).

ABBREVIATIONS aq aqueous
BINAP 2,2'-bis(diphenylphosphino)-1,1'-binaphthalene
Boc t-butoxycarbonyl
Brettphos 2-(dicyclohexylphosphino)-3,6-dimethoxy-2',4',6'-triisopropyl-1,1'-biphenyl
Brettphos precatalyst chloro[2-(dicyclohexylphosphino)-3,6-dimethoxy-2',4',6'-triisopropyl-1,1'-biphenyl][2-(2-aminoethyl)phenyl]-palladium(II)
nBuOH n-butanol
Cbz benzyloxycarbonyl
CDI carbonyldiimidazole
DAST diethylamino sulfur trifluoride
dba dibenylideneacetone
DCM dichloromethane
DCE 1,2-dichloroethane
DIPEA N, N-diisopropylethylamine
DMF N,N-dimethylformamide
DMSO dimethyl sulfoxide
Et ethyl
Et$_2$O diethyl ether ("ether")
EtOAc ethyl acetate
EtOH ethanol
eq equivalents
h hours
HPLC high performance liquid chromatography
LC liquid chromatography
Me methyl
Ms methanesulfonyl
MsCl methanesulfonylchloride
MS mass spectrometry
MS (ESI) mass spectrometry electrospray ionization
NMP N-methyl-2-pyrrolidone
NMR nuclear magnetic resonance
Pd/C palladium supported on carbon
rt room temperature
TEA triethylamine
TFA trifluoroacetic acid
THF tetrahydrofuran
TLC thin layer chromatography
Ts p-toluenesulfonyl Example 1.A. (−)-R-tert-butyl 4-(aminomethyl)-3,3-difluoropiperidine-1-carboxylate

Step 1: tert-butyl 3,3-difluoro-4,4-dihydroxypiperidine-1-carboxylate

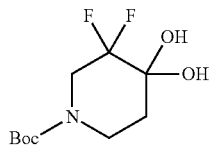

To a solution of 1-benzyl-3,3-difluoropiperidine-4,4-diol (100.0 g, 412 mmol) in ethanol (1850 mL) was added 10% Pd/C (10.0 g) and HCl (6.0 M, 69 mL, 414 mmol). The mixture was purged with H$_2$ three times and hydrogenated at room temperature under atmospheric pressure. After the starting material was consumed, the mixture was filtered through celite and the filter pad was extracted with EtOH. The combined filtrates were concentrated under reduced pressure and the crude 3,3-difluoropiperidine-4,4-diol hydrochloride product was used directly in the next step without purification. A stirred solution of the crude product 3,3-difluoropiperidine-4,4-diol hydrochloride (78 g) in water (1000 mL) and acetone (500 mL) was basified by Na$_2$CO$_3$ to pH 9. Di-tert-butyl dicarbonate (98.9 g, 453 mmol) was then added and the mixture was stirred at rt for 4 h. The mixture was concentrated under reduced pressure to remove the acetone cosolvent. The resulting mixture was extracted with EtOAc. The combined organic layers were dried over Na$_2$SO$_4$ and concentrated to afford the crude product as a brown oil. The oil was treated with hexane and the precipitated solid material was triturated and filtered to give the title compound as a white powder (94.3 g, 90% overall). $^1$H NMR (400 MHz, CD$_3$OD) δ 3.72 (t, J=11.6 Hz, 2H), 3.56-3.46 (m, 2H), 1.83-1.77 (m, 2H), 1.42 (s, 9H).

Step 2: tert-butyl 3,3-difluoro-4-(2-methoxy-2-oxo-ethylidene)piperidine-1-carboxylate

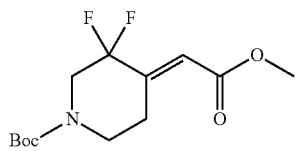 [SMILES: COC(=O)/C=C1\CCN(C(=O)OC(C)(C)C)CC1(F)F]

To a stirred solution of tert-butyl 3,3-difluoro-4,4-dihydroxypiperidine-1-carboxylate (80.0 g, 314 mmol) in toluene (1000 mL) was added methyl (triphenylphosphoranylidene)acetate (126 g, 377 mmol) and the reaction mixture was stirred at room temperature for 4 h. The reaction mixture was concentrated in vacuo and the residue was purified by column chromatography over silica gel (EtOAc/hexane=1/5) to afford the title compound as a colorless oil (79.6 g, 87%). $^1$H NMR (400 MHz, CDCl$_3$) δ 6.23 (s, 1H), 3.83-3.71 (m, 2H), 3.76 (s, 3H), 3.58-3.47 (m, 2H), 3.13-3.05 (m, 2H), 1.48 (s, 9H).

Step 3: 2-(1-(tert-butoxycarbonyl)-3, 3-difluoropiperidin-4-ylidene)acetic acid

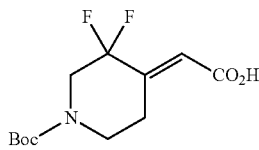 [SMILES: CC(C)(C)OC(=O)N1CC/C(=C\C(=O)O)C(F)(F)C1]

To a stirred solution of tert-butyl 3,3-difluoro-4-(2-methoxy-2-oxoethylidene)piperidine-1-carboxylate (590 g, 2.03 mol) in THF (1.5 L) was added a solution of NaOH (40.1 g, 1.0 mol) in water (1.5 L) at room temperature. The resulting mixture was heated to 50° C., and stirred for 1 h. After the starting material was consumed, the THF was concentrated under reduced pressure. The aqueous concentrate was extracted with ethyl acetate and acidified to pH 5 with 4.0M aqueous HCl under ice-water bath cooling. The aqueous phase was extracted with ethyl acetate three times. The combined organic phases were washed with water, brine, dried over Na$_2$SO$_4$, and concentrated under reduced pressure. The residue was triturated with hexane and the suspension was filtered to afford the title product as an off-white powder (492 g, 87%). $^1$H NMR (400 MHz, DMSO-d6) δ 12.99 (s, 1H), 6.11 (s, 1H), 3.81 (t, J=11.6 Hz, 2H), 3.50-3.42 (m, 2H), 2.94-2.88 (m, 2H), 1.42 (s, 9H).

Step 4: tert-butyl (R)-4-(2-(4-benzyl-2-oxooxazolidin-3-yl)-2-oxoethylidene)-3,3-difluoropiperidine-1-carboxylate

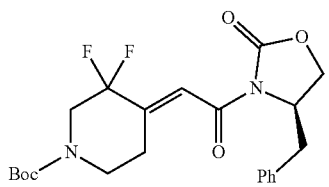

To a stirred solution of 2-(1-(tert-butoxycarbonyl)-3, 3-difluoropiperidin-4-ylidene)acetic acid (23.5 g, 84.8 mmol) in dry THF (250 mL) was added Et$_3$N (11.7 mL, 85.7 mmol) at 0° C. Pivaloyl chloride (10.5 mL, 89.0 mmol) was added dropwise and the mixture was stirred at 0° C. for 2 h. To the mixture at −78° C. was added a THF solution of one equivalent of (R)-4-benzyl-3-lithio-2-oxazolidinone (prepared from (R)-4-benzyl-2-oxazolidinone (15.0 g, 84.7 mmol) and n-BuLi (2.5 M in hexane, 34 mL, 85 mmol) in THF (150 mL) at −78° C.). The resulting mixture was allowed to warm to 0° C., stirred for 30 minutes at 0° C. and quenched with sat.NH$_4$Cl. The mixture was extracted with ethyl acetate. The combined organic layers were washed with water, brine, dried over Na$_2$SO$_4$ and concentrated in vacuo. The residue was recrystallized from ethyl acetate/hexane (60 mL/400 mL) to afford the title compound as a white powder (24.5 g, 66%). MS (ESI) calcd for C$_{22}$H$_{26}$F$_2$N$_2$O$_5$:436.2; found [459.3] [M+Na]; $^1$H NMR (400 MHz, CDCl$_3$) δ 7.39-7.32 (m, 3H), 7.31-7.29 (m, 1H), 7.22 (d, J=8.0 Hz, 2H), 4.76-4.70 (m, 1H), 4.27-4.19 (m, 2H), 3.84-3.79 (m, 2H), 3.63-3.52 (m, 2H), 3.35 (dd, J=3.2 and 13.2 Hz, 1H), 3.08-2.97 (m, 2H), 2.80 (dd, J=10.0 and 13.2 Hz, 1H), 1.49 (s, 9H).

Step 5: R-tert-butyl 4-(2-((R)-4-benzyl-2-oxooxazolidin-3-yl)-2-oxoethyl)-3,3-difluoropiperidine-1-carboxylate

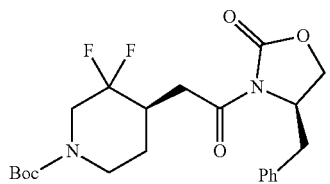 [SMILES: CC(C)(C)OC(=O)N1CC[C@H](CC(=O)N2C(=O)OC[C@H]2Cc2ccccc2)C(F)(F)C1]

To a suspension of ((R)-tert-butyl 4-(2-(4-benzyl-2-oxooxazolidin-3-yl)-2-oxoethylidene)-3,3-difluoropiperidine-1-carboxylate (10.0 g, 22.8 mmol) in ethyl acetate (150 mL) was added 10% palladium on carbon (1.0 g). The mixture was hydrogenated at room temperature for 13 hr at atmospheric pressure. The mixture was filtered through celite and the filter pad was extracted with ethyl acetate. The combined filtrates were concentrated in vacuo to afford a 12.0 g of a ca. 5:1 mixture mixture of the R title compound along with corresponding minor S diastereoisomer. The diastereomers were separated by column chromatography over silica gel (ethyl acetate/hexane=1/3). The major diastereoisomer eluted first and was obtained as white powder (5.20 g, 52%, >99% de) (Column: CHIRALPAKAD-H 4.6*150 mm, 5 um; Mobile Phase: A:Hexanes B:Ethanol=70:30; t=9.07). MS (ESI) calcd for C$_{22}$H$_{28}$F$_2$N$_2$O$_5$: 438.2; found: 461.2 [M+Na] $^1$H NMR (400 MHz, CDCl$_3$) δ 7.37-7.32 (m, 2H), 7.31-7.28 (m, 1H), 7.20 (d, J=8.0 Hz, 2H), 4.72-4.66 (m, 1H), 4.48-4.00 (m, 4H), 3.38-3.27 (m, 2H), 3.11-2.72 (m, 4H), 2.66-2.53 (m, 1H), 1.93-1.89 (m, 1H), 1.63-1.51 (m, 1H), 1.47 (s, 9H).

Step 6: R-2-(1-(tert-butoxycarbonyl)-3,3-difluoropiperidin-4-yl)acetic acid

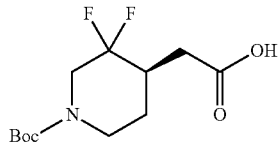 [SMILES: CC(C)(C)OC(=O)N1CC[C@H](CC(=O)O)C(F)(F)C1]

To a stirred mixture of R-tert-butyl 4-(2-((R)-4-benzyl-2-oxooxazolidin-3-yl)-2-oxoethyl)-3,3-difluoropiperidine-1-carboxylate (5.20 g, 11.8 mmol) in THF/H$_2$O (45 mL/45 mL) were added 30% aq. H$_2$O$_2$ (4.9 mL, 48 mmol) and lithium hydroxide monohydrate (800 mg, 19.0 mmol) at 0° C. After stirring for 90 min at 0° C., the reaction mixture was treated with 1M Na$_2$SO$_3$ solution (40 mL) and then extracted with ethyl acetate (2×100 mL) to remove the chiral auxiliary. The aqueous phase was acidified to pH=2~3 with 1M aq.HCl and then extracted with ethyl acetate (2×100 mL). The combined ethyl acetate phases were dried over Na₂SO₄ and concentrated in vacuo. The residue was recrystallized from ethyl acetate/hexane (5 mL/50 mL) to afford the title compound as a white powder (3.70 g, 79%). MS (ESI) calcd for $C_{12}H_{19}F_2NO_4$: 279.1; found 224 [M+H-56 (t-butyl group)]; ¹H NMR (400 MHz, CDCl₃) δ 4.51-4.01 (m, 2H), 3.10-2.70 (m, 3H), 2.45-2.28 (m, 2H), 1.93-1.89 (m, 1H), 1.58-1.50 (m, 1H), 1.46 (s, 9H).

Step 7: R-tert-butyl 4-((benzyloxycarbonylamino)methyl)-3,3-difluoropiperidine-1-carboxylate

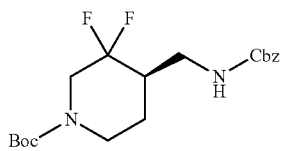 [SMILES: CC(C)(C)OC(=O)N1CC[C@H](CNC(=O)OCc2ccccc2)C(F)(F)C1]

To a stirred solution of R-2-(1-(tert-butoxycarbonyl)-3,3-difluoropiperidin-4-yl)acetic acid (6.05 g, 21.7 mmol) in dry toluene (50 mL) were added triethylamine (4.6 mL, 34 mmol) and diphenylphosphoryl azide (5.2 mL, 24 mmol) under nitrogen. After stirring for 20 min at 80° C., benzyl alcohol (1.4 mL, 25 mmol) was added and the reaction was stirred at 100° C. overnight. The mixture was allowed to cool to room temperature, concentrated and diluted with DCM (200 mL). The organic phase was washed with 0.5M aq. HCl (2×50 mL), water (2×50 mL) and brine (50 mL), dried over Na₂SO₄ and concentrated in vacuo. The residue was recrystallized from ethanol/H₂O (30 mL/90 mL) to afford the title compound as a white powder (6.91 g, 84%). MS (ESI) calcd for $C_{19}H_{26}F_2N_2O_4$: 384.2; found: 407.2 [M+Na]. ¹H NMR (400 MHz, CDCl₃) δ 7.39-7.30 (m, 5H), 5.10 (s, 2H), 5.02 (brs, 1H), 4.51-3.99 (m, 2H), 3.55-3.44 (m, 1H), 3.39-3.26 (m, 1H), 3.04-2.65 (m, 2H), 2.18-2.02 (m, 1H), 1.78-1.75 (m, 1H), 1.58-1.48 (m, 1H), 1.46 (s, 9H).

Step 8: (−)-R-tert-butyl 4-(aminomethyl)-3,3-difluoropiperidine-1-carboxylate

To a suspension of R-tert-butyl 4-((benzyloxycarbonylamino)methyl)-3,3-difluoropiperidine-1-carboxylate (7.01 g, 24.7 mmol) in ethyl acetate (45 mL) was added 10% palladium on carbon (700 mg). The mixture was hydrogenated at room temperature under atmospheric hydrogen pressure for 13 hr. The mixture was filtered through celite and the filter pad was extracted with ethyl acetate. The combined filtrates were concentrated in vacuo to afford the title compound as a brown oil (4.60 g, 93%). [α]_D=−18.3° (c=10 mg/mL, methanol, 20° C.), MS (ESI) calcd for $C_{11}H_{20}F_2N_2O_2$: 250.2; found: 195.2 [M+H-56 (t-butyl group)]; ¹H NMR (400 MHz, CDCl₃) δ 4.45-4.01 (m, 2H), 3.15 (dd, J=5.2, 12.8 Hz, 1H), 3.05-2.75 (m, 2H), 2.68 (dd, J=6.4, 12.8 Hz, 1H) 1.96-1.74 (m, 2H), 1.58-1.48 (m, 1H), 1.46 (s, 9H), 1.40 (brs, 2H).

Example 1.B. 2,5-dioxopyrrolidin-1-yl 4-methylbenzyl carbonate

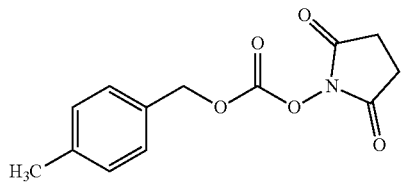 [SMILES: Cc1ccc(COC(=O)ON2C(=O)CCC2=O)cc1]

A mixture of p-tolylmethanol (2.40 g, 19.6 mmol) and bis(2,5-dioxopyrrolidin-1-yl) carbonate (5.03 g, 19.6 mmol) in a mixed solvent comprised of acetonitrile (30 mL) and CH₂Cl₂ (30 mL) was treated with 4-dimethylaminopyridine (1.20 g, 9.8 mmol). The reaction mixture was stirred for 2 h at room temperature. After the alcohol was consumed, the mixture was poured into water (100 mL), and the organic layer was separated, dried over anhydrous sodium sulfate and concentrated under vacuum. The solid thus obtained was triturated with ether and dried to afford the title compound as a white solid (3.40 g, 66%). ¹H NMR (400 MHz, CDCl₃) 7.29 (d, J=8.0 Hz, 2H), 7.20 (d, J=8.0 Hz, 2H), 5.28 (s, 2H), 2.82 (s, 4H), 2.36 (s, 3H).

Example 1.C. 2,5-dioxopyrrolidin-1-yl 4-ethylbenzyl carbonate

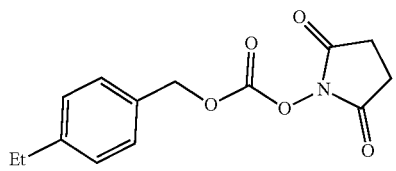 [SMILES: CCc1ccc(COC(=O)ON2C(=O)CCC2=O)cc1]

A mixture of 4-ethylbenzyl alcohol (1.0 g, 7.3 mmol) and bis(2,5-dioxopyrrolidin-1-yl) carbonate (1.88 g, 7.3 mmol) in a solvent mixture of acetonitrile (15.0 mL) and CH₂Cl₂ (15.0 mL) was treated with 4-dimethylaminopyridine (446 mg, 3.65 mmol). The reaction mixture was stirred for 2 h at room temperature. Then the mixture was diluted with ethyl acetate, washed with water, brine, dried over anhydrous Na₂SO₄ and concentrated under reduced pressure to afford the title compound as an off white powder (2.0 g, 99%) which was used without further purification.

Example 1.D. (+)-S-tert-butyl 4-(aminomethyl)-3,3-difluoropiperidine-1-carboxylate The title compound can be prepared in an analogous manner to (−)-R-tert-butyl 4-(aminomethyl)-3,3-difluoropiperidine-1-carboxylate as described in Example 1.A., but using (S)-4-benzyl-3-lithio-2-oxazolidinone (prepared from (S)-4-benzyl-2-oxazolidinone and n-BuLi) in place of the corresponding reagent having the (R) configuration.

Example 1.1. (+)-R-4-methylbenzyl 4-(([1,2,4]tri-azolo[4,3-a]pyrazin-8-ylamino)methyl)-3,3-difluoropiperidine-1-carboxylate (E1-1.2)

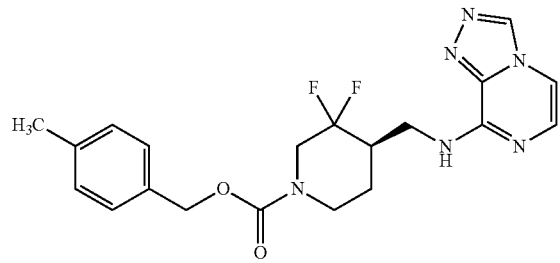 [SMILES: Cc1ccc(COC(=O)N2CC[C@H](CNc3nccn4cnnc34)C(F)(F)C2)cc1]

Step 1: R-tert-butyl 4-(([1,2,4]triazolo[4,3-a]pyrazin-8-ylamino)methyl)-3,3-difluoropiperidine-1-carboxylate

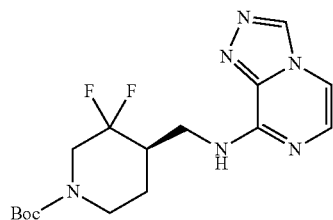 [SMILES: CC(C)(C)OC(=O)N1CC[C@H](CNc2nccn3cnnc23)C(F)(F)C1]

A stirred mixture of (−)-R-tert-butyl 4-(aminomethyl)-3,3-difluoropiperidine-1-carboxylate (230 mg, 0.92 mmol), 8-chloro-[1,2,4]triazolo[4,3-a]pyrazine (127 mg, 0.83 mmol) and DIPEA (0.30 mL, 1.8 mmol) in n-BuOH (5 mL) was heated to 95° C. under nitrogen for 13 hr. The reaction mixture was allowed to cool to room temperature and concentrated in vacuo. The residue was purified by column chromatography over silica gel (ethyl acetate/hexane=1/1) to afford the title compound as a white powder (210 mg, 62%). MS (ESI) calcd for $C_{16}H_{22}F_2N_6O_2$: 368.2; found: 369.1 [M+H]. $^1$H NMR (400 MHz, CDCl$_3$) δ 8.72 (s, 1H), 7.41 (d, J=4.8 Hz, 1H), 7.35 (d, J=4.8 Hz, 1H), 6.50-6.45 (m, 1H), 4.47-4.09 (m, 2H), 4.02-3.96 (m, 1H), 3.79-3.72 (m, 1H), 3.09-2.69 (m, 2H), 2.45-2.29 (m, 1H), 1.92-1.87 (m, 1H), 1.68-1.58 (m, 1H), 1.47 (s, 9H).

Step 2: R—N-((3,3-difluoropiperidin-4-yl)methyl)-[1,2,4]triazolo[4,3-a]pyrazin-8-amine trifluoroacetate

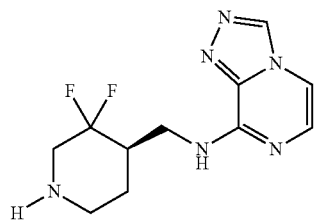

CF$_3$CO$_2$H

To stirred suspension of R-tert-butyl 4-(([1,2,4]triazolo[4,3-a]pyrazin-8-ylamino)-methyl)-3,3-difluoropiperidine-1-carboxylate (1.01 g, 2.72 mmol) in dichloromethane (15 mL) was added TFA (3 mL). The solution was then stirred at ambient temperature for 30 min. The resulting reaction mixture was concentrated under reduced pressure to afford the title compound as a yellow residue which was used in the next step without further purification. MS (ESI) calcd for $C_{11}H_{14}F_2N_6$: 268.1; found: 269.1 [M+H]. $^1$H NMR (400 MHz, CD$_3$OD) δ 9.26 (s, 1H), 7.87 (d, J=4.8 Hz, 1H), 7.33 (d, J=4.8 Hz, 1H), 4.16-4.05 (m, 1H), 3.82-3.75 (m, 2H), 3.52-3.46 (m, 2H), 3.20-3.13 (m, 1H), 2.92-2.76 (m, 1H), 2.36-2.26 (m, 1H), 1.95-1.87 (m, 1H).

Step 3: (+)-R-4-methylbenzyl 4-(([1,2,4]triazolo[4,3-a]pyrazin-8-ylamino)methyl)-3,3-difluoropiperidine-1-carboxylate

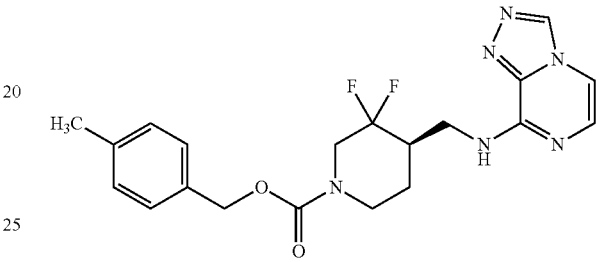

To a stirred solution of R—N-((3,3-difluoropiperidin-4-yl)methyl)-[1,2,4]triazolo[4,3-a]pyrazin-8-amine trifluoroacetate from the previous step (ca. 2.72 mmol) and triethylamine (2.1 mL, 15 mmol) in acetonitrile (20 mL) was added 2,5-dioxopyrrolidin-1-yl 4-methylbenzyl carbonate (750 mg, 2.85 mmol). The resulting mixture was stirred for 1 hr at room temperature. Then the mixture was diluted with ethyl acetate (100 mL), washed with water, brine, dried over anhydrous Na$_2$SO$_4$ and concentrated under reduced pressure. The residue was purified by column chromatography over silica gel (DCM/MeOH=35/1) to afford the title compound as an off-white powder (840 mg, 75%). $[α]_D$=+13.5° (c=10 mg/mL, MeOH, 20° C.). HPLC Chiral Purity >99% ee (CHIRALPAKAD-H 4.6*150 mm, 5 um; Mobile Phase: Hexane:Isopropanol=80:20; rt=6.88 min). MS (ESI) calcd for $C_{20}H_{22}F_2N_6O$: 416.2; found: 417.5 [M+H]. $^1$H NMR (400 MHz, CD$_3$OD) δ 9.11 (s, 1H), 7.71 (d, J=4.8 Hz, 1H), 7.34 (d, J=4.8 Hz, 1H), 7.26 (d, J=8.0 Hz, 2H), 7.19 (d, J=8.0 Hz, 2H), 5.11 (s, 2H), 4.38-4.26 (m, 1H), 4.18-4.14 (m, 1H), 4.01 (dd, J=5.2, 13.6 Hz, 1H), 3.62 (dd, J=8.8, 13.6 Hz, 1H), 3.29-3.11 (m, 1H), 3.03-2.89 (m, 1H), 2.65-2.50 (m, 1H), 2.35 (s, 3H), 2.00-1.94 (m, 1H), 1.62-1.52 (m, 1H).

Example 1.1a. R-4-methylbenzyl 4-(([1,2,4]triazolo[4,3-a]pyrazin-8-ylamino)methyl)-3,3-difluoropiperidine-1-carboxylate methanesulfonate (E1-1.2a)

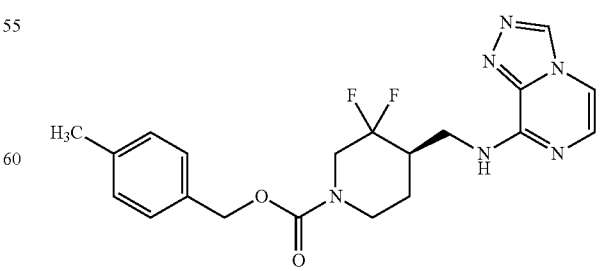

CH$_3$SO$_3$H

To a stirred solution of (+)-R-4-methylbenzyl 4-(([1,2,4]triazolo[4,3-a]pyrazin-8-ylamino)-methyl)-3,3-difluoropiperidine-1-carboxylate (1.8 g, 4.32 mmol) in 30 mL DCM/MeOH (1/1) was added methanesulfonic acid (420 mg, 4.32 mmol). The resulting solution was stirred at room temperature for 30 min. The solvent was evaporated, and the solid thus obtained was triturated with ether (25 mL) to give the title compound as a white solid (1.90 g, 86%). MS (ESI) calcd for $C_{20}H_{22}F_2N_6O_6$: 416.2; found: 417.5 [M+H]. $^1$H NMR (400 MHz, $CD_3OD$) δ 9.33 (s, 1H), 7.96 (d, J=4.8 Hz, 1H), 7.27 (d, J=4.8 Hz, 1H), 7.26 (d, J=8.0 Hz, 2H), 7.19 (d, J=8.0 Hz, 2H), 5.12 (s, 2H), 4.47-4.33 (m, 1H), 4.27-4.21 (m, 1H), 4.07-3.99 (m, 1H), 3.75-3.65 (m, 1H), 3.30-3.14 (m, 1H), 3.08-2.92 (m, 1H), 2.72 (s, 3H), 2.70-2.60 (m, 1H), 2.35 (s, 3H), 2.08-2.00 (m, 1H), 1.67-1.56 (m, 1H).

Example 1.2. (±)-4-methylbenzyl 4-(([1,2,4]triazolo[4,3-a]pyrazin-8-ylamino)methyl)-3,3-difluoropiperidine-1-carboxylate (C-1.2)

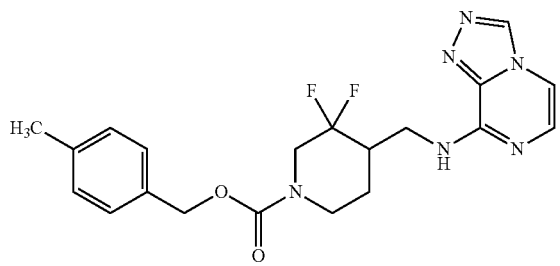 [SMILES: Cc1ccc(COC(=O)N2CCC(CNc3nccn4cnnc34)C(F)(F)C2)cc1]

Step 1: methyl 2-(1-benzyl-3,3-difluoropiperidin-4-ylidene)acetate

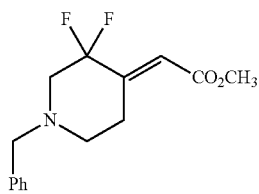 [SMILES: COC(=O)/C=C1\CCN(Cc2ccccc2)CC1(F)F]

To a stirred solution of 1-benzyl-3,3-difluoropiperidine-4,4-diol (10.9 g, 44.8 mmol) in toluene (350 mL) was added methyl (triphenylphosphoranylidene)acetate (18.0 g, 52 mmol) at room temperature. The reaction mixture was stirred at room temperature for 2 hrs. The reaction mixture was concentrated in vacuo and purified by column chromatography over silica gel (EtOAc/hexane=1/6) to afford the title compound as a white powder (10.9 g, 86%). MS (ESI) calcd for $C_{15}H_{17}F_2NO_2$: 281.1; found: 282.3 [M+H]. $^1$H NMR (400 MHz, $CDCl_3$) δ 7.36-7.27 (m, 5H), 6.19 (br s, 1H), 3.74 (s, 3H), 3.64 (s, 2H), 3.14-3.11 (m, 2H), 2.79 (t, J=11.2 Hz, 2H), 2.60 (t, J=5.6 Hz, 2H).

Step 2: methyl 2-(3,3-difluoropiperidin-4-yl)acetate

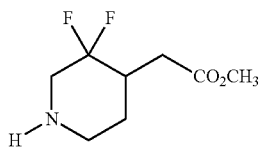 [SMILES: COC(=O)CC1CCNCC1(F)F]

To a stirred solution of methyl 2-(1-benzyl-3,3-difluoropiperidin-4-ylidene)acetate (10.9 g, 39 mmol) in MeOH (200 mL) was added 10% Pd/C (1.0 g, 10%). The reaction mixture was purged with $H_2$ three times, and hydrogenated at room temperature under atmospheric pressure. After the starting material was consumed, the mixture was filtered through celite and the filter pad was extracted with MeOH. The combined filtrates were concentrated and the residue was purified by column chromatography over silica gel (EtOAc/hexane=1/6) to afford the title compound as a clear oil (5.30 g, 70%). MS (ESI) calcd for $C_8H_{13}F_2NO_2$: 193.1; found: 194.4 [M+H]. $^1$HNMR (400 MHz, $CDCl_3$) δ 3.67 (s, 3H), 3.20-3.11 (m, 1H), 3.03-2.99 (m, 1H), 2.83-2.70 (m, 2H), 2.66-2.56 (m, 1H), 2.46-2.29 (m, 1H), 2.25-2.19 (m, 1H), 1.90-1.82 (m, 1H), 1.64 (br s, 1H), 1.45-1.34 (m, 1H).

Step 3: 4-methylbenzyl 3,3-difluoro-4-(2-methoxy-2-oxoethyl)piperidine-1-carboxylate

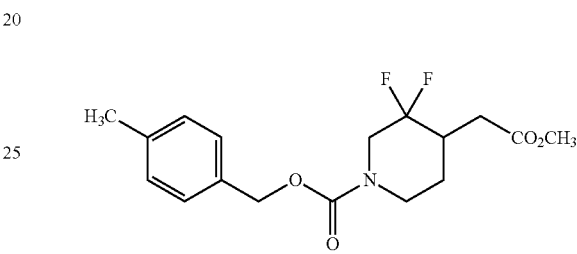

To a stirred solution of p-tolylmethanol (1.5 g, 12 mmol) in DMSO (20 mL) was added CDI (1.9 g, 11 mmol) at room temperature under $N_2$ atmosphere. The mixture was stirred for 1 hr and methyl 2-(3,3-difluoropiperidin-4-yl)acetate (2.0 g, 10 mmol) was added in DMSO (10 mL) at room temperature. The mixture was heated at 50° C. overnight, allowed to cool to room temperature and diluted with EtOAc. The organic layer was washed with water, brine, dried over $Na_2SO_4$ and concentrated. The concentrate was purified by column chromatography over silica gel (EtOAc/hexane=1/6) to afford the title compound as a clear oil (1.5 g, 43%). $^1$H NMR (400 MHz, $CDCl_3$) δ 7.26 (d, J=8.0 Hz, 2H), 7.17 (d, J=8.0 Hz, 2H), 5.09 (br s, 2H), 4.64 (d, J=5.2 Hz, 1H), 4.54-4.06 (m, 2H), 3.69 (d, J=12.0 Hz, 2H), 3.12-2.73 (m, 2H), 2.35 (s, 3H), 2.29-2.22 (m, 1H), 1.92-1.65 (m, 1H), 1.59 (s, 3H).

Step 4: 2-(3,3-difluoro-1-((4-methylbenzyloxy)carbonyl)piperidin-4-yl)acetic acid

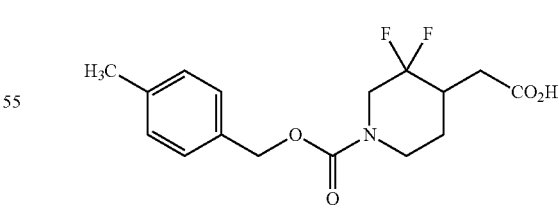

To a stirred solution of 4-methylbenzyl 3,3-difluoro-4-(2-methoxy-2-oxoethyl)piperidine-1-carboxylate (1.5 g, 4.4 mmol) in THF (20 mL) was added aqueous NaOH (1 M, 20 mL). The reaction mixture was stirred at room temperature for 5 hr and quenched with 1N HCl under ice-water bath cooling. The mixture was concentrated and extracted with ethyl acetate. The ethyl acetate layer was washed with water, brine, dried over Na$_2$SO$_4$ and concentrated to afford the title compound as a white solid (650 mg, 46%). $^1$H NMR (400 MHz, CDCl$_3$) δ 7.25 (d, J=8.0 Hz, 2H), 7.16 (d, J=8.0 Hz, 2H), 5.08 (s, 2H), 4.16 (br s, 2H), 2.91-2.71 (m, 2H), 2.35 (s, 3H), 2.31-2.26 (m, 1H), 2.01-1.88 (m, 1H), 1.80-1.69 (m, 1H), 1.25-1.14 (m, 2H).

Step 5: 4-methylbenzyl 4-(aminomethyl)-3,3-difluoropiperidine-1-carboxylate

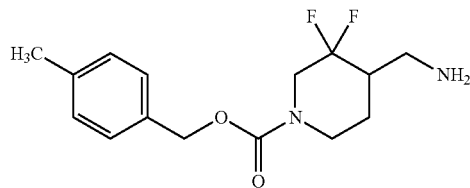 [SMILES: Cc1ccc(COC(=O)N2CCC(CN)C(F)(F)C2)cc1]

To a stirred solution of 2-(3,3-difluoro-1-((4-methylbenzyloxy)carbonyl)piperidin-4-yl)acetic acid (650 mg, 1.98 mmol) in toluene (3 mL) was added triethylamine (93 mg, 1.0 mmol) and DPPA (187 mg, 2.98 mmol). The reaction mixture was stirred at 70° C. for 1 hr. A mixture of dioxane (3 mL) and 1M aqueous NaOH (3 mL) was added and the reaction mixture was allowed to cool to room temperature. The mixture was concentrated under reduced pressure and diluted with EtOAc. The organic layer was washed with water, brine, dried over Na$_2$SO$_4$ and concentrated. The residue was taken up in dichloromethane and filtered. The filtrate was concentrated to afford crude product as a yellow oil (600 mg). MS (ESI) calcd for C$_{15}$H$_{20}$F$_2$N$_2$O$_2$: 298.2; found: 299.2 [M+H].

Step 6: (±)-4-methylbenzyl 4-(([1,2,4]triazolo[4,3-a]pyrazin-8-ylamino)methyl)-3,3-difluoropiperidine-1-carboxylate

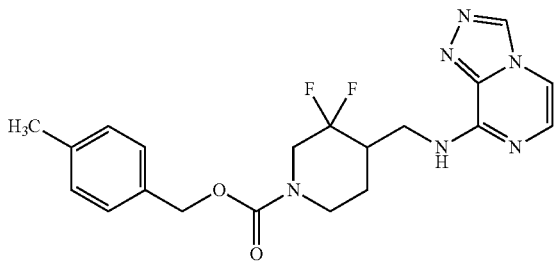 [SMILES: Cc1ccc(COC(=O)N2CCC(CNc3nccn4cnnc34)C(F)(F)C2)cc1]

A mixture of crude 4-methylbenzyl 4-(aminomethyl)-3,3-difluoropiperidine-1-carboxylate (600 mg, 2.0 mmol), 8-chloro-[1,2,4]triazolo[4,3-a]pyrazine (360 mg, 2.0 mmol) and DIPEA (0.76 mL, 4.0 mmol) in butyl alcohol (10 mL) was heated at 130° C. overnight. The mixture was allowed to cool to room temperature and concentrated under reduced pressure. The concentrate was purified by column chromatography over silica gel (100% ethyl acetate) to afford the title compound as a light gray powder (150 mg, 18%). MS (ESI) calcd for C$_{20}$H$_{22}$F$_2$N$_6$O$_2$: 416.2; found: 417.3 [M+H]. $^1$H NMR (400 MHz, CD$_3$OD) δ 9.16 (s, 1H), 7.77 (d, J=4.8 Hz, 1H), 7.29 (d, J=4.8 Hz, 1H), 7.24 (d, J=8.0 Hz, 2H), 7.17 (d, J=8.0 Hz, 2H), 5.09 (s, 2H), 4.33 (br s, 1H), 4.19-4.15 (m, 1H), 4.05-3.95 (m, 1H), 3.72-3.58 (m, 1H), 3.25-2.90 (m, 2H), 2.67-2.51 (m, 1H), 2.33 (s, 3H), 1.99-1.93 (m, 1H), 1.62-1.52 (m, 1H).

Example 1.3. (−)-S-4-methylbenzyl 4-(([1,2,4]triazolo[4,3-a]pyrazin-8-ylamino)methyl)-3,3-difluoropiperidine-1-carboxylate (E2-1.2)

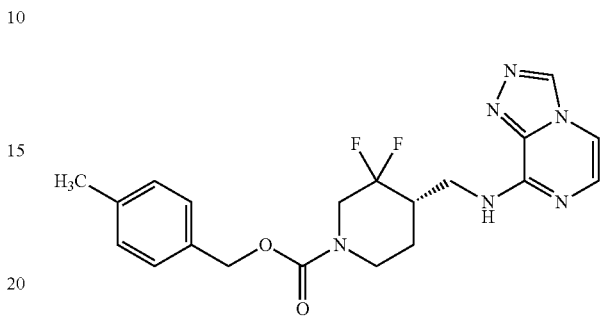

(±)-4-methylbenzyl 4-(([1,2,4]triazolo[4,3-a]pyrazin-8-ylamino)methyl)-3,3-difluoropiperidine-1-carboxylate was separated by chiral HPLC [CHIRALPAKAD-H4.6*150 mm, 5 um. Mobile phase: A:Hexanes B:(Ethanol/Methanol=2:1)=70:30] to give the respective pure enantiomers with (+)-R-4-methylbenzyl 4-(([1,2,4]triazolo[4,3-a]pyrazin-8-ylamino)methyl)-3,3-difluoropiperidine-1-carboxylate eluting first (rt=7.065 min) followed by (−)-S-4-methylbenzyl 4-(([1,2,4]triazolo[4,3-a]pyrazin-8-ylamino)methyl)-3,3-difluoropiperidine-1-carboxylate (rt=9.160 min).

(+)-R-4-methylbenzyl 4-(([1,2,4]triazolo[4,3-a]pyrazin-8-ylamino)methyl)-3,3-difluoropiperidine-1-carboxylate. CHIRALPAKAD rt=7.065 min, α$^{20}_D$=+13.5° (c=10 mg/mL, MeOH).

(−)-S-4-methylbenzyl 4-(([1,2,4]triazolo[4,3-a]pyrazin-8-ylamino)methyl)-3,3-difluoropiperidine-1-carboxylate. CHIRALPAKAD rt=9.160 min, α$^{20}_D$=−12.0° (c=10 mg/mL, MeOH).

Example. 1.4. 4-(([1,2,4]triazolo[4,3-a]pyrazin-5-ylamino)methyl)-3,3-difluoropiperidine-1-carboxylate (E1-2.2)

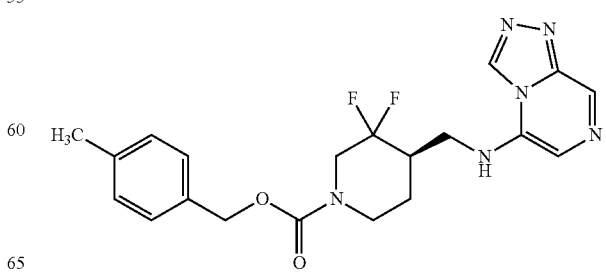

Step 1: R-tert-butyl 4-(([1,2,4]triazolo[4,3-a]pyrazin-5-ylamino)methyl)-3,3-difluoropiperidine-1-carboxylate

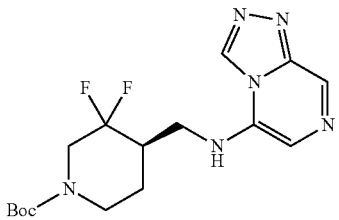 [SMILES: CC(C)(C)OC(=O)N1CC[C@H](CNc2cncc3nncn23)C(F)(F)C1]

A mixture of R-tert-butyl 4-(aminomethyl)-3,3-difluoropiperidine-1-carboxylate (300 mg, 1.20 mmol), 5-bromo-[1,2,4]triazolo[4,3-a]pyrazine (356 mg, 1.80 mmol) and DIPEA (0.42 mL, 2.40 mmol) in NMP (9 mL) was heated to 130° C. with stirring overnight. The orange solution was allowed to cool down to rt and diluted with ethyl acetate. The organic phase was washed with water, brine, dried over $Na_2SO_4$ and concentrated under vacuum. The concentrate was purified by column chromatography over silica gel (hexane/ethyl acetate=1/3) to afford the title compound as a yellow powder (210 mg, 48%). $^1$H NMR (400 MHz, $CDCl_3$) δ 9.25 (s, 1H), 8.85 (s, 1H), 7.27 (s, 1H), 6.17-6.01 (m, 1H), 4.51-4.17 (m, 2H), 3.93-3.84 (m, 1H), 3.52-3.44 (m, 1H), 3.11-2.71 (m, 2H), 2.52-2.37 (m, 1H), 2.03-1.92 (m, 1H), 1.73-1.63 (m, 1H), 1.48 (s, 9H).

Step 2: R—N-((3,3-difluoropiperidin-4-yl)methyl)-[1,2,4]triazolo[4,3-a]pyrazin-5-amine trifluoroacetate

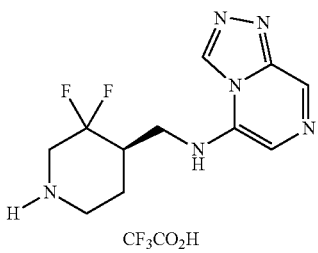

To a solution of R-tert-butyl 4-(([1,2,4]triazolo[4,3-a]pyrazin-5-ylamino)methyl)-3,3-difluoropiperidine-1-carboxylate (256 mg, 0.69 mmol) in dichloromethane (5 mL) was added TFA (2 mL) at room temperature. After stirring for 30 min, the mixture was concentrated to afford the title compound as a yellow oil which was directly used as crude salt in the next step. $^1$H NMR (400 MHz, $CD_3OD$) δ 9.38 (s, 1H), 8.71 (s, 1H), 7.33 (s, 1H), 3.99-3.92 (m, 1H), 3.84-3.75 (m, 1H), 3.57-3.46 (m, 3H), 3.18-3.11 (m, 1H), 2.83-2.69 (m, 1H), 2.40-2.33 (m, 1H), 1.92-1.81 (m, 1H).

Step 3: R-4-methylbenzyl 4-(([1,2,4]triazolo[4,3-a]pyrazin-5-ylamino)methyl)-3,3-difluoropiperidine-1-carboxylate

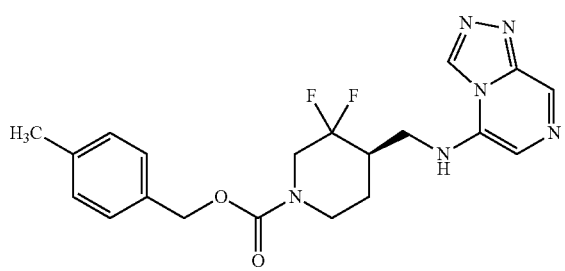 [SMILES: Cc1ccc(COC(=O)N2CC[C@H](CNc3cncc4nncn34)C(F)(F)C2)cc1]

To a solution of 2,5-dioxocyclopentyl 4-methylbenzyl carbonate (201 mg, 0.76 mmol) in MeCN (5 mL) was added R—N-((3,3-difluoropiperidin-4-yl)methyl)-[1,2,4]triazolo[4,3-a]pyrazin-5-amine trifluoroacetate (470 mg, 0.69 mmol) and triethylamine (0.32 mL, 2.30 mmol) at room temperature. After stirring for 1 hr, the mixture was diluted with EtOAc. The organic phase was washed with water, brine, dried over $Na_2SO_4$ and concentrated under vacuum. The concentrate was purified by column chromatography over silica gel (DCM/MeOH=40/1) to afford the title compound as a yellow powder (126 mg, two steps yield 43.6%). MS (ESI) calcd for $C_{20}H_{22}F_2N_6O_2$: 416.2; found: 417.5 [M+H]. $^1$H NMR (400 MHz, $CD_3OD$) δ 9.33 (s, 1H), 8.64 (s, 1H), 7.24 (d, J=8.0 Hz, 2H), 7.23 (s, 1H), 7.16 (d, J=8.0 Hz, 2H), 5.10 (s, 2H), 4.40-4.29 (m, 1H), 4.23-4.14 (m, 1H), 3.86 (dd, J=4.8 and 14.4 Hz, 1H), 3.41 (dd, J=4.8 and 14.4 Hz, 1H), 3.30-2.15 (m, 1H), 3.05-2.88 (m, 1H), 2.61-2.47 (m, 1H), 2.33 (s, 3H), 2.10-2.00 (m, 1H), 1.65-1.53 (m, 1H).

Example 1.4a. R-4-methylbenzyl 4-(([1,2,4]triazolo[4,3-a]pyrazin-5-ylamino)methyl)-3,3-difluoropiperidine-1-carboxylate methanesulfonate (E1-2.2a)

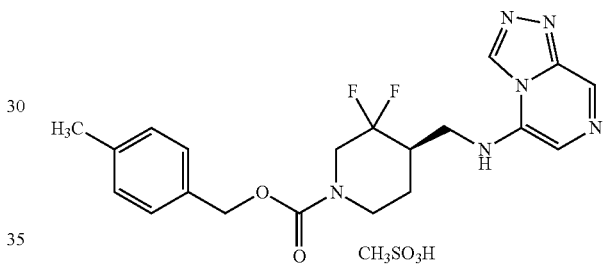

To a solution of R-4-methylbenzyl 4-(([1,2,4]triazolo[4,3-a]pyrazin-5-ylamino)methyl)-3,3-difluoropiperidine-1-carboxylate (127 mg, 0.31 mmol) in MeOH (3 mL) was added methanesulfonic acid (29 mg, 0.30 mmol). After stirring for 1 h at rt, the mixture was concentrated to afford the title compound as a white powder (131 mg, 84%). MS (ESI) calcd for $C_{20}H_{22}F_2N_6O_2$: 416.2; found: 417.5 [M+H]. $^1$H NMR (400 MHz, $CD_3OD$) δ 9.58 (s, 1H), 8.85 (s, 1H), 7.70 (s, 1H), 7.24 (d, J=8.0 Hz, 2H), 7.17 (d, J=8.0 Hz, 2H), 5.10 (s, 2H), 4.45-4.30 (m, 1H), 4.24-4.18 (m, 1H), 3.95 (dd, J=5.2 and 14.0 Hz, 1H), 3.57 (dd, J=8.0 and 14.0 Hz, 1H), 3.26-2.90 (m, 2H), 2.70 (s, 3H), 2.64-2.51 (m, 1H), 2.33 (s, 3H), 2.11-2.02 (m, 1H), 1.67-1.54 (m, 1H).

Example 1.5. (+)-R-4-methylbenzyl 4-(([1,2,4]triazolo[1,5-a]pyridin-2-ylamino)methyl)-3,3-difluoropiperidine-1-carboxylate (E1-9.2)

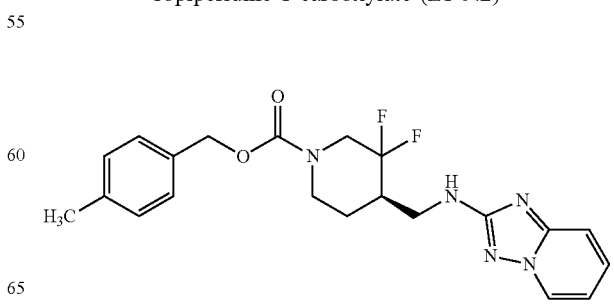

Step 1: R-tert-butyl 4-(([1,2,4]triazolo[1,5-a]pyridin-2-ylamino)methyl)-3,3-difluoropiperidine-1-carboxylate

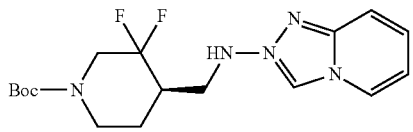

To a stirred suspension of 2-bromo-[1,2,4]triazolo[1,5-a]pyridine (500 mg, 2.53 mmol) in t-butyl alcohol (15 mL) were added (−)-R-tert-butyl 4-(aminomethyl)-3,3-difluoro piperidine-1-carboxylate (758 mg, 3.03 mmol), Brettphos precatalyst (75 mg), Brettphos (75 mg) and Cs$_2$CO$_3$ (2.25 g, 5.06 mmol) at room temperature under nitrogen. The reaction mixture was heated to 100° C. overnight. The mixture was allowed to cool to room temperature, diluted with DCM and filtered through celite. The filtrate was washed with water, dried over Na$_2$SO$_4$ and concentrated in vacuo. The residue was purified by column chromatography over silica gel (50% hexanes in EtOAc) to afford the title compound as an off-white powder (298 mg, 32%). MS (ESI) calcd for C$_{17}$H$_{23}$F$_2$N$_5$O$_2$: 367.2; found: 368.5 [M+H]. $^1$H NMR (400 MHz, CD$_3$OD) δ 8.45 (d, J=6.8 Hz, 1H), 7.53-7.48 (m, 1H), 7.37 (d, J=8.8 Hz, 1H), 6.96-6.92 (m, 1H), 4.28-4.14 (m, 1H), 4.12-4.04 (m, 1H), 3.77 (dd, J=14, 4.8 Hz, 1H), 3.36-3.33 (m, 1H), 3.18-3.07 (m, 1H), 2.92-2.84 (m, 1H), 2.48-2.35 (m, 1H), 1.98-1.91 (m, 1H), 1.56-1.48 (m, 1H), 1.47 (s, 9H).

Step 2: (+)-R-4-methylbenzyl 4-(([1,2,4]triazolo[1,5-a]pyridin-2-ylamino)methyl)-3,3-difluoropiperidine-1-carboxylate

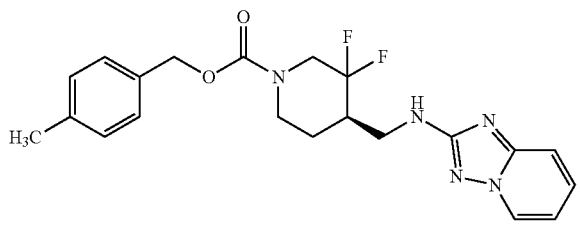 [SMILES: Cc1ccc(COC(=O)N2CC[C@H](CNc3nc4ccccn4n3)C(F)(F)C2)cc1]

To a solution of R-tert-butyl 4-(([1,2,4]triazolo[1,5-a]pyridin-2-ylamino)methyl)-3,3-difluoropiperidine-1-carboxylate (230 mg, 0.63 mmol) in DCM (6 mL) was added TFA (2 mL). The reaction solution was stirred at room temperature for 30 min. The solvent was evaporated to afford the intermediate R—N-((3,3-difluoropiperidin-4-yl)methyl)-[1,2,4]-triazolo[1,5-a]pyridin-2-amine trifluoroacetic acid salt as a yellow oil (260 mg) which was used in the next step without further purification. To a stirred solution of R—N-((3,3-difluoropiperidin-4-yl)methyl)-[1,2,4]-triazolo[1,5-a]pyridin-2-amine trifluoroacetate salt (260 mg) in acetonitrile (5 mL) were added triethylamine (0.26 mL) and 2,5-dioxopyrrolidin-1-yl 4-methylbenzyl carbonate (181 mg, 0.69 mmol). After stirring for 1 h at room temperature, the reaction mixture was concentrated in vacuo and the residue was taken up in EtOAc. The solution was washed with water, brine, dried over Na$_2$SO$_4$ and concentrated in vacuo. The residue was purified by column chromatography over silica gel (50% hexanes in EtOAc) to afford the title compound as a white powder (234 mg, 90%). [α]$_D$=+26.2° (c=7.5 mg/mL, MeOH, 28° C.). MS (ESI) calcd for C$_{21}$H$_{23}$F$_2$N$_5$O$_2$: 415.2; found: 416.6 [M+H]. $^1$H NMR (400 MHz, CD$_3$OD) δ 8.44 (d, J=6.4 Hz, 1H), 7.52-7.48 (m, 1H), 7.36 (d, J=8.8 Hz, 1H), 7.24 (d, J=8.0 Hz, 2H), 7.17 (d, J=8.0 Hz, 2H), 6.95-6.92 (m, 1H), 5.12-5.06 (m, 2H), 4.34-4.22 (m, 1H), 4.16-4.11 (m, 1H), 3.77 (dd, J=14, 4.8 Hz, 1H), 3.36-3.31 (m, 1H), 3.25-3.09 (m, 1H), 3.00-2.89 (m, 1H), 2.51-2.38 (m, 1H), 2.33 (s, 3H), 2.00-1.92 (m, 1H), 1.57-1.46 (m, 1H).

Example 1.6. (+)-R-4-methylbenzyl-4-((1H-pyrazolo[3,4-d]pyrimidin-6-ylamino)methyl)-3,3-difluoropiperidine-1-carboxylate (E1-8.2)

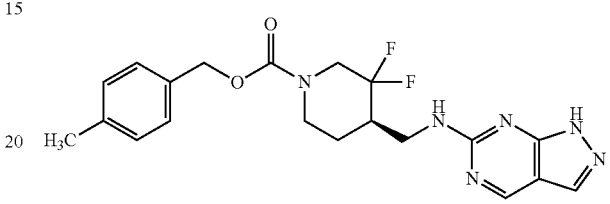

Step 1: R-tert-butyl 4-((1H-pyrazolo[3,4-d]pyrimidin-6-ylamino)methyl)-3,3-difluoropiperidine-1-carboxylate

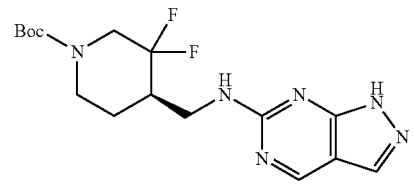 [SMILES: CC(C)(C)OC(=O)N1CC[C@H](CNc2ncc3cn[nH]c3n2)C(F)(F)C1]

A mixture of R-tert-butyl 4-(aminomethyl)-3,3-difluoropiperidine-1-carboxylate (440 mg, 1.60 mmol), 6-chloro-1H-pyrazolo[3,4-d]pyrimidine (272 mg, 1.76 mmol) and DIPEA (0.84 mL, 4.80 mmol) in i-PrOH (10 mL) was heated overnight at 85° C. The mixture was allowed to cool to room temperature and was concentrated under reduced pressure. The concentrate was purified by column chromatography over silica gel (hexane/ethyl acetate=1/3) to afford the title compound as a yellow powder (510 mg, 86%). MS (ESI) calcd for C$_{16}$H$_{22}$F$_2$N$_6$O$_2$: 368.2; found: 369.4 [M+H]. $^1$H NMR (400 MHz, CDCl$_3$) δ 10.88 (brs, 1H), 8.78 (s, 1H), 7.92 (s, 1H), 5.77-5.67 (m, 1H), 4.50-4.00 (m, 2H), 3.90-3.84 (m, 1H), 3.67-3.58 (m, 1H), 3.07-2.68 (m, 2H), 2.38-2.23 (m, 1H), 1.91-1.85 (m, 1H), 1.62-1.56 (m, 1H), 1.46 (s, 9H).

Step 2: R—N-((3,3-difluoropiperidin-4-yl)methyl)-1H-pyrazolo[3,4-d]pyrimidin-6-amine hydrochloride

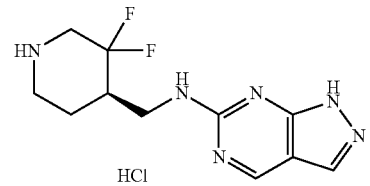 [SMILES: FC1(F)CNCC[C@@H]1CNc1ncc2cn[nH]c2n1 ; Cl]

To a solution of R-tert-butyl 4-((1H-pyrazolo[3,4-d]pyrimidin-6-ylamino)methyl)-3,3-difluoropiperidine-1-carboxylate (510 mg, 1.39 mmol) in DCM (4 mL) was added HCl in MeOH (10 mL, 2.0 M) at room temperature. After stirring overnight, the mixture was concentrated to afford the title compound as a pale-yellow powder (504 mg, 100%) which was used in the next step without further purification. MS (ESI) calcd for $C_{11}H_{14}F_2N_6$: 268.1; found: 269.2 [M+H]. $^1$H NMR (400 MHz, $CD_3OD$) δ 9.09 (s, 1H), 8.33 (s, 1H), 4.04 (dd, J=5.2, 14.0 Hz, 1H), 3.81-3.73 (m, 1H), 3.63-3.46 (m, 3H), 3.21-3.13 (m, 1H), 2.83-2.69 (m, 1H), 2.33-2.24 (m, 1H), 1.90-1.79 (m, 1H).

Step 3: (+)-R-4-methylbenzyl-4-((1H-pyrazolo[3,4-d]pyrimidin-6-ylamino)methyl)-3,3-difluoropiperidine-1-carboxylate

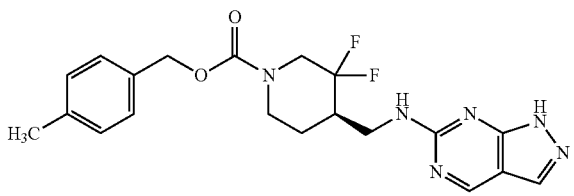 [SMILES: Cc1ccc(COC(=O)N2CC[C@H](CNc3ncc4cn[nH]c4n3)C(F)(F)C2)cc1]

To a solution of p-tolylmethanol (263 mg, 2.15 mmol) in DMSO (4 mL) was added CDI (349 mg, 2.15 mmol) at room temperature. After stirring for 1 hr, R—N-((3,3-difluoropiperidin-4-yl)-methyl)-1H-pyrazolo[3,4-d]pyrimidin-6-amine hydrochloride (504 mg, 1.66 mmol) was added. The mixture was heated to 80° C. under $N_2$ atmosphere. After stirring overnight, the mixture was diluted with EtOAc. The organic phase was washed with water and brine, dried over $Na_2SO_4$ and concentrated under vacuum. The concentrate was purified by column chromatography over silica gel (DCM/MeOH=40/1) to afford the title compound as a white powder (306 mg, 49%). $[α]_D$=+22° (c=8.5 mg/mL, 50% DCM in MeOH, 26° C.). MS (ESI) calcd for $C_{20}H_{22}F_2N_6O_2$: 416.2; found: 417.4 [M+H]. $^1$H NMR (400 MHz, $CD_3OD$) δ 8.77 (s, 1H), 7.92 (s, 1H), 7.24 (d, J=8.0 Hz, 2H), 7.17 (d, J=8.0 Hz, 2H), 5.09 (s, 2H), 4.33-4.23 (m, 1H), 4.16-4.10 (m, 1H), 3.87 (dd, J=5.2 and 14.0 Hz, 1H), 3.47-3.39 (m, 1H), 3.25-3.10 (m, 1H), 3.02-2.87 (m, 1H), 2.54-2.40 (m, 1H), 2.33 (s, 3H), 1.95-1.88 (m, 1H), 1.58-1.47 (m, 1H).

Example 1.6a. (+)-R-4-methylbenzyl4-((1H-pyrazolo[3,4-d]pyrimidin-6-ylamino)methyl)-3,3-difluoropiperidine-1-carboxylate methanesulfonate (E1-8.2a)

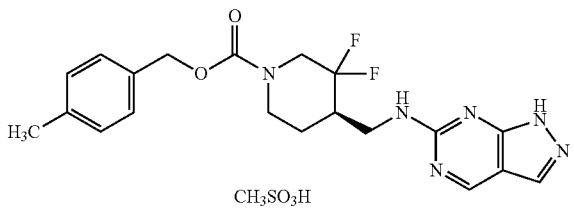 [SMILES: Cc1ccc(COC(=O)N2CC[C@H](CNc3ncc4cn[nH]c4n3)C(F)(F)C2)cc1 ; "CH3SO3H"]

To a solution of R-4-methylbenzyl4-((1H-pyrazolo[3,4-d]pyrimidin-6-ylamino)methyl)-3,3-difluoropiperidine-1-carboxylate (184 mg, 0.44 mmol) in DCM/MeOH (12 mL/4 mL) was added methanesulfonic acid (43 mg, 0.44 mmol). After stirring for 1 h at rt, the mixture was concentrated to afford the title compound as a white powder (191 mg, 84%). $[α]_D$=+11.2° (c=10 mg/mL, 50% DCM in MeOH, 26° C.). MS (ESI) calcd for $C_{20}H_{22}F_2N_6O_2$: 416.2; found: 417.5 [M+H]. $^1$H NMR (400 MHz, $CD_3OD$) δ 9.03 (s, 1H), 8.29 (s, 1H), 7.24 (d, J=8.0 Hz, 2H), 7.17 (d, J=8.0 Hz, 2H), 5.09 (s, 2H), 4.37-4.27 (m, 1H), 4.20-4.13 (m, 1H), 3.94 (dd, J=5.2 and 14.0 Hz, 1H), 3.58-3.53 (m, 1H), 3.24-3.10 (m, 1H), 3.03-2.92 (m, 1H), 2.72 (s, 3H), 2.56-2.44 (m, 1H), 2.33 (s, 3H), 1.99-1.90 (m, 1H), 1.61-1.50 (m, 1H).

Example 1.7. R-4-chlorobenzyl 4-((([1,2,4]triazolo[4,3-a]pyrazin-8-ylamino)methyl)-3,3-difluoropiperidine-1-carboxylate (E1-1.3)

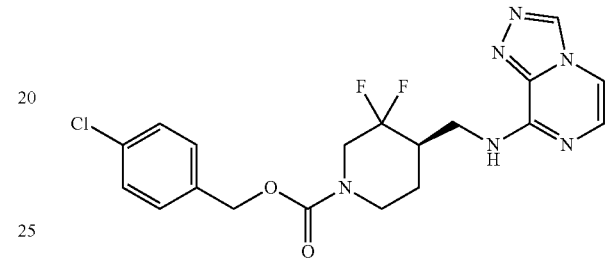

To a stirred solution of of 4-chlorobenzyl alcohol (115 mg, 0.81 mmol) and bis-(2,5-dioxopyrrolidin-1-yl)carbonate (207 mg, 0.81 mmol) in acetonitrile (3.0 mL) and $CH_2Cl_2$ (3.0 mL) was added 4-dimethylaminopyridine (49 mg, 0.40 mmol) and the mixture was stirred for 2 h at room temperature. N-((3,3-difluoropiperidin-4-yl)methyl)-[1,2,4]triazolo[4,3-a]pyrazin-8-amine trifluoroacetate salt (280 mg, 0.73 mmol) in MeCN (2 mL) and TEA (0.3 mL, 2.2 mmol) were added and the resulting mixture was stirred for 1 hour at room temperature. The mixture was then diluted with ethyl acetate (5 mL) and the organic phase was washed with water, brine, dried over anhydrous $Na_2SO_4$ and concentrated under reduced pressure. The residue was purified by column chromatography over silica gel (DCM/MeOH=50/1) to afford the title compound as a pale yellow powder (190 mg, 59%). MS (ESI) calcd for $C_{19}H_{19}ClF_2N_6O_2$: 436.1, 438.1; found: 437.4, 439.4 [M+H]. $^1$H NMR (400 MHz, $CD_3OD$) δ 9.08 (s, 1H), 7.69 (d, J=4.8 Hz, 1H), 7.39-7.33 (m, 4H), 7.32 (d, J=4.8 Hz, 1H), 5.16-5.09 (m, 2H), 4.37-4.26 (m, 1H), 4.19-4.11 (m, 1H), 4.01-3.95 (m, 1H), 3.65-3.57 (m, 1H), 3.27-3.07 (m, 1H), 3.07-2.88 (m, 1H), 2.65-2.47 (m, 1H), 1.99-1.91 (m, 1H), 1.63-1.49 (m, 1H).

Example 1.7a. R-4-chlorobenzyl 4-((([1,2,4]triazolo[4,3-a]pyrazin-8-ylamino)methyl)-3,3-difluoropiperidine-1-carboxylate methanesulfonate (E1-1.3a)

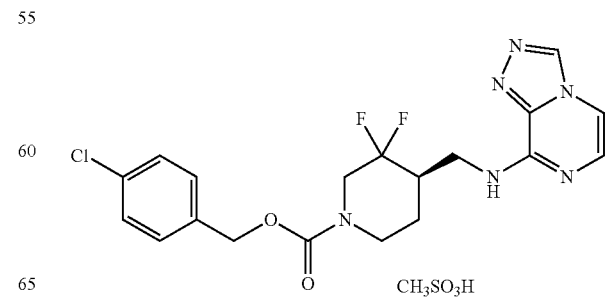

To a stirred solution of R-4-chlorobenzyl 4-(([1,2,4]triazolo[4,3-a]pyrazin-8-ylamino)methyl)-3,3-difluoropiperidine-1-carboxylate (99 mg, 0.23 mmol) in MeOH (2.0 mL) was added CH$_3$SO$_3$H (22 mg, 0.23 mmol) at rt. After stirring for 30 min, the mixture was concentrated to afford the title compound as an off-white powder (116 mg, 96%). MS (ESI) calcd for C$_{19}$H$_{19}$ClF$_2$N$_6$O$_2$: 436.1, 438.4; found: 437.4, 439.4[M+H]. $^1$H NMR (400 MHz, CD$_3$OD) δ 9.31 (s, 1H), 7.94 (d, J=4.8 Hz, 1H), 7.36 (s, 4H), 7.25 (d, J=4.8 Hz, 1H), 5.19-5.09 (m, 2H), 4.44-4.33 (m, 1H), 4.26-4.18 (m, 1H), 4.06-3.96 (m, 1H), 3.73-3.62 (m, 1H), 3.29-3.14 (m, 1H), 3.11-2.91 (m, 1H), 2.70 (s, 3H), 2.68-2.58 (m, 1H), 2.07-1.99 (m, 1H), 1.66-1.53 (m, 1H).

Example 1.8. R-4-fluorobenzyl 4-(([1,2,4]triazolo[4,3-a]pyrazin-8-ylamino)methyl)-3,3-difluoropiperidine-1-carboxylate (E1-1.4)

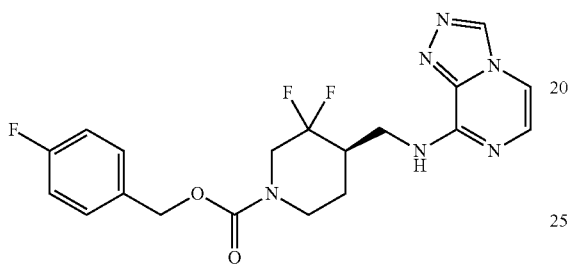

To a stirred solution of 4-fluorobenzyl alcohol (300 mg, 2.38 mmol) in DCM-MeCN (1:1 v/v, 10 mL) were added N,N'-disuccinimidyl carbonate (610 mg, 2.38 mmol) and DMAP (145 mg, 1.19 mmol) at ambient temperature. A clear solution was gradually obtained, and the mixture was stirred for 1 h at room temperature. Triethylamine (1.0 mL, 7.1 mmol) was then added followed by R—N-((3,3-difluoropiperidin-4-yl)methyl)-[1,2,4]triazolo[4,3-a]pyrazin-8-amine TFA salt (780 mg, 2.14 mmol) in acetonitrile (3 mL). The resulting mixture was stirred for 1 hr at room temperature and the mixture was concentrated in vacuo. The residue was dissolved in ethyl acetate and the organic phase was washed with water, brine, dried over Na$_2$SO$_4$, and concentrated in vacuo. The concentrate was purified by column chromatography over silica gel (ethyl acetate) to afford the title compound as an off-white powder (446 mg, 50%). MS (ESI) calcd for C$_{19}$H$_{19}$F$_3$N$_6$O$_2$: 420.2; found: 421.5 [M+H]. $^1$H NMR (400 MHz, CDCl$_3$) δ 8.71 (s, 1H), 7.40 (d, J=4.8 Hz, 1H), 7.36-7.31 (m, 3H), 7.04 (t, J=8.4 Hz, 2H), 6.51-6.51 (m, 1H), 5.11 (s, 2H), 4.54-4.10 (m, 2H), 4.04-3.96 (m, 1H), 3.82-3.72 (m, 1H), 3.14-2.96 (m, 1H), 2.94-2.78 (m, 1H), 2.49-2.33 (m, 1H), 1.95-1.87 (m, 1H), 1.71-1.61 (m, 1H).

Example 1.8a. R-4-fluorobenzyl 4-(([1,2,4]triazolo[4,3-a]pyrazin-8-ylamino)methyl)-3,3-difluoropiperidine-1-carboxylate methanesulfonate (E1-1.4a)

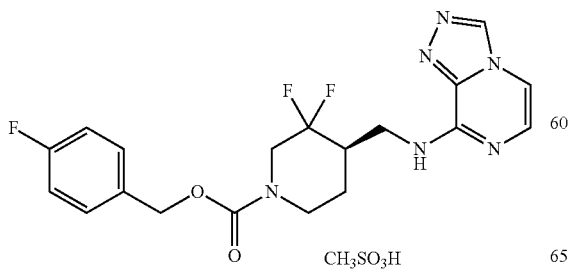

To a stirred solution of R-4-fluorobenzyl 4-(([1,2,4]triazolo[4,3-a]pyrazin-8-ylamino)-methyl)-3,3-difluoropiperidine-1-carboxylate (446 mg, 1.06 mmol) in DCM/MeOH (6 mL, 1:1) was added methylsulfonic acid (102 mg, 1.06 mmol) at room temperature. After stirring for 30 min, the mixture was concentrated. The obtained solid was washed with ether to afford the title compound as a pale brown solid (510 mg, 93%). MS (ESI) calcd for C$_{19}$H$_{19}$F$_3$N$_6$O$_2$: 420.2; found: 421.5 [M+H]. $^1$H NMR (400 MHz, CD$_3$OD) δ 9.31 (s, 1H), 7.94 (d, J=5.6 Hz, 1H), 7.43-7.37 (m, 2H), 7.25 (d, J=5.6 Hz, 1H), 7.09 (t, J=8.8 Hz, 2H), 5.13 (s, 2H), 4.43-4.32 (m, 1H), 4.24-4.17 (m, 1H), 4.06-3.95 (m, 1H), 3.73-3.63 (m, 1H), 3.32-3.10 (m, 1H), 3.09-2.92 (m, 1H), 2.70 (s, 3H), 2.68-2.58 (m, 1H), 2.06-1.98 (m, 1H), 1.65-1.53 (m, 1H).

Example 1.9. (+)-R-4-methylbenzyl 3,3-difluoro-4-((pyrimidin-2-ylamino)methyl)-piperidine-1-carboxylate (E1-22.2)

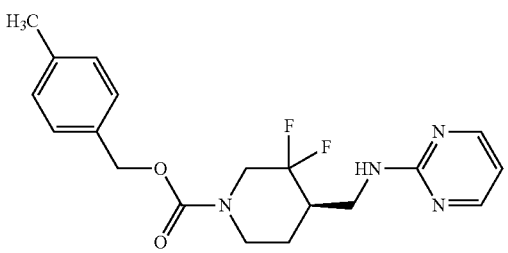 [SMILES: Cc1ccc(COC(=O)N2CC[C@H](CNc3ncccn3)C(F)(F)C2)cc1]

Step 1: R-tert-butyl 3,3-difluoro-4-((pyrimidin-2-ylamino)methyl)piperidine-1-carboxylate

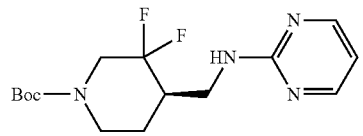 [SMILES: CC(C)(C)OC(=O)N1CC[C@H](CNc2ncccn2)C(F)(F)C1]

A solution of 2-chloropyrimidine (206 mg, 1.8 mmol), R-tert-butyl 4-(aminomethyl)-3,3-difluoropiperidine-1-carboxylate (500 mg, 1.8 mmol) and DIPEA (0.63 mL, 3.6 mmol) in n-BuOH (5 mL) was heated to 95° C. in a sealed tube overnight with stirring. The mixture was allowed to cool to rt and concentrated under reduced pressure. The residue was dissolved in ethyl acetate and the organic phase was washed with water and brine. The organic phase was dried over sodium sulfate, and concentrated in vacuo. The concentrate was treated with hexane and ethyl acetate (1.5 mL+5 mL). The resulting suspension was filtered to afford the title compound as an off-white powder (420 mg, 71%). MS (ESI) calcd for C$_{15}$H$_{22}$F$_2$N$_4$O$_2$: 328.2; found: 329.3[M+H]. $^1$H NMR (400 MHz, CDCl$_3$) δ 8.27 (d, J=4.8 Hz, 2H), 6.55 (t, J=4.8 Hz, 1H), 5.35-5.29 (m, 1H), 4.45-4.03 (m, 2H), 3.82-3.75 (m, 1H), 3.57-3.47 (m, 1H), 3.06-2.67 (m, 2H), 2.31-2.16 (m, 1H), 1.88-1.79 (m, 1H), 1.62-1.52 (m, 1H), 1.46 (s, 9H).

Step 2: R—N-((3,3-difluoropiperidin-4-yl)methyl)pyrimidin-2-amine hydrochloride

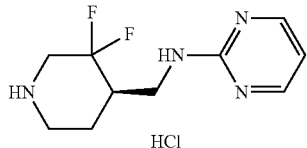 [SMILES: FC1(F)CNCC[C@@H]1CNc1ncccn1 ; Cl]

To a solution of R-tert-butyl 3,3-difluoro-4-((pyrimidin-2-ylamino)methyl)piperidine-1-carboxylate (410 mg, 1.24 mmol) in dichloromethane (2 mL) was added 2N methanolic HCl (7 mL) at room temperature. After stirring overnight at ambient temperature, the mixture was concentrated in vacuo to afford the title compound (285 mg, 76%) which was directly used in the next step. MS (ESI) calcd for $C_{10}H_{14}F_2N_4$: 228.1; found: 229.3[M+H]. $^1$H NMR (400 MHz, $CD_3OD$) δ 8.95-8.43 (m, 2H), 7.10 (t, J=5.6 Hz, 1H), 4.03 (dd, J=14.0, 5.6 Hz, 1H), 3.82-3.74 (m, 1H), 3.68 (dd, J=14.0, 5.6 Hz, 1H), 3.59-3.48 (m, 2H), 3.23-3.15 (m, 1H), 2.82-2.67 (m, 1H), 2.34-2.24 (m, 1H), 1.91-1.78 (m, 1H).

Step 3: (+)-R-4-methylbenzyl 3,3-difluoro-4-((pyrimidin-2-ylamino)methyl)-piperidine-1-carboxylate

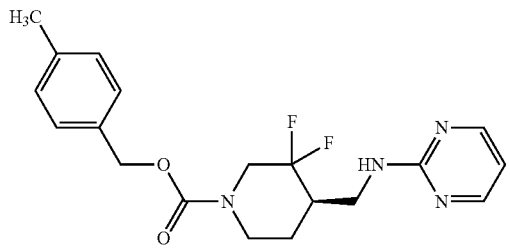 [SMILES: Cc1ccc(COC(=O)N2CC[C@H](CNc3ncccn3)C(F)(F)C2)cc1]

To a stirred solution of 4-methylbenzyl alcohol (199 mg, 1.62 mmol) in DMSO (5 mL) was added CDI (263 mg, 1.62 mmol). After stirring for 1 h at rt, (3,3-difluoro-piperidin-4-ylmethyl)-pyrimidin-2-yl-amine dihydrochloride (285 mg, 0.95 mmol) was added, and the reaction mixture was stirred overnight at 80° C. The reaction mixture was diluted with ethyl acetate, and the organic phase was washed with water and brine. The organic layer was dried over sodium sulfate, and concentrated in vacuo. The concentrate was purified by column chromatography over silica gel (hexane/EtOAc=1:1) to afford the title compound as a white powder (135 mg, 38%). %). [α]$_D$=+10.5° (c=3.7 mg/mL, MeOH, 26° C.). MS (ESI) calcd for $C_{19}H_{22}F_2N_4O_2$: 376.2; found: 377.4 [M+H]. $^1$H NMR (400 MHz, $CDCl_3$) δ 8.27 (d, J=4.8 Hz, 2H), 7.25 (d, J=8.0 Hz, 2H), 7.17 (d, J=8.0 Hz, 2H), 6.55 (t, J=4.8 Hz, 1H), 5.37-5.26 (m, 1H), 5.16-5.05 (m, 2H), 4.57-4.10 (m, 2H), 3.84-3.74 (m, 1H), 3.59-3.47 (m, 1H), 3.12-2.76 (m, 2H), 2.35 (s, 3H), 2.32-2.17 (m, 1H), 1.92-1.78 (m, 1H), 1.62-1.52 (m, 1H).

Example 1.9a. R-4-methylbenzyl 3,3-difluoro-4-((pyrimidin-2-ylamino)methyl)piperidine-1-carboxylate methanesulfonate (E1-22.2a)

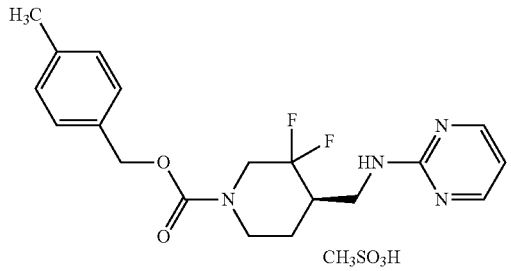

To a stirred solution of (+)-R-4-methylbenzyl 3,3-difluoro-4-((pyrimidin-2-ylamino)methyl)-piperidine-1-carboxylate (123 mg, 0.33 mmol) in MeOH (2.0 mL) was added $CH_3SO_3H$ (32 mg, 0.33 mmol) at rt. After stirring for 30 min, the mixture was concentrated to afford the title compound as an off-white powder (150 mg, 97%). MS (ESI) calcd for $C_{19}H_{22}F_2N_4O_2$: 376.2; found: 377.4[M+H]. $^1$H NMR (400 MHz, $CD_3OD$) δ 8.90-8.40 (m, 2H), 7.24 (d, J=8.0 Hz, 2H), 7.17 (d, J=8.0 Hz, 2H), 7.00 (t, J=5.6 Hz, 1H), 5.09 (s, 2H), 4.39-4.25 (m, 1H), 4.21-4.12 (m, 1H), 3.91 (dd, J=5.6 and 14.0 Hz, 1H), 3.57 (dd, J=7.6 and 14.0 Hz, 1H), 3.27-3.08 (m, 1H), 3.06-2.87 (m, 1H), 2.71 (s, 3H), 2.54-2.39 (m, 1H), 2.33 (s, 3H), 1.97-1.89 (m, 1H), 1.60-1.48 (m, 1H).

Example 1.10. R-4-methylbenzyl 3,3-difluoro-4-((pyrazin-2-ylamino)methyl)piperidine-1-carboxylate (E1-21.2)

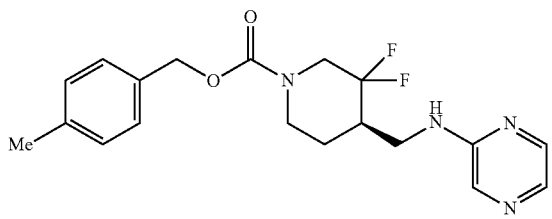 [SMILES: Cc1ccc(COC(=O)N2CC[C@H](CNc3cnccn3)C(F)(F)C2)cc1]

Step 1: R-tert-butyl 3,3-difluoro-4-((pyrazin-2-ylamino)methyl)piperidine-1-carboxylate

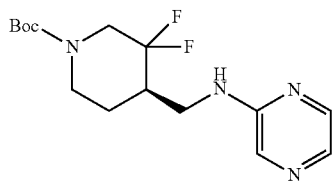 [SMILES: CC(C)(C)OC(=O)N1CC[C@H](CNc2cnccn2)C(F)(F)C1]

A mixture of R-tert-butyl 4-(aminomethyl)-3,3-difluoropiperidine-1-carboxylate (200 mg, 0.80 mmol), 2-bromopyrazine (140 mg, 0.88 mmol) and DIPEA (0.42 mL, 2.40 mmol) in NMP (6 mL) was heated with stirring overnight at 130° C. The mixture was allowed to cool to rt, and diluted with ethyl acetate. The organic phase was washed with water and brine, dried over Na₂SO₄ and concentrated under vacuum. The concentrate was purified by column chromatography over silica gel (hexane/ethyl acetate=1/1) to afford the title compound as a yellow oil (196 mg, 50%). MS (ESI) calcd for $C_{15}H_{22}F_2N_4O_2$: 328.2; found: 329.2[M+H]. ¹H NMR (400 MHz, CDCl₃) δ 7.98 (dd, J=2.8 and 1.2 Hz, 1H), 7.89 (d, J=1.2 Hz, 1H), 7.81 (d, J=2.8 Hz, 1H), 4.80-4.70 (m, 1H), 4.45-4.10 (m, 2H), 3.76-3.69 (m, 1H), 3.57-3.49 (m, 1H), 3.04-2.70 (m, 2H), 2.31-2.16 (m, 1H), 1.87-1.79 (m, 1H), 1.63-1.53 (m, 1H), 1.47 (s, 9H).

Step 2: R-4-methylbenzyl 3,3-difluoro-4-((pyrazin-2-ylamino)methyl)piperidine-1-carboxylate

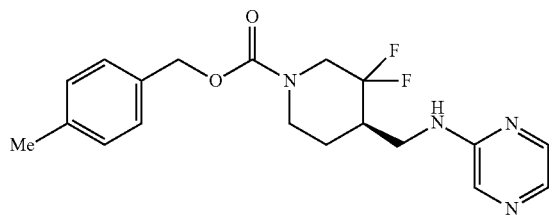 [SMILES: Cc1ccc(COC(=O)N2CC[C@H](CNc3cnccn3)C(F)(F)C2)cc1]

To a solution of R-tert-butyl 3,3-difluoro-4-((pyrazin-2-ylamino)methyl)-piperidine-1-carboxylate (196 mg, 0.59 mmol) in DCM (3 mL) was added TFA (2 mL) at room temperature. After stirring for 30 min, the mixture was concentrated to afford crude product R—N-((3,3-difluoropiperidin-4-yl)methyl)pyrazin-2-amine trifluoroacetate as a yellow oil which was directly used in the next step without further purification. To a solution of the crude R—N-((3,3-difluoropiperidin-4-yl)methyl)pyrazin-2-amine trifluoroacetate in MeCN (6 mL) were added triethylamine (0.8 mL, 5.8 mmol) and 2,5-dioxocyclopentyl 4-methylbenzyl carbonate (386 mg, 1.44 mmol) at room temperature. After stirring for 1 hr, the mixture was diluted with EtOAc. The organic phase was washed with water, brine, dried over Na₂SO₄ and concentrated under vacuum. The concentrate was purified by column chromatography over silica gel (100% EtOAc) to afford the title compound as a yellow oil (167 mg, 52%). MS (ESI) calcd for $C_{19}H_{22}F_2N_4O_2$: 376.2; found: 377.5 [M+H]. ¹H NMR (400 MHz, CD₃OD) δ 7.97 (dd, J=2.8 and 1.2 Hz, 1H), 7.88 (d, J=1.2 Hz, 1H), 7.64 (d, J=2.8 Hz, 1H), 7.24 (d, J=8.0 Hz, 2H), 7.17 (d, J=8.0 Hz, 2H), 5.09 (s, 2H), 4.31-4.21 (m, 1H), 4.17-4.07 (m, 1H), 3.76 (dd, J=14.0 and 5.2 Hz, 1H), 3.35 (dd, J=14.0 and 5.2 Hz, 1H), 3.27-2.85 (m, 2H), 2.44-2.34 (m, 1H), 2.33 (s, 3H), 1.96-1.85 (m, 1H), 1.54-1.43 (m, 1H).

Example 1.10a. R-4-methylbenzyl 3,3-difluoro-4-((pyrazin-2-ylamino)methyl)piperidine-1-carboxylate methanesulfonate (E1-21.2a)

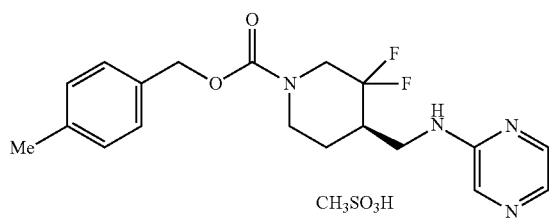

To a solution of R-4-methylbenzyl 3,3-difluoro-4-((pyrazin-2-ylamino)methyl)piperidine-1-carboxylate (118 mg, 0.31 mmol) in MeOH (2 mL) was added methanesulfonic acid (27 mg, 0.28 mmol). After stirring for 1 h at rt, the mixture was concentrated to afford the title compound as a yellow powder (127 mg, 87%). MS (ESI) calcd for $C_{19}H_{22}F_2N_4O_2$: 376.2; found: 377.4 [M+H]. ¹H NMR (400 MHz, CD₃OD) δ 8.6 (dd, J=2.8 and 1.2 Hz, 1H), 8.23 (d, J=1.2 Hz, 1H), 7.85 (d, J=2.8 Hz, 1H), 7.24 (d, J=8.0 Hz, 2H), 7.17 (d, J=8.0 Hz, 2H), 5.09 (s, 2H), 4.40-4.27 (m, 1H), 4.22-4.14 (m, 1H), 3.85 (dd, J=14.0 and 5.2 Hz, 1H), 3.49 (dd, J=14.0 and 5.2 Hz, 1H), 3.30-2.90 (m, 2H), 2.72 (s, 3H), 2.55-2.36 (m, 1H), 2.33 (s, 3H), 1.99-1.89 (m, 1H), 1.60-1.47 (m, 1H).

Example 1.11. R-4-methylbenzyl 3,3-difluoro-4-((5-methylpyrazin-2-ylamino)-methyl)piperidine-1-carboxylate (E1-21.26)

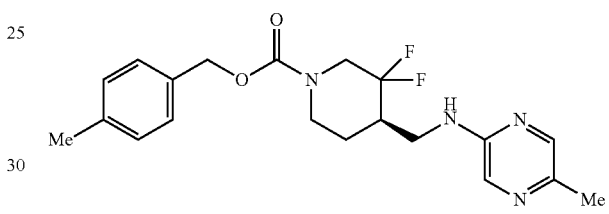

Step 1: R-tert-butyl 3,3-difluoro-4-((5-methylpyrazin-2-ylamino)methyl)-piperidine-1-carboxylate

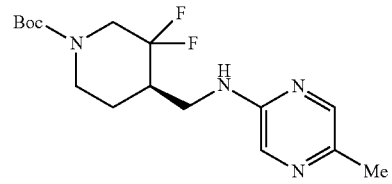 [SMILES: Cc1cnc(NC[C@H]2CCN(C(=O)OC(C)(C)C)CC2(F)F)cn1]

To a solution of R-tert-butyl 4-(aminomethyl)-3,3-difluoropiperidine-1-carboxylate (188 mg, 0.75 mmol) in dioxane (3 mL) were added 2-chloro-5-methylpyrazine (100 mg, 0.78 mmol), Pd₂(dba)₃.CHCl₃ (21 mg, 0.02 mmol), Xantphos (23 mg, 0.04 mmol) and Cs₂CO₃ (329 mg, 1.0 mmol). The mixture was heated to 90° C. under N₂. After stirring overnight, the reaction solution was treated with ethyl acetate. The organic phase was washed with water, brine, dried over Na₂SO₄ and concentrated in vacuo. The residue was purified by column chromatography over silica gel (ethyl acetate/hexane=1/1) to afford the title compound as a pale-yellow powder (115 mg, 45%). MS (ESI) calcd for $C_{16}H_{24}F_2N_4O_2$: 342.2; found: 343.4[M+H]. ¹H NMR (400 MHz, CDCl₃) δ 7.86 (s, 1H), 7.83 (s, 1H), 4.63-4.53 (m, 1H), 4.48-4.04 (m, 2H), 3.73-3.67 (m, 1H), 3.52-3.45 (m, 1H), 3.00-2.89 (m, 1H), 2.79-2.70 (m, 1H), 2.38 (s, 3H), 2.28-2.15 (m, 1H), 1.85-1.80 (m, 1H), 1.47 (s, 9H).

Step 2: R-4-methylbenzyl 3,3-difluoro-4-((5-methylpyrazin-2-ylamino)-methyl)piperidine-1-carboxylate

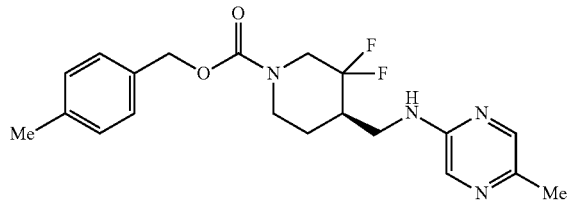 [SMILES: Cc1ccc(COC(=O)N2CC[C@H](CNc3cnc(C)cn3)C(F)(F)C2)cc1]

To a solution of R-tert-butyl 3,3-difluoro-4-((5-methylpyrazin-2-ylamino)methyl)piperidine-1-carboxylate (115 mg, 0.34 mmol) in DCM (3 mL) was added TFA (1 mL) at room temperature. After stirring for 30 min, the mixture was concentrated to afford R—N-((3,3-difluoropiperidin-4-yl)methyl)-5-methylpyrazin-2-amine trifluoroacetate as a yellow oil which was directly used in the next step without further purification. To a solution of the crude R—N-((3,3-difluoropiperidin-4-yl)methyl)-5-methylpyrazin-2-amine trifluoroacetate in MeCN (4 mL) were added triethylamine (1 mL) and 2,5-dioxocyclopentyl 4-methylbenzyl carbonate (98 mg, 0.37 mmol) at room temperature. After stirring for 1 hr, the mixture was diluted with EtOAc. The organic phase was washed with water, brine, dried over $Na_2SO_4$ and concentrated under vacuum. The concentrate was purified by column chromatography over silica gel (ethyl acetate/hexane=2/1) to afford the title compound as pale-yellow powder (61 mg, 46%). MS (ESI) calcd for $C_{20}H_{24}F_2N_4O_2$: 390.2; found: 391.2 [M+H]. $^1$H NMR (400 MHz, $CDCl_3$) δ 7.86 (s, 1H), 7.82 (s, 1H), 7.24 (d, J=8.0 Hz, 2H), 7.17 (d, J=8.0 Hz, 2H), 5.10 (s, 2H), 4.66-4.60 (m, 1H), 4.49-4.16 (m, 2H), 3.73-3.67 (m, 1H), 3.51-3.44 (m, 1H), 3.07-2.95 (m, 1H), 2.87-2.79 (m, 1H), 2.38 (s, 3H), 2.35 (s, 3H), 2.30-2.18 (m, 1H), 1.85-1.81 (m, 1H), 1.63-1.53 (m, 1H).

Example 1.11a. R-4-methylbenzyl 3,3-difluoro-4-((5-methylpyrazin-2-ylamino)methyl)-piperidine-1-carboxylate methanesulfonate (E1-21.26a)

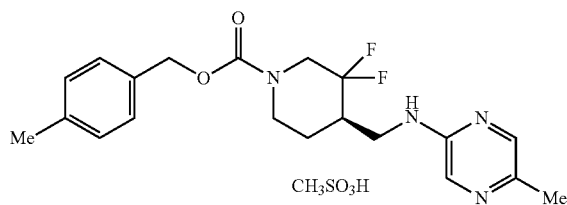

To a solution of R-4-methylbenzyl 3,3-difluoro-4-((5-methylpyrazin-2-ylamino)-methyl)piperidine-1-carboxylate (54 mg, 0.138 mmol) in DCM (2 mL) was added methylsulfonic acid in MeOH (0.14 mL, 1.0 M, 0.14 mmol). After stirring for 15 min at rt, the mixture was concentrated to afford the title compound as a pale-yellow powder (127 mg, 87%). MS (ESI) calcd for $C_{20}H_{24}F_2N_4O_2$: 390.2; found: 391.2 [M+H]. $^1$H NMR (400 MHz, $CD_3OD$) δ 8.22 (s, 1H), 8.10 (s, 1H), 7.24 (d, J=8.0 Hz, 2H), 7.17 (d, J=8.0 Hz, 2H), 5.09 (s, 2H), 4.37-4.26 (m, 1H), 4.19-4.15 (m, 1H), 3.82 (dd, J=14.0 and 5.6 Hz, 1H), 3.46 (dd, J=14.0 and 5.6 Hz, 1H), 3.30-3.12 (m, 1H), 3.02-2.91 (m, 1H), 2.71 (s, 3H), 2.48 (s, 3H), 2.46-2.36 (m, 1H), 2.33 (s, 3H), 1.95-1.91 (m, 1H), 1.58-1.48 (m, 1H).

Example 1.12. R-4-fluorobenzyl 4-((1H-pyrazolo[3,4-d]pyrimidin-6-ylamino)methyl)-3,3-difluoropiperidine-1-carboxylate (E1-8.4)

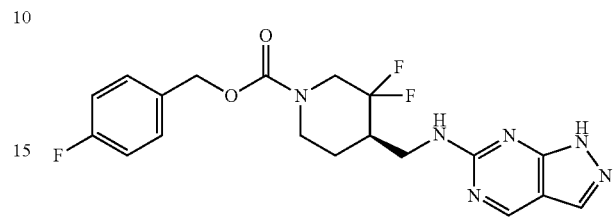

Step 1: R—N-((3,3-difluoropiperidin-4-yl)methyl)-1H-pyrazolo[3,4-d]pyrimidin-6-amine trifluoroacetate

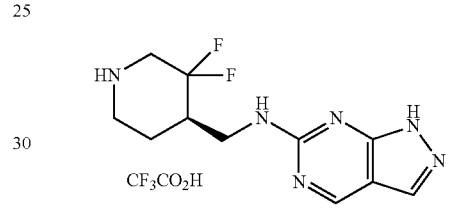

To a solution of R-tert-butyl 4-((1H-pyrazolo[3,4-d]pyrimidin-6-ylamino)methyl)-3,3-difluoropiperidine-1-carboxylate (340 mg, 0.92 mmol) in DCM (5 mL) was added TFA (3 mL) at room temperature. After stirring for 30 min, the mixture was concentrated to afford the title compound as a pale-yellow oil which was used in the next step without further purification.

Step 2: R-4-fluorobenzyl 4-((1H-pyrazolo[3,4-d]pyrimidin-6-ylamino)methyl)-3,3-difluoropiperidine-1-carboxylate

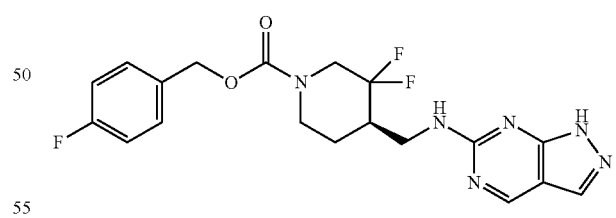

To a solution of R—N-((3,3-difluoropiperidin-4-yl)methyl)-1H-pyrazolo[3,4-d]pyrimidin-6-amine trifluoroacetate salt from the previous step (ca. 0.92 mmol) in MeCN (5 mL) was added triethylamine (0.6 mL, 4.6 mmol), followed by addition of 2,5-dioxopyrrolidin-1-yl 4-fluorobenzyl carbonate (296 mg, 1.10 mmol). The resulting mixture was stirred for 1 hour at room temperature. Then the mixture was diluted with ethyl acetate, washed with water, brine, dried over anhydrous $Na_2SO_4$ and concentrated under reduced pressure. The residue was purified by column chromatography over silica gel (ethyl acetate/hexane=1/1)

to afford the title compound as an off white powder (160 mg, 41% for two steps). MS (ESI) calcd for $C_{19}H_{19}F_3N_6O_2$: 420.2; found: 421.4 [M+H]. $^1$H NMR (400 MHz, $CD_3OD$) δ 8.77 (s, 1H), 7.92 (s, 1H), 7.42-7.36 (m, 2H), 7.12-7.05 (m, 2H), 5.12 (s, 2H), 4.33-4.21 (m, 1H), 4.16-4.10 (m, 1H), 3.86 (dd, J=13.6 and 4.4 Hz, 1H), 3.50-3.43 (m, 1H), 3.25-2.85 (m, 2H), 2.54-2.40 (m, 1H), 1.95-1.88 (m, 1H), 1.58-1.47 (m, 1H).

Example 1.13. R-4-methylbenzyl 4-((1H-pyrazolo[3,4-d]pyrimidin-4-ylamino)methyl)-3,3-difluoropiperidine-1-carboxylate (E1-6.2)

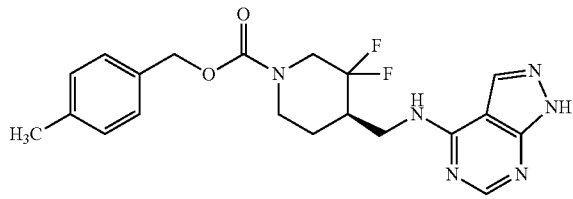

Step 1: R-tert-butyl 4-(([1,2,4]triazolo[4,3-a]pyrazin-8-ylamino)methyl)-3,3-difluoropiperidine-1-carboxylate

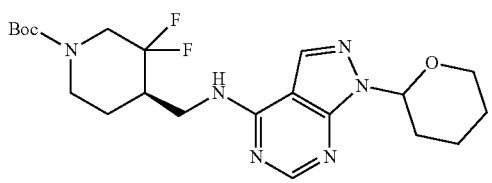 [SMILES: CC(C)(C)OC(=O)N1CC[C@H](CNc2ncnc3c2cnn3C2CCCCO2)C(F)(F)C1]

To a stirred solution of R-tert-butyl 4-(aminomethyl)-3,3-difluoropiperidine-1-carboxylate (600 mg, 2.4 mmol) in n-BuOH (5 mL) were added 4-chloro-1-(tetrahydro-2H-pyran-2-yl)-1H-pyrazolo[3,4-d]pyrimidine (571 mg, 2.4 mmol) and DIPEA (0.84 mL, 4.8 mmol). The mixture was heated to 100° C. under nitrogen for 13 hours. The reaction mixture was allowed to cool to room temperature and concentrated in vacuo. The residue was dissolved in ethyl acetate and the organic phase was washed with water, brine, dried over $Na_2SO_4$, and concentrated under reduced pressure. The concentrate was purified by column chromatography over silica gel (ethyl acetate/hexane=1/1) to afford the title compound as a yellow powder (800 mg, 80%). MS (ESI) calcd for $C_{21}H_{30}F_2N_6O_3$: 452.2; found: 453.6 [M+H]. $^1$H NMR (400 MHz, $CDCl_3$) δ 8.42 (s, 1H), 7.95 (s, 1H), 5.98-5.95 (m, 1H), 5.81-5.60 (brs, 1H), 4.49-4.09 (m, 3H), 3.99-3.87 (m, 1H), 3.83-3.76 (m, 2H), 3.06-2.67 (m, 2H), 2.63-2.53 (m, 1H), 2.40-2.23 (m, 1H), 2.16-2.08 (m, 1H), 1.96-1.92 (m, 1H), 1.93-1.54 (m, 6H), 1.47 (s, 9H).

Step 2: R—N-((3,3-difluoropiperidin-4-yl)methyl)-1H-pyrazolo[3,4-d]pyrimidin-4-amine dihydrochloride salt

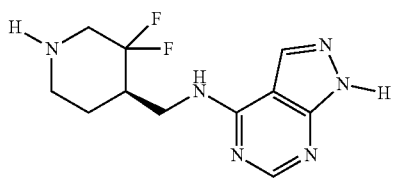

2 HCl

R-tert-butyl 3,3-difluoro-4-((1-(tetrahydro-2H-pyran-2-yl)-1H-pyrazolo[3,4-d]-pyrimidin-4-ylamino)methyl)piperidine-1-carboxylate (0.80 g, 1.76 mmol) was dissolved in methanolic HCl solution (2N, 15 mL) at room temperature. After stirring overnight, the resulting reaction mixture was concentrated under reduce pressure to afford the title compound as a yellow solid (600 mg, 99%) which was used in the next step without further purification. MS (ESI) calcd for $C_{11}H_{14}F_2N_6$: 268.1; found: 269.2 [M+H]. $^1$H NMR (400 MHz, $CD_3OD$) δ 8.72 (s, 1H), 8.64 (s, 1H), 4.19 (dd, J=14.0 and 5.6 Hz, 1H), 3.90 (dd, J=14.0 and 5.6 Hz, 1H), 3.83-3.75 (m, 1H), 3.61-3.48 (m, 2H), 3.24-3.18 (m, 1H), 2.93-2.78 (m, 1H), 2.35-2.29 (m, 1H), 1.94-1.84 (m, 1H).

Step 3: R-4-methylbenzyl 4-((1H-pyrazolo[3,4-d]pyrimidin-4-ylamino)methyl)-3,3-difluoropiperidine-1-carboxylate

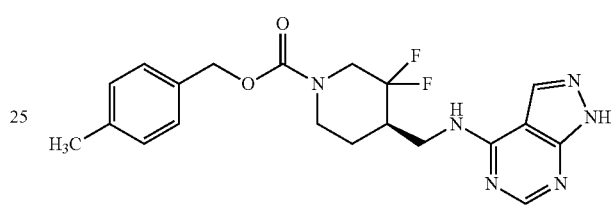

To a stirred solution of R—N-((3,3-difluoropiperidin-4-yl)methyl)-1H-pyrazolo[3,4-d]pyrimidin-4-amine dihydrochloride (400 mg, 1.17 mmol) and TEA (0.37 mL, 2.6 mmol) in a MeCN (15 mL) and DMF (4 mL) solvent mixture was added 2,5-dioxopyrrolidin-1-yl 4-methylbenzyl carbonate (307 mg, 1.17 mmol). The resulting mixture was stirred for 1 hour at room temperature and then diluted with ethyl acetate (50 mL). The organic phase was washed with water, brine, dried over anhydrous $Na_2SO_4$ and concentrated under reduced pressure. The residue was purified by column chromatography over silica gel (DCM/MeOH=35/1) to afford the title compound as a yellow powder (250 mg, 51%). MS (ESI) calcd for $C_{20}H_{22}F_2N_6O_6$: 416.2; found: 417.5 [M+H]. $^1$H NMR (400 MHz, $CD_3OD$) δ 8.27 (s, 1H), 8.09 (s, 1H), 7.26 (d, J=8.0 Hz, 2H), 7.18 (d, J=8.0 Hz, 2H), 5.11 (s, 2H), 4.38-4.26 (brs, 1H), 4.18-4.12 (m, 1H), 3.99-3.95 (m, 1H), 3.67-3.61 (m, 1H), 3.28-3.10 (m, 1H), 3.03-2.89 (m, 1H), 2.60-2.44 (m, 1H), 2.35 (s, 3H), 1.96-1.93 (m, 1H), 1.60-1.49 (m, 1H).

Example 1.13a. (+)-R-4-methylbenzyl 4-((1H-pyrazolo[3,4-d]pyrimidin-4-ylamino)methyl)-3,3-difluoropiperidine-1-carboxylate methanesulfonate (E1-6.2a)

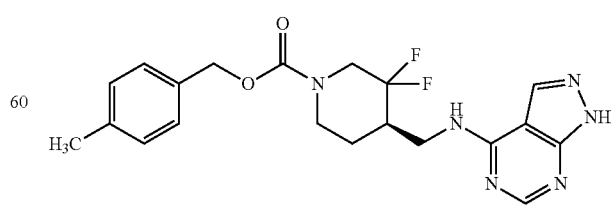

$CH_3SO_3H$

To a stirred solution of R-4-methylbenzyl 4-((1H-pyrazolo[3,4-d]pyrimidin-4-ylamino)methyl)-3,3-difluoropiperidine-1-carboxylate (230 mg, 0.55 mmol) in DCM (3 mL) was added a solution of methanesulfonic acid (53 mg, 0.55 mmol) in methanol (3 mL). The mixture was stirred at room temperature for 30 min. The solvent was evaporated, and the solid thus obtained was triturated with ether (10 mL) and filtered to give the title compound as yellow powder (270 mg, 95%). $[\alpha]_D$=+13.5 (c=10 mg/mL, MeOH, 20° C.). MS (ESI) calcd for $C_{20}H_{22}F_2N_6O_6$: 416.2; found: 417.5 [M+H]. $^1$H NMR (400 MHz, CD$_3$OD) δ 8.55 (s, 1H), 8.50 (s, 1H), 7.26 (d, J=8.0 Hz, 2H), 7.19 (d, J=8.0 Hz, 2H), 5.11 (s, 2H), 4.41-4.29 (m, 1H), 4.23-4.15 (m, 1H), 4.11-4.06 (m, 1H), 3.84-3.78 (m, 1H), 3.26-3.14 (m, 1H), 3.07-2.91 (m, 1H), 2.72 (s, 3H), 2.63-2.50 (m, 1H), 2.35 (s, 3H), 2.00-1.92 (m, 1H), 1.64-1.53 (m, 1H).

Example 1.14. (+)-R-4-methylbenzyl 4-((7H-pyrrolo[2,3-d]pyrimidin-4-ylamino)methyl)-3,3-difluoropiperidine-1-carboxylate (E1-7.2)

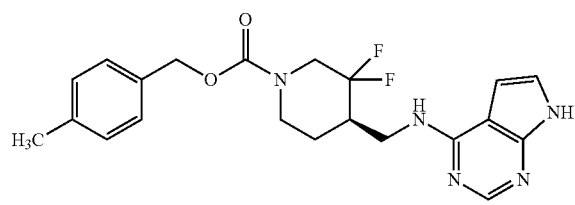 [SMILES: Cc1ccc(COC(=O)N2CC[C@H](CNc3ncnc4[nH]ccc34)C(F)(F)C2)cc1]

Step 1: R-tert-butyl 3,3-difluoro-4-((7-tosyl-7H-pyrrolo[2,3-d]pyrimidin-4-ylamino)methyl)piperidine-1-carboxylate

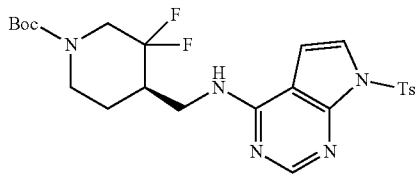 [SMILES: Cc1ccc(S(=O)(=O)n2ccc3c(NC[C@H]4CCN(C(=O)OC(C)(C)C)CC4(F)F)ncnc32)cc1]

A mixture of 4-chloro-7-tosyl-7H-pyrrolo[2,3-d]pyrimidine (615 mg, 1.99 mmol), R-tert-butyl 4-(aminomethyl)-3,3-difluoropiperidine-1-carboxylate (600 mg, 2.39 mmol) and DIPEA (0.66 mL, 3.99 mmol) in n-BuOH (8 mL) was heated to 130° C. under nitrogen atmosphere overnight. The mixture was allowed to cool to rt and concentrated under vacuum. The concentrate was partitioned into ethyl acetate and water. The organic layer was washed with water, brine, dried over Na$_2$SO$_4$ and concentrated in vacuo. The residue was purified by column chromatography over silica gel (hexane/EtOAc=3/2) to afford the title compound as an off-white powder (850 mg, 82%). MS (ESI) calcd for $C_{24}H_{29}F_2N_5O_4S$: 521.2; found: 522.5 [M+H]. $^1$H NMR (400 MHz, CDCl$_3$) δ 8.44 (s, 1H), 8.07 (d, J=8.0 Hz, 2H), 7.47 (d, J=4.0 Hz, 1H), 7.29 (d, J=8.0 Hz, 2H), 6.41 (d, J=4.0 Hz, 1H), 5.23-5.16 (m, 1H), 4.45-4.25 (m, 2H), 3.88-3.70 (m, 2H), 3.02-2.67 (m, 2H), 2.39 (s, 3H), 2.35-2.19 (m, 1H), 1.85-1.77 (m, 1H), 1.62-1.50 (m, 1H), 1.46 (s, 9H).

Step 2: R—N-((3,3-difluoropiperidin-4-yl)methyl)-7-tosyl-7H-pyrrolo[2,3-d]pyrimidin-4-amine trifluoroacetate

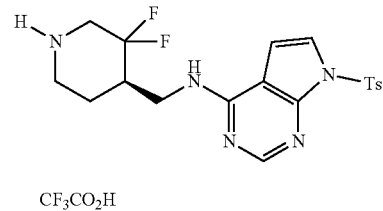 [SMILES: "CF3CO2H" ; Cc1ccc(S(=O)(=O)n2ccc3c(NC[C@H]4CCNCC4(F)F)ncnc32)cc1]

To a solution of R-tert-butyl 3,3-difluoro-4-((7-tosyl-7H-pyrrolo[2,3-d]pyrimidin-4-ylamino)methyl)piperidine-1-carboxylate (850 mg, 1.63 mmol) in DCM (8 mL) was added TFA (4 mL). The resulting solution was stirred for 30 min at room temperature and then concentrated under vacuum to give the title compound (2.19 g) which was directly used in the next step without further purification. MS (ESI) calcd for $C_{19}H_{21}F_2N_5O_2S$: 421.1; found: 422.7 [M+H].

Step 3: R-4-methylbenzyl 3,3-difluoro-4-((7-tosyl-7H-pyrrolo[2,3-d]pyrimidin-4-ylamino)methyl)piperidine-1-carboxylate

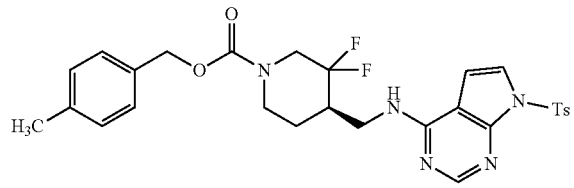 [SMILES: Cc1ccc(COC(=O)N2CC[C@H](CNc3ncnc4c3ccn4S(=O)(=O)c3ccc(C)cc3)C(F)(F)C2)cc1]

The crude R—N-((3,3-difluoropiperidin-4-yl)methyl)-7-tosyl-7H-pyrrolo[2,3-d]pyrimidin-4-amine trifluoroacetate salt (2.19 g, ca. 1.6 mmol) was dissolved in acetonitrile (9 mL), followed by addition of triethylamine (1.2 mL, 8.16 mmol). Then 2,5-dioxocyclopentyl 4-methylbenzyl carbonate (515 mg, 1.95 mmol) was added and the resulting mixture was stirred at room temperature overnight. The mixture was concentrated, and the concentrate was dissolved in ethyl acetate. The organic phase was washed with water, brine, dried over Na$_2$SO$_4$ and concentrated in vacuo. The residue was purified by column chromatography over silica gel (hexane/EtOAc=3/2) to afford the title compound as a white powder (847 mg, 80%). MS (ESI) calcd for $C_{28}H_{29}F_2N_5O_4S$: 569.2; found: 570.5 [M+H]. $^1$H NMR (400 MHz, CDCl$_3$) δ 8.43 (s, 1H), 8.06 (d, J=8.0 Hz, 2H), 7.47 (d, J=4.0 Hz, 1H), 7.29 (d, J=8.0 Hz, 2H), 7.24 (d, J=8.0 Hz, 2H), 7.16 (d, J=8.0 Hz, 2H), 6.40 (d, J=4.0 Hz, 1H), 5.23-5.15 (m, 1H), 5.13-5.05 (m, 2H), 4.55-4.10 (m, 2H), 3.87-3.71 (m, 1H), 3.07-2.90 (m, 1H), 2.87-2.74 (m, 1H), 2.39 (s, 3H), 2.35 (s, 3H), 2.37-2.22 (m, 2H), 1.87-1.77 (m, 1H), 1.64-1.51 (m, 1H).

Step 4: (+)-R-4-methylbenzyl 4-((7H-pyrrolo[2,3-d]pyrimidin-4-ylamino)methyl)-3,3-difluoropiperidine-1-carboxylate

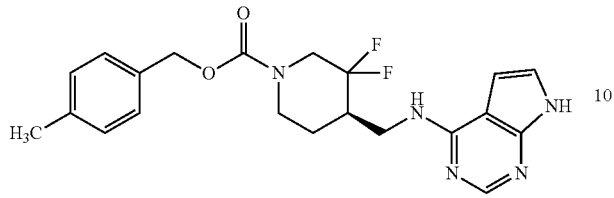

To a solution of R-4-methylbenzyl 3,3-difluoro-4-((7-tosyl-7H-pyrrolo[2,3-d]pyrimidin-4-ylamino)methyl)piperidine-1-carboxylate (777 mg, 1.36 mmol) in THF (8 mL) was added 50% aqueous NaOH (2 mL). The resulting mixture was stirred overnight at ambient temperature and concentrated under vacuum to remove the THF solvent. The residual solution was adjusted to pH=9 with HCl (6N) under ice-water bath cooling. The aqueous phase was extracted with ethyl acetate. The combined organic phases were washed with brine, dried over $Na_2SO_4$ and concentrated in vacuo. The residue was purified by column chromatography over silica gel (hexane/acetone=1/1) to afford the title compound as a pale brown powder (390 mg, 70%). $[\alpha]_D$=+22.5° (c=10 mg/mL, MeOH, 26° C.). MS (ESI) calcd for $C_{21}H_{23}F_2N_5O_2$: 415.2; found: 416.5 [M+H]. $^1$H NMR (400 MHz, $CDCl_3$) δ 10.08-9.98 (brs, 1H), 8.34 (s, 1H), 7.25 (d, J=8.0 Hz, 2H), 7.17 (d, J=8.0 Hz, 2H), 7.07 (d, J=2.7 Hz, 1H), 6.37 (d, J=2.7 Hz, 1H), 5.31-5.25 (m, 1H), 5.14-5.07 (s, 2H), 4.56-4.10 (m, 2H), 3.98-3.89 (m, 1H), 3.88-3.77 (m, 1H), 3.12-2.93 (m, 1H), 2.91-2.77 (m, 1H), 2.45-2.28 (m, 1H), 2.35 (s, 3H), 1.95-1.85 (m, 1H), 1.70-1.56 (m, 1H).

Example 1.15. R-4-ethylbenzyl 4-(([1,2,4]triazolo[4,3-a]pyrazin-8-ylamino)methyl)-3,3-difluoropiperidine-1-carboxylate (E1-1.5)

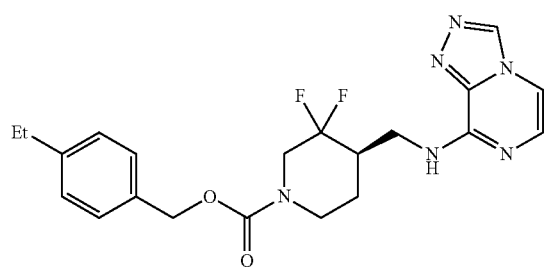

To a solution of previously described crude N-((3,3-difluoropiperidin-4-yl)methyl)-[1,2,4]triazolo[4,3-a]pyrazin-8-amine trifluoroacetate (373 mg, ca. 1.0 mmol) in MeCN (5 mL) was added TEA (0.7 mL, 5.05 mmol), followed by 2,5-dioxopyrrolidin-1-yl 4-ethylbenzyl carbonate (335.8 mg, 1.21 mmol). The resulting mixture was stirred for 1 hour at room temperature. The mixture was diluted with ethyl acetate and the organic phase was washed with water, brine, dried over anhydrous $Na_2SO_4$ and concentrated under reduced pressure. The residue was purified by column chromatography over silica gel (ethyl acetate/hexane=1/1) to afford the title compound as an off white powder (302 mg). MS (ESI) calcd for $C_{21}H_{24}F_2N_6O_2$: 430.2; found: 431.4 [M+H]. $^1$H NMR (400 MHz, $CD_3OD$) δ 9.08 (s, 1H), 7.69 (d, J=4.8 Hz, 1H), 7.32 (d, J=4.8 Hz, 1H), 7.26 (d, J=8.0 Hz, 2H), 7.19 (d, J=8.0 Hz, 2H), 5.10 (s, 2H), 4.37-4.26 (m, 1H), 4.19-4.11 (m, 1H), 3.98 (dd, J=14.0 and 5.2 Hz, 1H), 3.62 (dd, J=14.0 and 8.4 Hz, 1H), 3.27-3.07 (m, 1H), 3.07-2.88 (m, 1H), 2.64 (q, J=7.6 Hz, 2H), 2.59-2.48 (m, 1H), 1.98-1.93 (m, 1H), 1.61-1.51 (m, 1H), 1.22 (t, J=7.6 Hz, 3H).

Example 1.15a. (+)-R-4-ethylbenzyl 4-(([1,2,4]triazolo[4,3-a]pyrazin-8-ylamino)methyl)-3,3-difluoropiperidine-1-carboxylate methanesulfonate (E1-1.5a)

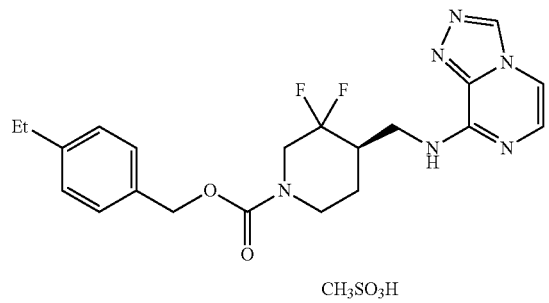

To a stirred solution of R-4-ethylbenzyl 4-(([1,2,4]triazolo[4,3-a]pyrazin-8-ylamino)-methyl)-3,3-difluoropiperidine-1-carboxylate (302 mg, 0.70 mmol) in MeOH/DCM (4.0 mL, v/v=1:1) was added a solution of $CH_3SO_3H$ (68 mg, 0.70 mmol) in methanol (1 mL) at rt. After stirred for 30 min, the mixture was concentrated to afford the product as off-white powder (335 mg, 90.6%). $[\alpha]_D$=+2.4° (c=10 mg/mL, MeOH, 23° C.). MS (ESI) calcd for $C_{21}H_{24}F_2N_6O_2$: 430.2; found: 431.5 [M+H]. $^1$H NMR (400 MHz, $CD_3OD$) δ 9.32 (s, 1H), 7.95 (d, J=5.6 Hz, 1H), 7.27 (d, J=8.0 Hz, 2H), 7.24 (d, J=5.6 Hz, 1H), 7.19 (d, J=8.0 Hz, 2H), 5.10 (s, 2H), 4.45-4.36 (m, 1H), 4.24-4.20 (m, 1H), 4.04-3.99 (m, 1H), 3.71-3.66 (m, 1H), 3.25-2.93 (m, 2H), 2.70 (s, 3H), 2.68-2.60 (m, 3H), 2.08-1.98 (m, 1H), 1.65-1.55 (m, 1H), 1.22 (t, J=7.6 Hz, 3H).

Example 1.16 Single Crystal X-Ray Diffraction (SCXRD) of (R)-XVIa

Data were collected on a Oxford Diffraction Supernova Dual Source, Cu at Zero, Atlas CCD diffractometer equipped with an Oxford Cryosystems Cobra cooling device. The data was collected using CuKα radiation. Structures were typically solved using either the SHELXS or SHELXD programs and refined with the SHELXL program as part of the Bruker AXS SHELXTL suite (V6.10). Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

A sample of (R)-XVIa was re-crystallized (ca. 10 mg) from 2-methyl-1-propanol (400 μL, 40 vol.) by slow evaporation at room temperature. A crystal of sufficient size and quality for analysis by single crystal X-ray diffraction was isolated with approximate dimensions 0.20×0.15×0.10 mm.

The structure was determined at 100 K in the orthorhombic system, space group $P2_12_12_1$ with the final R1 [I>σ2(l)] =4.52%. A summary of all structural data can be found in Tables A through D. The compound was identified as a non-solvated form of (R)-XVIa.

TABLE A

Sample and crystal data for (R)-XVIa.

| | |
|---|---|
| Crystallisation solvents | 2-methyl-1-propanol |
| Crystallisation method | Slow evaporation |
| Empirical formula | $C_{22}H_{28}F_2N_2O_5$ |
| Formula weight | 438.46 |
| Temperature | 100(2) K |
| Wavelength | 1.54178 Å |
| Crystal size | 0.200 × 0.150 × 0.100 mm |
| Crystal habit | Colourless Prism |
| Crystal system | Orthorhombic |
| Space group | $P2_12_12_1$ |
| Unit cell dimensions | a = 5.47256(9) Å, α = 90° |
| | b = 11.73866(17) Å, β = 90° |
| | c = 34.1360(5) Å, γ = 90° |
| Volume | 2192.91(6) Å$^3$ |
| Z | 4 |
| Density (calculated) | 1.328 Mg/m$^3$ |
| Absorption coefficient | 0.886 mm$^{-1}$ |
| F(000) | 928 |

TABLE B

Data collection and structure refinement for (R)-XVIa.

| | |
|---|---|
| Diffractometer | SuperNova, Dual, Cu at zero, Atlas |
| Radiation source | SuperNova (Cu) X-ray Source, CuKα |
| Data collection method | Omega scans |
| Theta range for data collection | 8.941 to 74.419° |
| Index ranges | −6 ≤ h ≤ 6, −14 ≤ k ≤ 14, −42 ≤ l ≤ 42 |
| Reflections collected | 43577 |
| Independent reflections | 4457 [R(int) = 0.0698] |
| Coverage of independent reflections | 99.4% |
| Variation in check reflections | n/a |
| Absorption correction | Semi-empirical from equivalents |
| Max. and min. transmission | 1.00000 and 0.56116 |
| Structure solution technique | Direct methods |
| Structure solution program | SHELXTL (Sheldrick, 2013) |
| Refinement technique | Full-matrix least-squares on F$^2$ |
| Refinement program | SHELXTL (Sheldrick, 2013) |
| Function minimized | $\Sigma w(F_o^2 - F_c^2)^2$ |
| Data/restraints/parameters | 4457/0/283 |
| Goodness-of-fit on F$^2$ | 1.082 |
| $\Delta/\sigma_{max}$ | 0.001 |

TABLE B-continued

Data collection and structure refinement for (R)-XVIa.

| Final R indices | |
|---|---|
| 4253 data; I > 2σ (I) | R1 = 0.0452, wR2 = 0.1191 |
| all data | R1 = 0.0469, wR2 = 0.1207 |
| Weighting scheme | $w = 1/[\sigma^2(F_o^2) + (0.0637P)^2 + 0.8591P]$ where $P = (F_o^2 + 2F_c^2)/3$ |
| Absolute structure parameter | −0.04(6) |
| Extinction coefficient | n/a |
| Largest diff. peak and hole | 0.259 and −0.189 eÅ$^{-3}$ |

TABLE C

Atomic coordinates and equivalent isotropic atomic displacement parameters, (Å$^2$), for (R)-XVIa. U(eq) is defined as one third of the trace of the orthogonalized U$_{ij}$ tensor.

| | x/a | y/b | z/c | U(eq) |
|---|---|---|---|---|
| F1 | 0.7976(4) | 0.47723(15) | 0.84220(6) | 0.0440(4) |
| F2 | 1.1649(4) | 0.49906(16) | 0.86598(5) | 0.0464(5) |
| O1 | 0.7099(5) | 0.31705(19) | 0.73129(6) | 0.0410(5) |
| O2 | 0.8636(4) | 0.49684(18) | 0.73493(6) | 0.0395(5) |
| O3 | 1.0565(4) | 0.12527(18) | 0.91034(6) | 0.0345(5) |
| O4 | 0.4735(4) | 0.32754(17) | 0.95057(7) | 0.0388(5) |
| O5 | 0.4084(4) | 0.17168(17) | 0.98667(6) | 0.0344(4) |
| N1 | 0.9942(6) | 0.3583(2) | 0.77608(7) | 0.0429(7) |
| N2 | 0.7173(4) | 0.16508(18) | 0.94441(6) | 0.0262(4) |
| C1 | 0.5884(6) | 0.3317(3) | 0.69316(8) | 0.0376(7) |
| C2 | 0.4246(6) | 0.4362(3) | 0.69245(12) | 0.0496(8) |
| C3 | 0.7802(6) | 0.3375(5) | 0.66140(10) | 0.0594(11) |
| C4 | 0.4369(8) | 0.2240(3) | 0.68976(11) | 0.0523(9) |
| C5 | 0.8538(6) | 0.3995(2) | 0.74621(8) | 0.0339(6) |
| C6 | 1.1272(7) | 0.4357(3) | 0.80100(9) | 0.0390(7) |
| C7 | 1.0279(6) | 0.4298(2) | 0.84224(8) | 0.0341(6) |
| C8 | 1.0144(5) | 0.3107(2) | 0.85927(8) | 0.0299(5) |
| C9 | 0.8847(7) | 0.2319(2) | 0.83005(9) | 0.0381(7) |
| C10 | 0.9968(8) | 0.2401(3) | 0.78948(9) | 0.0468(9) |
| C11 | 0.8919(6) | 0.3113(2) | 0.89942(8) | 0.0346(6) |
| C12 | 0.9000(5) | 0.1951(2) | 0.91797(7) | 0.0287(5) |
| C13 | 0.5282(5) | 0.2322(2) | 0.95928(8) | 0.0299(5) |
| C14 | 0.5338(5) | 0.0654(2) | 0.99436(8) | 0.0311(6) |
| C15 | 0.6961(5) | 0.0475(2) | 0.95830(7) | 0.0258(5) |
| C16 | 0.5776(5) | −0.0257(2) | 0.92593(7) | 0.0278(5) |
| C17 | 0.5697(5) | −0.1508(2) | 0.93511(7) | 0.0251(5) |
| C18 | 0.7557(5) | −0.2228(2) | 0.92237(7) | 0.0289(5) |
| C19 | 0.7448(5) | −0.3390(2) | 0.92911(9) | 0.0350(6) |
| C20 | 0.5484(6) | −0.3857(2) | 0.94909(9) | 0.0366(7) |
| C21 | 0.3642(5) | −0.3151(3) | 0.96252(9) | 0.0351(6) |
| C22 | 0.3740(5) | −0.1989(2) | 0.95534(8) | 0.0299(5) |

TABLE D

Anisotropic atomic displacement parameters, (Å$^2$), for (R)-XVIa. The anisotropic atomic displacement factor exponent takes the form:
$-2\pi^2 [h^2 a^{*2} U_{11} + \ldots + 2hka^* b^* U_{12}]$

| | U11 | U22 | U33 | U23 | U13 | U12 |
|---|---|---|---|---|---|---|
| F1 | 0.0490(11) | 0.0289(9) | 0.0540(10) | 0.0059(7) | 0.0020(9) | 0.0083(8) |
| F2 | 0.0640(13) | 0.0364(9) | 0.0388(9) | −0.0027(7) | −0.0061(9) | −0.0202(9) |
| O1 | 0.0562(13) | 0.0333(11) | 0.0336(10) | 0.0030(8) | −0.0078(10) | −0.0040(10) |
| O2 | 0.0410(12) | 0.0331(11) | 0.0443(11) | 0.0104(9) | −0.0017(9) | 0.0000(9) |
| O3 | 0.0300(10) | 0.0330(10) | 0.0404(10) | 0.0050(8) | 0.0049(8) | 0.0074(8) |
| O4 | 0.0386(11) | 0.0234(9) | 0.0545(12) | −0.0019(9) | 0.0059(10) | 0.0071(9) |
| O5 | 0.0357(10) | 0.0268(10) | 0.0407(10) | −0.0032(8) | 0.0088(8) | 0.0023(9) |
| N1 | 0.069(2) | 0.0284(12) | 0.0314(12) | 0.0003(9) | −0.0113(12) | −0.0010(13) |
| N2 | 0.0277(10) | 0.0208(10) | 0.0302(10) | −0.0009(8) | 0.0004(8) | 0.0033(9) |
| C1 | 0.0307(14) | 0.0498(18) | 0.0324(13) | 0.0041(12) | −0.0014(11) | 0.0035(14) |
| C2 | 0.0293(16) | 0.054(2) | 0.066(2) | 0.0023(17) | −0.0032(15) | 0.0043(15) |
| C3 | 0.0282(15) | 0.115(4) | 0.0351(16) | −0.0011(19) | −0.0024(12) | 0.008(2) |

TABLE D-continued

Anisotropic atomic displacement parameters, (Å$^2$), for (R)-XVIa.
The anisotropic atomic displacement factor exponent takes the form:
$-2\pi^2 [h^2 a^{*2} U_{11} + \ldots + 2hka^* b^* U_{12}]$

|     | U11        | U22        | U33        | U23         | U13         | U12         |
|-----|------------|------------|------------|-------------|-------------|-------------|
| C4  | 0.058(2)   | 0.049(2)   | 0.0497(18) | −0.0038(15) | −0.0136(17) | −0.0017(18) |
| C5  | 0.0416(16) | 0.0313(14) | 0.0289(13) | 0.0023(10)  | 0.0036(11)  | 0.0043(12)  |
| C6  | 0.0492(18) | 0.0319(15) | 0.0357(14) | 0.0021(11)  | −0.0038(13) | −0.0055(14) |
| C7  | 0.0411(16) | 0.0257(13) | 0.0356(14) | −0.0023(11) | −0.0062(12) | −0.0054(12) |
| C8  | 0.0338(13) | 0.0253(12) | 0.0306(12) | 0.0002(10)  | −0.0041(10) | 0.0006(11)  |
| C9  | 0.0512(18) | 0.0211(13) | 0.0421(15) | 0.0027(11)  | −0.0147(13) | −0.0042(13) |
| C10 | 0.078(2)   | 0.0274(14) | 0.0349(14) | −0.0014(11) | −0.0172(16) | 0.0040(16)  |
| C11 | 0.0420(15) | 0.0245(13) | 0.0371(14) | 0.0017(10)  | 0.0039(12)  | 0.0027(12)  |
| C12 | 0.0282(12) | 0.0276(13) | 0.0303(12) | −0.0008(10) | −0.0018(10) | 0.0021(11)  |
| C13 | 0.0298(13) | 0.0234(13) | 0.0366(13) | −0.0062(10) | 0.0025(10)  | −0.0001(11) |
| C14 | 0.0363(14) | 0.0260(12) | 0.0311(12) | −0.0032(10) | 0.0016(11)  | −0.0003(11) |
| C15 | 0.0285(12) | 0.0214(12) | 0.0277(11) | −0.0018(9)  | −0.0026(10) | 0.0031(10)  |
| C16 | 0.0313(13) | 0.0246(12) | 0.0277(11) | −0.0017(10) | −0.0038(10) | 0.0026(11)  |
| C17 | 0.0260(12) | 0.0251(12) | 0.0242(11) | −0.0035(9)  | −0.0039(9)  | 0.0006(10)  |
| C18 | 0.0263(13) | 0.0302(13) | 0.0303(12) | −0.0040(10) | 0.0006(10)  | 0.0001(11)  |
| C19 | 0.0334(15) | 0.0282(14) | 0.0433(15) | −0.0058(12) | −0.0059(12) | 0.0078(11)  |
| C20 | 0.0428(16) | 0.0230(13) | 0.0441(16) | 0.0014(11)  | −0.0124(13) | −0.0023(12) |
| C21 | 0.0308(13) | 0.0342(14) | 0.0404(14) | 0.0004(11)  | −0.0018(11) | −0.0086(12) |
| C22 | 0.0238(12) | 0.0316(14) | 0.0342(13) | −0.0045(10) | −0.0010(10) | −0.0006(11) |

Figure 11:
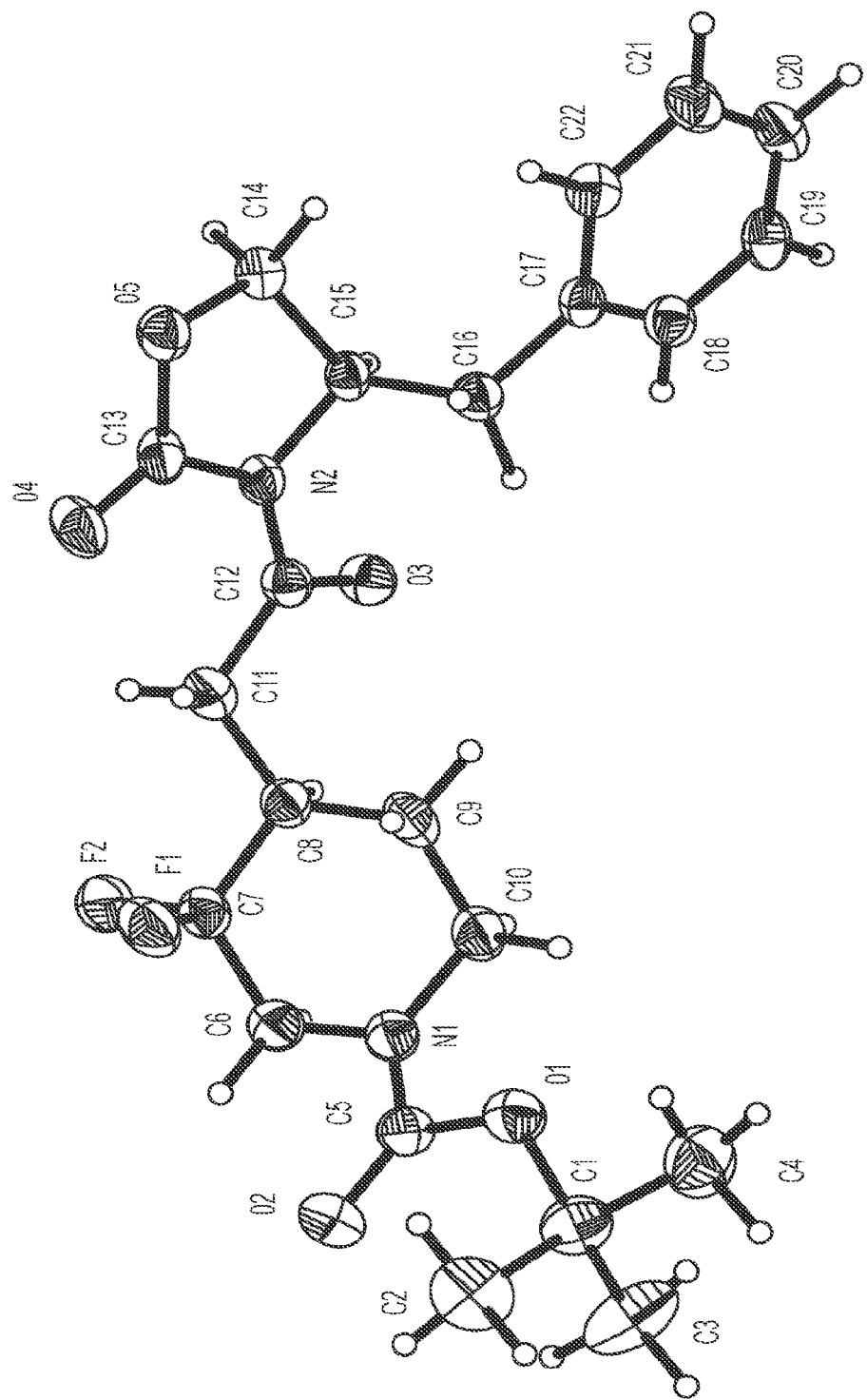
FIG. 11 shows a ball-and-stick diagram of intermediate (R)-XVIa showing the numbering scheme employed in Tables A-D.

The asymmetric unit contains a single fully ordered molecule of (R)-XVIa. Anisotropic atomic displacement ellipsoids for the non-hydrogen atoms are shown at the 50% probability level. Hydrogen atoms are displayed with an arbitrarily small radius (FIG. 11). For the structure as presented with C8 and C15 in the R configuration, the Flack parameter=−0.04(6) (Parsons and Flack, *Acta Cryst.* 2004, A60, s61). For the inverted structure with C8 and C15 in the S configuration, the Flack parameter=1.04(6). Determination of the absolute structure using Bayesian statistics on Bijvoet differences (Hooft et al., *J. Appl. Cryst.,* 2008, 41, 96-103), reveals that the probability of the absolute structure as presented being correct is 1.000, while the probabilities of the absolute structure being a racemic twin or false are both 0.000. The Flack equivalent and its uncertainty are calculated through this program to be −0.01(5). The calculation was based on 1853 Bijvoet pairs with a coverage of 100%. Based on the Flack parameter, the bayesian statistic analysis and the a priori knowledge that the chirality at C15 is R the absolute stereochemistry.

Example 2. Assays

Example 2.1. NR2B Antagonist Activity

HEK293 cell lines stably expressing cloned human NR1/NR2B and NR1/NR2A, respectively, were established according to standard previously described methods (Hansen et al., *Comb. Chem High Throughput Screen.* 11:304, 2008). Activation of the NR2A or NR2B subtype of NMDA receptor with glutamate as an agonist and glycine co-agonist on these cells results in calcium influx, which can be monitored with fluorescent indicator Fluo-4. A cell based assay has been implemented to evaluate the effect of a compound on NR2A and NR2B receptors by measuring the fluorescent changes (Hansen et al., *Comb. Chem High Throughput Screen.* 11:304, 2008).

HEK293 cells stably expressing NR2A or NR2B receptors were cultured at 37° C. in a humidified $CO_2$ incubator in DMEM supplemented with 10% fetal bovine serum (FBS) (Hyclone), 10 μM MK801 (Sigma-Aldrich) and 50 μM AP-5 (Tocris). For experiments, the cells were seeded onto poly-D-lysine-coated 96-well black plates with clear bottom (Corning) at a density of ~50,000 cells/well. After overnight culture, the growth medium was removed from the wells and the cells were incubated at 37° C. for 60 min in Hanks buffer containing 4 μM fluo-4-AM (Invitrogen) and 0.1% bovine serum albumin (BSA). After dye-loading, the cells were washed three times with Hanks buffer and incubated for 10 min at room temperature with various concentrations of test compounds prepared in Hanks buffer with 0.1% BSA. The cell plates were placed onto FDSS pCell fluorescence reader (Hamamatsu). After 20 sec reading of background fluorescence, agonist glutamate at final 100 μM and co-agonist glycine at final 50 μM were added to the cells to activate the receptor, and the resulting fluorescence changes were recorded and quantified. Based on the changes in fluorescence intensity, the pharmacological effect of test compounds were analyzed and the $IC_{50}$ values derived from a non-linear least squares fitting of the concentration-dependent response to a standard logistic equation using Prism (Graphpad, Inc):

Amplitude=Max Amplitude/(1+($IC_{50}$/[antagonist])$^n$).

Results are shown in the Table 2.1.

TABLE 2.1

| Cmpd. No. | NR2B $IC_{50}$ (nM) | NR2A $IC_{50}$ |
|-----------|---------------------|----------------|
| E1-1.2    | 21.0                | >10 μM         |
| E2-1.2    | 156                 | >10 μM         |
| E1-2.2    | 10.4                | >10 μM         |
| E1-9.2    | 48.2                | >10 μM         |
| E1-8.2    | 17                  | >10 μM         |
| E1-1.3    | 14.8                | >10 μM         |
| E1-1.4    | 20.5                | >10 μM         |
| E1-22.2   | 42.4                | >10 μM         |
| E1-21.2   | 14.4                | >10 μM         |
| E1-21.26  | 38.7                | >10 μM         |

Example 2.1.1. Radioligand Binding Assay

This example describes NMDA receptor binding assays using two different radioligands, [$^3$H] MK-801 and [$^3$H] (E)-N1-(2-methoxybenzyl)-cinnamidine (see below). An established binding assay using the non-selective NMDA receptor ligand [$^3$H] MK-801 serves as a measure of total NMDA receptor binding activity across all NMD receptor subtypes in native rat brain receptors. The binding assay method using the NR2B selective receptor ligand [$^3$H] (E)-N1-(2-methoxybenzyl)-cinnamidine was adapted from a previously described cellular human NR2B cloned receptor assay (Kiss et al., Neurochemistry International. 46, p 453-464, 2005) to rat brain tissue. This assay serves as a selective measure of NR2B receptor binding activity in native rat brain receptors. Briefly, the brains of Male Wistar rats were homogenized (Polytron) before centrifugation at 40,000×g for 15 minutes at 4° C. After 2 washes, the final pellet was homogenized and stored at −80° C. The protein concentration was determined by Bradford assay.

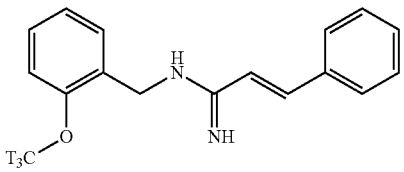

[$^3$H] (E)-N1-(2-methoxybenzyl)-cinnamidine

[$^3$H] MK-801 was used at one concentration, 2 nM, with 400 μg of membrane proteins. Non-specific binding (NS) was assessed in presence of excess (10 μM) unlabelled MK-801. A single binding site was observed with a $K_i$ value of 5.75 nM.

[$^3$H] (E)-N1-(2-methoxybenzyl)-cinnamidine was used at 2 different concentrations, 0.5 and 30 nM, with 30 μg of membrane proteins. Non-specific binding (NS) was assessed in presence of excess (10 μM) (E)-N1-(2-methoxybenzyl)-cinnamidine. A high affinity site was identified, for which a $K_i$ value of 0.18 nM was determined for (E)-N1-(2-methoxybenzyl)-cinnamidine. Thus, using [$^3$H] (E)-N1-(2-methoxybenzyl)-cinnamidine as the NR2B receptor radioligand (Kiss et al., Neurochemistry International. 46, p 453-464, 2005), a $K_i$ value of 1.0 nM at cloned NR2B receptors was determined. (Clairborne, C. F. Bioorganic and Medicinal Chemistry Letters, 13, 697-700, 2003) while using [$^3$H]-ifenprodil as the NR2B receptor radioligand $K_i$ value of 0.7 nM at cloned NR2B receptors (Curtis N. R. et al., Bioorganic and Medicinal Chemistry Letters, 13, 693-696, 2003).

Test compounds were solubilized at 10 mM in DMSO. Then the dilutions were performed with a constant solvent concentration (1% DMSO) in the assay.

After incubation for 4.5 h at room temperature, the assays were filtered on GF/B filters pretreated with 0.3% (v/v) PEI with a Brandel system for [$^3$H] MK-801, and with a Packard system for [$^3$H] (E)-N1-(2-methoxybenzyl)-cinnamidine. The experiment was performed in duplicate (n=2).

Compound E1-1.2 exhibited only a partial effect (40%) on [$^3$H] MK-801 binding consistent with selective binding to the NR2B receptor subtype. Compound E1-1.2 exhibited a complete displacement of [$^3$H] (E)-N1-(2-methoxybenzyl)-cinnamidine at the NR2B receptor high affinity site (96%; Ki=5.23 nM).

Compound E2-1.2 exhibited only a partial effect (36%) on [$^3$H] MK-801 binding consistent with selective binding to the NR2B receptor subtype. Compound E2-1.2 exhibited a complete displacement of [$^3$H] (E)-N1-(2-methoxybenzyl)-cinnamidine at the NR2B receptor high affinity site (98%; Ki=74.3 nM).

Compound E1-1.3 exhibited only a partial effect (41%) on [$^3$H] MK-801 binding consistent with selective binding to the NR2B receptor subtype. Compound E1-1.3 exhibited a complete displacement of [$^3$H] (E)-N1-(2-methoxybenzyl)-cinnamidine at the NR2B receptor high affinity site (97%; Ki=2.34 nM).

Compound E1-1.4 exhibited only a partial effect (32%) on [$^3$H] MK-801 binding consistent with selective binding to the NR2B receptor subtype. Compound E1-1.4 exhibited a complete displacement of [$^3$H] (E)-N1-(2-methoxybenzyl)-cinnamidine at the NR2B receptor high affinity site (98%; Ki=18.2 nM).

Compound E1-1.5 exhibited only a partial effect (48%) on [$^3$H] MK-801 binding consistent with selective binding to the NR2B receptor subtype. Compound E1-1.5 exhibited a complete displacement of [$^3$H] (E)-N1-(2-methoxybenzyl)-cinnamidine at the NR2B receptor high affinity site (97%; Ki=0.854 nM).

Compound E1-8.2 exhibited only a partial effect (33%) on [$^3$H] MK-801 binding consistent with selective binding to the NR2B receptor subtype. Compound E1-8.2 exhibited a complete displacement of [$^3$H] (E)-N1-(2-methoxybenzyl)-cinnamidine at the NR2B receptor high affinity site (95%; Ki=1.71 nM).

Compound E1-9.2 exhibited only a partial effect (34%) on [$^3$H] MK-801 binding consistent with selective binding to the NR2B receptor subtype. Compound E1-9.2 exhibited a complete displacement of [$^3$H] (E)-N1-(2-methoxybenzyl)-cinnamidine at the NR2B receptor high affinity site (97%; Ki=11.3 nM).

Compound E1-21.2 exhibited only a partial effect (49%) on [$^3$H] MK-801 binding consistent with selective binding to the NR2B receptor subtype. Compound E1-21.2 exhibited a complete displacement of [$^3$H] (E)-N1-(2-methoxybenzyl)-cinnamidine at the NR2B receptor high affinity site (98%; Ki=0.716 nM).

Compound E1-21.26 exhibited only a partial effect (41%) on [$^3$H] MK-801 binding consistent with selective binding to the NR2B receptor subtype. Compound E1-21.26 exhibited a complete displacement of [$^3$H] (E)-N1-(2-methoxybenzyl)-cinnamidine at the NR2B receptor high affinity site (99%; Ki=1.02 nM).

Example 2.2. hERG Channel Inhibition

The assay was performed on hERG channel stably expressed in HEK293 cells. The cells were cultured at 37° C. in a humidified $CO_2$ incubator in the growth medium consisting of DMEM, 10% fetal bovine serum and antibiotics. Prior to the assay, the cells were seeded onto a 12 mm PDL-coated glass coverslip and cultured in a 35 mm Petri dish. After 16 to 40 hr culture, the cover slip was transferred into the chamber of OctaFlow perfusion system (ALA Instrument) and under a constant flow of extracellular solution (140 mM NaCl, 4 mM KCl, 1 mM $MgCl_2$, 2 mM $CaCl_2$, 10 mM HEPES, 10 mM D-glucose, pH 7.35, osmolarity 290). Whole cell patch clamping was performed with a glass micropipette filled with intracellular solution (120 mM KCl, 1.75 mM $MgCl_2$, 5.4 mM $CaCl_2$, 10 mM HEPES, 10 mM EGTA, and 4 mM ATP-$K_2$, PH 7.2, osmolarity 310). Giga-seal was maintained during the test. The voltage control and current measurement were carried out using Axon amplifier 700B, Digidata 1440A and CLAMPEX10 software (Molecular Devices). Whole-cell hERG currents were recorded following the Petroski protocol: the cell was held at −80 mV, and the voltage step jumped from −80 to 30 mV and stay for 2 sec with a 20 ms prepulse at −40 mV. After depolarization, the voltage was decreased to −40 mV and stay for 2 sec, and returned back to −80 mV. Test compound was applied by quartz capillary tubes tip (200 μm inner diameter), and the flow rate was controlled at 2-3 ml/min with OctaFlow perfusion system. Different concentrations of the compound were applied to the cells for 5 min and the hERG current was measured three times before, during and after compound treatment. The data were analyzed using Clampfit 10 software (Molecular Devices) to generate $IC_{50}$ values. Results are shown in Table 2.2.

TABLE 2.2

| Cmpd. No. | NR2B $IC_{50}$ (nM) | hERG $IC_{50}$ (μM) | hERG @ 10 μM (%) |
|---|---|---|---|
| LX-1 | 24 | 4.5 | 61 |
| E1-1.2 | 21.0 | 40 | 17 |
| E2-1.2 | 156 | | 22 |
| E1-2.2 | 10.4 | | 32 |
| E1-9.2 | 48.2 | | 38 |
| E1-8.2 | 17 | 6.8 | 57 |
| E1-1.3 | 14.8 | | 19 |
| E1-1.4 | 20.5 | | 11 |
| E1-22.2 | 42.4 | >10 | |
| E1-21.2 | 14.4 | | 27 |
| E1-21.26 | 38.7 | | 39 |

Example 2.3. CYP P450 Enzyme Inhibition

Inhibitory activities of test compounds on 5 major isoforms of CYP P450 were evaluated by using pooled human liver microsome (HLM, purchased from BD Gentest) and selective substrates for those isoforms. Those CYP isoforms and their corresponding probe substrates are as follows: CYP1A2 (phenacetin, 30 μM), CYP2C9 (tolutamide, 100 μM), CYP2C19 (S-mephenytoin, 40 μM), CYP2D6 (dextromethorphan, 5 μM) and CYP3A4 (midazolam, 1 μM). All probe substrates were used at concentrations near or below their $K_{ms}$. For experiment, a reaction mixture of test compound at 10 μM or in serial dilution, CYP probe substrate described above and 0.2 mg/mL pooled HLM in phosphate buffer, pH 7.4 in a final volume of 200 μL was pre-incubated at 37° C. for 10 minutes in triplicate. The reaction was initiated by addition of NADPH at final concentration of 1 mM. The reaction was terminated after 10 minutes (CYP1A2, CYP2D6 and CYP3A4) or 30 minutes (CYP2C9 and CYP2C19) by addition of 100 μL ice-cold acetonitrile with internal standard (IS). The samples were then centrifuged at 13,000 rpm and the supernatants were injected to LC-MS/MS (Agilent Technologies) to quantify the concentration of the specific metabolites of the probe substrates formed by individual CYP450 isoforms. The inhibition ratio is calculated as:

$$(M_t - M_0)/M_{water} \times 100\%$$

in which $M_t$ and $M_0$ represent the concentrations of the specific probe substrate metabolite, which was formed by individual CYP450 isoform, at the beginning and end of the reaction in the presence of test compound; while $M_{water}$ represents the concentration of the specific metabolite at the end of the reaction in the absence of test compound. Test compound concentration-dependent response data experiments performed in triplicate. Mean CYP2D6 $IC_{50}$ values were derived from non-linear, least-squares fitting of dose-dependent response data to a standard logistic equation (Prism, GraphPad Software, Inc) to generate the CYP2D6 $IC_{50}$ results shown in Table 2.3

TABLE 2.3

| Cmpd. No. | NR2B $IC_{50}$ (nM) | CYP2D6 $IC_{50}$ (μM) | CYP2D6 @ 10 μM (%) |
|---|---|---|---|
| LX-1 | 24 | 1.0 | 93 |
| E1-1.2 | 21.0 | | 14 |
| E2-1.2 | 156 | | |
| E1-2.2 | 10.4 | | 18 |
| E1-9.2 | 48.2 | | 14 |
| E1-8.2 | 17 | 5.9 | 83 |
| E1-1.3 | 14.8 | | 37 |
| E1-1.4 | 20.5 | | 19 |
| E1-22.2 | 42.4 | | |
| E1-21.2 | 14.4 | | 97 |
| E1-21.26 | 38.7 | | 32 |

Example 2.4. Forced Swim Test (FST)

The forced swim test (FST) also known at the behavioural despair test was used to evaluate antidepressant activity (Porsolt et al., 1977 *Arch. Int. Pharmacodyn.* 229: 327-336, Porsolt et al., 1977, *Eur. J. Pharmacol.* 47:379-391). Mice or rats that are forced to swim in a situation from which they cannot escape, rapidly become immobile. Drugs with antidepressant activity, such as imipramine, reduce the amount of time spent in the immobile state. Therefore, the amount of immobility time during a test conducted after drug administration represents a useful indicator of antidepressant activity (Lucki et al 2001 *Psychopharmacology* 155: 315-322; Porsolt et al., 1977, *Nature* 266:730-732).

Test compounds E1-1.2 and E1-21.26 were administered as mesylate salts (mpk based on molecular weight of the free base). Test compound E1-8.2 was administered as the free base.

Testing for antidepressant activity was conducted in rats or mice according to the general procedures below.

Mice were evaluated in a single swimming test session of 6 minutes. Mice were placed in a transparent plastic cylinder 24 cm high with a diameter of 13 cm containing 10 cm of water with ambient temperature control generally from 22±2° C. Mice were placed in the water for 6 minutes and the duration of immobility during the last 4 minutes was measured.

Male Wistar rats weighing 197-251 g were used for the rat test. Rats were evaluated according to a two-session procedure with a swimming session of 15 minutes on the first day of the experiment (Session 1) followed 24 hours later by a 5-minute swimming test (Session 2). Rats were individually forced to swim inside 40 cm×18 cm vertical transparent plexiglass cylinders containing 15 cm of water maintained at 25° C. (Session 1). After 15 min in the water, the rats were removed and allowed to dry for 15 min in a heated enclosure (32° C.) before being returned to their cages. Rats were placed in the water 24 h later for 5 minutes (Session 2) and the duration of immobility was measured.

Animals were observed by a blinded observer. The observer judged the animal to be immobile when it ceased all activity (struggling, swimming, jumping etc.) and floated passively atop the water. The amount of time each animal spent in the immobile state (and the latency to the first bout of immobility) was recorded and used for statistical analysis of compound effect. Group differences were evaluated by student's t-test (reference substance) or one-way ANOVA followed by post-hoc Dunnett's test (test substances).

In a given experiment (for both mouse and rat experiments) a test compound, vehicle control solution and positive control reference compound imipramine were administered. Test compounds were administered in one or more doses by either oral gavage (p.o.) or by intraperitoneal injection (i.p.) dosing routes after dissolving in 0.5% dimethylsulfoxide, 4% hydroxypropyl-b-cyclodextrin water as a vehicle. Test compound doses ranged from 1 to 30 milligrams per kilogram (expressed in the accompanying Figures either as mpk or mg/kg).

Imipramine control compound was dissolved in physiological saline solution. Imipramine was dosed as indicated in the particular Examples.

Test compound dose solutions and vehicle control solutions were administered 20 minutes before placing the animals in the water cylinder for both oral and intraperitoneal experiments. Imipramine was dosed as indicated in the particular Examples below.

Male mice (strain NLMN) weighing 25-35 g were used for testing. All animals were housed in a temperature (22-24° C.) and humidity (50-60%) controlled environment with free access to food and water on a 12-hour light-dark cycle. Test compounds were dissolved in 0.5% dimethylsulfoxide, 4% hydroxypropyl-b-cyclodextrin water to generate the appropriate dosing solution. Drugs were administered by intraperitoneal injection at a dose volume of 10 mL/kg. Testing was initiated 20-60 minutes after dosing. Testing for antidepressant activity was conducted as described by Darci et al. (Darci et al., 2004, Eur. J. Pharmacol. 499:135-146). Mice were placed in a white plastic cylinder 20 cm high with a diameter of 21 cm containing 10 cm of water at 25±2° C. The mice were videotaped for 6 minutes, and the last 4 minutes of video were analyzed by a blinded observer off-line. The observer judged the animal to be immobile when it ceased all activity (struggling, swimming, jumping etc.) and floated passively atop the water. The amount of time each animal spent in the immobile state was recorded and used for statistical analysis of compound effect. Group differences were evaluated by student's t-test or one-way ANOVA followed by post-hoc Dunnett's test.

Example 2.4.1. Compound E1-1.2 in Mice

Results are shown in FIG. 1A. Bars represent the mean±SEM immobility time for each dose group (n=10, ***: different from vehicle group, $p<0.001$, One-way ANOVA, Dunnett's post-test). Doses are given as milligram per kilogram (mpk). The dose of imipramine was 32 mpk.

Figure 1B:
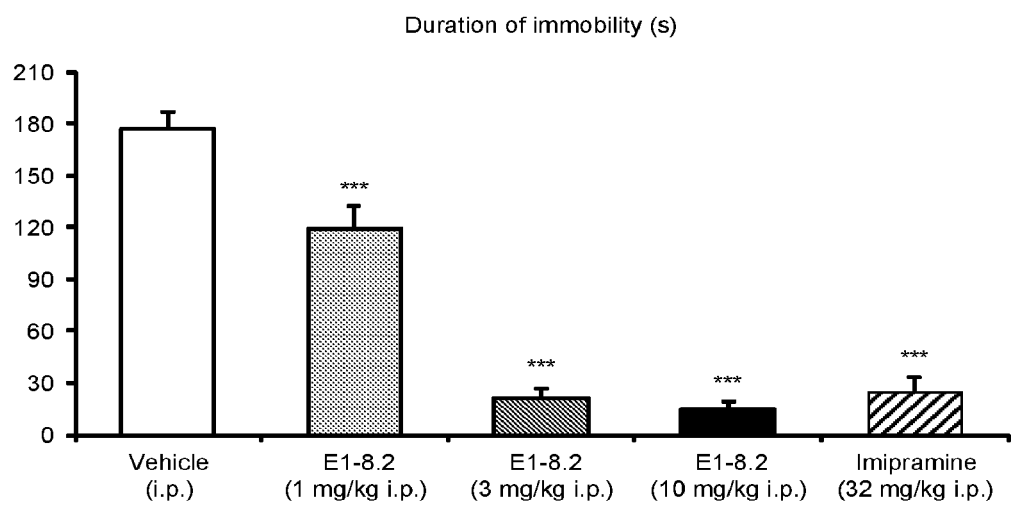
FIG. 1B shows results of the Forced Swim Test in mice as described in Example 2.4.2 with compound E1-8.2 by i.p. administration.

Example 2.4.2. Compound E1-8.2 Administered by Intraperitoneal Injection in Mice Results are shown in FIG. 1B. Bars represent the mean±SEM immobility time for each dose group (***: different from vehicle group, $p<0.001$, One-way ANOVA, Dunnett's post-test). In the present Example the positive control compound, imipramine (32 mpk i.p.) administered once 30 min before the test, showed the expected antidepressant activity.

Figure 1C:
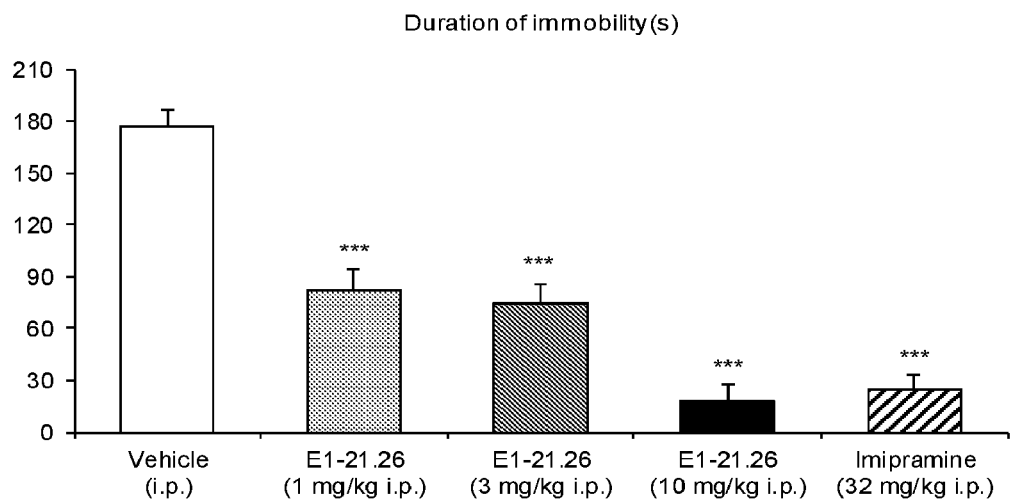
FIG. 1C shows results of the Forced Swim Test in mice as described in Example 2.4.3 with compound E1-21.26 by i.p. administration.

Example 2.4.3. Compound E1-21.26 Administered by Intraperitoneal Injection in Mice Results are shown in FIG. 1C. Bars represent the mean±SEM immobility time for each dose group (***: different from vehicle group, $p<0.001$, One-way ANOVA, Dunnett's post-test). In the present Example the positive control compound, imipramine (32 mpk i.p.) administered once 30 min before the test, showed the expected antidepressant activity.

Example 2.4.4. Compound E1-1.2 Administered Orally in Mice

Figure 1D:
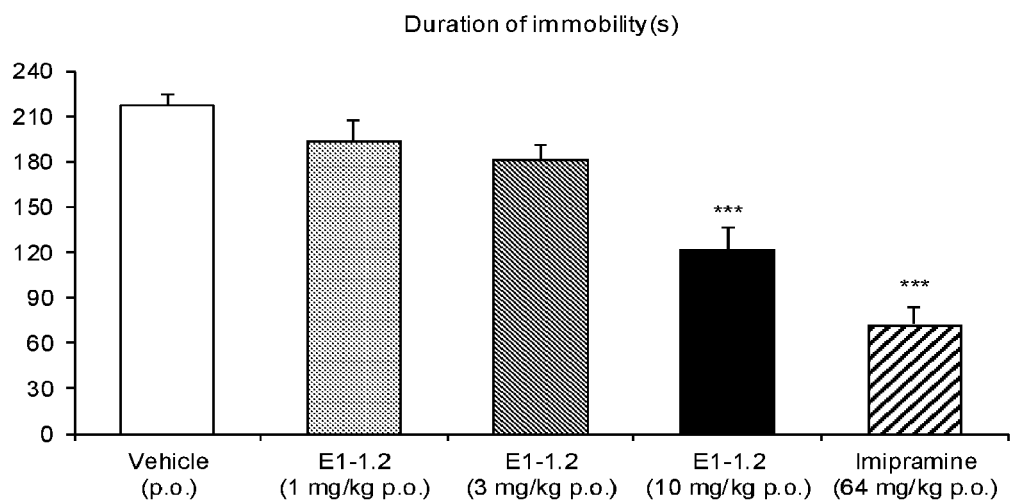
FIG. 1D shows results of the Forced Swim Test in mice as described in Example 2.4.4 with compound E1-1.2 by oral (p.o.) administration.

Results are shown in FIG. 1D. Bars represent the mean±SEM immobility time for each dose group (***: different from vehicle group, $p<0.001$, One-way ANOVA, Dunnett's post-test). In the present Example the positive control compound, imipramine (64 mpk p.o.) administered once 60 min before the test, showed the expected antidepressant activity.

Figure 1E:
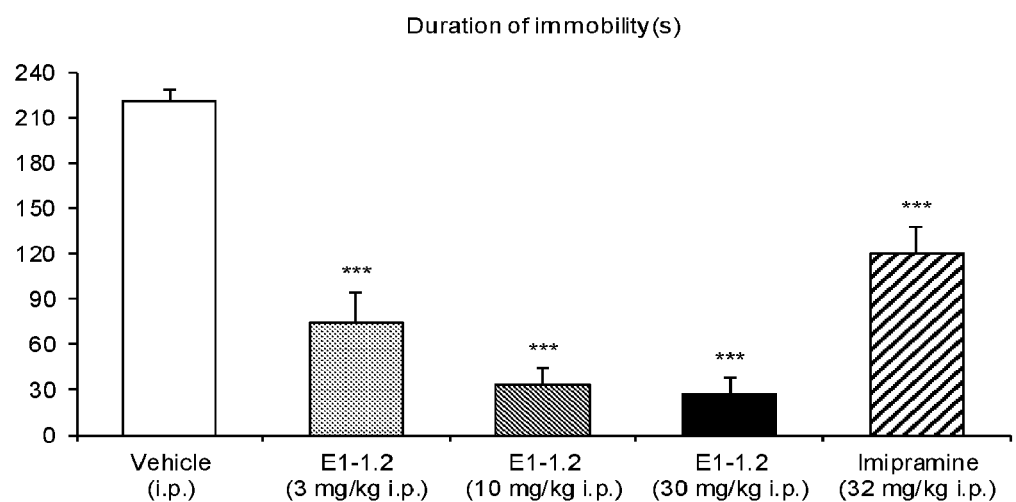
FIG. 1E shows results of the Forced Swim Test in rats as described in Example 2.4.5 with compound E1-1.2 by i.p. administration.

Example 2.4.5. Compound E1-1.2 Administered by Intraperitoneal Injection in Rats Results are shown in FIG. 1E. Bars represent the mean±SEM immobility time for each dose group (***: different from vehicle group, $p<0.001$, One-way ANOVA, Dunnett's post-test).). In the present Example the positive control compound, imipramine (32 mpk i.p.) administered 3 times: at 24 h, 4 h and 30 min before the test (Session 2), showed the expected antidepressant activity.

Example 2.4.6. Compound E1-21.26 Administered Orally in Rats

Figure 1F:
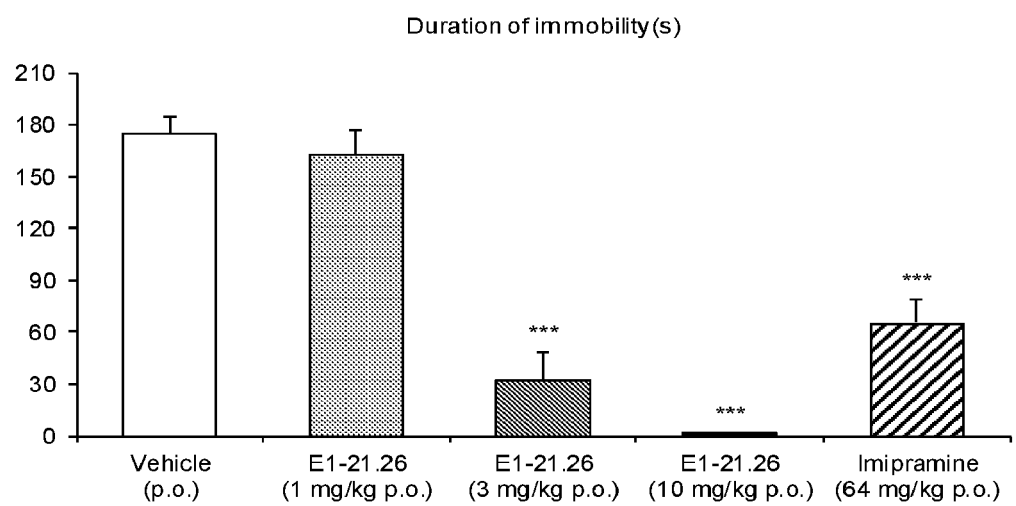
FIG. 1F shows results of the Forced Swim Test in rats as described in Example 2.4.6 with compound E1-21.26 by p.o. administration.

Results are shown in FIG. 1F. Bars represent the mean±SEM immobility time for each dose group (***: different from vehicle group, $p<0.001$, One-way ANOVA, Dunnett's post-test). In the present Example the positive control compound, imipramine (64 mpk p.o.) administered 3 times: at 24 h, 4 h and 60 min before the test (Session 2), showed the expected antidepressant activity.

Example 2.4.7. Chronic Dosing of Mice in Forced Swim Test

Mice were individually placed in a cylinder (height=24 cm; diameter=13 cm) containing 10 cm water (22° C.) from which they cannot escape. The mice were placed in the water for 6 minutes and the duration of immobility during the last 4 minutes was measured. The latency to the first bout of immobility was also recorded starting from the beginning of the test.

The compound was evaluated at 2 doses (3 and 10 mg/kg), administered either acutely p.o. 20 minutes before the test on Day 7 or daily during 7 days with the last administration 20 minutes before the test on Day 7, and compared with a vehicle control group. Vehicle was administered daily when a drug was not due. Imipramine (128 mg/kg p.o.), administered once 60 minutes before the test on Day 7, was used as reference substance.

Figure 1G:
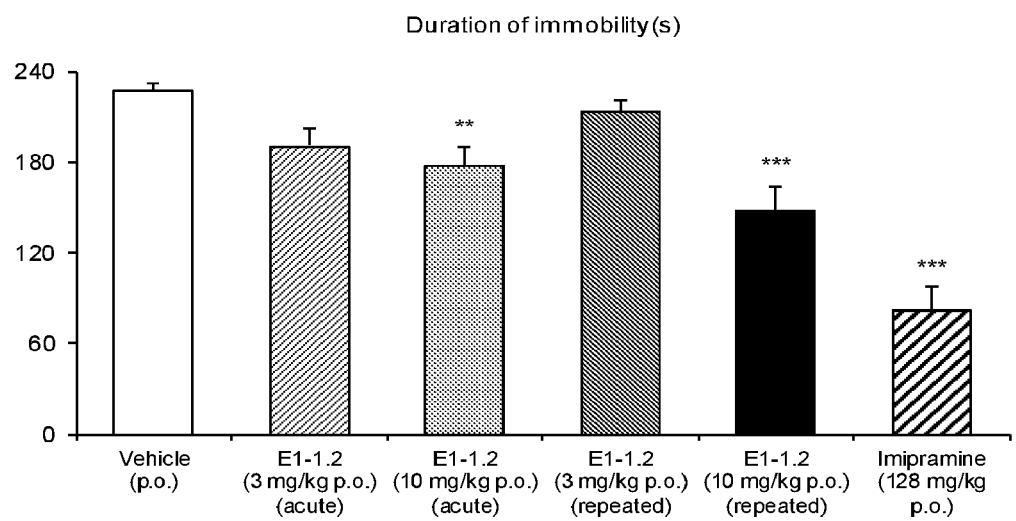
FIG. 1G shows results of the Forced Swim Test as described in Example 2.4.7 with compound E1-1.2.

Results are shown in FIG. 1G. Bars represent the mean±SEM immobility time for each dose group (/*: different from vehicle group, $p<0.01/p<0.001$, One-way ANOVA, Dunnett's post-test). In the present Example the positive control compound, imipramine (128 mpk p.o.) administered once 60 minutes before the test on Day 7, showed the expected antidepressant activity.

These results indicate that provided compounds exhibit antidepressant activity when tested in standard models for human depression. These data demonstrate that the test compounds exhibit antidepressant activity when dosed chronically. Furthermore these results indicate that provided compounds exhibit antidepressant activity when dosed acutely and chronically.

Example 2.5. Electroconvulsive Threshold Test (ECT)

The Electroconvulsive Threshold Test, which detects proconvulsant or anticonvulsant activity, was generally conducted as described by Swinyard et al., (*J. Pharmacol. Exp. Ther.*, 106, 319-330, 1952). Test compounds E1-1.2 and E1-21.26 were administered as mesylate salts (mpk based on molecular weight of the free base). Test compound E1-8.2 was administered as the free base.

Rats were administered ECS (rectangular current: 0.6 ms pulse width, 1.5 s duration, 200 Hz) via earclip electrodes connected to a constant current shock generator (Ugo Basile: type 7801). Test compounds were administered by oral gavage (p.o.) 1 hour before the test at a dose volume of 5 mL/kg.

Treatment groups of 20 rats were exposed to ECS as follows: The first animal was exposed to 30 mA of ECS. If this animal did not convulse (tonic convulsions) within 5 seconds maximum, animal no2 is exposed to 35 mA, etc. . . . (increases of 5 mA) until the first tonic convulsion was observed. Once the first tonic convulsion was observed, the intensity of ECS was decreased by 2 mA for the next animal and then decreased or increased by 2 mA from animal to animal depending on whether the previous animal convulsed or not. If the first animal did convulse (tonic convulsions) within 5 seconds, animal no2 is exposed to 25 mA, etc. . . . (decreases of 5 mA) until the absence of tonic convulsions was observed. At this point, the intensity of ECS was increased by 2 mA for the next animal and then decreased or increased by 2 mA from animal to animal depending on whether the previous animal convulsed or not. The minimum current intensity applied is 5 mA and the maximum 95 mA. The first 5 animals serve to approach threshold current and were not included in the analysis. The results are presented as the mean current intensity administered to the final 15 animals of a group. The test was performed blind. A positive percent change indicates an anticonvulsant effect. A negative percent change indicates a proconvulsant effect. The test substance was evaluated at 4 doses, typically using 0.5% dimethylsulfoxide, 4% hydroxypropyl-b-cyclodextrin water as a vehicle, and administered p.o. 60 minutes before ECS, and compared with a vehicle control group. Diazepam (16 mg/kg p.o.), administered under the same experimental conditions, was used as reference substance. The experiment included 6 groups. Data with the test substance was analyzed by comparing treated groups with vehicle control using one-way ANOVA followed by Dunnett's t tests.

In Example 2.5.1 the anticonvulsant positive control compound diazepam (16 mpk p.o.) showed the expected anticonvulsant activity. The proconvulsant positive control compound theophylline (128 mpk p.o.) showed the expected proconvulsant activity. In Example 2.5.2 only the anticonvulsant positive control was included in the study.

Example 2.5.1. Compound E1-1.2

Figure 2:
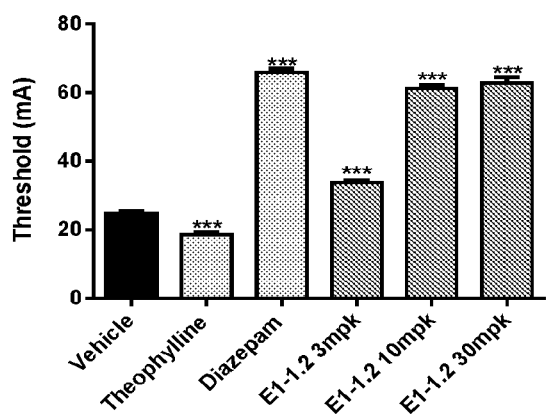
FIG. 2 shows results of the Electroconvulsive Threshold Test (ECT) as described in Example 2.5.1 with compound E1-1.2.

The results are shown in FIG. 2. Bars represent the mean±SEM electroconvulsive threshold for each dose group (n=15, ***: different from vehicle group, $p<0.001$, One-way ANOVA, Dunnett's post-test). Doses are given as milligram per kilogram (mpk). The dose of diazepam was 16 mpk. The dose of theophylline was 128 mpk.

Compound E1-1.2 showed robust anticonvulsant activity at doses tested, 3, 10 and 30 mpk.

Example 2.5.2. Compound E1-8.2

Figure 3:
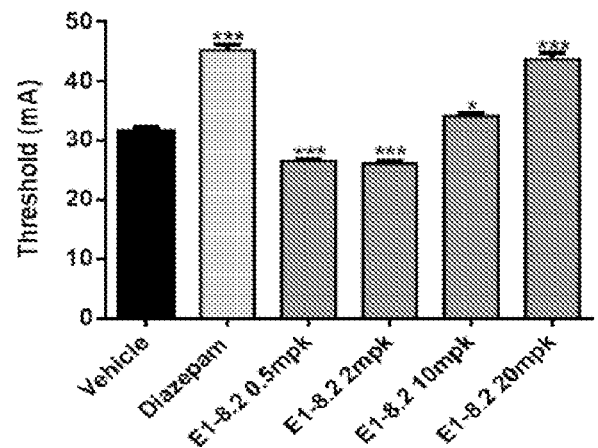
FIG. 3 shows results of the Electroconvulsive Threshold Test (ECT) as described in Example 2.5.2 with compound E1-8.2.

The results are shown in FIG. 3. Bars represent the mean±SEM electroconvulsive threshold for each dose group (n=15, ***/*: different from vehicle group, $p<0.001/0.05$ respectively, One-way ANOVA, Dunnett's post-test). Doses are given as milligram per kilogram (mpk). The dose of diazepam was 16 mpk.

Compound E1-8.2 showed modest proconvulsant activity after administration of 0.5 and 2 mpk, and anticonvulsant activity at 10 and 20 mpk doses.

Example 2.5.3. Compound E1-21.26

Figure 4:
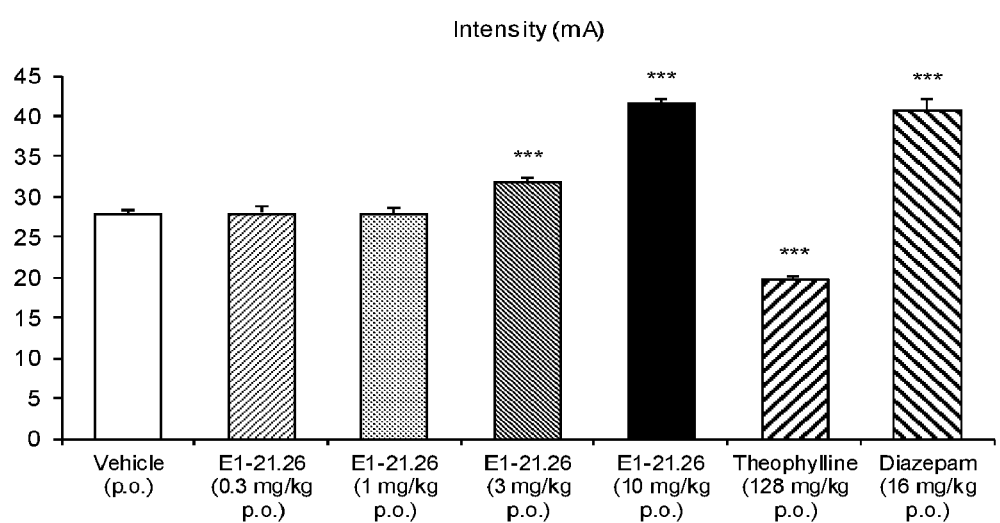
FIG. 4 shows results of the Electroconvulsive Threshold Test (ECT) as described in Example 2.5.3 with compound E1-21.26.
Figure 5A:
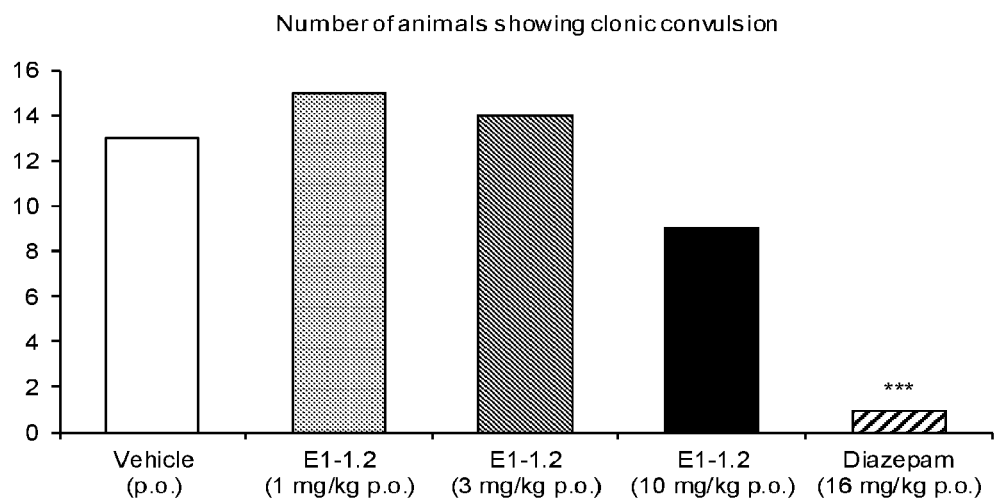
FIG. 5A shows the number of animals showing clonic convulsions in the Pentylenetetrazole (PTZ) Seizure Test as described in Example 2.6.1 with compound E1-1.2.
Figure 5B:
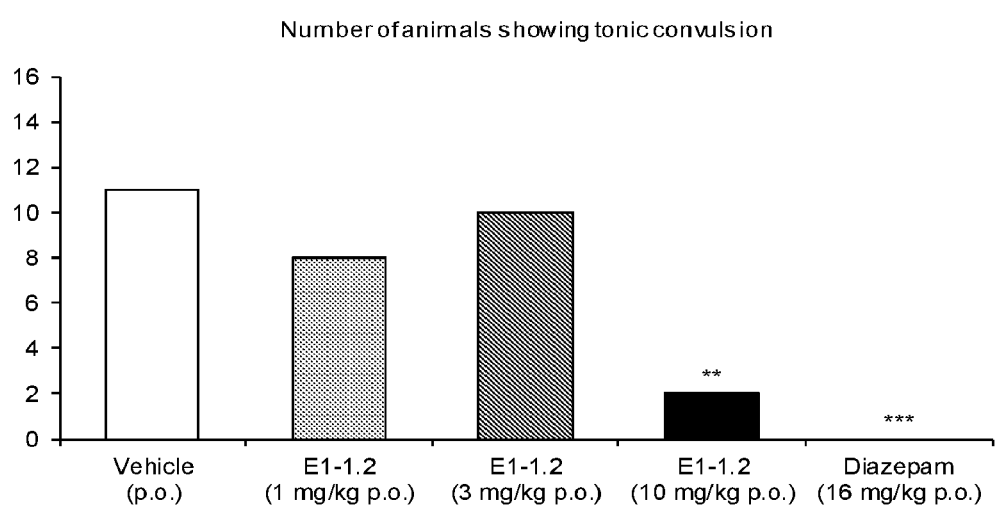
FIG. 5B shows the number of animals showing tonic convulsions in the PTZ Seizure Test with compound E1-1.2.
Figure 5C:
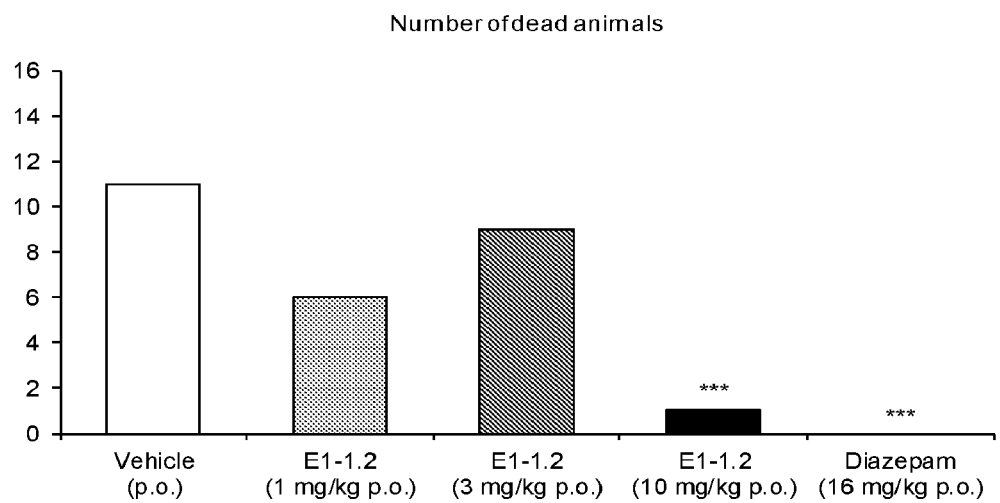
FIG. 5C shows number of dead animals in the PTZ Seizure Test with compound E1-1.2.
Figure 5D:
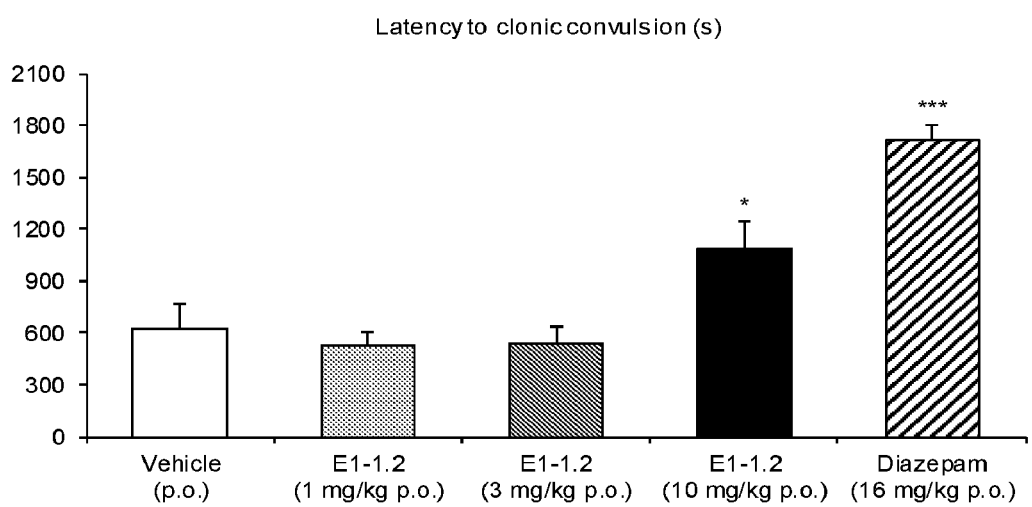
FIG. 5D shows latency to clonic convulsions in the PTZ Seizure Test with compound E1-1.2.
Figure 5E:
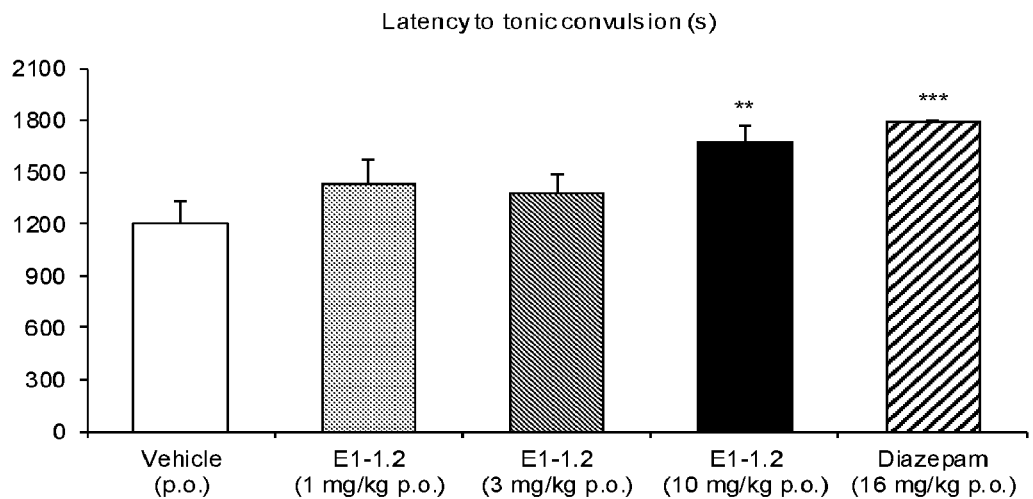
FIG. 5E shows latency to tonic convulsions in the PTZ Seizure Test with compound E1-1.2.
Figure 5F:
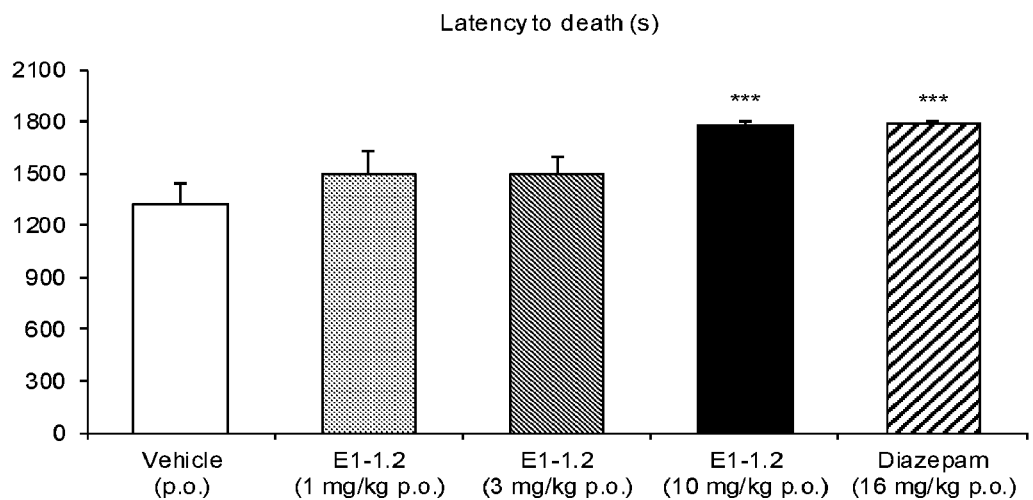
FIG. 5F shows latency to death in the PTZ Seizure Test with compound E1-1.2.
Figure 6A:
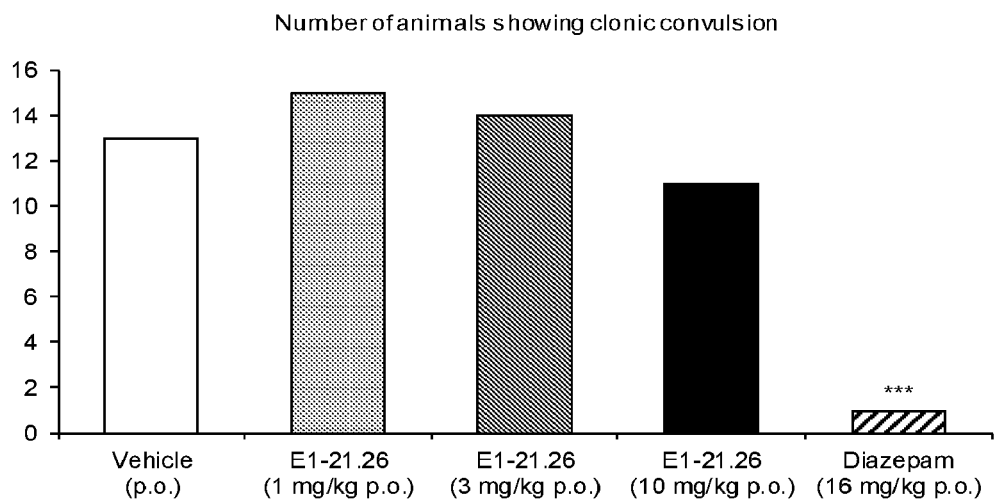
FIG. 6A shows the number of animals showing clonic convulsions in the Pentylenetetrazole (PTZ) Seizure Test as described in Example 2.6.2 with compound E1-21.26.
Figure 6B:
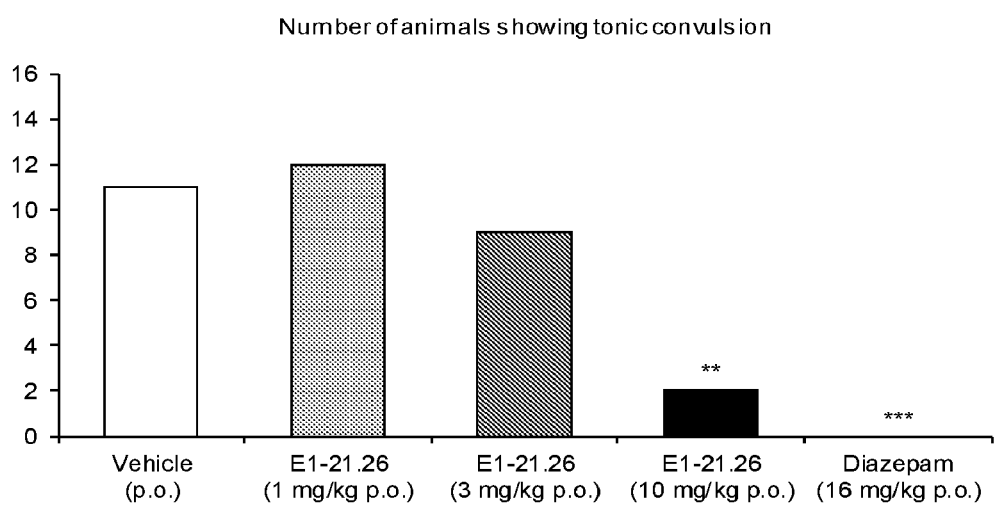
FIG. 6B shows the number of animals showing tonic convulsions in the PTZ Seizure Test with compound E1-21.26.
Figure 6C:
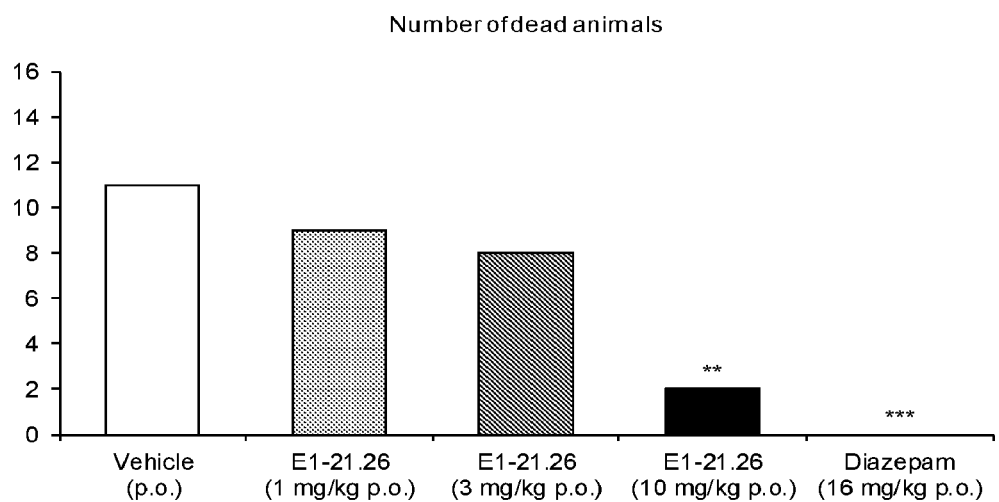
FIG. 6C shows number of dead animals in the PTZ Seizure Test with compound E1-21.26.
Figure 6D:
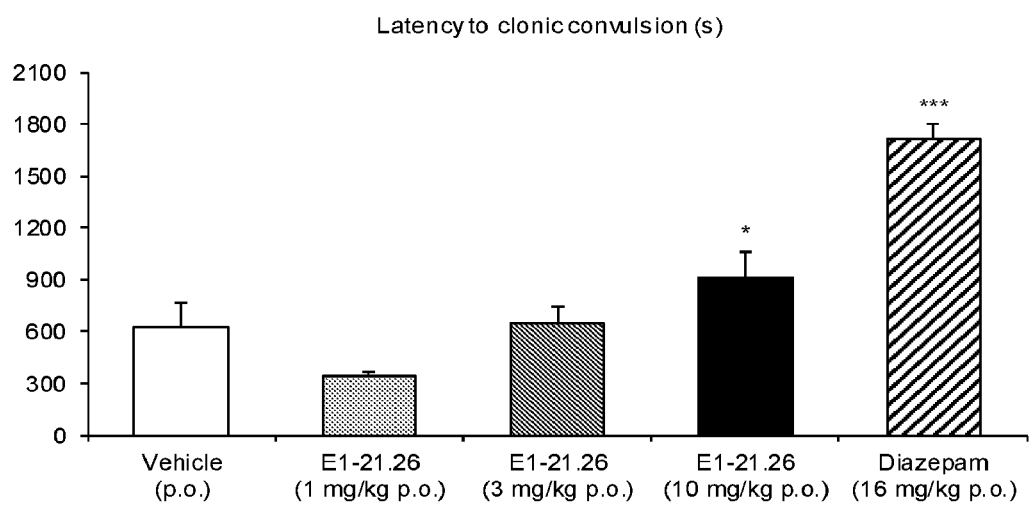
FIG. 6D shows latency to clonic convulsions in the PTZ Seizure Test with compound E1-21.26.
Figure 6E:
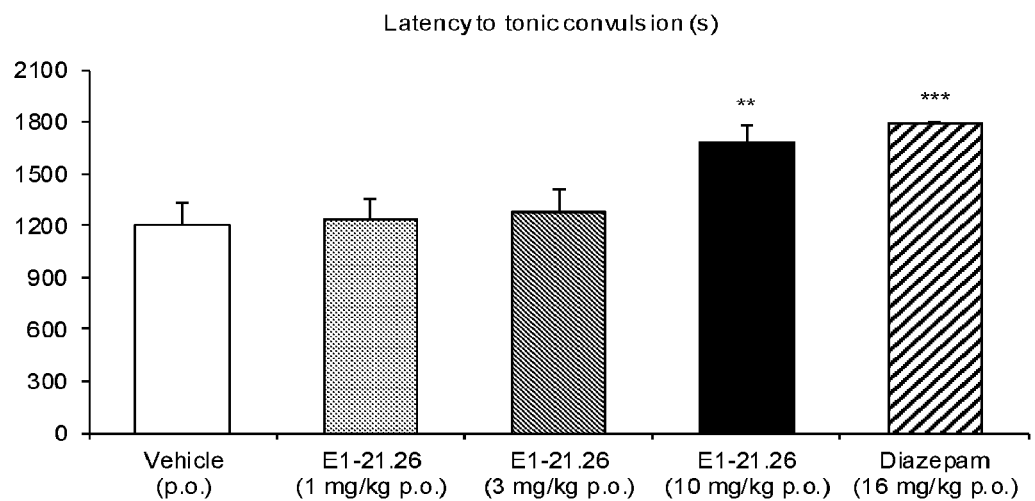
FIG. 6E shows latency to tonic convulsions in the PTZ Seizure Test with compound E1-21.26.
Figure 6F:
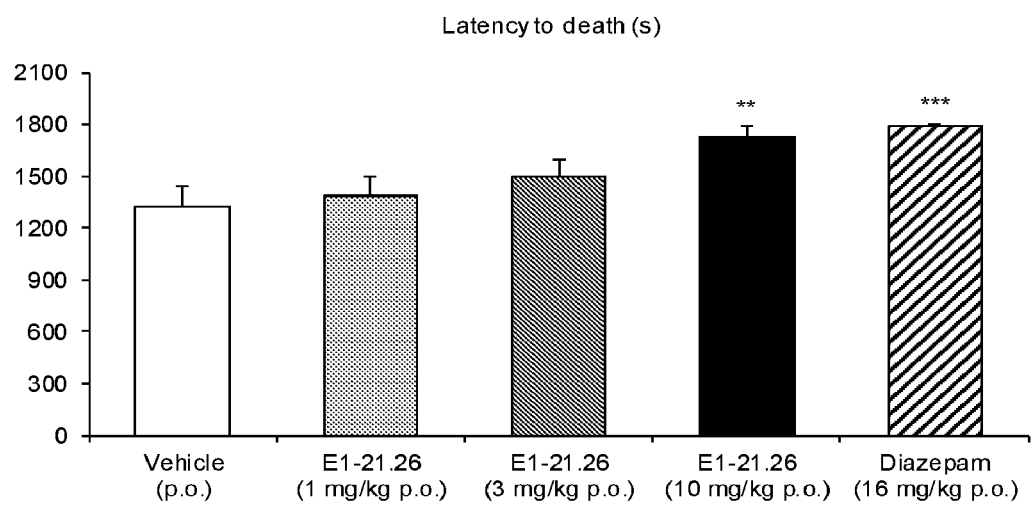
FIG. 6F shows latency to death in the PTZ Seizure Test with compound E1-21.26.

The results are shown in FIG. 4. Bars represent the mean±SEM electroconvulsive threshold for each dose group (n=15, ***/*: different from vehicle group, $p<0.001/0.05$ respectively, One-way ANOVA, Dunnett's post-test).

Compound E1-21.26 showed anticonvulsant activity at 3 and 10 mpk doses.

Example 2.6. Pentylenetetrazole (PTZ) Seizure Test

The method, which detects proconvulsant or anticonvulsant activity related to a GABAergic mechanism, follows that described by Krall (*Epilepsia*, 19, 409-428, 1978). Rats, placed in individual macrolon cages (25×19×13 cm), were injected with pentylenetetrazole (PTZ) (100 mg/kg s.c.). The occurrence and latency of clonic and tonic convulsions and death were noted over a 30 minute period. 15 rats were studied per group. The test was performed blind.

Test compounds E1-1.2 and E1-21.26 were administered as mesylate salts (mpk based on molecular weight of the free base). Test compound E1-8.2 was administered as the free base.

Compounds were evaluated typically using 0.5% dimethylsulfoxide, 4% hydroxypropyl-b-cyclodextrin water as a vehicle at 1 or more doses (e.g., 1, 3 and 10 mg/kg), administered p.o. 30 minutes before PTZ, and compared with a vehicle control group. Diazepam (16 mg/kg p.o.), administered 60 minutes before PTZ, was used as reference substance. The experiment was performed over 2 separate sub-experiments with N=7 to 8 animals per group and per sub-experiment. Quantitative data (latencies) with the test substance was analyzed by comparing treated groups with vehicle control using Kruskal-Wallis test followed by Mann-Whitney U test. Quantitative data with the reference substance was analyzed using Mann-Whitney U test. Quantal data (frequencies) was analyzed by comparing treated groups with vehicle control using Fisher's Exact Probability tests (*=$p<0.05$; =$p<0.01$; *=$p<0.001$).

Example 2.6.1. Compound E1-1.2

The results are shown in FIG. 5A, FIG. 5B, FIG. 5C, FIG. 5D, FIG. 5E, and FIG. 5F.

Compound E1-1.2 at a 10 mg/kg p.o. dose decreased the number of rats showing tonic convulsions (−82%, $p<0.01$) and the number of deaths (−91%, $p<0.001$) as compared with vehicle controls. Compound E1-1.2 also increased the latencies to induce clonic and tonic convulsions and the latency to death (+72%, $p<0.05$; +39%, $p<0.01$ and +35%, $p<0.001$, respectively). These results confirm the anticonvulsant activity for compound E1-1.2 at 10 mg/kg p.o. in the Pentylenetetrazole Seizure Test in the rat.

Example 2.6.2. Compound E1-21.26

The results are shown in FIG. 6A, FIG. 6B, FIG. 6C, FIG. 6D, FIG. 6E, and FIG. 6F.

Compound E1-21.26 at a 10 mg/kg p.o. dose decreased the number of rats showing tonic convulsions (−82%, p<0.01) and the number of deaths (−82%, p<0.01) as compared with vehicle controls. Compound E1-21.26 also increased the latencies to induce clonic and tonic convulsions and the latency to death (+45%, p<0.05; +40%, p<0.01 and +31%, p<0.01, respectively). These results confirm the anticonvulsant activity for compound E1-21.26 at 10 mg/kg p.o. in the Pentylenetetrazole Seizure Test in the rat.

Example 2.7. 6 Hz Seizure Test

The 6 Hz seizure test, which detects anticonvulsant activity of test compounds, was conducted according to methods described by Brown et al. (*J. Pharmacol. Exp. Ther.* 107, 273-283, 1953) and Barton et al. (*Epilepsy Res.* 47, 217-227, 2001). Mice were administered a rectangular current (44 mA, rectangular pulse: 0.2 ms pulse width, 3 s duration, 6 Hz) via corneal electrodes connected to a constant current shock generator (Ugo Basile: type 7801). The results for the number of seizures as reflected by forelimb clonus were recorded during the first minute following current administration. Forelimb clonus was scored as absent (0), mild (1) and strong (2). 15 mice were studied per group. The test was performed partially blind (test substance vs vehicle). Test substances were administered typically using 0.5% dimethylsulfoxide, 4% hydroxypropyl-b-cyclodextrin water as a vehicle p.o. 30 minutes before the test and compared with a vehicle control group. Test compounds E1-1.2 and E1-21.26 were administered as mesylate salts (mpk based on molecular weight of the free base). Test compound E1-8.2 was administered as the free base.

Diazepam, administered 60 minutes before the test, was used as a positive control reference substance. Quantitative data (scores) with the test substance was analyzed by comparing treated groups with vehicle control using Kruskall-Wallis test followed by Mann-Whitney U tests.

Example 2.7.1. Compound E1-1.2

Figure 7A:
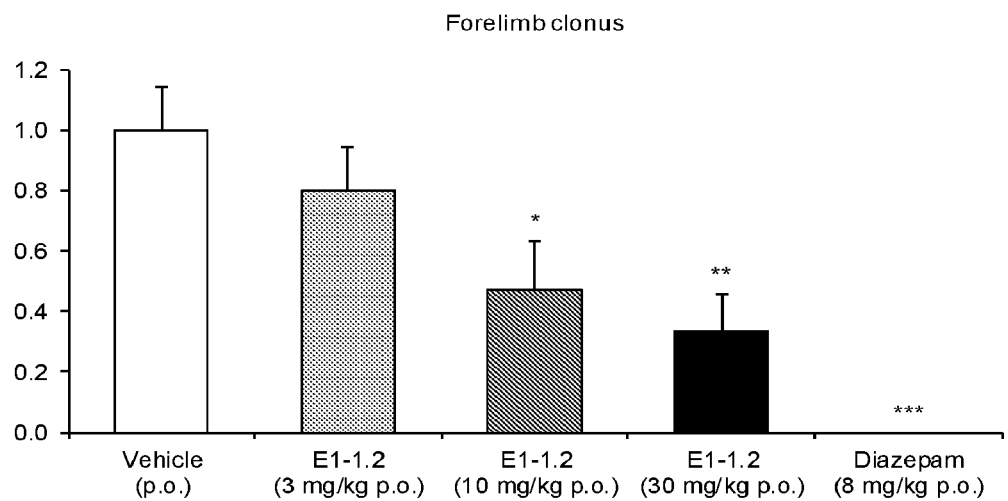
FIG. 7A shows the forelimb clonus score in the 6 Hz Seizure Test as described in Example 2.7.1 for compound E1-1.2.
Figure 7B:
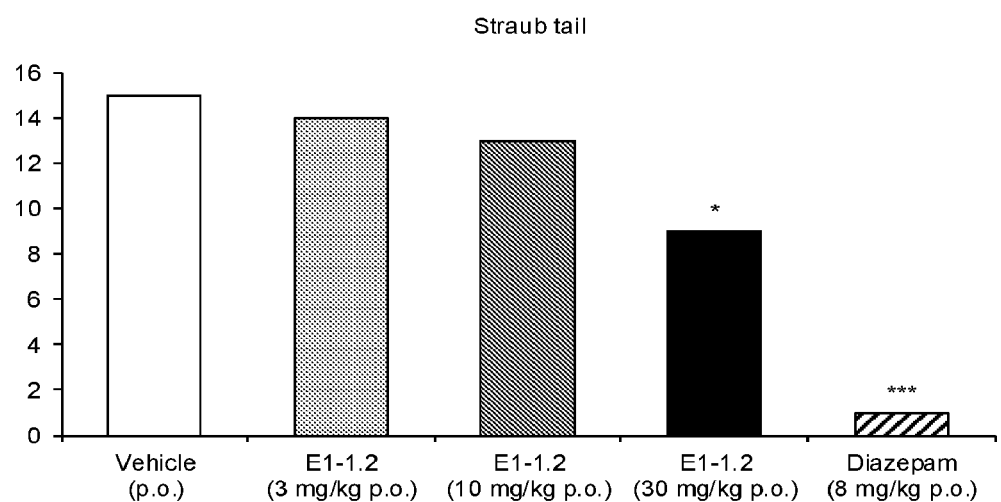
FIG. 7B shows the number of mice with Straub tail in the 6 Hz Seizure Test as described in Example 2.7.1 for compound E1-1.2.

Results are shown in FIG. 7A. Bars represent the mean±SEM forelimb clonus score (arbitrary units) for each dose group (*//*: different from vehicle group, p<0.05/ 0.01/0.001, One-way ANOVA, Dunnett's post-test). Doses are given as milligram per kilogram (mpk). The dose of diazepam was 8 mpk (p.o.). Compound E1-1.2 showed a dose-response reduction in forelimb clonus. (10 and 30 mg/kg), administered p.o. 30 minutes before the test, significantly and dose-dependently decreased the forelimb seizure score, as compared with vehicle control (−50%, p<0.05 and −70%, p<0.01, respectively). It also dose-dependently decreased the number of mice with Straub tail with a significant effect observed at 30 mg/kg (10 mg/kg: −13%, NS and 30 mg/kg: −40%, p<0.05) (FIG. 7B).

Example 2.8. Haloperidol-Induced Catalepsy (HIC) Model

The Haloperidol-induced Catalepsy (HIC) model detects antipsychotic activity and the action of NR2B selective antagonists (Steece-Collier et al. *Exp. Neurol.* 163: 239, 2000) and was based on methods described by Chermat and Simon (*J. Pharmacol.*, 6, 493-496, 1975). The capacity to induce catalepsy serves as an index of the liability of a test substance to induce extrapyramidal side-effects, in particular Parkinsonism. Antagonism of antipsychotic-induced catalepsy can thus serve to detect anti-Parkinson potential.

Rats were injected with haloperidol (1 mg/kg i.p.) and were examined for catalepsy at 30 minute intervals up to 360 minutes. Presence (+) or absence (−) of catalepsy was assessed by three procedures: 1) imposed crossing of the ipsilateral fore- and hind-limbs; 2) placing the animal in the Buddha position; 3) the tilting board, an automatic device that, 5 seconds after positioning the rat, displaces the rat from a horizontal to vertical position and back while it clings to a wire grid with its front paws. Akinesia and catalepsy were assessed depending on whether or not the animal moves before (akinesia) or during operation of the board (catalepsy).

The 4 scores were cumulated over time to give a global catalepsy score per animal. Six rats were studied per group. The test was performed blind (test substances versus vehicle). Test substances were evaluated at 1 or more doses, administered typically using 0.5% dimethylsulfoxide, 4% hydroxypropyl-b-cyclodextrin water as a vehicle p.o. 15 minutes before haloperidol (i.e. 45 minutes before the first measurement), and compared with a vehicle control group. Test compounds E1-1.2 and E1-21.26 were administered as mesylate salts (mpk based on molecular weight of the free base).

Amphetamine (8 mg/kg p.o.), administered 60 minutes before the test (i.e. 90 minutes before the first measurement), was used as reference substance. Data with the test substances were analyzed by comparing treated groups with vehicle control using Kruskal-Wallis Test followed by Mann-Whitney U tests at each time and for cumulated score. Data with the reference substance were analyzed using Mann-Whitney U tests.

Example 2.8.1. Compound E1-1.2

Figure 8A:
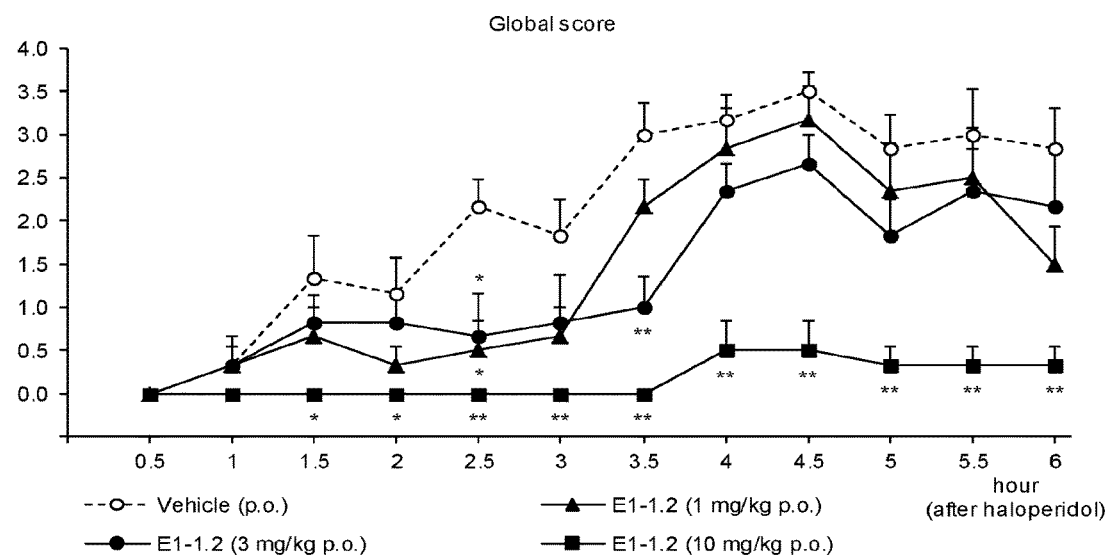
FIG. 8A shows the results of the haloperidol-induced catalepsy model as described in Example 2.8.1 for compound E1-1.2.

The results are shown in FIG. 8A. Doses were given as milligram per kilogram (mpk). The dose of amphetamine was 8 mpk (FIG. 8B).

Figure 8B:
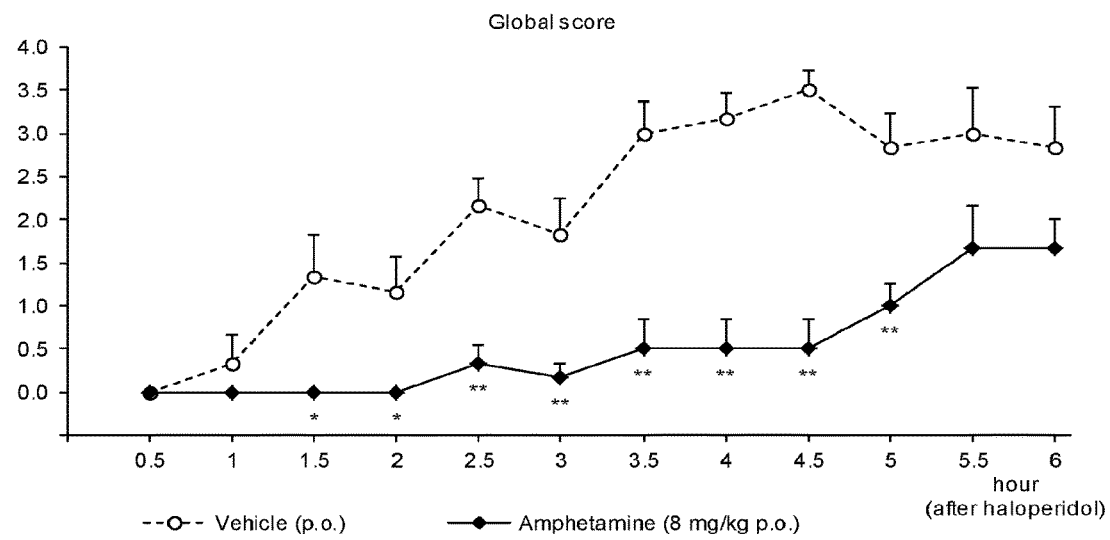
FIG. 8B shows the results of the haloperidol-induced catalepsy model for amphetamine.

The positive control compound amphetamine (8 mg/kg p.o.) showed the expected robust anticataleptic activity (FIG. 8B). Compound E1-1.2 significantly decreased the cumulated score of catalepsy over 360 mins, as compared with vehicle controls (2.0, p<0.01). At 1 and 3 mg/kg, Compound E1-1.2 tended to decrease the cumulated score of catalepsy over 360 mins (17.0, p=0.0898 and 15.8, p=0.0526, respectively) with significant effects at 2.5 hours at 1 mg/kg (p<0.05) and at 2.5 and 3.5 hours at 3 mg/kg (p<0.05 and p<0.01, respectively). Catalepsy was observed between 4 and 6 hours at 10 mg/kg. These results suggest the presence of significant anti-cataleptic activity for compound E1-1.2 in the Haloperidol-induced Catalepsy test in the rat.

Example 2.8.2. Compound E1-21.26

Figure 8C:
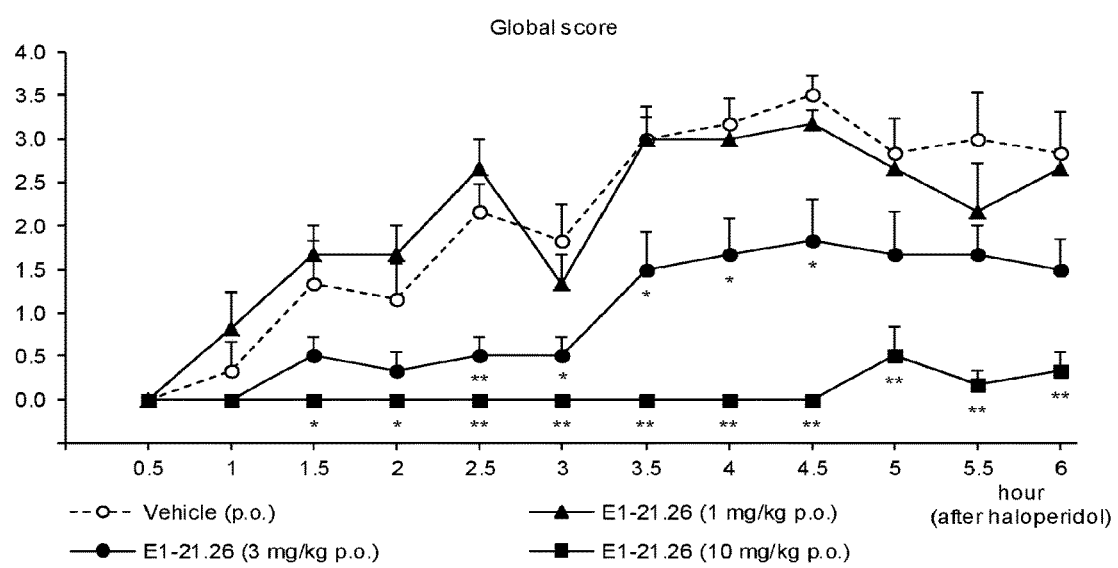
FIG. 8C shows the results of the haloperidol-induced catalepsy model as described in Example 2.8.2 for compound E1-21.26.

The results are shown in FIG. 8C. Doses were given as milligram per kilogram (mpk). The positive control compound amphetamine (8 mg/kg p.o.) showed the expected robust anticataleptic activity (FIG. 8B). Compound E1-21.26 at 3 mg/kg and 10 mg/kg significantly and dose-dependently decreased the cumulated score of catalepsy over 360 mins, as compared with vehicle controls (11.7 and 1.0, respectively, p<0.01). Catalepsy was observed between 1.5 and 6 hours at 3 mg/kg. Catalepsy was also observed between 5 and 6 hours at 10 mg/kg. These results suggest the presence of significant anti-cataleptic activity for compound E1-21.26 in the Haloperidol-induced Catalepsy test in the rat.

Example 2.9. Rat Formalin Model

The rat formalin model is a tonic model of continuous pain resulting from formalin-induced spontaneous nociceptive behaviors. Intra-paw injection of formalin is a commonly used model to measure spontaneous nociceptive behaviors in rodents (Dubuisson, D. and Dennis, S. G. Pain 4:161, 1977). Subcutaneous plantar injection of formalin causes a bi-phasic nocifensive behavioral response in rodents. The early phase (phase-1) lasts for about 5-10 min following which an interphase occurs without any discernible nociceptive reactions after which the late phase (phase-II) nociceptive reaction ensues continuing from about 20-60 min following formalin injection. Formalin model is a model of tonic, persistent pain, and is widely used for rapid screening of novel analgesic compounds. The model encompasses inflammatory, neurogenic and central mechanisms of nociception, and the late phase in particular is considered as a pharmacodynamic surrogate of central sensitization. In the present example, effects of test item were assessed in 0-5 minutes from the early phase (phase-I) and 20-35 minutes from the late phase (phase-II) of formalin-induced nociceptive behavior. 20 mins before injection of formalin, the animals were administered with vehicle, test compound (10, 30, 60 mpk i.p.) typically using 0.5% dimethylsulfoxide, 4% hydroxypropyl-b-cyclodextrin water as a vehicle and positive control Duloxetine (30 mpk).

For all groups, animals were acclimated to the observation chamber for 15 minutes immediately prior to formalin injection. All animals received an intraplantar subcutaneous injection of 50 µL of 5% formalin into the left hind paw and then placed immediately into an observation chamber and formalin-evoked spontaneous nociceptive behaviors in the rats were continuously recorded for 0-60 min using a commercial camcorder.

Scoring from the recorded video files was performed off-line using a PC by an observer who was validated to score such nociceptive behavior in rodents. The total time spent in a 5 min bin was recorded using a stop-watch for the following nociceptive behavior: flinching, shaking, biting and licking of the injected paw.

Test compound E1-1.2 was administered as a mesylate salt (mpk based on molecular weight of the free base).

Effects of the test compound was assessed in the following bins: 0-5 minutes from early phase (phase-1) and 20-35 minutes from late phase (phase-II).

Figure 9A:
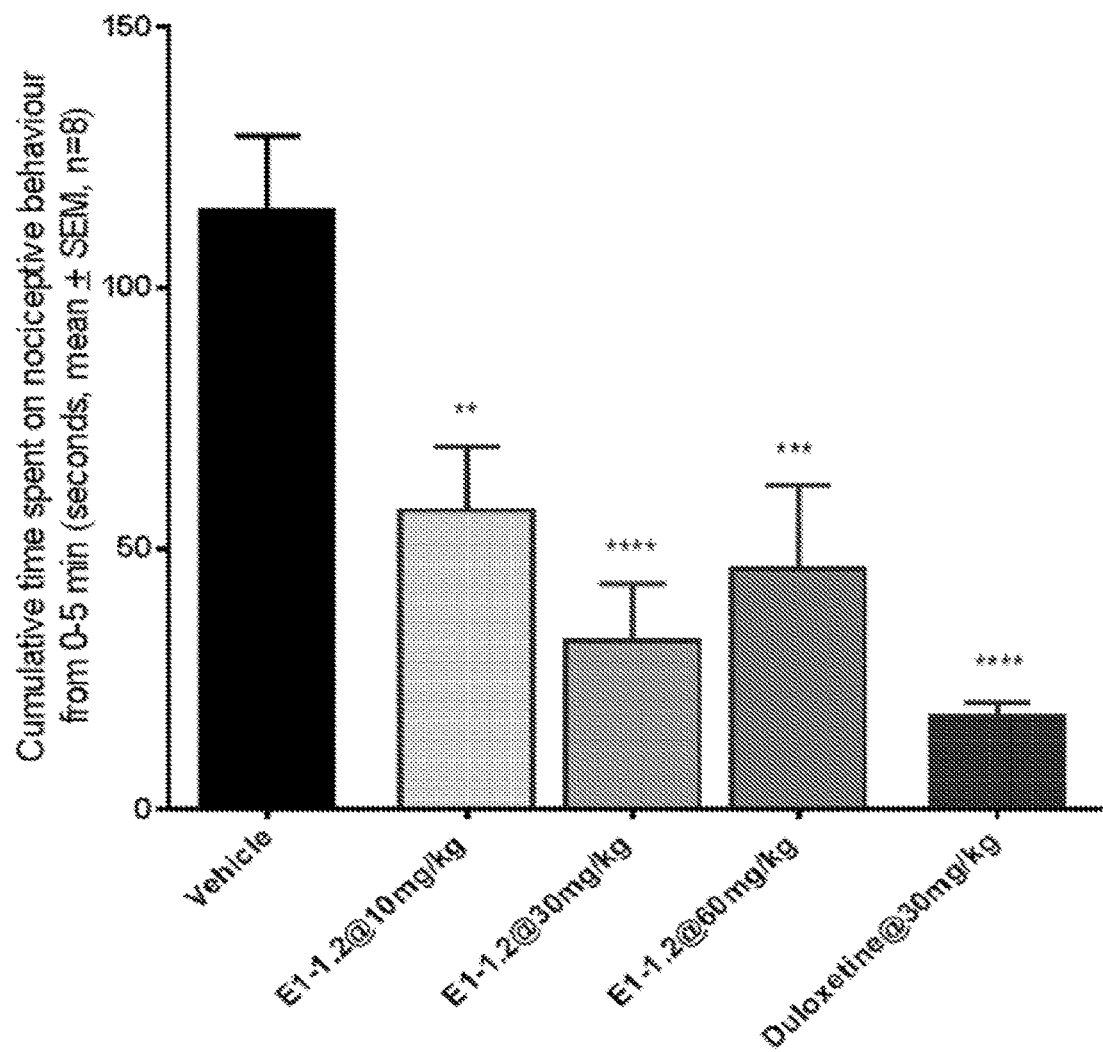
FIG. 9A shows the rat formalin model nociceptive behavior in phase I as described in Example 2.9 for compound E1-1.2.
Figure 9B:
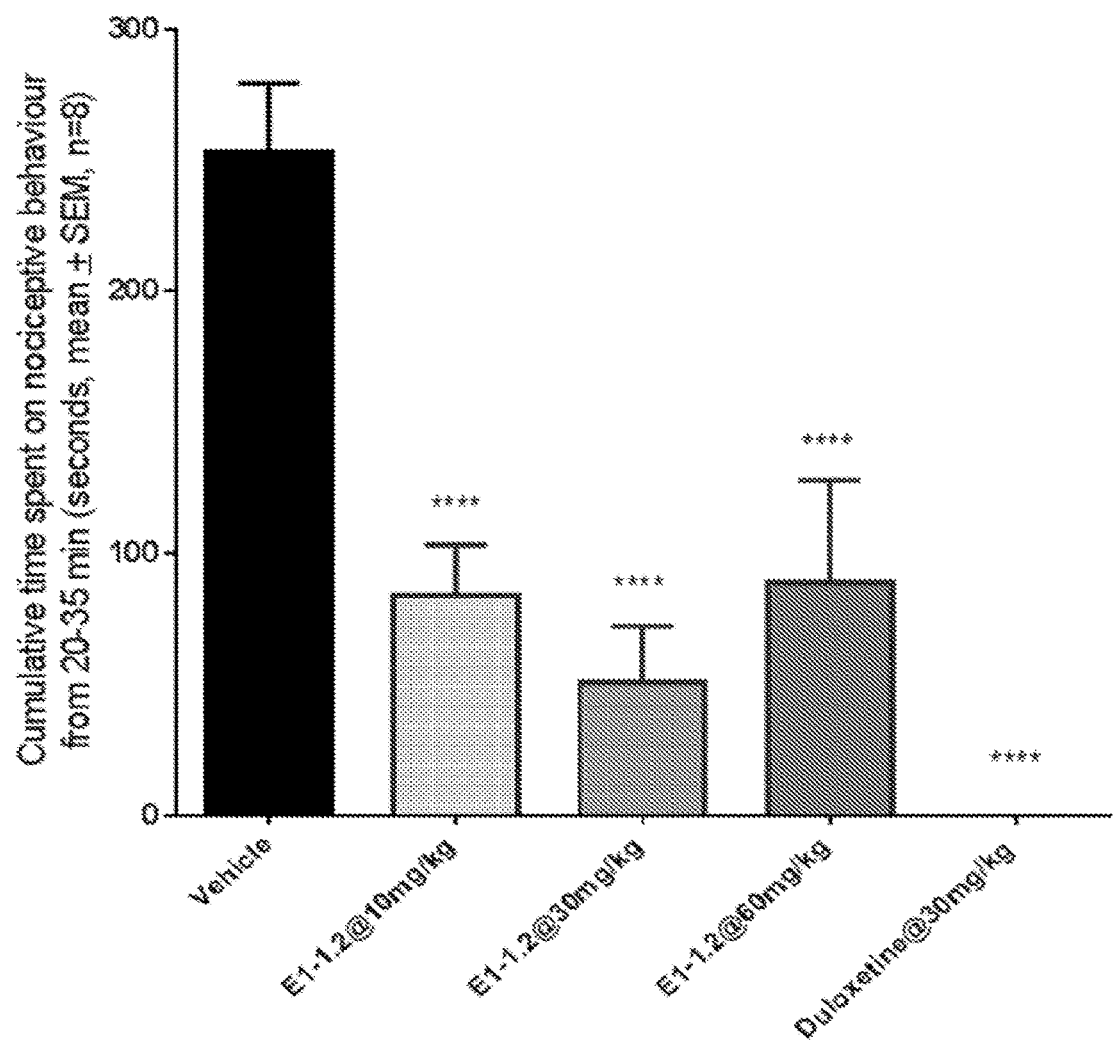
FIG. 9B shows the rat formalin model nociceptive behavior in phase II as described in Example 2.9 for compound E1-1.2.

The results are shown in FIGS. 9A and 9B. Bars represent the mean±SEM for each dose group (n=8, ****: different from vehicle group, p<0.0001, One-way ANOVA, Dunnett's post-test). Doses are given as milligram per kilogram (mpk).

At each of the doses (10, 30 and 60 mpk i.p.), Compound E1-1.2 decreased the cumulative time spent on nociceptive behavior in phase 1 (0-5 mins) (FIG. 9A) and phase 11 (20-35 mins) (FIG. 9B).

Example 2.10. Cortical Spreading Depression (CSD), Aura Phase of Migraine Model

The cortical spreading depression model is utilized to investigate whether treatment with compounds of the present invention affect electrophysiological and hemodynamic events in a rat model of migraine.

Rats were anesthetized with 5% isoflurane (in 70% $N_2O$ and 30% $O_2$; flow 300 ml/min) and placed in a stereotactic frame. During the operation and CSD the concentration of anesthetic was reduced to 1-1.5%. The rectal temperature was maintained at 37.0±1.0° C. with a homeothermic blanket system. The skin was opened by a medial incision and retracted laterally. Three burr holes were drilled under saline cooling over the right hemisphere at the following coordinates (mm from bregma): (1) posterior 4.5, lateral, 2.0 (occipital cortex): KCl application site; (2) posterior 0.5, lateral 2.0 (parietal cortex): LDF recording site; (3) anterior 2, lateral 2 (frontal cortex): DC potential recording site. A laser-Doppler flow probe (Oxyflow, Oxford Optronics, UK) to monitor CBF and an invasive Ag/AgCl electrode for measuring direct current (DC) potential shifts were placed in the parietal and frontal cortex burr holes on the intact dura and in the cortex, respectively. The laser-Doppler flow probe was positioned in an area free of large pial and dural vessels to minimize a large-vessel contribution to the signal. For the DC-potential measurement, a reference electrode was fixed in the neck. Dura overlying the occipital cortex was gently removed and care was taken to avoid bleeding. After surgical preparation, the cortex was allowed to recover for 15 minutes under saline irrigation. A cotton ball (2 mm diameter) soaked with 1M KCl was placed on the pial surface and kept moist by placing 5 µl of KCl solution every 15 minutes. Test compound or vehicle was administered ten (10) minutes prior to CSD initiation. Positive control MK-801 was administrated 30 min prior to CSD initiation. The number of KCl-induced CSDs was counted for 2 hours. The CBF and DC-potentials were monitored continuously starting from 5 minutes before KCl exposure.

Test compound E1-1.2 was administered as a mesylate salt (mpk based on molecular weight of the mesylate salt).

The data was collected in Windaq acquisition software (Dataq Instruments, USA) at 20 kHz. The raw data was analyzed in Clampfit program (Axon Instruments, USA). The signals were low pass filtered (cut off range 5-10000 Hz) that CSD episodes in DC and CBF could be confirmed. The following parameters were analyzed: i) the number, duration and amplitude of DC-potentials, and ii) the number and amplitude of CBF events.

Figure 10:
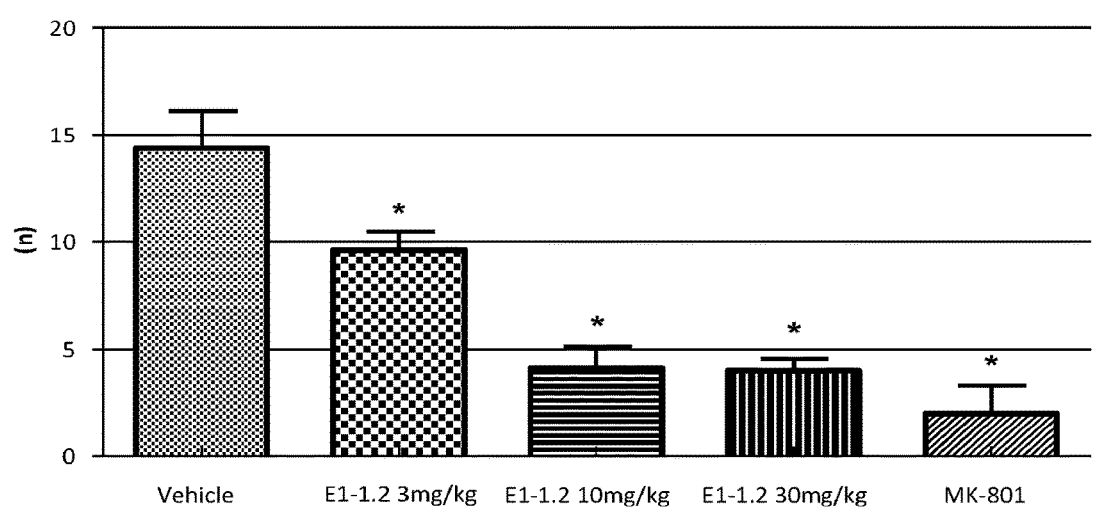
FIG. 10 shows the number of DC potentials for compound E1-1.2 in the cortical spreading depression (migraine) model as described in Example 2.10.

The results for number of DC potentials is shown in FIG. 10. Doses were given as milligram per kilogram (mpk). The dose of MK-801, the positive control, was 1.25 mg/kg. Bars represent mean±Standard Error of Mean (SEM), and differences were considered to be statistically significant at the P<0.05 level (n=8, * different from vehicle group). Statistical analysis was performed using StatsDirect statistical software. Differences between groups were analyzed by using 1-way ANOVA and Dunnett's post hoc test.

Amplitude of DC potentials for compound E1-1.2 at various doses and MK-801 was not statistically different compared to vehicle (not shown). Duration of DC potentials for compound E1-1.2 at various doses was not statistically different compared to vehicle (not shown). Duration of DC potentials for MK-801 was increased compared to vehicle (p<0.05, not shown).

The magnitude of CBF was unchanged for compound E1-1.2 compared to vehicle. The number of CBF events was decreased for compound E1-1.2 at 10 mg/kg and for MK-801 at 1.25 mg/kg with a statistically significant difference from vehicle (* p<0.05 vs vehicle group) (not shown).

Compound E1-1.2 (at 3 mpk, 10 mpk and 30 mpk) significantly decreased the number of DC potentials when compared to the vehicle group (* $p<0.05$ for all doses vs vehicle group, data presented as mean±SEM). The present data demonstrate that compound E1-1.2 was effective in a model of migraine.

What is claimed is:

1. A chemical entity, which is a compound of formula:

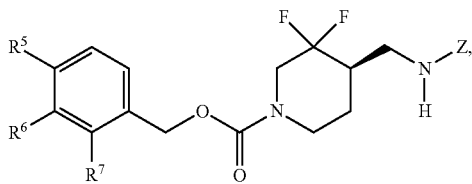

wherein:
$R^5$ is selected from the group consisting of —H, —CH$_3$, —F, —Cl, —CH$_2$CH$_3$, —CF$_2$H, —CH$_2$F, —CF$_3$, —CF$_2$CH$_3$, —CH$_2$CF$_3$, cyclopropyl, —OCF$_3$, —OCF$_2$H, —SCH$_3$, —SO$_2$CH$_3$, and ethynyl;
$R^6$ is selected from the group consisting of —H and —F;
$R^7$ is selected from the group consisting of —H, —F, —Cl, and —CH$_3$; and
Z is

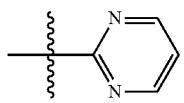 [SMILES: *c1ncccn1]

2. A pharmaceutical composition comprising the chemical entity of claim 1 and a pharmaceutically acceptable carrier.

3. The pharmaceutical composition of claim 2, which is suitable for oral administration.

4. The chemical entity of claim 1, wherein $R^5$ is —H, $R^6$ is —H, and $R^7$ is —H.

5. The chemical entity of claim 1, wherein $R^5$ is —CH$_3$, $R^6$ is —H, and $R^7$ is —H.

6. The chemical entity of claim 1, wherein $R^5$ is —Cl, $R^6$ is —H, and $R^7$ is —H.

7. The chemical entity of claim 1, wherein $R^5$ is —F, $R^6$ is —H, and $R^7$ is —H.

8. The chemical entity of claim 1, wherein $R^5$ is —CH$_2$CH$_3$, $R^6$ is —H, and $R^7$ is —H.

9. The chemical entity of claim 1, wherein $R^5$ is —CF$_2$H, $R^6$ is —H, and $R^7$ is —H.

10. The chemical entity of claim 1, wherein $R^5$ is —CH$_2$F, $R^6$ is —H, and $R^7$ is —H.

11. The chemical entity of claim 1, wherein $R^5$ is —CF$_3$, $R^6$ is —H, and $R^7$ is —H.

12. The chemical entity of claim 1, wherein $R^5$ is —CF$_2$CH$_3$, $R^6$ is —H, and $R^7$ is —H.

13. The chemical entity of claim 1, wherein $R^5$ is —CH$_2$CF$_3$, $R^6$ is —H, and $R^7$ is —H.

14. The chemical entity of claim 1, wherein $R^5$ is cyclopropyl, $R^6$ is —H, and $R^7$ is —H.

15. The chemical entity of claim 1, wherein $R^5$ is —OCF$_3$, $R^6$ is —H, and $R^7$ is —H.

16. The chemical entity of claim 1, wherein $R^5$ is —OCF$_2$H, $R^6$ is —H, and $R^7$ is —H.

17. The chemical entity of claim 1, wherein $R^5$ is —Cl, $R^6$ is —H, and $R^7$ is —F.

18. The chemical entity of claim 1, wherein $R^5$ is —CH$_3$, $R^6$ is —H, and $R^7$ is —F.

19. The chemical entity of claim 1, wherein $R^5$ is —CH$_3$, $R^6$ is —F, and $R^7$ is —H.

20. The chemical entity of claim 1, wherein $R^5$ is —Cl, $R^6$ is —F, and $R^7$ is —H.

21. The chemical entity of claim 1, wherein $R^5$ is —F, $R^6$ is —F, and $R^7$ is —H.

22. The chemical entity of claim 1, wherein $R^5$ is —F, $R^6$ is —H, and $R^7$ is —F.

23. The chemical entity of claim 1, wherein $R^5$ is —F, $R^6$ is —H, and $R^7$ is —Cl.

24. The chemical entity of claim 1, wherein $R^5$ is —F, $R^6$ is —H, and $R^7$ is —CH$_3$.

25. The chemical entity of claim 1, wherein $R^5$ is —Cl, $R^6$ is —H, and $R^7$ is —CH$_3$.

26. The chemical entity of claim 1, wherein $R^5$ is —SCH$_3$, $R^6$ is —H, and $R^7$ is —H.

27. The chemical entity of claim 1, wherein $R^5$ is —SO$_2$CH$_3$, $R^6$ is —H, and $R^7$ is —H.

28. The chemical entity of claim 1, wherein $R^5$ is ethynyl, $R^6$ is —H, and $R^7$ is —H.

* * * * *